US012025622B2

(12) United States Patent
Ranum et al.

(10) Patent No.: US 12,025,622 B2
(45) Date of Patent: Jul. 2, 2024

(54) USE AND TREATMENT OF DI-AMINO ACID REPEAT-CONTAINING PROTEINS ASSOCIATED WITH ALS

(71) Applicant: University of Florida Research Foundation, Incorporated, Gainesville, FL (US)

(72) Inventors: Laura Ranum, Gainesville, FL (US); Tao Zu, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 630 days.

(21) Appl. No.: 17/322,604

(22) Filed: May 17, 2021

(65) Prior Publication Data

US 2021/0285970 A1 Sep. 16, 2021

Related U.S. Application Data

(62) Division of application No. 16/851,690, filed on Apr. 17, 2020, now Pat. No. 11,035,867, which is a division of application No. 16/362,908, filed on Mar. 25, 2019, now Pat. No. 10,663,475, which is a division of application No. 14/775,278, filed as application No. PCT/US2014/022670 on Mar. 10, 2014, now Pat. No. 10,295,547.

(60) Provisional application No. 61/883,219, filed on Sep. 27, 2013, provisional application No. 61/786,258, filed on Mar. 14, 2013.

(51) Int. Cl.

| | |
|---|---|
| ***G01N 33/68*** | (2006.01) |
| ***A61K 35/28*** | (2015.01) |
| ***B01D 21/26*** | (2006.01) |
| ***C07K 16/18*** | (2006.01) |
| ***C12Q 1/6883*** | (2018.01) |

(52) U.S. Cl.

CPC ......... *G01N 33/6896* (2013.01); *A61K 35/28* (2013.01); *B01D 21/262* (2013.01); *C07K 16/18* (2013.01); *C12Q 1/6883* (2013.01); *C07K 2317/34* (2013.01); *C12Q 2600/158* (2013.01); *G01N 2800/2835* (2013.01); *G01N 2800/285* (2013.01)

(58) Field of Classification Search

None

See application file for complete search history.

(56) References Cited

U.S. PATENT DOCUMENTS

| | | | |
|---|---|---|---|
| 5,011,912 A | 4/1991 | Hopp et al. | |
| 6,204,008 B1 * | 3/2001 | Borneman | C07K 14/415 435/219 |
| 6,342,581 B1 | 1/2002 | Rosen et al. | |
| 7,481,997 B1 | 1/2009 | Hardy | |
| 8,993,633 B2 | 3/2015 | Megeney et al. | |
| 9,448,232 B2 | 9/2016 | Petrucelli et al. | |
| 10,295,547 B2 | 5/2019 | Ranum et al. | |
| 10,509,045 B2 | 12/2019 | Ranum et al. | |
| 10,663,475 B2 | 5/2020 | Ranum et al. | |
| 10,940,161 B2 | 3/2021 | Ranum et al. | |
| 11,034,974 B2 | 6/2021 | Ling et al. | |
| 11,345,911 B2 | 5/2022 | Ranum et al. | |
| 2002/0165355 A1 | 11/2002 | Meheus et al. | |
| 2003/0233675 A1 | 12/2003 | Cao et al. | |
| 2006/0068434 A1 | 3/2006 | Stoerker | |
| 2007/0004729 A1 | 1/2007 | Timmer et al. | |
| 2007/0014810 A1 | 1/2007 | Baker et al. | |
| 2007/0036760 A1 | 2/2007 | Wilson et al. | |
| 2007/0093426 A1 | 4/2007 | Wormser | |
| 2008/0227699 A1 | 9/2008 | Chiba et al. | |
| 2009/0074721 A1 | 3/2009 | Kim et al. | |
| 2009/0143418 A1 | 6/2009 | Dixon et al. | |
| 2009/0312395 A1 | 12/2009 | El-Tanani et al. | |
| 2012/0076785 A1 | 3/2012 | Nikolaev et al. | |
| 2012/0094299 A1 | 4/2012 | Ranum et al. | |
| 2012/0220534 A1 | 8/2012 | Levin et al. | |
| 2013/0115603 A9 | 5/2013 | Ranum et al. | |
| 2014/0336133 A1 | 11/2014 | Miller et al. | |
| 2015/0361166 A1 | 12/2015 | Edbauer et al. | |
| 2016/0025747 A1 | 1/2016 | Ranum et al. | |
| 2016/0096800 A1 | 4/2016 | Walter et al. | |
| 2018/0292416 A1 | 10/2018 | Ranum et al. | |
| 2019/0142858 A1 | 5/2019 | Ranum et al. | |
| 2019/0153445 A1 | 5/2019 | Seow et al. | |
| 2019/0285652 A1 | 9/2019 | Ranum et al. | |
| 2020/0140846 A1 | 5/2020 | Ranum et al. | |

(Continued)

FOREIGN PATENT DOCUMENTS

| | | |
|---|---|---|
| EP | 2837390 A1 | 2/2015 |
| EP | 2948471 A1 | 12/2015 |

(Continued)

OTHER PUBLICATIONS

Extended European Search Report, dated Sep. 30, 2016, in connection with Application No. EP 14776090.4.

(Continued)

*Primary Examiner* — Agnieszka Boesen

(74) *Attorney, Agent, or Firm* — Wolf, Greenfield & Sacks, P.C.

(57) ABSTRACT

Disclosed herein are methods and compositions for identifying and/or treating subjects having or likely to have amyotrophic lateral sclerosis (ALS) or frontotemporal dementia (FTD). Antibodies specific for one or more di-amino acid repeat-containing proteins are also provided herein.

3 Claims, 35 Drawing Sheets

Specification includes a Sequence Listing.

(56) References Cited

U.S. PATENT DOCUMENTS

| | | | |
|---|---|---|---|
| 2020/0206255 A9 | 7/2020 | Ranum et al. |
| 2020/0232925 A1 | 7/2020 | Ranum et al. |
| 2020/0241013 A1 | 7/2020 | Ranum et al. |
| 2020/0268691 A1 | 8/2020 | Ranum et al. |
| 2020/0341012 A1 | 10/2020 | Ranum et al. |
| 2021/0236535 A1 | 8/2021 | Ranum et al. |

FOREIGN PATENT DOCUMENTS

| | | |
|---|---|---|
| EP | 3440100 A1 | 2/2019 |
| WO | WO 2001/75067 A2 | 10/2001 |
| WO | WO 2006/083800 A2 | 8/2006 |
| WO | WO 2010/115033 A2 | 10/2010 |
| WO | WO 2010/132982 A1 | 11/2010 |
| WO | WO 2013/030588 A1 | 3/2013 |
| WO | WO 2014/114303 A1 | 7/2014 |
| WO | WO 2014/114660 A1 | 7/2014 |
| WO | WO 2014/116865 A1 | 7/2014 |
| WO | WO 2014/159247 A1 | 10/2014 |
| WO | WO 2016/025692 A1 | 2/2016 |
| WO | WO 2017/176813 A1 | 10/2017 |
| WO | WO 2018/035408 A1 | 2/2018 |
| WO | WO 2018/195110 A1 | 10/2018 |
| WO | WO 2019/060918 A1 | 3/2019 |

OTHER PUBLICATIONS

International Search Report and Written Opinion, dated Aug. 22, 2014, in connection with Application No. PCT/US2014/022670.
International Preliminary Report on Patentability, dated Sep. 24, 2015, in connection with Application No. PCT/US2014/022670.
International Search Report and Written Opinion, dated Sep. 21, 2016, in connection with Application No. PCT/US2016/034738.
International Preliminary Report on Patentability, dated Dec. 14, 2017, in connection with Application No. PCT/US2016/034738.
Supplementary Partial European Search Report, dated Oct. 18, 2019, in connection with Application No. EP 17779695.0.
Extended European Search Report, dated Jan. 7, 2020, in connection with Application No. EP 17779695.0.
Extended European Search Report, dated Dec. 17, 2020, in connection with Application No. EP 18786964.9.
International Preliminary Report on Patentability, dated Oct. 31, 2019, in connection with Application No. PCT/US2018/028015.
Extended European Search Report, dated Nov. 26, 2021, in connection with Application No. EP 18860923.4.
International Search Report and Written Opinion, dated Jan. 15, 2019, in connection with Application No. PCT/US2018/052913.
International Preliminary Report on Patentability, dated Apr. 9, 2020, in connection with Application No. PCT/US2018/052913.
Extended European Search Report, dated Jun. 11, 2021, in connection with Application No. EP 18859783.5.
International Search Report and Written Opinion, dated Dec. 6, 2018, in connection with Application No. PCT/US2018/052745.
International Preliminary Report on Patentability, dated Apr. 9, 2020, in connection with Application No. PCT/US2018/052745.
Invitation to Pay Additional Fees, mailed Nov. 30, 2020, in connection with Application No. PCT/US2020/051671.
International Search Report and Written Opinion, dated Feb. 9, 2021, in connection with Application No. PCT/US2020/051671.
International Preliminary Report on Patentability, dated Mar. 31, 2022, in connection with Application No. PCT/US2020/051671.
International Search Report and Written Opinion, dated Dec. 31, 2020, in connection with Application No. PCT/US2020/051670.
International Preliminary Report on Patentability, dated Apr. 7, 2022, in connection with Application No. PCT/US2020/051670.
Invitation to Pay Additional Fees, mailed Feb. 19, 2021, in connection with Application No. PCT/US2020/054976.
International Search Report and Written Opinion, dated Apr. 23, 2021, in connection with Application No. PCT/US2020/054976.
International Preliminary Report on Patentability, dated Apr. 21, 2022, in connection with Application No. PCT/US2020/054976.
[No Author Listed] Amersham ECL Western Blotting Detection Reagent. Retrieved from the internet under https://www.cytivalifesciences.com/en/us/shop/protein-analysis/blotting-and-detection/blotting-standards-and-reagents/amersham-ecl-western-blotting-detection-reagent-p-05748 on Feb. 22, 2022, 6 pages.
[No Author Listed] EBNA1—Epstein-Barr nuclear antigen 1—Epstein-Barr virus (strain GD1) (HHV-4)—EBNA1 gene & protein, 2018 Jan. 2018. Retrieved from the internet under https://www.uniprot.org/uniprot/Q3KSS4 on Sep. 12, 2018. 6 pages.
[No Author Listed], Abstracts. Medizinische Genetik, Berufsverband Nedizinische Genetik, Muchen, DE. Medgen. Mar. 4, 2016; 28(1):84-232. DOI: 10.1007/s11825-016-0083-5.
Ash et al., Unconventional translation of C9ORF72 GGGGCC expansion generates insoluble polypeptides specific to c9FTD/ALS. Neuron. Feb. 20, 2013;77(4):639-46. doi: 10.1016/j.neuron.2013.02.004. Epub Feb. 12, 2013.
Ashizawa et al., GGCCTG repeats put a hex on Purkinje cells and motor neurons in SCA36. Neurology. Jul. 24, 2012;79(4):302-3. doi: 10.1212/WNL.0b013e31826043d9. Epub Jun. 27, 2012.
Ayhan et al., SCA8 RAN polySer protein preferentially accumulates in white matter regions and is regulated by eIF3F. EMBO J. Oct. 1, 2018;37(19). pii: e99023. doi: 10.15252/embj.201899023. Epub Sep. 11, 2018.
Baboonian et al., Cross reaction of antibodies to a glycine/alanine repeat sequence of Epstein-Barr virus nuclear antigen-1 with collagen, cytokeratin, and actin. Ann Rheum Dis. Nov. 1991;50(11):772-5.
Bae et al., Antibody-aided clearance of extracellular α-synuclein prevents cell-to-cell aggregate transmission. J Neurosci. Sep. 26, 2012;32(39):13454-69.
Bañez-Coronel et al., A pathogenic mechanism in Huntington's disease involves small CAG-repeated RNAs with neurotoxic activity. PLoS Genet. 2012;8(2):e1002481. doi: 10.1371/journal.pgen.1002481. Epub Feb. 23, 2012.
Batra et al., Partners in crime: bidirectional transcription in unstable microsatellite disease. Hum Mol Genet. Apr. 15, 2010;19(R1):R77-82. doi: 10.1093/hmg/ddq132. Epub Apr. 4, 2010.
Carroll et al., Potent and selective antisense oligonucleotides targeting single-nucleotide polymorphisms in the Huntington disease gene / allele-specific silencing of mutant huntingtin. Mol Ther. Dec. 2011;19(12):2178-85. doi: 10.1038/mt.2011.201. Epub Oct. 4, 2011.
Chen et al., Functional genomics in *Drosophila* models of human disease. Briefings in Functional Genomics. Aug. 22, 2012;11(5):405-415.
Cleary et al., Repeat-associated non-ATG (RAN) translation in neurological disease. Hum Mol Genet. Oct. 15, 2013;22(R1):R45-51. doi: 10.1093/hmg/ddt371. Epub Aug. 4, 2013.
Donnelly et al., RNA toxicity from the ALS/FTD C9ORF72 expansion is mitigated by antisense intervention. Neuron. Oct. 16, 2013;80(2):415-28. doi: 10.1016/j.neuron.2013.10.015.
Duan et al., Generation of polyclonal antiserum for the detection of methylarginine proteins. J Immunol Methods. Mar. 30, 2007;320(1-2):132-42. Epub Feb. 6, 2007.
Duellman et al., Antigen-binding properties of monoclonal antibodies reactive with EBNA1 and use in immunoaffinity chromatography. PLoS One. 2009;4(2):e4614. doi: 10.1371/journal.pone.0004614. Epub Feb. 26, 2009.
Gkogkas et al., Pharmacogenetic inhibition of eIF4E-dependent Mmp9 mRNA translation reverses fragile X syndrome-like phenotypes. Cell Rep. Dec. 11, 2014;9(5):1742-1755. doi: 10.1016/j.celrep.2014.10.064. Epub Nov. 26, 2014.
Gómez-Tortosa et al., C9ORF72 hexanucleotide expansions of 20-22 repeats are associated with frontotemporal deterioration. Neurology. Jan. 22, 2013;80(4):366-70. doi: 10.1212/WNL.0b013e31827f08ea. Epub Jan. 2, 2013.
Hock et al., Antibodies against beta-amyloid slow cognitive decline in Alzheimer's disease. Neuron. May 22, 2003;38(4):547-54.
Jin et al., Metformin Protects Cells from Mutant Huntingtin Toxicity Through Activation of AMPK and Modulation of Mitochondrial

(56) References Cited

OTHER PUBLICATIONS

Dynamics. Neuromolecular Med. Dec. 2016;18(4):581-592. doi: 10.1007/s12017-016-8412-z. Epub May 25, 2016. Author Manuscript, 19 pages.

Kearse et al., CGG Repeat-Associated Non-AUG Translation Utilizes a Cap-Dependent Scanning Mechanism of Initiation to Produce Toxic Proteins. Mol Cell. Apr. 21, 2016;62(2):314-322. doi: 10.1016/j.molcel.2016.02.034. Epub Mar. 31, 2016.

Leitman et al., ER stress-induced eIF2-alpha phosphorylation underlies sensitivity of striatal neurons to pathogenic huntingtin. PLoS One. Mar. 3, 2014;9(3):e90803. doi: 10.1371/journal.pone.0090803.

Ma et al., Metformin therapy in a transgenic mouse model of Huntington's disease. Neurosci Lett. Jan. 10, 2007;411(2):98-103. doi: 10.1016/j.neulet.2006.10.039. Epub Nov. 15, 2006.

Mirkin, Expandable DNA repeats and human disease. Nature. Jun. 21, 2007;447(7147):932-40. doi: 10.1038/nature05977.

Mori et al., The C9orf72 GGGGCC repeat is translated into aggregating dipeptide-repeat proteins in FTLD/ALS. Science. Mar. 15, 2013;339(6125):1335-8. doi: 10.1126/science.1232927. Epub Feb. 7, 2013. Supplementary information included.

Satoh et al., Dystrophic neurites express C9orf72 in Alzheimer's disease brains. Alzheimers Res Ther. Aug. 16, 2012;4(4):33. doi: 10.1186/alzrt136. 13 pages.

Sha et al., Treatment implications of C9ORF72. Alzheimer's Res Ther. Nov. 27, 2012;4(6):46. doi: 10.1186/alzrt149. eCollection 2012.

Shoesmith et al., Amyotrophic lateral sclerosis: update for family physicians. Can Fam Physician. Dec. 2006;52(12):1563-9.

Trouth et al., Myasthenia gravis: a review. Autoimmune Dis. ;2012:874680. doi: 10.1155/2012/874680. Epub Oct. 31, 2012.

Vaughn et al., Inhibition of PKR protects against tunicamycin-induced apoptosis in neuroblastoma cells. Gene. Feb. 15, 2014;536(1):90-6. doi: 10.1016/j.gene.2013.11.074. Epub Dec. 14, 2013.

Wang et al., Comparative Analysis of VOCs in Exhaled Breath of Amyotrophic Lateral Sclerosis and Cervical Spondylotic Myelopathy Patients. Sci Rep. 2016;6:26120. Published May 23, 2016. doi:10.1038/srep26120.

Xiao et al., Isoform-specific antibodies reveal distinct subcellular localizations of C9orf72 in amyotrophic lateral sclerosis. Ann Neurol. Oct. 2015;78(4):568-83. doi: 10.1002/ana.24469. Epub Aug. 29, 2015.

Yanagisawa et al., Protein Binding of a DRPLA Family Through Arginine-Glutamic Acid Dipeptide repeats is Enhanced by Extended polyglutamine. Human Molecular Genetics. 2000;9(9):1433-1442.

Yu et al., Developing therapeutic antibodies for neurodegenerative disease. Neurotherapeutics. Jul. 2013;10(3):459-72. doi: 10.1007/s13311-013-0187-4.

Zhang et al., Aggregation-prone c9FTD/ALS poly(GA) RAN-translated proteins cause neurotoxicity by inducing ER stress. Acta Neuropathol. 2014;128:505-24.

Zhou et al., Antibodies inhibit transmission and aggregation of C9orf72 poly-GA dipeptide repeat proteins. EMBO Mol Med. May 2017;9(5):687-702. doi: 10.15252/emmm.201607054.

Zu et al., RAN proteins and RNA foci from antisense transcripts in C9ORF72 ALS and frontotemporal dementia. Proc Natl Acad Sci U S A. Dec. 17, 2013;110(51):E4968-77. doi: 10.1073/pnas.1315438110. Epub Nov. 18, 2013.

* cited by examiner

| | Case Information | | | | | | RAN Inclusions | | | | |
|---|---|---|---|---|---|---|---|---|---|---|---|
| | Case | C9 EXP | Age | Sex/Race | PMD | DX | GP | PA | PR | GR | GA |
| Hippocampus | 1 | + | 59 | F/W | 4 | ALS | +++ | + | + | ++ | ++ |
| | 2 | + | 42 | M/W | 10 | A/F | +++ | + | NA | NA | NA |
| | 3 | + | 74 | F/W | 16 | FTD | +++ | +++* | +++* | ++ | + |
| | 4 | + | 45 | M/W | 3 | ALS | +++ | - | + | ++ | + |
| | 5 | + | 82 | F/W | 17 | FTD | +++ | + | + | ++ | + |
| | 6 | + | 86 | F/W | 10 | A/F | ++ | - | + | ++ | - |
| | 7 | - | 76 | M/W | 7 | ALS | - | - | - | - | - |
| | 8 | - | 55 | M/W | 7.5 | ALS | - | - | NA | NA | NA |
| | 9 | - | 60 | M/W | 16 | CON | - | - | NA | NA | NA |
| | 10 | - | 81 | M/W | 6 | FTD | - | NA | NA | - | - |
| | 11 | - | 83 | M/W | 17 | FTD+ | - | - | - | - | - |
| | 12 | - | 77 | M/W | 16 | CON | - | - | - | - | - |
| Motor Cortex | 1 | + | 59 | F/W | 4 | ALS | +++ | - | - | ++ | ++ |
| | 2 | + | 42 | M/W | 10 | A/F | +++ | + | + | + | - |
| | 7 | - | 76 | M/W | 7 | ALS | - | - | - | - | - |
| | 8 | - | 55 | M/W | 7.5 | ALS | - | - | - | - | - |
| | 9 | - | 60 | M/W | 16 | CON | - | - | - | - | - |
| Spinal Cord | 2 | + | 42 | M/W | 6 | A/F | + | - | - | - | - |
| | 13 | + | 53 | M/W | 10 | ALS | + | - | - | - | - |
| | 14 | + | 55 | F/W | ? | A/F | + | - | - | - | - |
| | 7 | - | 76 | M/W | 7 | ALS | - | - | - | - | - |
| | 8 | - | 55 | M/W | 7.5 | ALS | - | - | - | - | - |
| | 9 | - | 60 | M/W | 16 | CON | - | - | - | - | - |
| | 15 | - | 64 | F/W | 0 | ALS | - | - | - | - | - |
| | 16 | - | 79 | M/W | 33 | ALS | - | - | - | - | - |
| | 17 | - | 79 | M/W | 10 | ALS | - | - | - | - | - |

(-) no inclusions, (+) occasional, (++) moderate, (+++) numerous inclusions. (-) Variable staining from section to section. DX =diagnosis. FTD=frontrotemporal dementia, ALS=amyotrophic lateral sclerosis, F=female, M-Male. PMD=post-mortem interval. NA = not available. HIPPO=hippocampus, M Cortex = motor cortex. The apparent differences in the frequencies of the various inclusions may reflect differences in protein conformation and epitope availability or differences in the affinities of these antibodies.

*FIG. 18*

A
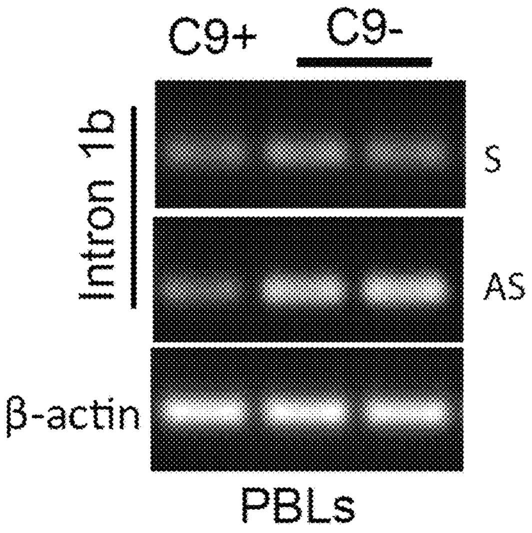
B
| 5' start site to repeat(bp) | PCR clones |
|---|---|
| 251 | 2 |
| 263 | 1 |
| 295 | 7 |
| 322 | 1 |
| 429 | 3 |
| 455 | 1 |
C
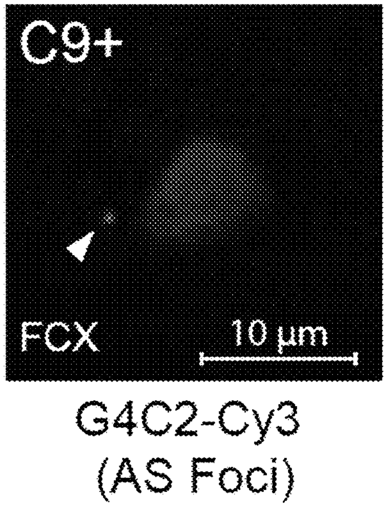
*FIG. 19A-C*

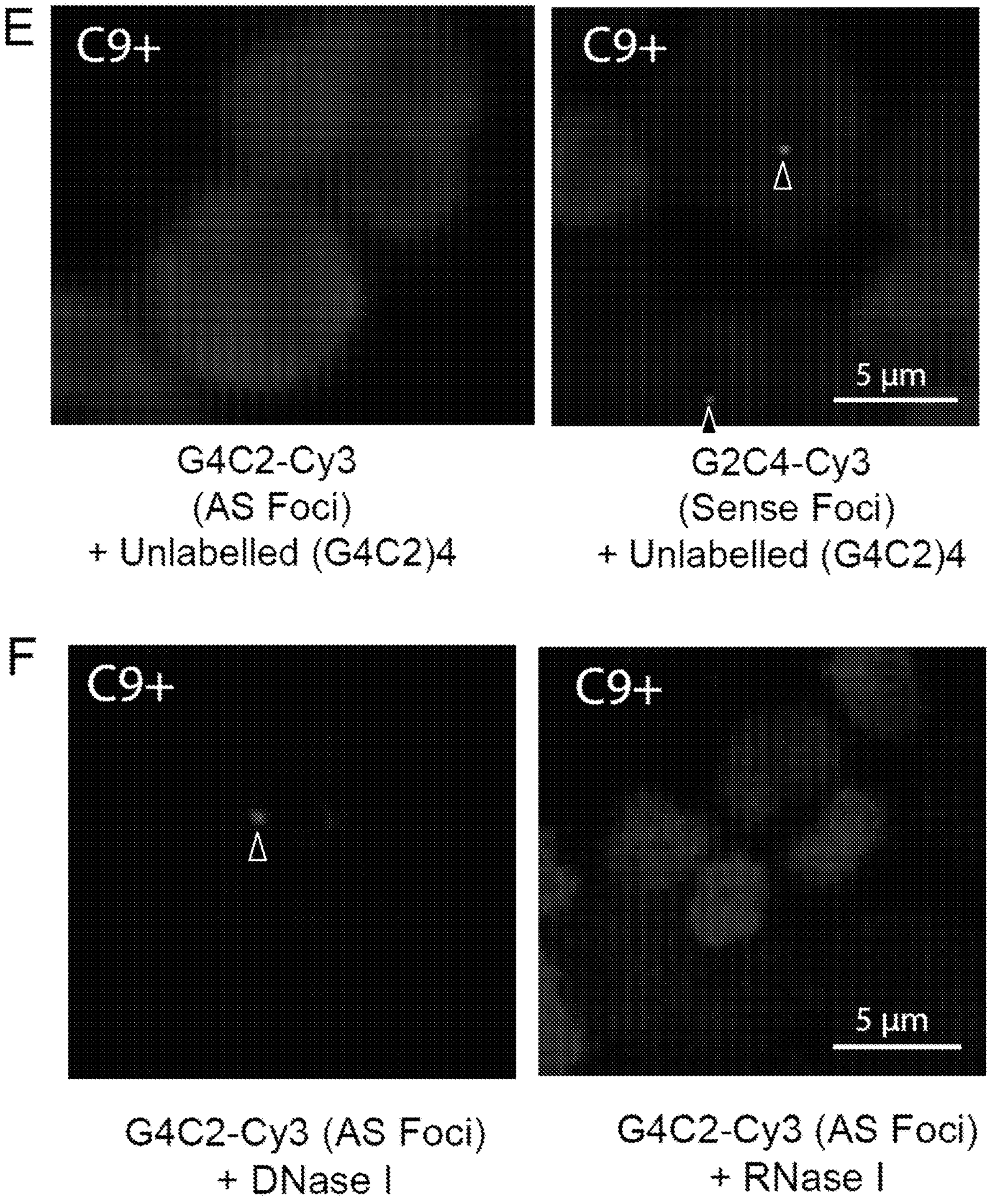
*FIG. 19E-F*

$G_2C_4$ strand

Frame 1

*GEPPLLPAPLPGSRTPNSHPPGCRLLTHPLATACASAAAGAGTATAAPPRARPRARPDHAPAPA
PAPAPAPAPAPAPA(PA)$_{exp}$PAPAPSARLLSSRACYRLRLFPSLFSSG*

Frame 2

MQAIPPVARGESPTPSFGQRNERESKNASSSEESPRFYPRLFPAAEPQTATRQDAASSLTHSPPP
APPPPRAQAPQPQPRPGPAPGPAPTTPRPRPRPRPRPRPRPR(PR)$_{exp}$PRPRPLARDS*

Frame 3

MRGKVKMRRALRRAPASTRASSRQPNPKQPPARMPPPHSPTRHRLRLRRRGRRHRNRSPAPGPPP
GPPRPRPGPGPGPGPGPGPGPGP(GP)$_{exp}$GPGP*

$G_4C_2$ strand

Frame 1

*GPGPGPGPGPGPGPGP(GP)$_{exp}$GPGPGRGRGGPGGGPGAGLRLRCLRPRRRRRRWRVGE*

Frame 2

*RLTRRKQGGKQPQPVASSGTQESRARGRGRGRGRGRGRGRGR(GR)$_{exp}$GRGRGVVGAGPGAG
PGRGCGCGACARGGGGAGGGEWVSEEAASWRVAVWGSAAGKRRG*

Frame 3

*QALELRSRALGAGAGAGAGAGAGAGAGA(GA)$_{exp}$GAGAWSGRARGRARGGAAVAVPAPAAAE
AQAVASG*

*FIG. 21*

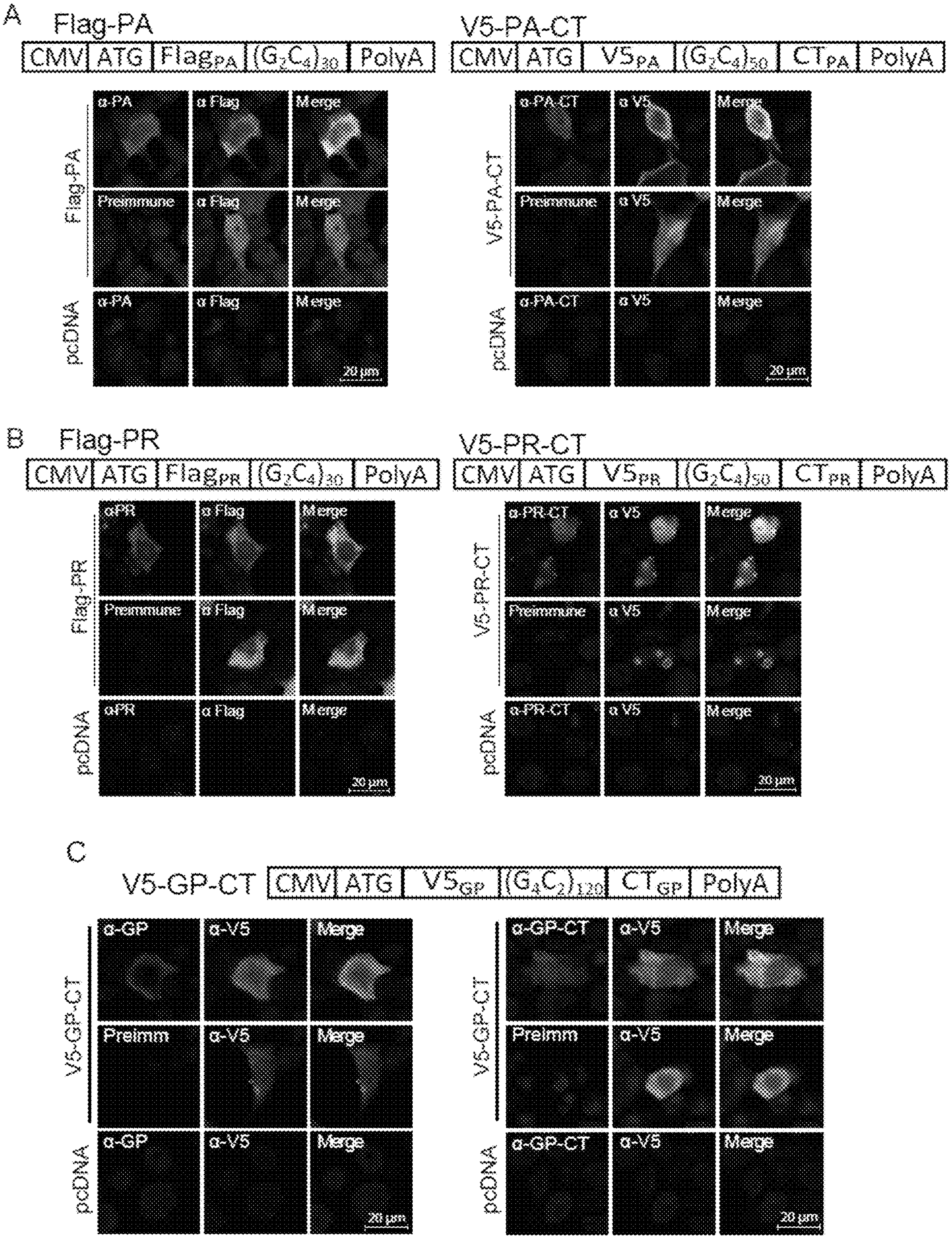
FIG. 22A-C

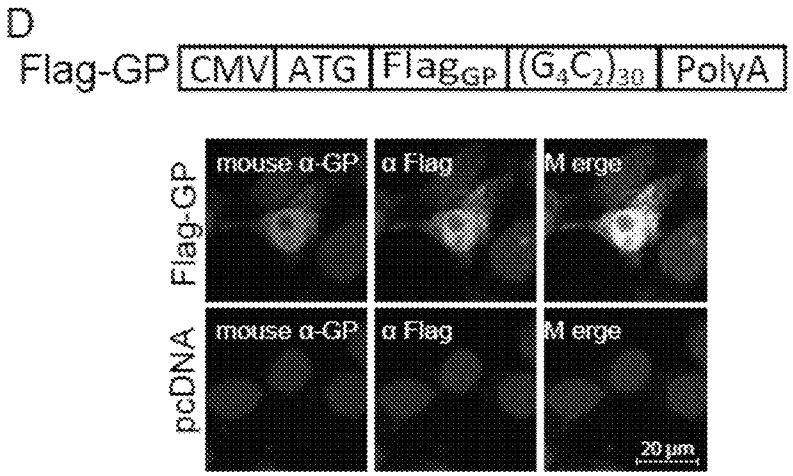
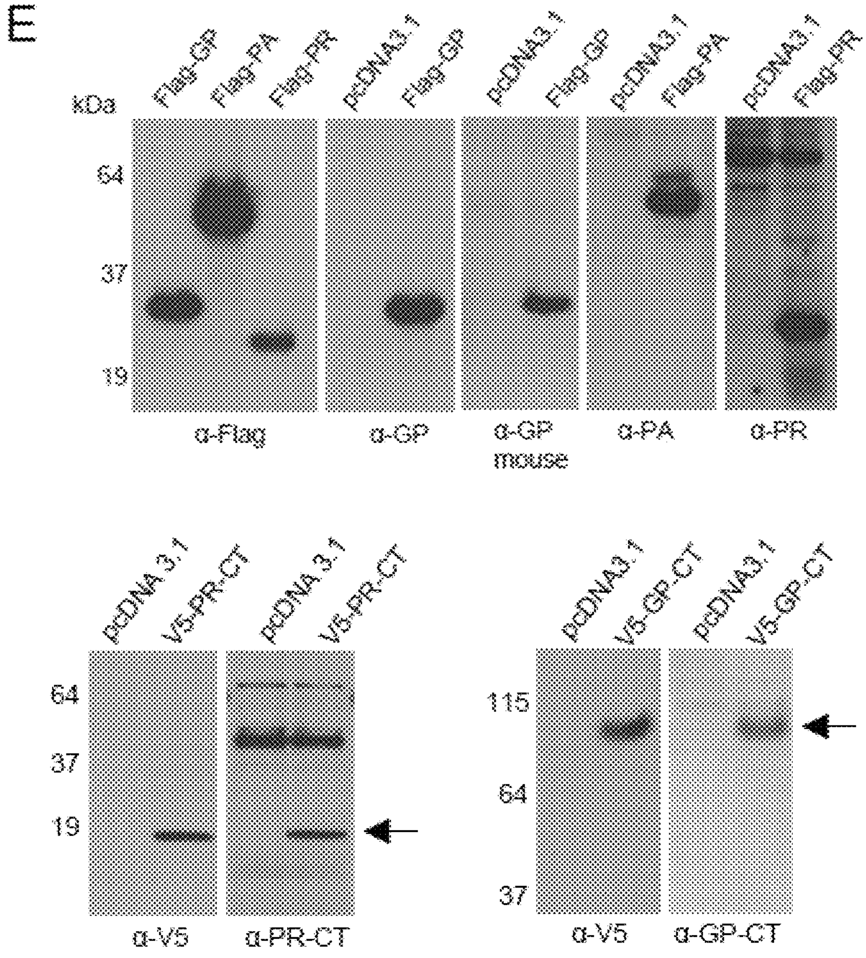
*FIG. 22D-E*

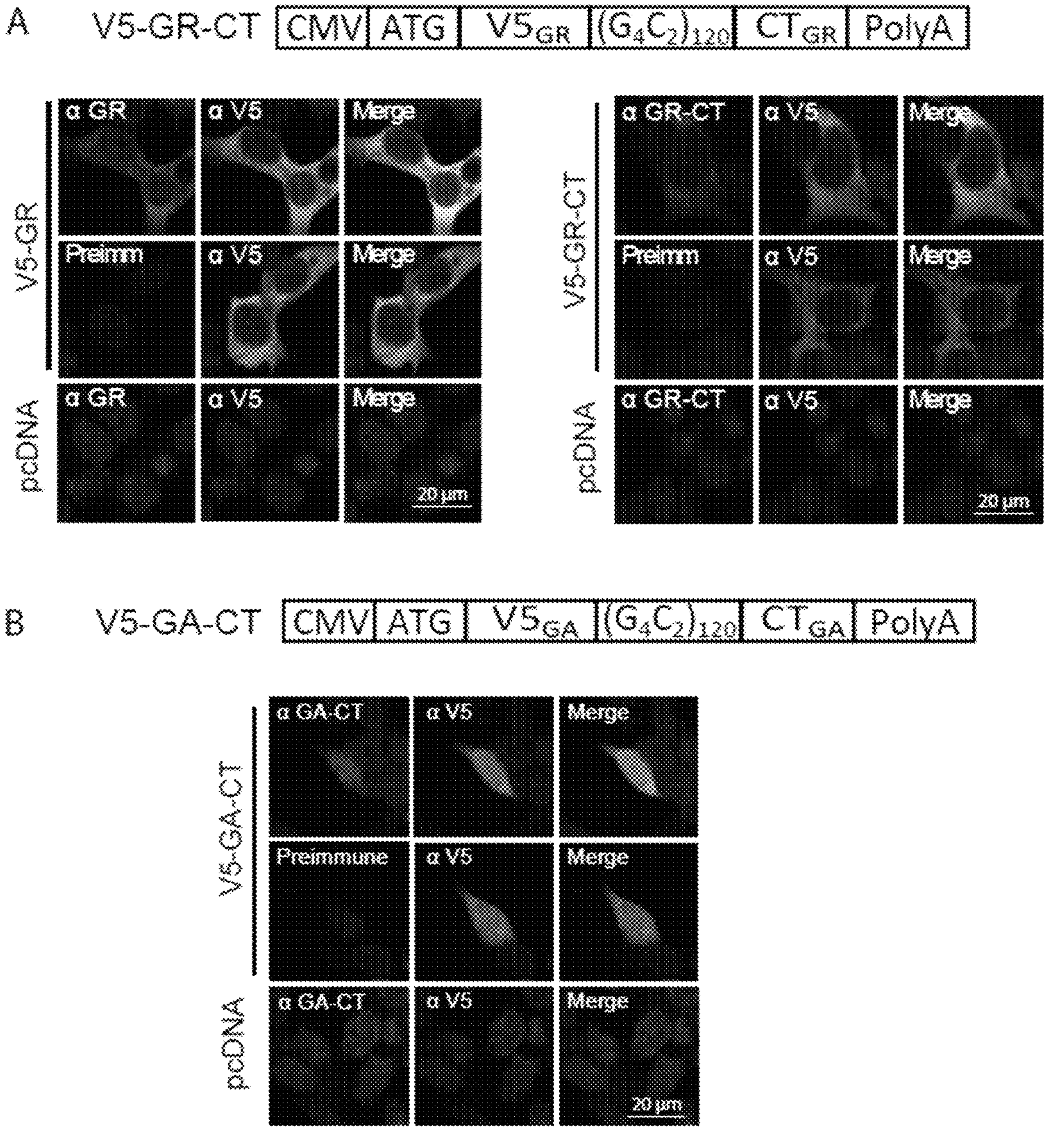
*FIG. 23A-B*

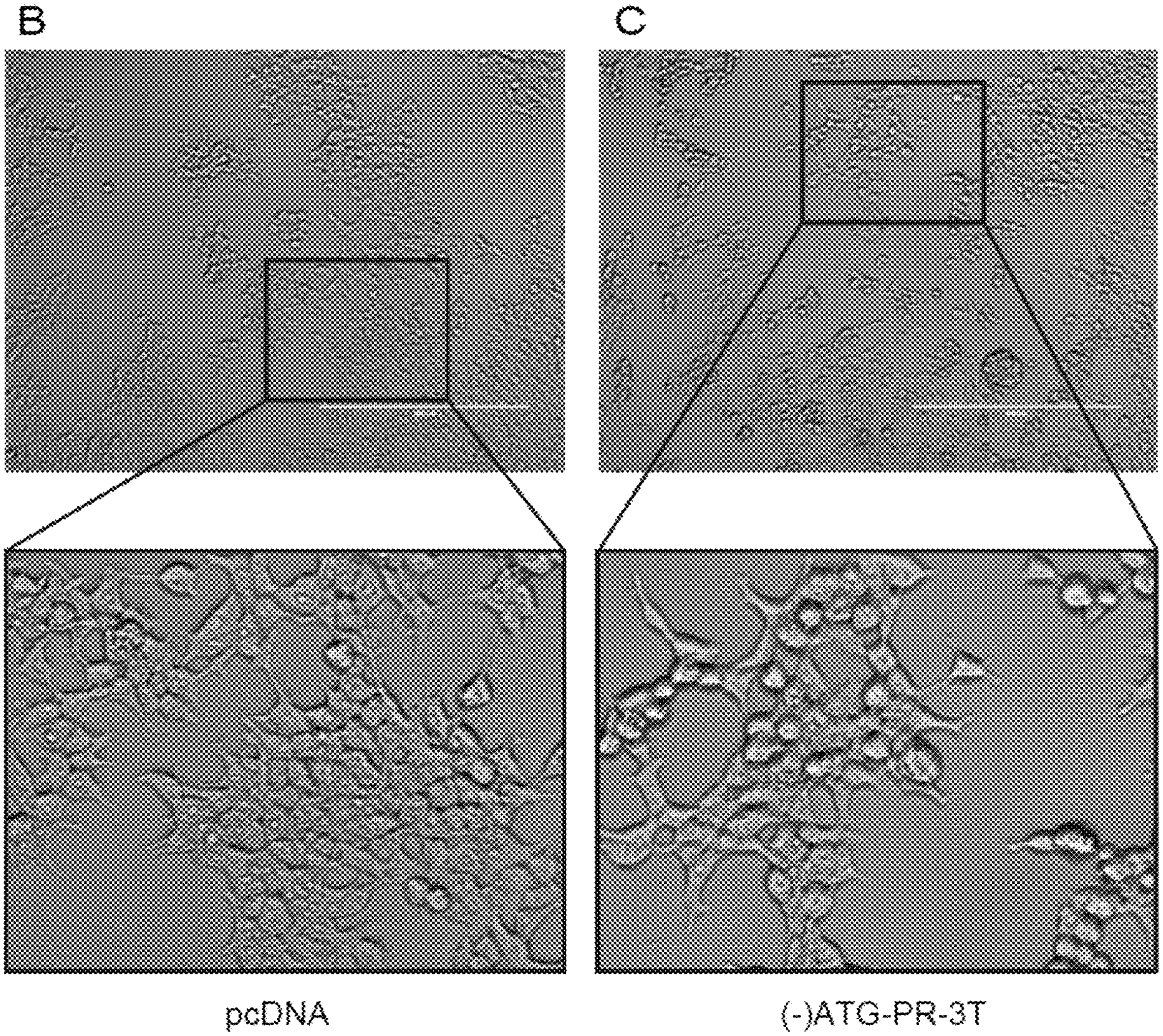
FIG. 26B-C (+)ATG-PR-3T

| Primer Name | Primer Sequence (5' to 3') |
|---|---|
| ASORF-F | AGTCGCTAGAGGCGAAAGC |
| ASORF-R | CGAGTGGGTGAGTGAGGAG |
| LK-ASORF-R | CGACTGGAGCACGAGGACACTGACGAGTGGGTGAGTGAGGAG |
| LK-ASORF-F | CGACTGGAGCACGAGGACACTGAAGTCGCTAGAGGCGAAAGC |
| 1a-F | GCCCACGTAAAAGATGACGC |
| 1a-R | CCTCCTAAACCCACACCTGC |
| LK-1a-R | CGACTGGAGCACGAGGACACTGACCTCCTAAACCCACACCTGC |
| LK-1a-F | CGACTGGAGCACGAGGACACTGAGCCCACGTAAAAGATGACGC |
| LK | CGACTGGAGCACGAGGACACTGA |
| 5'GSP1 | GCTTTCGCCTCTAGCGACT |
| 5'GSP2 | TCTAGCGACTGGTGGAATTGCCT |
| 3'GSP1 | CTGCGGTTGTTTCCCTCCTT |
| 3'GSP2 | TTTCTTGTTCACCCTCAGCGA |
| ACTB3 | CTGGAACGGTGAAGGTGACA |
| ACTB4 | GGGAGAGGACTGGGCCATT |
| 3xTag-Fw | ACGACATCGATTACAAGGACG |
| 3xTag-RV | ATCAGCTTCTGCTCGCTATG |

*FIG. 27*

| Strand | Antigen | ID # | Sequence | Species | IB | IHC | IF |
|---|---|---|---|---|---|---|---|
| AS-$G_2C_4$ | poly(PA) | H3152 | H2N-APAPAPAPAPAPAPACKKKK-amide | Rabbit | Y | Y | Y |
| | PA C-term | H3159 | Ac-CYRLRLFPSLFSSG-OH | Rabbit | Y | Y | Y |
| | poly(PR) | H3150 | Ac-RPRPRPRPRPRPRPRPRPRC-amide | Rabbit | Y | Y | Y |
| | PR C-term | H3162 | Ac-CRPRPLARDS-OH | Rabbit | Y | Y | Y |
| Both Strands | poly(GP) | H3154 | H2N-GPGPGPGPGPGPGPGPGCKK-amide | Rabbit | Y | Y | Y |
| | poly(GP) | F3M1 | H2N-GPGPGPGPGPGPGPGPGCKK-amide | Mouse | Y | Y | Y |
| S-$G_4C_2$ | GP C-term | H3157 | Ac-CRRRRWRVGE-OH | Rabbit | Y | Y | Y |
| | poly(GR) | H3148 | Ac-RGRGRGRGRGRGRGRGRGRC-amide | Rabbit | Y | Y | Y |
| | GR C-term | H3160 | Ac-CRVAVWGSAAGKRRG-OH | Rabbit | Y | Y | Y |
| | GA C-term | H3164 | Ac-CSGRARGRARGGA-amide | Rabbit | Y | Y | Y |

Summary of sense and antisense antibodies including antigen recognized, identification number (ID#), and peptide sequence used for injections in rabbits or mice. Detection of recombinant proteins by various methods is summarized on right. IB=immunoblot, IHC=immunohistochemistry, IF=immunofluorescence, Y=yes, N=no, AS=Antisense, S=Sense.

*FIG. 28*

*Map of BAC insert used to make mouse models*

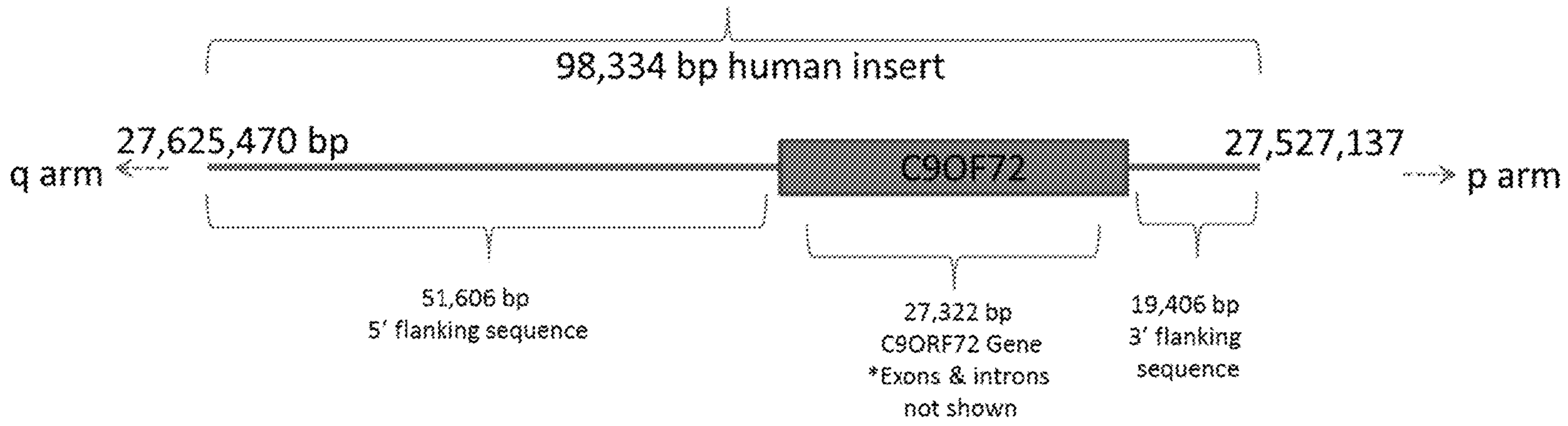

1) BAC insert extends from bp27,625,470 to 27,527,137 of human genome reference sequence on Chromosome 9.
2) The insert was cloned from a patient with ~800 GGGGCC repeats - size estimate above does not include extra repeats from this patient.
3) BAC insert DNA contains about 800 repeats in some clone preps but is very unstable
4) BAC repeat size in the mice is ~500 repeats but this varies between progeny and may grow or shrink in size as mouse colony is expanded and additional generations of mice are propagated in the laboratory.
5) BAC expansion mice express both sense and antisense versions of the C9ORF72 gene

*FIG. 29*

AS-RNA foci (GGCCCC) in 558 &561 lines

USE AND TREATMENT OF DI-AMINO ACID REPEAT-CONTAINING PROTEINS ASSOCIATED WITH ALS

CROSS-REFERENCE TO RELATED APPLICATIONS

This application is a Divisional Application of U.S. application Ser. No. 16/851,690, filed Apr. 17, 2020, which is a Divisional Application of U.S. application Ser. No. 16/362,908, filed Mar. 25, 2019 and issued as U.S. Pat. No. 10,663,475, which is a Divisional Application of U.S. application Ser. No. 14/775,278, filed Sep. 11, 2015 and issued as U.S. Pat. No. 10,295,547, which is a national stage filing under 35 U.S.C. § 371 of International PCT application PCT/US2014/022670, filed Mar. 10, 2014, which claims the benefit of the filing date of U.S. Provisional Application No. 61/786,258, filed Mar. 14, 2013, and the benefit of the filing date of U.S. Provisional Application No. 61/883,219, filed Sep. 27, 2013. The entire contents of each of these referenced applications are incorporated by reference herein.

FEDERALLY SPONSORED RESEARCH OR DEVELOPMENT

This invention was made with government support under NS058901 and NS040389, awarded by the National Institutes of Health. The Government has certain rights in the invention.

BACKGROUND OF THE INVENTION

Expansion of a GGGGCC hexanucleotide sequence within the intron of the human C9ORF72 gene is associated with both amyotrophic lateral sclerosis and frontotemporal dementia in humans. Amyotrophic lateral sclerosis (ALS) is a debilitating disease with varied etiology characterized by rapidly progressing weakness, muscle atrophy, muscle spasticity, difficulty speaking (dysarthria), difficulty swallowing (dysphagia), and difficulty breathing (dyspnea). Although the order and rate of symptoms varies from person to person, eventually most subjects are not able to walk, get out of bed on their own, or use their hands and arms. Most subjects with ALS will eventually die from respiratory failure, usually within three to five years from the onset of symptoms. Riluzole (Rilutek) is the only currently available treatment for ALS and only slows progression and increases survival to a modest extent. Frontotemporal dementia (FTD) is also a devestating group of disorders resulting from atrophy or shrinkage of the frontal and temporal lobes of the brain. This shrinkage or atrophy results in severe behavioral changes. There is currently no cure for FTD and limited medications for managing the symptoms of FID. New methods for diagnosing and treating ALS and/or FTD would greatly benefit ALS and FTD subjects.

SUMMARY OF THE INVENTION

Expansion of a GGGGCC hexanucleotide sequence within the intron of the human C9ORF72 gene is associated with both amyotrophic lateral sclerosis and frontotemporal dementia in humans. As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. These sense and anti-sense transcripts were found to be translated to produce di-amino acid repeat-containing proteins. The sense transcript (containing 5'-GGGGCC-3' hexanucleotide repeats) was found to be translated through repeat-associated non-ATG (RAN) translation such that poly-(Gly-Ala), poly-(Gly-Pro), and poly-(Gly-Arg) proteins were produced. The anti-sense transcript (containing 5'-GGCCCC-3' hexanucleotide repeats) was found to be translated through repeat-associated non-ATG (RAN) translation such that poly-(Pro-Ala), poly-(Pro-Arg), poly-(Gly-Pro) proteins were produced. Additionally, the anti-sense transcript was found to be translated through ATG-initiated translation to produce Met . . . poly-(Pro-Arg) and Met . . . poly-(Gly-Pro) proteins.

These di-amino acid repeat-containing proteins were found to be present in ALS subject blood samples. Accordingly, aspects of the disclosure relate to a method of detection of di-amino acid-repeat containing protein levels in sample (e.g., blood) obtained from a subject, the method comprising measuring di-amino acid-repeat-containing protein levels in the sample of the subject. In some aspects, detection of di-amino acid-repeat containing protein levels may identify (or diagnose) or aid in identification (or aid in diagnosis) of a subject having ALS or FTD or likely to develop ALS or FTD. Alternatively or additionally, detection of di-amino acid-repeat containing protein levels, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject. Aspects of the disclosure also relate to treatment of a subject having ALS or FTD by decreasing or stabilizing di-amino acid-repeat-containing protein levels in the blood of the subject.

Additionally, expression of the anti-sense transcript (containing 5'-GGCCCC-3' hexanucleotide repeats) was found to be highly elevated in subjects having the expanded GGGGCC hexanucleotide repeat compared to controls. Foci of sense and anti-sense transcripts were also detectable using fluorescent in situ hybridization (FISH) in brain and blood cells of patients having the expanded GGGGCC hexanucleotide repeat sequence within the intron of the C9ORF72 gene. Thus, other aspects of the disclosure relate to a method of detection of a hexanucleotide repeat-containing transcript, the method comprising measuring a level a hexanucleotide repeat-containing transcript and/or measuring the presence or absence of a hexanucleotide repeat-containing transcript focus. In some aspects, detection of a hexanucleotide repeat-containing transcript may identify (or diagnose) or aid in identification (or aid in diagnosis) of a subject as having ALS or FTD or likely to develop ALS or FTD. Alternatively or additionally, detection of a hexanucleotide repeat-containing transcript, e.g., in a blood sample of the subject, may identify (or diagnose) or aid in identification (or aid in diagnosis) of a subject as having a risk factor of ALS or FTD, such as an elevated level of a di-amino acid-repeat containing protein or proteins in the cerebrospinal fluid of the subject.

In some aspects, the disclosure relates to a method for identifying a subject as having ALS or FTD or likely to develop ALS or FTD, the method comprising determining, in a blood sample obtained from a subject, a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid repeat-containing proteins that is elevated compared to a control level indicates that the subject has ALS or FTD or is likely to develop ALS or FTD. In some embodiments, the level of the one or more di-amino acid repeat-containing proteins is determined by performing an assay. In some embodiments, the assay comprises an immuno-based assay. In some embodiments, the immuno-based assay comprises an isolated antibody specific for an antigen comprising a sequence as set for in Tables 1, 2, or 3. In some embodiments, the immuno-based assay comprises an isolated antibody specific for the C-terminus of the one or more di-amino acid repeat-containing protein.

In some embodiments, the method further comprises identifying the subject as having ALS or FTD or likely to develop ALS or FTD if the level of the di-amino acid repeat-containing protein is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant.

In some embodiments, the one or more di-amino acid repeat-containing proteins is selected from the poly-(Pro-Ala), poly-(Pro-Arg), Met . . . poly-(Pro-Arg) or Met . . . poly-(Gly-Pro) protein. In some embodiments, the one or more di-amino acid repeat-containing proteins is two or more di-amino acid repeat-containing proteins.

Other aspects of the disclosure relate to a method for treating a subject with ALS or FTD, the method comprising decreasing or preventing an increase in a level of one or more di-amino acid repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein in the blood of the subject. In some embodiments, decreasing or preventing an increase of the level of one or more di-amino acid repeat-containing proteins comprises removing the one or more di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, the bone marrow transplantation is an allogeneic bone marrow transplantation.

In yet another aspect, the disclosure relates to an isolated antibody specific for one or more di-amino acid repeat proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. In some embodiments, the di-amino acid repeat protein is selected from a poly-(Pro-Ala), poly-(Pro-Arg), Met . . . poly-(Pro-Arg) or Met . . . poly-(Gly-Pro) protein. In some embodiments, the isolated antibody is specific for an antigen comprising a sequence or fragment of a sequence as set for in Tables 1, 2, or 3.

Other aspects of the disclosure relate to a method for identifying a subject as having ALS or FTD or likely to develop ALS or FTD, the method comprising determining, in a sample obtained from a subject, a level of a 5'-GGGGCC-3' hexanucleotide repeat-containing RNA and/or a 5'-GGCCCC-3' hexanucleotide repeat-containing RNA, wherein a level of the 5'-GGGGCC-3' hexanucleotide repeat-containing RNA and/or a 5'-GGCCCC-3' hexanucleotide repeat-containing RNA that is elevated compared to a control level indicates that the subject has ALS or FTD or is likely to develop ALS or FTD. In some embodiments, the level is determined by performing an assay. In some embodiments, the assay comprises a nucleic acid-based assay, such as in-situ hybridization (e.g., FISH) or RT-PCR (e.g., quantitative RT-PCR or strand specific quantitative RT-PCR). In some embodiments, the method further comprises identifying the subject as having ALS or FTD or likely to develop ALS or FTD if the level of a 5'-GGGGCC-3' hexanucleotide repeat-containing RNA and/or a 5'-GGCCCC-3' hexanucleotide repeat-containing RNA is elevated compared to a control level. In some embodiments, the method further comprises treating the subject having ALS or FTD or likely to develop ALS or FTD. In some embodiments, treating comprises administering to the subject an effective amount of one or more of riluzole, baclofen, diazepam, phenytoin, trihexyphenidyl or amitriptyline. In some embodiments, treating comprises performing a procedure selected from plasmapheresis or a bone marrow transplant. In some embodiments, the level of a 5'-GGGGCC-3' hexanucleotide repeat-containing RNA and/or a 5'-GGCCCC-3' hexanucleotide repeat-containing RNA is a level of a 5'-GGCCCC-3' hexanucleotide repeat-containing RNA.

Yet other aspects of the disclosure relate to a method for identifying a subject as having ALS or FTD or likely to develop ALS or FTD, the method comprising determining, in a sample obtained from a subject, the presence or absence of foci containing 5'-GGGGCC-3' hexanucleotide repeat-expansion-containing RNA and/or a 5'-GGCCCC-3' hexanucleotide repeat-expansion-containing RNA, wherein the presence of the foci of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. In some embodiments, presence or absence of foci or elevated C9ORF72 sense or antisense RNA levels is determined by performing an assay. In some embodiments, the assay comprises a nucleic acid-based assay, such as strand specific RT-PCR or in-situ hybridization (e.g., FISH).

Yet other aspects of the disclosure relate to transgenic mice. In some embodiments, the transgenic mouse comprises a human C9ORF72 gene and optionally human flanking sequences. In some embodiments, the transgenic mouse comprises SEQ ID NO: 63.

These and other aspects are described in more detail herein and illustrated by the non-limiting figures and examples.

BRIEF DESCRIPTION OF THE DRAWINGS

The drawings are first described.

FIG. 18 is a table summarizing histopathological findings in C9ORF72 positive ALS/FTD cases and controls.

FIGS. 19A-19F are a series of images and datasets. (A) shows strand-specific RT-PCR detection of sense (S) and antisense (AS) transcripts (across intron 1) of PBLs of C9(+) patient and normal controls. (B) is a summary of 5' RACE products. (C) shows FISH staining of frontal cortex from a C9(+) case showing an example of cytoplasmic RNA foci.

(D) shows FISH staining of peripheral blood leukocytes showing the accumulation of antisense (AS) $G_2C_4$ and sense (S) $G_4C_2$ RNA foci in C9(+) but not C9(−) cells. (E) shows antisense foci specificity assay showing excess unlabeled $(G_4C_2)_4$ oligo blocks labeling of G4C2-Cy3 antisense (AS) but not $G_2C_4$-Cy3 labeled sense foci. (F) shows additional controls for antisense RNA foci showing expected DNase I resistance and RNase I sensitivity.

Figure 20:
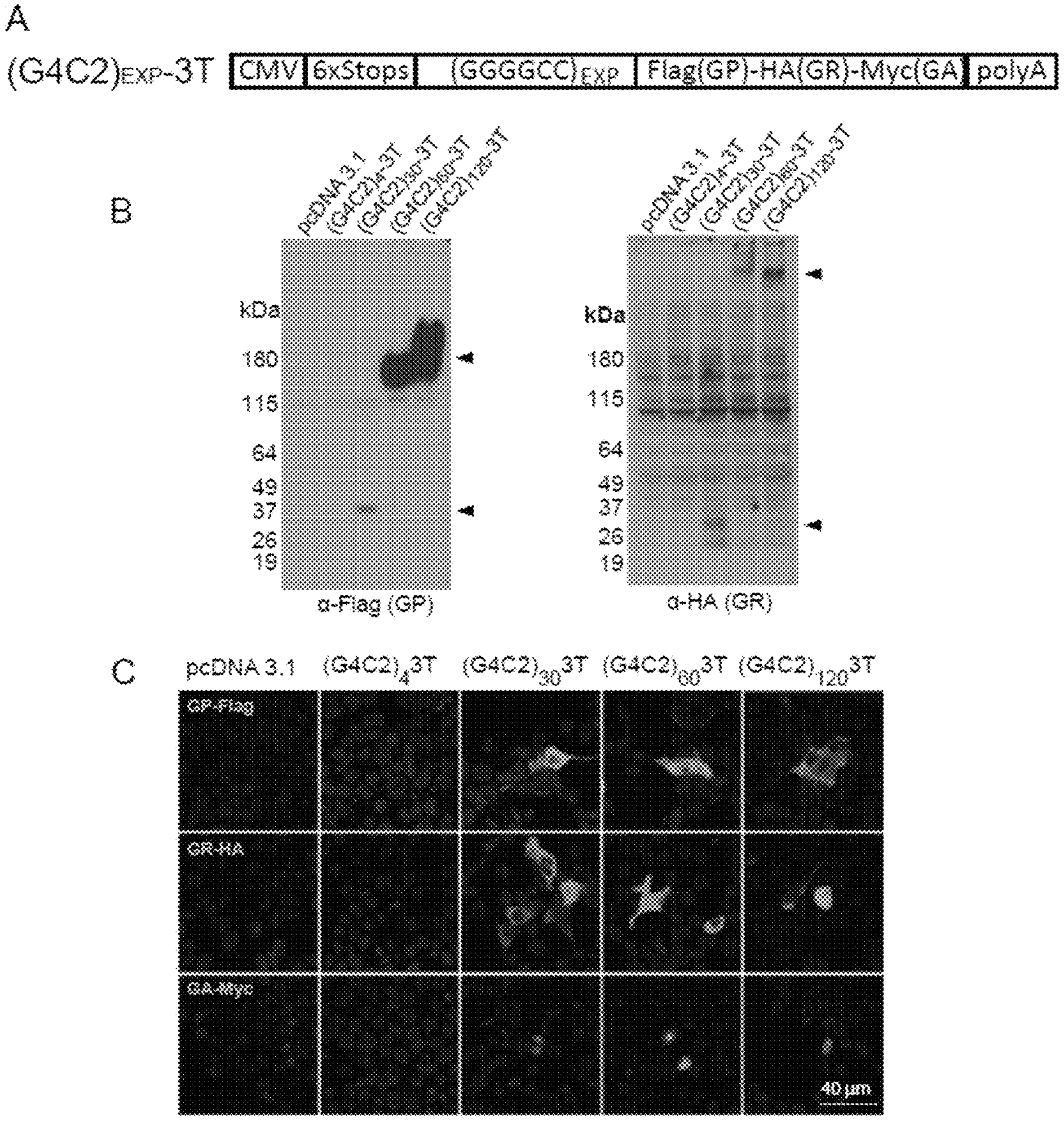

FIG. 20 is a series of images of in vitro evidence for RAN translation of the sense GGGGGCC repeat expansion. (A) shows constructs containing varying GGGGCC repeat lengths with upstream 6× Stop cassette and 3' tags in each reading frame. Immunoblots (B) and/or immunofluorescence staining (C) showing RAN translation occurs in all three frames (GP, OR, GA) in cells transfected with constructs containing 30, 60 and 120 repeats.

FIG. 21 is a schematic of putative protein products in sense and antisense directions for all reading frames SEQ ID NOs: 57-62, from top to bottom. Underlined sequences were used to generate polyclonal antibodies. *=Stop codon.

FIGS. 22A-22E are a series of images showing validation of dual antibodies to detect putative polyPA, polyPR, polyGP proteins by immunofluorescence and protein blot (A-D Top)l Schematic diagrams of constructs expressing ATG-initiated N-terminal epitope-tagged (V5 or Flag) repeat proteins with or without endogenous C-terminal sequences. (A-D Bottom panels), co-localization of a-Flag or a-V5 staining in transfected HEK293T cells with staining using the following newly developed antibodies: (A) α-PA or α-PA-CT (antisense); (B) α-PR or α-PR-CT (C) rabbit α-GP or α-GP-CT (sense); (D) mouse α-GP. Similar staining was not seen in preimmune or pcDNA3.1 empty vector controls; (E) Corresponding immunoblots showing six of the seven antibodies tested also detect recombinant proteins by Western.

Figure 23C:
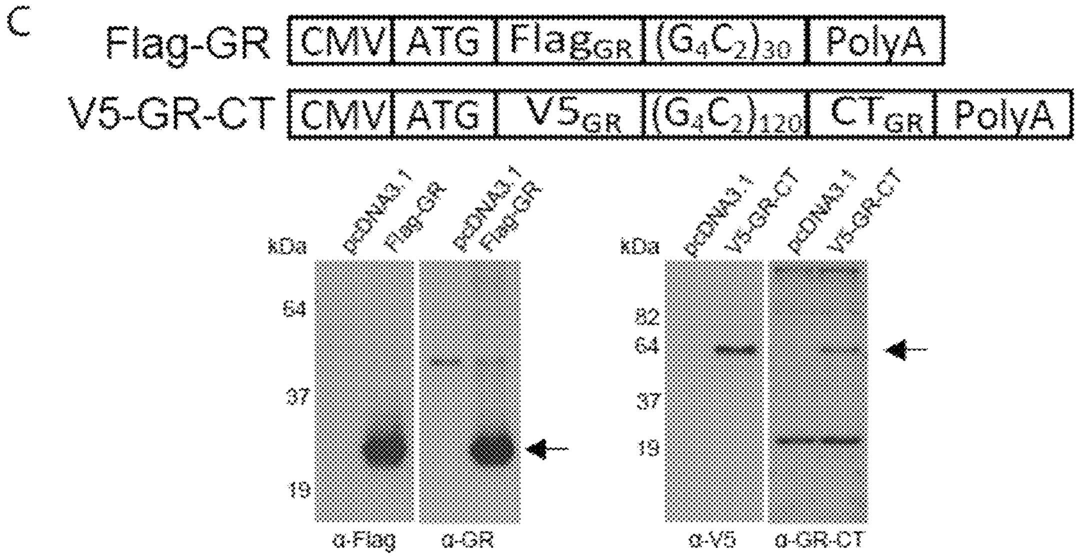

FIGS. 23A-23C are a series of images showing validation of additional sense repeat and C-terminal polyclonal antibodies. (A, B Top): Schematic diagrams of constructs expressing ATG-initiated N-terminal V5-epitope tagged GR or GA repeat proteins with endogenous C-terminal sequences. (A-B Bottom panels), co-localization of a-V5 staining in transfected HEK293T cells with α-GR, α-GR-CT and α-GP-CT respectively. Similar staining was not seen in preimmune or pcDNA3.1 empty vector controls. (C) a-OR detection of recombinant protein in Flag-OR transfected cells by protein blot.

Figure 24:
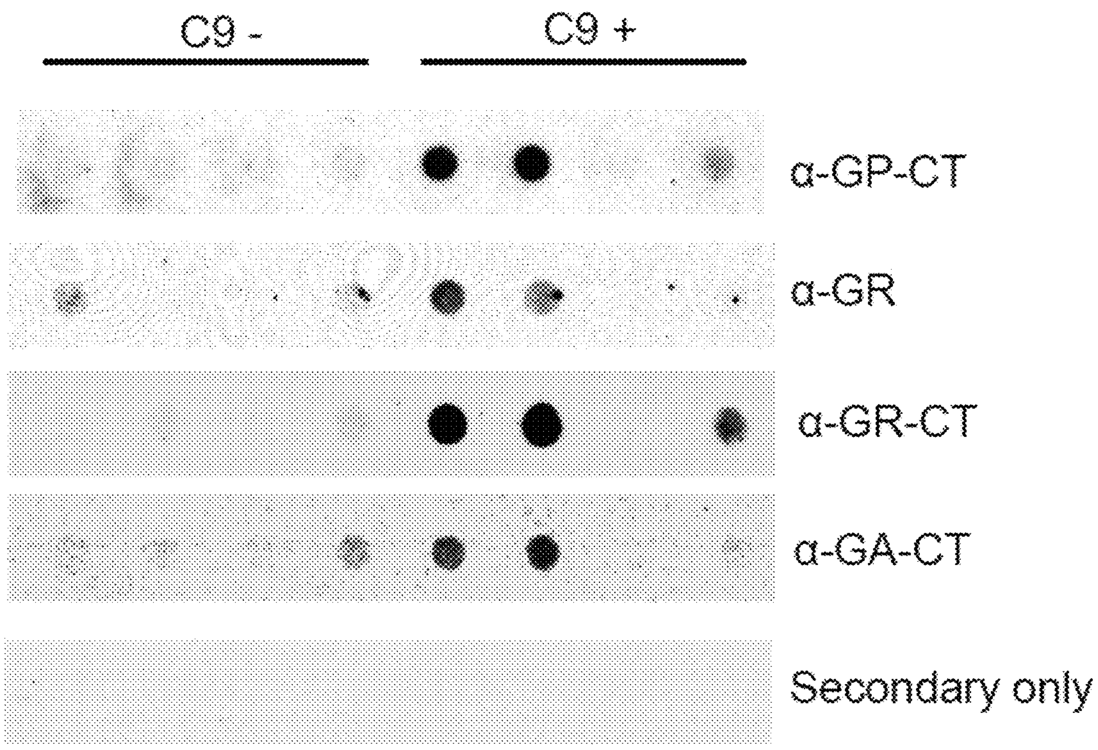

FIG. 24 is a series of images of immunoblots of 2% soluble lysates from C9(+) and C9(−) ALS frontal cortices with α-GP-CT, α-GR, α-GR-CT and α-GA antibodies.

Figure 25:
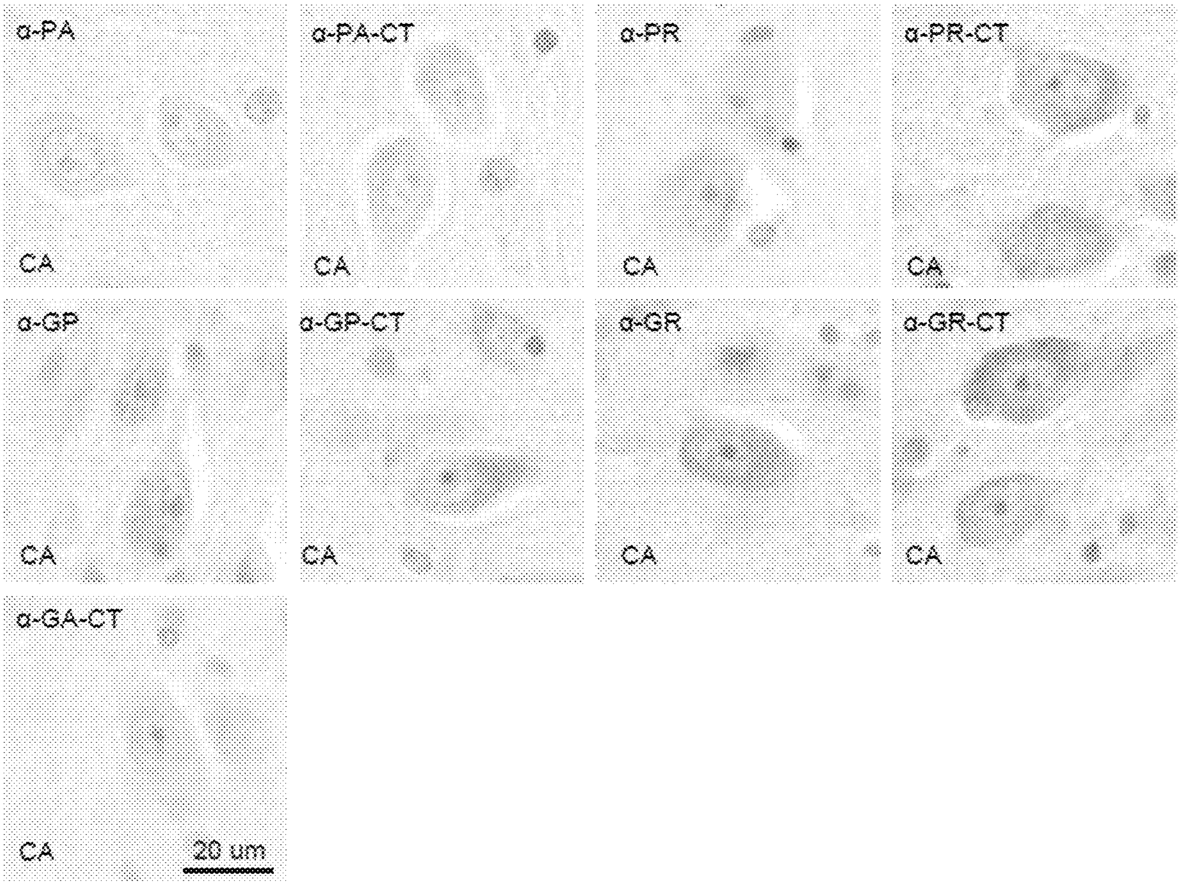

FIG. 25 is a series of images showing negative IHC staining of C9(−) ALS/FTD hippocampal sections with antibodies against sense and antisense proteins.

FIGS. 26A-26D are a graph and a series showing images RAN translation and PR protein expression affect cell viability. (A) qRT-PCR shows expression of expansion transcripts are similar in HEK293T cells transfected with (−)ATG-PR-3T and (+)ATG-PR-3T constructs. (B-D) Bright-field microscopy images showing changes in cell morphology in cells expressing RNA and RAN proteins from (−)ATG-PR-3T constructs compared to empty vector control (pcDNA3.1) and worsening effects in (+)ATG-PR-3T cells expressing increased levels of PR protein.

FIG. 27 is a table describing primers used for RT-PCR and RACE (SEQ ID NOs: 17 of them (in order. SEQ ID NOs: 36, 37, 39, 38, 45-47, 40, 48-56).

FIG. 28 is a table describing novel sense and antisense antibodies. (in order SEQ ID NOs: 20, 23, 19, 25, 21, 21, 22, 18).

FIG. 29 is a schematic of the BAC insert used to make transgenic mice.

Figure 30:
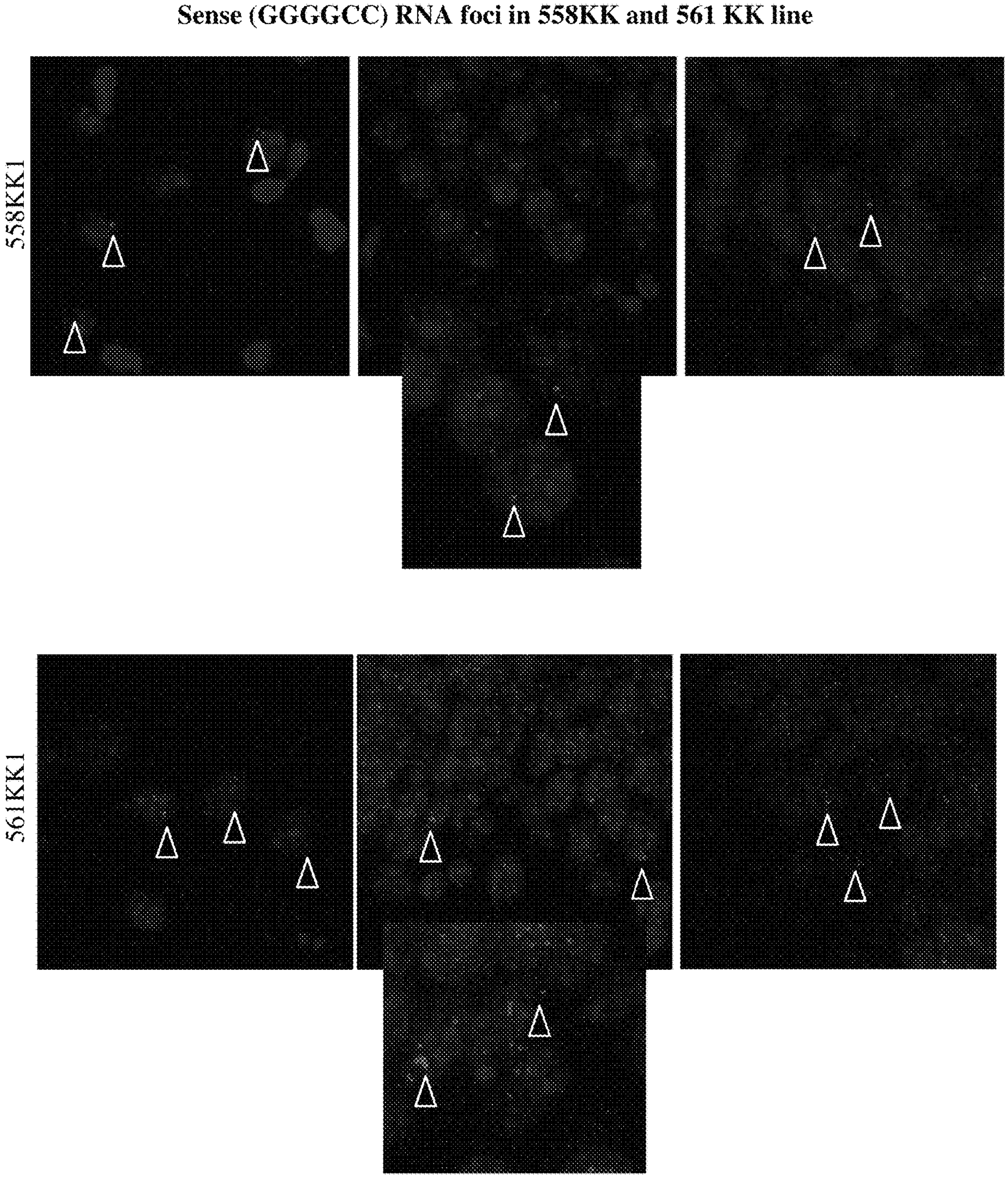

FIG. 30 is a series of photographs showing sense RNA foci in transgenic mice expressing a human C9ORF72 gene containing GGGGCC repeats. Exemplary foci are indicated by arrowheads.

Figure 31:
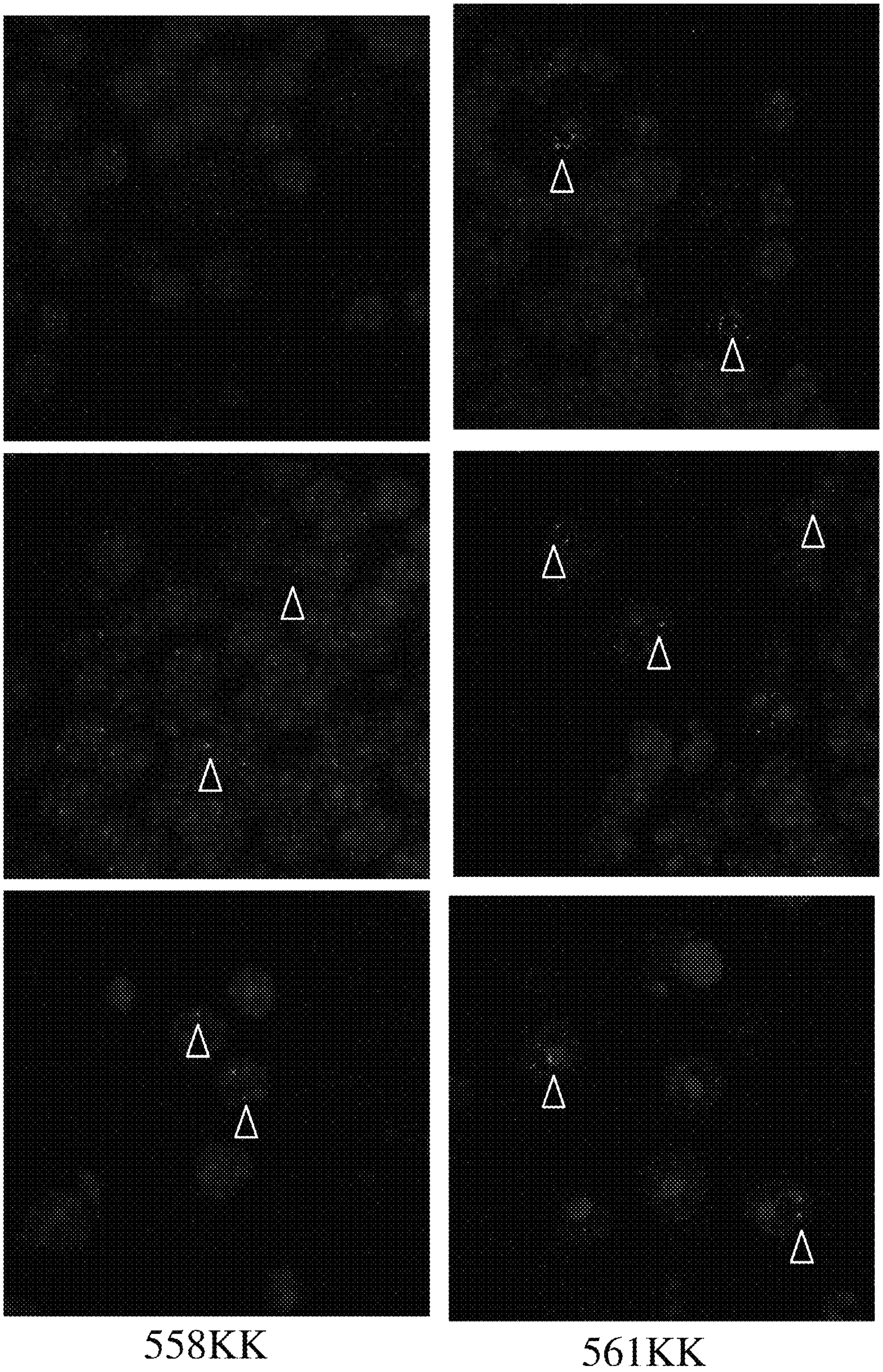

FIG. 31 is a series of photographs showing anti-sense (AS) RNA foci in transgenic mice expressing a human C9ORF72 gene containing GGGGCC repeats. Exemplary foci are indicated by arrowheads.

DETAILED DESCRIPTION OF THE INVENTION

Well-established rules of translational initiation have been used as a cornerstone in molecular biology to understand gene expression and to predict the consequences of disease causing mutations. In general, microsatellite expansion mutations (e.g., CAG, CTG) located in predicted coding- and non-coding regions have been thought to cause disease by protein gain-, or loss-, of-function or RNA gain-of-function mechanisms. It has been previously reported that the canonical rules of translation do not apply for CTG·CAG repeat expansions and that CAG and CUG expansion transcripts express homopolymeric expansion proteins in all three frames without an AUG start codon (see, e.g., T. Zu et al., Non-ATG-initiated translation directed by microsatellite expansions. PNAS 108, 260 (2011)). This translation independent of an AUG start codon is termed repeat-associated non-ATG (RAN) translation. RAN translation is hairpin dependent and occurs without frameshifting or RNA editing. RAN translation has been observed from trinucleotide, tetranucleotide, and pentanucleotide repeats associated with myotonic dystrophy 1, myotonic dystrophy 2, spinocerebellar ataxia type 3, spinocerebellar ataxia type 8 and Huntington disease (see PCT publication WO/2010/115033, which is incorporated herein by reference).

Expansion of a GGGGCC hexanucleotide repeat within the intron of the C9ORF72 gene has been previously associated with both amyotrophic lateral sclerosis and frontotemporal dementia. As described herein, it has been found that this expanded hexanucleotide repeat is contained within RNA transcripts expressed in both the sense and anti-sense direction from the C9ORF72 locus. These hexanucleotide repeat-containing transcripts were found to undergo RAN translation such that poly-(Gly-Ala), poly-(Gly-Pro), poly-(Gly-Arg), poly-(Pro-Ala), or poly-(Pro-Arg) proteins were produced, depending on the frame of the hexanucleotide repeat being mad from the RNA (5'-GGGGCC-3', 5'-GGGCCG-3', and 5'-GGCCGG-3' on the sense transcript, 5'-GGCCCC-3', 5'-GCCCCG-3', and 5'-CCCCGG-3' on the anti-sense transcript, see FIG. 1). In addition, the anti-sense transcript was found to be translated through ATG-initiated translation to produce Met . . . poly-(Pro-Arg) and Met . . . poly-(Gly-Pro) proteins. These RAN and ATG-initiated proteins are referred to as di-amino acid-repeat-containing proteins herein. The sense and anti-sense hexanucleotide repeat-containing transcripts are referred to herein as 5'-GGGGCC-3' hexanucleotide repeat-containing RNA (sense) and 5'-GGCCCC-3' hexanucleotide repeat-containing RNA (anti-sense).

As further described herein, these di-amino acid-repeat-containing proteins unexpectedly were found to be present in blood samples from subjects with ALS. Additionally, expression of the anti-sense 5'-GGCCCC-3' hexanucleotide repeat-containing RNA transcript was found to be highly elevated in subjects having a C9ORF72 gene containing the expanded GGGGCC hexanucleotide repeat sequence. Further, foci of both the sense and anti-sense hexanucleotide repeat-expansion-containing RNA transcripts were found to be present in subjects having a C9ORF72 gene containing the expanded GGGGCC hexanucleotide repeat sequence. Without wishing to be bound by theory or mechanism, it is believed that di-amino acid-repeat-containing proteins in the blood of subjects with ALS accumulate within the brain parenchyma over time, leading to neuroinflammatory changes, CNC dysfunction, and neuronal death. Accordingly, aspects of the disclosure relate to identification of a subject as having ALS or likely to develop ALS by providing novel assays for determining di-amino acid-repeat-containing protein levels in the blood of the subject and/or hexanucleotide repeat-containing RNA levels in a sample from the subject. Aspects of the disclosure also relate to treatment of a subject having ALS or FTD by decreasing or stabilizing di-amino acid-repeat-containing protein levels in the blood of the subject.

Identification of a Subject Having ALS or FTD or Likely to Develop ALS or FTD

Aspects of the disclosure relate to identification of a subject having ALS or FTD or likely to develop ALS or FTD based on a level of one or more di-amino acid-repeat-containing proteins in a blood sample from a subject. In some embodiments, a method comprises, determining, in a blood sample obtained from a subject, a level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a level of the one or more di-amino acid-repeat-containing proteins that is elevated compared to a control level indicates that the subject has ALS or FTD or is likely to develop ALS or FTD. In some embodiments, a level of one or more di-amino acid-repeat-containing proteins is determined by performing an assay. Non-limiting assays are described herein.

Other aspects of the disclosure relate to identification of a subject having ALS or FTD or likely to develop ALS or FTD based on a level of a 5'-GGGCC-3' hexanucleotide repeat-containing RNA and/or a 5'-GGCCCC-3' hexanucleotide repeat-containing RNA in a sample from a subject. In some embodiments, identification of a subject having ALS or FTD or likely to develop ALS or FTD is based on a level of a 5'-GGCCCC-3' hexanucleotide repeat-containing RNA in a sample from a subject. The sample may be, e.g., a fluid or tissue sample obtained from the subject. In some embodiments, a method comprises, determining, in a sample obtained from a subject, a level of a 5'-GGGGCC-3' hexanucleotide repeat-containing RNA and/or a 5'-GGCCCC-3' hexanucleotide repeat-containing RNA, wherein a level of the hexanucleotide repeat-containing RNA that is elevated compared to a control level indicates that the subject has ALS or FTD or is likely to develop ALS or FTD. In some embodiments, a level of a hexanucleotide repeat-containing RNA is determined by performing an assay. Non-limiting assays are described herein.

Yet other aspects of the disclosure relate to identification of a subject having ALS or FTD or likely to develop ALS or FTD based on the presence or absence of RNA foci containing a 5'-GGGGCC-3' hexanucleotide repeat-expansion-containing RNA and/or a 5'-GGCCCC-3' hexanucleotide repeat-expansion-containing RNA in a sample from a subject, wherein the presence of the focus of the 5'-GGGGCC-3' hexanucleotide repeat-expansion-containing RNA and/or a 5'-GGCCCC-3' hexanucleotide repeat-expansion-containing RNA indicates that the subject has ALS or FTD or is likely to develop ALS or FTD. As used herein, a focus of a 5'-GGGGCC-3' hexanucleotide repeat-expansion-containing RNA and/or a 5'-GGCCCC-3' hexanucleotide repeat-expansion-containing RNA refers to an area of accumulation of the 5'-GGGGCC-3' hexanucleotide repeat-expansion-containing RNA and/or the 5'-GGCCCC-3' hexanucleotide repeat-expansion-containing RNA, which may be detectable using a nucleic acid-based assay, such as FISH. In some embodiments, the focus may be, e.g., 0.1 to 2 micrometers in diameter, 0.1 to 1.5 micrometers in diameter, or 0.1 to 1 micrometers in diameter. In some embodiments, the focus may be at least 0.1 micrometers in diameter. It is to be appreciated that a sample may contain more than one focus and that each focus may be a different size. For example, one focus may be 0.2 micrometers in diameter, while second focus may be 1 micrometer in diameter. Non-limiting examples of foci and methods detecting such foci are provided in Example 3.

It is to be understood that a subject may be identified based on a level of one or more di-amino acid-repeat-containing proteins, a level of a hexanucleotide repeat-expansion containing RNA, the presence or absence of a hexanucleotide repeat-expansion containing RNA, or any combination thereof. In some embodiments, the method further comprises identifying the subject as having ALS or FTD or likely to develop ALS or FTD if the level of the di-amino acid-repeat-containing protein or hexanucleotide repeat-containing RNA is elevated compared to a control level. In some embodiments, the method further comprises identifying the subject as having ALS or FTD or likely to develop ALS or FTD if the focus or foci of the hexanucleotide repeat-expansion-containing RNA are present in the sample. In some embodiments, the method further comprises identifying the subject as not having ALS or FTD or unlikely to develop ALS or FTD if the level of the di-amino acid-repeat-containing protein or hexanucleotide repeat-containing RNA is decreased or the same compared to a control level. In some embodiments, the method further comprises identifying the subject as not having ALS or FTD or unlikely to develop ALS or FTD if the focus or foci of the hexanucleotide repeat-expansion-containing RNA are absent in the sample.

In some embodiments, a level of one or more di-amino acid-repeat-containing proteins or the identity of a subject may be recorded. In some embodiments, recordation comprises inputting a level or identity of subject into a computer, such as a medical record database.

Other aspects of the disclosure relate to treatment of a subject identified as having ALS or FTD or likely to develop ALS or FTD. As used herein, "treat" or "treatment" refers to (a) preventing or delaying the onset of ALS or FTD; (b) reducing the severity of ALS or FTD; (c) reducing or preventing development of symptoms characteristic of ALS or FTD; (d) preventing worsening of symptoms characteristic of ALS or FTD; and/or (e) reducing or preventing recurrence of ALS or FTD symptoms in subjects that were previously symptomatic for ALS or FTD.

In some embodiments, treatment comprises administering an effective amount of a known ALS therapeutic agent, such as Riluzole (Rilutek. Sanofi-Aventis), to a subject identified as having ALS. In some embodiments, treatment comprises administering an effective amount of a known FTD therapeutic agent, such as trazodone (Desyrel, Oleptro) or a selective serotonin reuptake inhibitor (SSRI), to a subject identified as having FTD. In some embodiments, treatment comprises administering an effective amount of a therapeutic agent, such as baclofen, diazepam, phenytoin, trihexyphenidyl and/or amitriptyline, which reduces one or more symptoms of ALS or FTD in a subject identified as having ALS or FTD. In some embodiments, treatment comprises one or more of physical therapy, occupational therapy, or speech therapy. In some embodiments, treatment comprises a method as described herein for decreasing or stabilizing di-amino acid-repeat-containing protein levels in the blood of the subject, such as bone marrow transplantation or plasmapheresis. In some embodiments, treatment comprises any combination of the above-mentioned treatments or any other treatments described herein.

An effective amount is a dosage of a therapeutic agent sufficient to provide a medically desirable result, such as treatment of ALS or FTD. The effective amount will vary with the age and physical condition of the subject being treated, the severity of ALS or FTD in the subject, the duration of the treatment, the nature of any concurrent therapy, the specific route of administration and the like factors within the knowledge and expertise of the health practitioner.

Administration of a treatment may be accomplished by any method known in the art (see, e.g., Harrison's Principle of Internal Medicine, McGraw Hill Inc.). Administration may be local or systemic. Administration may be parenteral (e.g., intravenous, subcutaneous, or intradermal) or oral. Compositions for different routes of administration are well known in the art (see, e.g., Remington's Pharmaceutical Sciences by E. W. Martin). Dosage will depend on the subject and the route of administration. Dosage can be determined by the skilled artisan.

Other aspects of the disclosure relate to methods for monitoring responsiveness to a treatment in a subject having ALS or FTD or suspected of having ALS or FTD. In some embodiments, the method comprises: determining, in a blood sample obtained from the subject at a first time point, a first level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein; and determining, in a blood sample obtained from the subject at a second time point, a second level of one or more di-amino acid-repeat-containing proteins selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein, wherein a second level that is elevated or the same compared to a first level indicates that the subject is unresponsive or likely unresponsive to treatment and wherein a second level that is decreased compared to a first level indicates that the subject is responsive or likely responsive to treatment. In some embodiments, the first blood sample is obtained before treatment of the subject and the second blood sample is obtained during or after treatment of the subject. This method may also be performed by determining a level of a hexanucleotide repeat-containing RNA or the presence or absence of a focus or foci of a hexanucleotide repeat-expansion-containing RNA in addition to or in place of the level of di-amino acid protein.

As used herein, "elevated" means that the level of one or more di-amino acid-repeat-containing proteins or a hexanucleotide repeat-containing RNA is above a control level, such as a pre-determined threshold or a level of one or more di-amino acid-repeat-containing proteins or a hexanucleotide repeat-containing RNA in a control sample. Controls and control levels are described in detail herein. An elevated level includes a level that is, for example, 1%, 5%, 10%, 20%, 30%, 40%, 50%, 60%, 70%, 80%, 90%, 100%, 150%, 200%, 300%, 400%, 500%, or more above a control level. An elevated level also includes increasing a phenomenon from a zero state (e.g., no or undetectable di-amino acid-repeat-containing protein expression or hexanucleotide repeat-containing RNA expression) to a non-zero state (e.g., some or detectable di-amino acid-repeat-containing protein expression or hexanucleotide repeat-containing RNA).

As used herein, "decreased" means that the level of one or more di-amino acid-repeat-containing proteins or a hexanucleotide repeat-containing RNA is below a control level, such as a pre-determined threshold or a level of one or more di-amino acid-repeat-containing proteins or a hexanucleotide repeat-containing RNA in a control sample. Controls and control levels are described in detail herein. A decreased level includes a level that is, for example, 1%, 5%, 10%, 20%, 30%, 40%, 50%, 60%, 70%, 80%, 90%, 100%, 150%, 200%, 300%, 400%, 500%, or more below a control level. A decreased level also includes decreasing a phenomenon from a non-zero state (e.g., some or detectable di-amino acid-repeat-containing protein expression or hexanucleotide repeat-containing RNA) to a zero state (e.g., no or undetectable di-amino acid-repeat-containing protein expression or hexanucleotide repeat-containing RNA expression).

Hexanucleotide Repeat-Containing RNAs and Di-Amino Acid Repeat-Containing Proteins As described herein, an expanded GGGGCC hexanucleotide repeat sequence within the intron of the C9ORF72 gene was found to be transcribed such that RNA transcripts containing the hexanucleotide repeat in both the sense and anti-sense direction were produced. The GenBank Gene JD for the human C90R-72 gene is 203228. Both the sense and anti-sense hexanucleotide repeat-containing transcripts were found to undergo translation independent of an AUG start codon (repeat-associated non-ATG (RAN) translation) such that poly-(Gly-Ala), poly-(Gly-Pro), poly-(Gly-Arg), poly-(Pro-Ala), or poly-(Pro-Arg) di-amino acid repeat-containing proteins were produced, depending on the frame of the hexanucleotide repeat being read (5'-GGGGCC-3', 5'-GGGCCG-3', and 5'-GGCCGG-3' on the sense transcript, 5'-GGCCCC-3', 5'-GCCCCG-3', and 5'-CCCCGG-3' on the anti-sense transcript, see FIG. 1). In addition, the anti-sense hexanucleotide repeat-containing transcript was found to be translated through ATG-initiated translation to produce Met . . . poly-(Pro-Arg) and Met . . . poly-(Gly-Pro) proteins.

Accordingly, aspects of the invention relate to the sense and anti-sense RNAs containing an expanded hexanucleotide repeat and uses thereof. The sense RNA is a 5'-GGGGCC-3' hexanucleotide repeat-containing RNA and the anti-sense RNA is a 5'-GGCCCC-3' hexanucleotide repeat-containing RNA.

The 5'-GGGGCC-3' and 5'GGCCCC-3' hexanucleotide repeat-containing RNAs comprise a repeat nucleic acid sequence of the formula $(GGGGCC)_x$ or $(GCCCCC)_x$, respectively, where X may be at least 10, at least 20, at least 25, or at least 30, or in a range selected from 10-100,000, 10-50,000, 10-5,000, 20-1,000, 20-100,000, 20-50,000, 20-5,000, 20-1,000, 25-100,000, 25-50.000, 25-5,000, or 25-1,000. The hexanucleotide repeat-containing RNA may further comprise additional N- and/or C-terminal nucleic acids. In some embodiments, an N-terminal nucleic sequence comprises a nucleic acid sequence upstream of the 5'-GGGGCC-3' hexanucleotide repeat within the intron of the C9ORF72 for the sense transcript or a nucleotide sequence upstream of the 5'-GGCCCC-3' hexanucleotide repeat within the intron of the C9ORF72 for the anti-sense transcript. In some embodiments, a C-terminal nucleic acid sequence comprises a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript.

Each di-amino acid repeat-containing protein comprises a repeat amino acid sequence, which contains a di-amino acid repeat unit of the formula $(YZ)_x$, where X can be from 2-10.000, 5-10,000, 2-5,000, 5-5,000, 2-1000, 5-1000, 5-500, 5-300, 5-200, 10-500, 10-300, or 10-200. The di-amino acid repeat unit for each di-amino acid repeat-containing protein is provided in Table 1.

TABLE 1

Di-Amino Acid-Repeat-Containing Proteins

| Di-Amino Acid-Repeat-Containing Protein | Di-Amino Acid Repeat Unit | Predicted C-terminus |
|---|---|---|
| poly-(Gly-Ala) | $(GA)_x$ or $(AG)_x$ | WSGRARGRARGGAAVAVPAPAAAEAQAVASG (SEQ ID NO: 1) or AWSGRARGRARGGAAVAVPAPAAAEAQAVASG (SEQ ID NO: 27) |
| poly-(Gly-Pro) | $(GP)_x$ or $(PG)_x$ | GRGRGGPGGGPGAGLRLRCLRPRRRRRRRWRVGE (SEQ ID NO: 2, sense), PGRGRGGPGGGPGAGLRLRCLRPRRRRRRRWRVGE (SEQ ID NO: 28, sense) or none (anti-sense) |
| poly-(Gly-Arg) | $(GR)_x$ or $(RG)_x$ | GVVGAGPGAGPGRGCGCGACARGGGGAGGGEWVSEEAASWRVAVWGSAAGKRRG (SEQ ID NO: 3) or RGVVGAGPGAGPGRGCGCGACARGGGGAGGGEWVSEEAASWRVAVWGSAAGKRRG (SEQ ID NO: 29) |
| poly-(Pro-Ala) | $(AP)_x$ or $(PA)_x$ | PSARLLSSRACYRLRLFPSLFSSG (SEQ ID NO: 4) OR APSARLLSSRACYRLRLFPSLFSSG (SEQ ID NO: 30) |
| poly-(Pro-Arg) | $(PR)_x$ or $(RP)_x$ | PLARDS (SEQ ID NO: 5) or RPLARDS (SEQ ID NO: 31) |
| Met . . . poly-(Pro-Arg) | $(PR)_x$ | PLARDS (SEQ ID NO: 5) |
| Met . . . poly-(Gly-Pro) | $(GP)_x$ | None |

X = number of repeats of the sequence in the parentheses

Other aspects of the invention relate to one or more di-amino acid repeat-containing proteins and uses thereof. The one or more di-amino acid repeat-containing proteins are selected from poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) proteins.

The sense 5'-GGGGCC-3' hexanucleotide repeat-containing RNA and the anti-sense 5'-GGCCCC-3' hexanucleotide repeat-containing RNA both encode poly-(Gly-Pro) proteins. Accordingly a poly-(Gly-Pro) protein may include a protein translated from the sense strand, the anti-sense strand, or both. It is predicted that the C-terminus of the sense and anti-sense translated poly-(Gly-Pro) proteins may differ (see Table 1). Accordingly, a sense poly-(Gly-Pro) protein may comprise the poly-(Gly-Pro) a C-terminal sequence as described in Table 1, while an anti-sense poly-(Gly-Pro) protein may comprise the repeat region with no additional C-terminal sequence. Methods described herein may comprise use of a poly-(Gly-Pro) protein translated from the sense strand, the anti-sense strand, or both. Antibodies described herein may be specific for a poly-(Gly-Pro) protein translated from the sense strand, the anti-sense strand, or both.

Each di-amino acid repeat-containing protein may further comprise an N- and/or C-terminal amino acid sequence that comprises a non-di-amino acid repeat sequence. In some embodiments, a N-terminal amino acid sequence comprises an amino acid sequence translated from a nucleotide sequence of a C9ORF72 RNA transcript, such as a nucleotide sequence upstream of the 5'-GGGGCC-3' hexanucleotide repeat within the intron of the C9ORF172 for the sense transcript or a nucleotide sequence upstream of the 5'-GGCCCC-3' hexanucleotide repeat within the intron of the C9ORF72 for the anti-sense transcript. In some embodiments, a C-terminal amino acid sequence comprises an amino acid sequence translated from a nucleotide sequence of a C9ORF72 RNA transcript, such as a nucleotide sequence downstream of the 5'-GGGGCC-3' hexanucleotide repeat within the intron of the C9ORF72 for the sense transcript or a nucleotide sequence downstream of the 5'-GGCCCC-3' hexanucleotide repeat within the intron of the C9ORF72 for the anti-sense transcript. Such a nucleotide sequence downstream of the 5'-GGGGCC-3' or 5'-GGCCCC-3' hexanucleotide repeat may be translated until a stop codon or multiple stop codons are reached.

A portion of a C9ORF72 gene sequence (sense and anti-sense) is shown below. The 5'-GGGGCC-3' or 5'-GGCCCC-3' hexanucleotide repeat is underlined and in bold. The nucleotide sequence upstream of the 5'-GGGGCC-3' or 5'-GGCCCC-3' hexanucleotide repeat precedes the underlined and bolded sequence. The nucleotide sequence downstream of the 5'-GGGGCC-3' or 5'-GGCCCC-3' hexanucleotide repeat follows the underlined and bolded sequence. It is to be understood that this 5'-GGGGCC-3' or 5'-GGCCCC-3' hexanucleotide repeat can be repeated more than the number of times present in these sequences.

```
C9ORF72 (partial sequence, sense)
                                        (SEQ ID NO: 6)
CCCCATTTCGCTAGCCTCGTGAGAAAACGTCATCGCACATAGAAAACAGA

CAGACGTAACCTACGGTGTCCCGCTAGGAAAGAGAGGTGCGTCAAACAGC

GACAAGTTCCCCCCACGTAAAAGATGACGCTTGGTGTGTCAGCCGTCCCT

GCTGCCCGGTTGCTTCTCTTTTGGGGGCGGGGTCTAGCAAGAGCAGGTGT

GGGTTTAGGAGGTGTGTGTTTTTGTTTTTCCCACCCTCTCTCCCCACTAC

TTGCTCTCACAGTACTCGCTGAGGGTGAACAAGAAAAGACCTGATAAAGA

TTAACCAGAAGAAAACAAGGAGGGAAACAACCGCAGCCTGTAGCAAGCTC

TGGAACTCAGGAGTCGCGCGCTAGGGGCCGGGGCCGGGGCCGGGGCGTGG

TCGGGGGGGGCCCGGGGGCGGGCCCGGGGCGGGGCTGCGGTTGCGGTGCC

TGCGCCCGCGGCGGCGGAGGCGCAGGCGGTGGCGAGTGGGTGAGTGAGGA

GGCGGCATCCTGGCGGGTGGCTGTTTGGGGTTCGGCTGCCGGGAAGAGGC

GCGGGTAGAAGCGGGGGCTCTCCTCAGAGCTCGACGCATTTTTACTTTCC

CTCTCATTTCTCTGACCGAAGCTGGGTGTCGGGCTTTCGCCTCTAGCGAC

TGGTGGAATTGCCTGCATCCGGGCCCCGGGCTTCCCGGCGGCGGCGGCGG

CGGCGGCGGCGCAGGGACAAGGGATGGGGATCTGGCCTCTTCCTTGCTTT

CCCGCCCTCAGTACCCGAGCTGTCTCCTTC

C9ORF72 (partial sequence, anti-sense)
                                        (SEQ ID NO: 7)
GAAGGAGACAGCTCGGGTACTGAGGGCGGGAAAGCAAGGAAGAGGCCAGA

TCCCCATCCCTTGTCCCTGCGCCGCCGCCGCCGCCGCCGCCGGGAAG

CCCGGGGCCCGGATGCAGGCAATTCCACCAGTCGCTAGAGGCGAAAGCCC

GACACCCAGCTTCGGTCAGAGAAATGAGAGGGAAAGTAAAAATGCGTCGA

GCTCTGAGGAGAGCCCCCGCTTCTACCCGCGCCTCTTCCCGGCAGCCGAA

CCCCAAACAGCCACCCGCCAGGATGCCGCCTCCTCACTCACCCACTCGCC

ACCGCCTGCGCCTCCGCCGCCGCGGGCGCAGGCACCCCAACCGCAGCCCC

GCCCCGGGCCCGCCCCCGGGCCCGCCCCGACCACGCCCCGGCCCCGGCCC

CGGCCCCTAGCGCGCGACTCCTGAGTTCCAGAGCTTGCTACAGGCTGCGG

TTGTTTCCCTCCTTGTTTTCTTCTGGTTAATCTTTATCAGGTCTTTTCTT

GTTCACCCTCAGCGAGTACTGTGAGAGCAAGTAGTGGGGAGAGAGGGTGG

GAAAAACAAAAACACACACCTCCTAAACCCACACCTGCTCTTGCTAGACC

CCGCCCCCAAAAGAGAAGCAACCGGGCAGCAGGGACGGCTGACACACCAA

GCGTCATCTTTTACGTGGGCGGAACTTGTCGCTGTTTGACGCACCTCTCT

TTCCTAGCGGGACACCGTAGGTTACGTCTGTCTGTTTTCTATGTGCGATG

ACGTTTTCTCACGAGGCTAGCGAAATGGGG
```

In some embodiments, a Met . . . poly-(Pro-Arg) or Met . . . poly-(Gly-Pro) protein comprises an N-terminal amino acid sequence comprising an N-terminal methionine. In some embodiments, a Met . . . poly-(Pro-Arg) protein comprises an N-terminal amino acid sequence comprising MQAIPPVARGESPTPSFGQRNERESKNASSSEESPRFYPRLFPAAEPQTATRQDAASSL THSPPPAPPPPRAQAPQPQPRPGPAPGPAPTT (SEQ ID NO: 41) or a fragment thereof, wherein the sequence is N-terminal to a poly-(Pro-Arg) repeat amino acid sequence. In some embodiments, a Met . . . poly-(Gly-Pro) protein comprises an N-terminal amino acid sequence comprising MRGKVKMRRALRRAPASTRASSRQPNPKQPPARMPPPHSPTRHRLRLRRRGRRHRN RSPAPGPPPGPPRPRP (SEQ ID NO: 42), MRRALRRAPASTRASSRQPNPKQPPARMPPPHSPTRHRLRLRRRGRRHRNRSPAPGP PPGPPRPRP (SEQ ID NO: 43), MPPPHSPTRHRLRLRRRGRRHRNRSPAPGPPPGPPRPRP (SEQ ID NO: 44), or a fragment thereof, wherein the sequence is N-terminal to a poly-(Gly-Pro) repeat amino acid sequence.

In some embodiments, a C-terminal amino acid sequence comprises a C-terminus amino acid sequence shown in Table 1 or a fragment of a C-terminus amino acid sequence shown in Table 1. It is to be understood that C-terminal amino acid sequences other than those in Table 1 are also contemplated.

Exemplary di-amino acid repeat-containing proteins may comprise a sequence provided in Table 2.

TABLE 2

| |
|---|
| (GA)$_x$WSGRARGRARGGAAVAVPAPAAAEAQAVASG (SEQ ID NO: 8) |
| (AG)$_x$AWSGRARGRARGGAAVAVPAPAAAEAQAVASG (SEQ ID NO: 9) |
| (GP)$_x$GRGRGGPGGGPGAGLRLRCLRPRRRRRRRWRVGE (SEQ ID NO: 10) |
| (PG)$_x$PGRGRGGPGGGPGAGLRLRCLRPRRRRRRRWRVGE (SEQ ID NO: 11) |
| (GP)$_x$ |
| (PG)$_x$ |
| (GR)$_x$GVVGAGPGAGPGRGCGCGACARGGGGAGGGEWVSEEAASWRVAVWGSAAGKRRG (SEQ ID NO: 12) |
| (RG)$_x$RGVVGAGPGAGPGRGCGCGACARGGGGAGGGEWVSEEAASWRVAVWGSAAGKRRG (SEQ ID NO: 13) |
| (AP)$_x$APSARLLSSRACYRLRLFPSLFSSG (SEQ ID NO: 14) |
| (PA)$_x$PSARLLSSRACYRLRLFPSLFSSG (SEQ ID NO: 15) |
| (PR)$_x$PLARDS (SEQ ID NO: 16) |
| (RP)$_x$RPLARDS (SEQ ID NO: 17) |
| MQAIPPVARGESPTPSFGQRNERESKNASSSEESPRFYPRLFPAAEPQTATRQDAASSLTHSPPPAPPPPRAQAPQPQPRPGPAPGPAPTT(PR)xPLARDS (SEQ ID NO: 32) |
| MRGKVKMRRALRRAPASTRASSRQPNPKQPPARMPPPHSPTRHRLRLRRRGRRHRNRSPAPGPPPGPPRPRP(GP)x (SEQ ID NO: 33) |

TABLE 2-continued

| |
|---|
| MRRALRRAPASTRASSRQPNPKQPPARMPPPHSPTRHRLRLRRRGRRHRN RSPAPGPPPGPPRPRP(GP)x (SEQ ID NO: 34) |
| MPPPHSPTRHRLRLRRRGRRHRNRSPAPGPPPGPPRPRP(GP)x (SEQ ID NO: 35) |

X = a number between 2-10,000, 5-10,000, 2-5,000, 5-5,000, 2-1000, 5-1000, 5-500, 5-300, 5-200, 10-500, 10-300, or 10-200.

In some embodiments, the one or more di-amino acid repeat-containing proteins are selected from the poly-(Pro-Ala), poly-(Gly-Pro), poly-(Pro-Arg), Met . . . poly-(Pro-Arg) or Met . . . poly-(Gly-Pro) protein. In some embodiments, the one or more di-amino acid repeat-containing proteins are selected from the poly-(Pro-Ala), poly-(Pro-Arg) protein, Met . . . poly-(Pro-Arg) or Met . . . poly-(Gly-Pro) protein.

In some embodiments, the one or more di-amino acid repeat-containing proteins is two or more, three or more, four or more, or five or more, or six or more, seven or more, or eight di-amino acid repeat-containing proteins.

Subjects

Aspects of the disclosure relate to identification and treatment of a subject, such as a human, with ALS or FTD or likely to develop ALS or FTD. In some embodiments, a subject may have ALS. In some embodiments, a subject may have one or more symptoms of ALS, such as difficulty breathing, difficulty swallowing, muscle cramps, muscle contractions, muscle weakness, paralysis, speech problems, or weight loss. In some embodiments, a subject may not have any symptoms of ALS. In some embodiments, a subject may have a family history of ALS.

In some embodiments, a subject may have frontotemporal dementia (FTD). In some embodiments, a subject may have one or more symptoms of FTD, such as lethargy, aspontaneity, disinhibition, loss of empathy and other interpersonal skills, apathy, progressive nonfluent aphasia, semantic dementia, binge eating, compulsive behavior, tremor, rigidity, muscle spasums, poor coordination, difficulty swallowing, and muscle weakness. In some embodiments, a subject may not have any symptoms of FTD. In some embodiments, a subject may have a family history of FTD.

In some embodiments, a subject may have GGGGCC hexanucleotide repeats within one or both alleles of a C9ORF72 gene (NCBI Entrez Gene ID: 203228). In some embodiments. GGGGCC hexanucleotide repeats are within a promoter and/or intron of the C9ORF72 gene. In some embodiments, the number of GGGGCC hexanucleotide repeats is greater than 25, 50, 100, 150, 200, 250, 300, 500, 5,000, 10,000 or more. The number of repeats may be detected using any assay known in the art, e.g., using as a nucleic acid-based assay such as a southern blot (see, e.g., Dejesus-Hernandez et al. Expanded GGGGCC hexanucleotide repeat in noncoding region of C9ORF72 causes chromosome 9p-linked FTD and ALS. Neuron 72, 245 (2011); Renton et al. A hexanucleotide repeat expansion in C9ORF72 is the cause of chromosome 9p21-linked ALS-FTD. Neuron 72, 257 (2011); and Gijselink et al. A C9orf72 promoter repeat expansion in a Flanders-Belgian cohort with disorders of the frontotemporal lobar degeneration-amyotrophic lateral sclerosis spectrum: A gene identification study. Lancet Neurol. 11, 54 (2011)).

Controls and Control Levels

Aspects of the disclosure relate to comparison of a level of one or more di-amino acid repeat-containing proteins and/or hexanucleotide repeat-containing RNAs to a control level. In some embodiments, the control level is a level of one or more di-amino acid repeat-containing proteins and/or hexanucleotide repeat-containing RNAs in sample, such as a fluid sample or tissue sample, obtained from a healthy subject or population of healthy subjects. In some embodiments, the sample is a blood sample. As used herein, a healthy subject is a subject that is apparently free of disease and has no history of disease, such as ALS or FTD. In some embodiments, a healthy subject is a subject that has 25 or fewer GGGGCC hexanucleotide repeats within a C9ORF72 gene.

In some embodiments, a control level is a level of one or more di-amino acid repeat-containing proteins and/or hexanucleotide repeat-containing RNAs that is undetectable or below a background/noise level obtained using standard methods of detection (e.g., Western blot, qPCR, northern blot, or immunohistochemistry). Such a level could be obtained, for example, by measuring a level of one or more di-amino acid repeat-containing proteins and/or hexanucleotide repeat-containing RNAs in a sample that is known to be free of the di-amino acid repeat-containing proteins and/or hexanucleotide repeat-containing RNAs.

The disclosure also involves comparing the level of one or more di-amino acid repeat-containing proteins and/or hexanucleotide repeat-containing RNAs with a predetermined level or value, such that a control level need not be measured every time. The predetermined level or value can take a variety of forms. It can be single cut-off value, such as a median or mean. It can be established based upon comparative groups, such as where one defined group is known not to have ALS or FTD and another defined group is known to have ALS or FTD. It can be a range, for example, where the tested population is divided equally (or unequally) into groups, such as a subject that has 25 or fewer GGGGCC hexanucleotide repeats, a subject that has 25-50 GGGGCC hexanucleotide repeats, and a subject that has 50 or more GGGGCC hexanucleotide repeats.

Samples

Aspects of the disclosure relate to determining a level of one or more di-amino acid repeat-containing proteins in a blood sample (e.g., whole blood, plasma, or serum) obtained from a subject. The blood sample may be obtained by any method known in the art, e.g., using a needle or fingerprick device. The blood may be processed before use in the methods described herein. Such processing includes, for example, addition of an anti-coagulant, removal of blood cells, and/or freezing of the blood. However, it should be appreciated that other samples may be used, such as a tissue sample (e.g., brain tissue) or other fluid samples such as saliva, or urine.

Other aspects of the disclosure relate to determining a level of hexanucleotide repeat-containing RNA in sample obtained from a subject. The sample may be a fluid or tissue sample. In some embodiments, the tissue sample is brain tissue. In some embodiments, the fluid sample is blood (e.g., whole blood, plasma, or serum), saliva, or urine. In some embodiments, the fluid sample is a blood sample (e.g., whole blood, plasma, or serum).

Assays

Aspects of the disclosure relate to performing an assay to determine a level or presence/absence of one or more di-amino acid repeat-containing proteins and/or hexanucleotide repeat-containing RNAs. Assays known in the art for detecting proteins and RNAs (see, e.g., Molecular Cloning: A Laboratory Manual, J. Sambrook, et al., eds., Third Edition. Cold Spring Harbor Laboratory Press, Cold Spring Harbor, New York, 2001, Current Protocols in Molecular Biology, F. M. Ausubel, et al., eds., John Wiley & Sons, Inc., New York. Microarray technology is described in Microarray Methods and Protocols. R. Matson, CRC Press, 2009, or Current Protocols in Molecular Biology, F. M. Ausubel, et al., eds., John Wiley & Sons, Inc., New York) can be used alone or in combination with techniques and compositions described herein for measuring a di-amino acid repeat-containing protein level.

Assays for detecting protein levels include, but are not limited to, immunoassays (also referred to herein as immune-based or immuno-based assays, e.g., Western blot, immunohistochemistry and ELISA assays), Mass spectrometry, and multiplex bead-based assays. Such assays for protein level detection are well-known in the art. Other examples of protein detection and quantitation methods include multiplexed immunoassays as described for example in U.S. Pat. Nos. 6,939,720 and 8,148,171, and published US Patent Application No. 2008/0255766, and protein microarrays as described for example in published US Patent Application No. 2009/0088329, all of which are incorporated herein by reference in their entirety.

Any suitable binding partner for a di-amino acid repeat-containing protein is contemplated for detection of a di-amino acid repeat-containing protein level. In some embodiments, the binding partner is any molecule that binds specifically to a di-amino acid repeat-containing protein as described herein. As described herein. "binds specifically to a di-amino acid repeat-containing protein" means that the molecule is more likely to bind to a portion of or the entirety of a di-amino acid repeat-containing protein than to a portion of or the entirety of a non-di-amino acid repeat-containing protein.

In some embodiments, the binding partner is an antibody or antigen-binding fragment thereof, such as Fab, F(ab)2, Fv, single chain antibodies, Fab and sFab fragments, F(ab')2, Fd fragments, scFv, or dAb fragments. Methods for producing antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London. New York (1989), WO2006/040153, WO2006/122786, and WO2003/002609). Binding partners also include other peptide molecules and aptamers that bind specifically to a di-amino acid repeat-containing protein. Methods for producing peptide molecules and aptamers are well known in the art (see, e.g., published US Patent Application No. 2009/0075834, U.S. Pat. Nos. 7,435,542, 7,807,351, and 7,239,742). The binding partner may comprise a label including, but not limited to, a fluorescent, enzymatic, affinity or isotopic label.

In some embodiments, an assay comprises an immuno-based assay. In some embodiments, the immuno-based assay comprises an isolated antibody specific for one or more di-amino acid repeat-containing proteins. In some embodiments, the isolated antibody specific for one or more di-amino acid repeat-containing proteins is an isolated antibody as described herein in further detail. In some embodiments, the isolated antibody specific for one or more di-amino acid repeat-containing proteins is an isolated antibody specific for an antigen or sequence, or a fragment of an antigen or sequence described in Table 1, Table 2 or Table 3.

Accordingly, a di-amino acid repeat-containing binding partner (e.g., a di-amino acid repeat-containing-specific antibody) can be labeled with a detectable moiety.

Assays for detecting RNA include, but are not limited to, hybridization-based assays such as Northern blot analysis, RT-PCR, sequencing technology, RNA in situ hybridization (using e.g., DNA or RNA probes to hybridize to RNA molecules present in the sample as in FISH), in situ RT-PCR (e.g., as described in Nuovo G J, et al. Am J Surg Pathol. 1993, 17: 683-90; Komminoth P, et al. Pathol Res Pract. 1994, 190: 1017-2.5), and oligonucleotide microarray (e.g., by hybridization of polynucleotide sequences derived from a sample to oligonucleotides attached to a solid surface (e.g., a glass wafer) with addressable locations, such as an Affymetrix microarray (Affymetrix®, Santa Clara, CA)). Methods for designing nucleic acid binding partners, such as probes, are well known in the art. In some embodiments, the nucleic acid binding partners bind to a part of or an entire nucleic acid sequence of a hexanucleotide repeat-containing RNA provided herein.

Treatment

As described herein, it was found that di-amino acid repeat-containing proteins were present in samples of blood from patients with ALS. Without wishing to be bound by theory or mechanism, it is believed that di-amino acid repeat-containing proteins in the blood of subjects with ALS accumulate within the brain parenchyma over time, leading to neuroinflammatory changes, CNS dysfunction, and neuronal death. Accordingly, aspects of the disclosure relate to treatment of a subject having ALS or FTD by decreasing or stabilizing di-amino acid repeat-containing protein levels in the blood of the subject.

In some embodiments, decreasing or preventing an increase of the level of one or more di-amino acid repeat-containing proteins comprises removing the one or more (e.g., 1, 2, 3, 4, 5, 6, 7 or 8) di-amino acid repeat-containing proteins from the blood of the subject. In some embodiments, the one or more di-amino acid repeat-containing proteins from the blood of the subject is removed using a procedure selected from plasmapheresis or a bone marrow transplantation. In some embodiments, it may be advantageous to decrease or prevent an increase of the level of all di-amino acid repeat-containing proteins expressed by a subject. Accordingly, in some embodiments, a method comprises decreasing or preventing an increase of the level of all forms of di-amino acid repeat-containing proteins expressed by a subject.

In some embodiments, the one or more di-amino acid repeat-containing from the blood of the subject is removed using a hematopoietic stem cell (HSC) transplantation. HSC transplantation is the transplantation of hematopoietic stem cells, usually derived from bone marrow, peripheral blood, or umbilical cord blood, into a subject. The source of hematopoietic stem cells may be allogeneic (e.g., from a donor such as a healthy subject). Methods of HSC transplantation are well known in the art (see, e.g., Bishop M R, Pavletic S Z. Hematopoietic stem cell transplantation. In: Abeloff M D, Armitage J O, Niederhuber J E, Kastan M B, McKena W G, eds. Clinical Oncology. 4th ed. Philadelphia, Pa: Elsevier Churchill Livingstone; 2008:chap 32; and Vose J M. Pavletic S Z. Hematopoietic stem cell transplantation. In: Goldman L, Schafer A1. Cecil Medicine. 24th ed. Philadelphia, Pa: Saunders Elsevier; 2011:chap 181).

In order to prepare a subject for HSC transplantation, the HSCs present in the subject may be removed or depleted so that the transplanted cells can become the dominant HSC population in the subject. HSCs in the subject may be depleted, for example, by treating the subject with a chemotherapy, radiation, or both in order to cause the HSC cells of the subject to undergo apoptosis or cell cycle arrest.

In allogeneic HSC transplantation, the HSCs are obtained from a donor. The donor is preferably a healthy subject, such as a subject that is apparently free of disease and has no history of disease, such as ALS or FTD. It is preferable that the donor is HLA-compatible with the subject receiving the transplant in order to reduce the risk of graft versus host disease. HLA-compatibility can be determined, e.g., using HLA typing. HLA typing generally involves examination of at least 8 HLA markers: two A, two B, two C, and two DRB1 markers, and optionally also two DQ markers. HLA typing can be accomplished, e.g., through a blood test. HLA allele identities can be determined using serology or a nucleic acid-based assay. Generally, a match of at least 4-6 markers between host and donor is preferred. In some embodiments, the donor is a subject that has 25 or fewer GGGGCC hexanucleotide repeats within a C9ORF72 gene.

HSCs can be obtained from a donor using any method known in the art. Exemplary methods include bone marrow harvest and leukapheresis (see, e.g., Transfusion, 2003 February; 43(2):259-64. Leukapheresis after high-dose chemotherapy and autologous peripheral blood progenitor cell transplantation: a novel approach to harvest a second autograft. Schwella N, Braun A, Ahrens N, Rick O, Salama A). In a bone marrow harvest, the bone marrow is typically removed from the back of one or both hip bones of the donor. Leukapheresis involves separation of HSCs from blood obtained from the donor using, e.g., continuous flow centrifugation or filtering. The growth factor G-CSF may be administered to the donor to stimulate the growth of new HSCs so that more HSCs are present in the blood. Once obtained, the allogeneic HSCs are then administered to the subject receiving the transplant. Any suitable method of administration known in the art is contemplated. e.g., by central venous catheter.

In some embodiments, during or after HSC transplantation, the subject receiving the HSC transplant may receive additional treatments and/or therapies, such as antibiotics, antifungals, antivirals, blood transfusions and/or immunosuppressive therapies. Such treatments and/or therapies may help to prevent infection and/or graft versus host disease during a HSC transplant recovery period.

In some embodiments, the HSC transplantation is bone marrow transplantation. In some embodiments, the bone marrow transplantation is an allogeneic bone marrow transplantation.

Plasmapheresis is a medical procedure that occurs outside the body (an "extracorporeal therapy") and refers to the removal, treatment, and return of (components of) blood plasma from blood circulation. Plasmapheresis is well-known in the art and has been used to treat several diseases including Goodpasture's syndrome, myasthenia gravis, Guillain-Barre syndrome, lupus, and thrombotic thrombocytopenic purpura (see, e.g., Madore, Plasmapheresis Technical aspects and indications, Crit Care Clin 18: 375-392, 2002). During plasmapheresis, blood is initially taken out of the body, e.g., through a needle or previously implanted catheter. Plasma is then separated from the blood cells, e.g., by using a cell separator. After plasma separation, the blood cells are combined with a replacement fluid and readministered to the subject. The replacement fluid may be either the separated plasma treated to remove disease-associated components or a replacement plasma (also called plasma exchange).

Exemplary procedures used to separate the plasma from the blood cells include:

1) Discontinuous flow centrifugation: One venous catheter line is used. Typically, one or more batches of blood are removed at a time and centrifuged to separate plasma from blood cells. The blood cells are then combined with the replacement fluid and returned to the subject.

2) Continuous flow centrifugation: Two venous lines are used. Plasma is continuously spun out of the blood and the separated blood cells are fed through a line that combines with a replacement fluid before return to the subject.

3) Plasma filtration: Two venous lines are used. The plasma is filtered using standard hemodialysis equipment, e.g., a parallel-plate or hollow-fiber filter. The separated blood cells are fed through a line that combines with a replacement fluid before return to the subject. The filters usually have pores of 0.2-0.6 μm diameter, sufficient to allow passage of plasma, while retaining cells. Several membrane plasma separators are commercially available (e.g., Plasmaflo from Asahi Medical Co., Ltd., Tokyo, Japan; Plasmax from Toray Industries, Tokyo, Japan; CPS-10 from Baxter. Deerfield, IL, USA; Plasmaflux from Fresenius Medical Care AG, Bad Homburg, Germany; Prisma TPE 2000 from Hospal, Lyon, France).

If the separated plasma is to be used as the replacement fluid, the separated plasma is first treated to decrease the levels of di-amino acid repeat-containing proteins present in the separated plasma. In some embodiments, decreasing the levels of di-amino acid repeat-containing proteins present in the separated plasma comprises contacting the separated plasma with one or more isolated antibodies specific for a di-amino acid repeat-containing protein as described herein, whereby the di-amino acid repeat-containing proteins present in the separated plasma bind to the one or more isolated antibodies. In some embodiments, a binding partner for the one or more isolated antibodies is contacted with the separated plasma. A binding partner for the one or more isolated antibodies may be, for example, a capture moiety such as biotin or streptavidin, protein A, or a secondary antibody specific for the one or more isolated antibodies. Such binding partners allow for the one or more isolated antibodies to be removed from the separated plasma.

In some embodiments, the one or more isolated antibodies are attached to a filter, column, and/or solid support. In such embodiments, the separated plasma is contacted with the filter, column, and/or solid support, whereby the di-amino acid repeat-containing proteins bind to the isolated antibodies attached to the filter, column and/or solid support. Without wishing to be bound by theory, it is believed that the di-amino acid repeat-containing proteins may form aggregates in the blood. Accordingly, the di-amino acid repeat-containing proteins may be removed from the separated plasma using a filter, such that the aggregates are isolated from the separated plasma.

In in some embodiments, a subject expressing one or more di-amino acid repeat-containing proteins may develop autoantibodies. In some embodiments, autoantibodies to one or more di-amino acid repeat-containing proteins may be removed from the separated plasma. Autoantibodies may be removed using any method known in the art, e.g., using a binding partner (e.g., bound to a solid support or attached to a tag) that recognizes the autoantibodies. In some embodiments, the binding partner may be one or more di-amino acid repeat-containing proteins as described herein.

If plasma exchange is to be used, the subject receives replacement plasma. Replacement plasma may be, e.g., donor plasma or a solution of albumin (e.g., 5-70% albumin in saline). An exemplary replacement plasma is 5% albumin combined with 0.9% saline in a 50%:50% (vol:vol) solution. Medication to keep the blood from clotting (e.g., an anticoagulant such as citrate, acid-citrate dextrose or heparin) may be given to the subject or contacted with the blood of the subject during the procedure.

In some embodiments, decreasing or preventing an increase of the level of one or more di-amino acid repeat-containing proteins comprises decreasing a level of a hexanucleotide repeat-containing RNA. Decreasing a level of a hexanucleotide repeat-containing RNA may comprise administration of an effective amount of an inhibitory nucleic acid molecule such as an shRNA, an siRNA, miRNA, or an antisense nucleic acid molecule that targets the hexanucleotide repeat-containing RNA.

Methods for producing shRNAs, siRNAs, miRNAs, and antisense nucleic acid molecules are well known in the art (see e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition). In some embodiments, a nucleic acid inhibitor comprises or corresponds to at least a portion of sequence of a target hexanucleotide repeat-containing RNA sequence or comprises at least a portion of a sequence complementary to a target hexanucleotide repeat-containing RNA sequence.

In some embodiments, treatment may comprise decreasing or stabilizing a level of an autoantibody to one or more di-amino acid repeat-containing proteins in a subject. A level of autoantibody may be decreased or stabilized using any method known in the art. In some embodiments, decreasing or stabilizing a level of an autoantibody comprises administration of an effective amount of atacicept, belimumab, blisibimod, BR3-Fe, rituximab, ocrelizumab, atumumab, epratuzumab, corticosteroid (e.g., prednisone), mycophenolic acid, methotrexate, cyclophosphamide, azathioprine, and/or cyclosporin. In some embodiments, decreasing or stabilizing a level of an autoantibody comprises plasmapheresis.

Antibodies

Aspects of the disclosure relate to isolated antibodies specific for a di-amino acid repeat-containing protein (e.g., a RAN protein) selected from a poly-(Gly-Ala), poly-(Gly-Pro), poly-(Gly-Arg), poly-(Pro-Ala), poly-(Pro-Arg), Met . . . poly-(Pro-Arg) or Met . . . poly-(Gly-Pro) protein. The isolated antibody may recognize a region or regions of the di-amino acid repeat-containing protein (such as a repeat sequence or the C-terminus) or may recognize the entire di-amino acid repeat-containing protein.

An antibody that "specifically binds" to a target or an epitope is a term understood in the art, and methods to determine such specific binding are also known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically binds to a poly-(Gly-Ala) protein or an epitope therein is an antibody that binds this target antigen with greater affinity, avidity, more readily, and/or with greater duration than it binds to other antigens or other epitopes in the same antigen. It is also understood by reading this definition that, for example, an antibody that specifically binds to a first target antigen may or may not specifically bind to a second target antigen. As such, "specific binding" does not necessarily require (although it can include) exclusive binding. Generally, but not necessarily, reference to binding means specific binding. In some embodiments, antibodies described herein have a suitable binding affinity to a di-amino acid repeat-containing protein (e.g., a RAN protein). As used herein, "binding affinity" refers to the apparent association constant or $K_A$. The $K_A$ is the reciprocal of the dissociation constant ($K_D$). The antibody described herein may have a binding affinity ($K_D$) of at least $10^{-5}$, $10^{-6}$, $10^{-7}$, $10^{-8}$, $10^{-9}$, $10^{-10}$ M, or lower. An increased binding affinity corresponds to a decreased $K_D$. Higher affinity binding of an antibody to a first target relative to a second target can be indicated by a higher $K_A$ (or a smaller numerical value $K_D$) for binding the first target than the $K_A$ (or numerical value $K_D$) for binding the second target. In such cases, the antibody has specificity for the first target (e.g., a protein in a first conformation or mimic thereof) relative to the second target (e.g., the same protein in a second conformation or mimic thereof: or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or 10 fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in, e.g., TRIS-buffer (50 mM TRIS, 150 mM NaCl, 5 mM CaCl2) at pH7.5). These techniques can be used to measure the concentration of bound binding protein as a function of target protein concentration. The concentration of bound binding protein ([Bound]) is related to the concentration of free target protein ([Free]) and the concentration of binding sites for the binding protein on the target where (N) is the number of binding sites per target molecule by the following equation:

$$[Bound]=[N][Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the isolated antibody is specific for a di-amino acid repeat-containing protein selected from a poly-(Pro-Ala) poly-(Pro-Arg), Met . . . poly-(Pro-Arg) or Met . . . poly-(Gly-Pro) protein.

In some embodiments, the isolated antibody is specific for an antigen comprising a di-amino acid repeat and/or C-terminus sequence or fragment thereof as defined in Table 1. In some embodiments, the isolated antibody is specific for an antigen comprising a sequence or fragment of a sequence defined in Table 2.

In some embodiments, the isolated antibody is specific for an antigen in Table 3 or in FIG. 28. In some embodiments, an antigen in Table 3 does not contain an N- and/or C-terminal modification.

TABLE 3

Di-Amino Acid Repeat-Containing Protein Antigens

| di-amino acid repeat-containing protein | Label | Antigen | Antigen location in di-amino acid repeat-containing protein |
|---|---|---|---|
| Poly-(Gly-Arg) | GGGGCC F1 repeat | Ac-RGRGRGRGRGRGRGRC-amide (SEQ ID NO: 18) | Repeat sequence |
| Poly-(Pro-Arg) | GGGGCC-AS F2 repeat | Ac-RPRPRPRPRPRPRPRPRC-amide (SEQ ID NO: 19) | Repeat sequence |
| Poly-(Pro-Ala) | GGGGCC-AS F1 repeat | H2N-APAPAPAPAPAPAPAPACKKKK-amide (SEQ ID NO: 20) | Repeat sequence |
| Poly-(Gly-Pro) | GGGGCC F3 repeat | H2N-GPGPGPGPGPGPGPGPGCKK-amide (SEQ ID NO: 21) | Repeat sequence |
| Poly-(Gly-Pro) | GGGGCC F3 CT | Ac-CRRRWRVGE-OH (SEQ ID NO: 22) | C-terminus |
| Poly-(Pro-Ala) | GGGGCC-AS F1 CT | Ac-CYRLRLFPSLFSSG-OH (SEQ ID NO: 23) | C-terminus |
| Poly-(Gly-Arg) | GGGGCC F1 CT | Ac-CRVAVWGSAAGKRRG-OH (SEQ ID NO: 24) | C-terminus |
| Poly-(Pro-Arg) | GGGGCC-AS F2 CT | Ac-CRPRPLARDS-OH (SEQ ID NO: 25) | C-terminus |
| Poly-(Gly-Ala) | GGGGCC F2 CT | Ac-CSGRARGRARGGA-amide (SEQ ID NO: 26) | C-terminus |

F1 = reading frame 1,
F2 = reading frame 2,
F3 = reading frame 3,
AS F1 = anti-sense reading frame 1,
AS F2 = anti-sense reading frame 2,
AS F3 = anti-sense reading frame 3.

An isolated antibody may be a monoclonal or polyclonal antibody, or an antigen-binding fragment thereof. An antigen-binding fragment thereof includes, for example, an Fab, F(ab)2, F(ab')2, Fv, single chain antibody, Fab fragment, sFab fragment, Fd fragment, scFv, or dAb fragment. Methods for producing polyclonal and monoclonal antibodies and antigen-binding fragments thereof are well known in the art (see, e.g., Sambrook et al, "Molecular Cloning: A Laboratory Manual" (2nd Ed.), Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), WO2006/040153, WO2006/122786, and WO2003/002609). Also encompassed are antibodies made by recombinant means such as chimeric antibodies (variable region and constant region derived from different species) and CDR-grafted antibodies (complementary determining region derived from a different species) as described in U.S. Pat. Nos. 4,816,567 and 5,225,539, which are incorporated herein by reference in their entirety. Also encompassed are humanized antibodies, typically produced by recombinant methods, wherein the human sequences comprise part or all of the antibody. Also included are fully human antibodies, such as those produced in genetically-altered mice (see PCT Application No. 93/12227, which is incorporated herein by reference in its entirety). In some embodiments, an isolated antibody specific for a di-amino acid repeat-containing protein is a rabbit polyclonal antibody as listed in Table 4.

TABLE 4

Di-Amino Acid Repeat-Containing Protein Rabbit Polyclonal Antibodies

| Antigen | Animal | Titer |
|---|---|---|
| GGGGCC F1 repeat | H3147 | 1,575,500 |
| GGGGCC F1 repeat | H3148 | 1,956,500 |
| GGGGCC-AS F2 repeat | H3149 | 2,399,600 |
| GGGGCC-AS F2 repeat | H3150 | 3,225,000 |
| GGGGCC-AS F1 repeat | H3151 | 660,200 |
| GGGGCC-AS F1 repeat | H3152 | 2,082,600 |
| GGGGCC F3 repeat | H3154 | 752,300 |
| GGGGCC F3 repeat | H3155 | 590,500 |
| GGGGCC F3 CT | H3156 | 231,300 |
| GGGGCC F3 CT | H3157 | 616,700 |
| GGGGCC-AS F1 CT | H3158 | 6,300 |
| GGGGCC-AS F1 CT | H3159 | 32,800 |
| GGGGCC F1 CT | H3160 | 573,900 |
| GGGGCC F1 CT | H3161 | 363,000 |
| GGGGCC-AS F2 CT | H3162 | 2,261,700 |
| GGGGCC-AS F2 CT | H3163 | 176,300 |
| GGGGCC F2 CT | H3164 | 1,549,500 |
| GGGGCC F2 CT | H3165 | 115,700 |

Antibodies may be produced in bacterial cells, e.g., *E. coli*, or eukaryotic cells, such as yeast cells or mammalian cells. In one embodiment, antibodies are produced in mammalian cells. Mammalian host cells for expressing the antibodies or antigen-binding fragments thereof include Chinese Hamster Ovary (CHO cells) (including dhfr− CHO cells, described in Urlaub and Chasin, 1980. Proc. Natl. Acad. Sci. USA 77:4216-4220, used with a DHFR selectable marker, e.g., as described in Kaufman and Sharp, 1982, Mol. Biol. 159:601 621), lymphocytic cell lines, e.g., NS0 myeloma cells and SP2 cells, COS cells, and a cell from a transgenic animal, e.g., a transgenic mammal. Antibodies can also be produced by a transgenic animal. For example, U.S. Pat. No. 5,849,992 describes a method of expressing an antibody in the mammary gland of a transgenic mammal.

Isolated antibodies of the disclosure may also have a detectable label attached thereto. The label may be, for example, a fluorescent, enzymatic, affinity or isotopic label. Examples include fluorescein isothiocyanate (FITC) for detection by fluorescence, horseradish peroxidase which allows detection by cleavage of a chromogenic substrate, radioisotopes such as $I^{125}$ for detection by autoradiography and avidin/biotin for antibody detection and affinity purification of antigens and antigen-bearing cells.

Also encompassed by the disclosure are hybridoma cell lines producing a monoclonal antibody specific for a di-amino acid repeat-containing protein selected from a poly-(Gly-Ala), poly-(Gly-Pro), poly-(Gly-Arg), poly-(Pro-Ala), poly-(Pro-Arg) protein, Met . . . poly-(Pro-Arg), Met . . . poly-(Gly-Pro), a C-terminal peptide of a di-amino acid repeat-containing protein as described herein, and/or a combination of two or more thereof.

In some embodiments, an isolated antibody is an isolated auto-antibody obtained from a subject having ALS, wherein the isolated auto-antibody is specific for one or more di-amino acid repeat-containing proteins as described herein.

In some embodiments, an isolated antibody described herein is contained within a buffered solution. In some embodiments, an isolated antibody described herein is attached to a solid support (e.g., the surface of a plate or a bead).

Transgenic Mouse

In another aspect, the disclosure relates to a transgenic mouse comprising a human C9ORF72 gene comprising a GGGGCC hexanucleotide repeat sequence. In some embodiments, the mouse comprises a human C9ORF72 gene comprising a GGGGCC hexanucleotide repeat sequence and flanking human sequences on the 5' and 3' end of the human C9ORF72 gene. In some embodiments, the flanking human sequences on the 5' and 3' end are each independently at least 1 kilobases (kB), at least 5 kB, at least 10 kB, at least 20 kB, at least 30 kB, at least 40 kB, or at least 50 kB in length. In some embodiments, the flanking human sequences on the 5' and 3' end each independently comprise a promoter capable of driving transcription of the human C9ORF72 gene in the sense and anti-sense direction, respectively. Accordingly, in some embodiments, the transgenic mouse expresses both sense and anti-sense transcripts (e.g., 5'-GGGGCC-3' and 5'GGCCCC-3' hexanucleotide repeat-containing RNAs described herein). In some embodiments, the human C9ORF72 gene and flanking sequences comprise the sequence below, wherein (GGGGCC)$_n$ indicates the location of the GGGGCC hexanucleotide repeat sequence:

Chr9: 27, 527, 137-27, 625, 470 (reverse complement)

(SEQ ID NO. 63)

```
AAGCTTGATAATATTATCAAATATTAGATAAATGTAATATTAGAAGAAAACTTTTTTGAAAAGATATATAAAAAT

AATTTCATTCAAAATTTTTATATTTAATTTAAATTTTTAATGAAAATATATCTAAGTTTTGTACGCTTTAAATGT

AATTATGTTTGATAATTTAATCATTTACTATTCGTTCTCTATTGCTGCCCTAACAAATTACCATAGTTCAGTGGC

TTACAAAACACAAATTTATTATCTTACCATTCTGTGAGTCAAAATTCCAAAATAGGTGTCACTAGGCTAAAATGA

AGGACTGCATTTCTTCCTGCAGGCTCCAGGAGAGATCTATGTCTTACTCTTTTCGGCTTCTAAAGGCTGCCCACA

TTCCTCGACTAGTGGCGTCCCTCCTTCGTCTCTAAACCCAGCAACAACAGGTTGAGTCCTCATGTCACATCTTTC

TTACCTTTCTGTCATCTCATCTCGCTGACTGCTGCTGGGAAAAATTCTCCACTTTTAAGGGCTATCATGATTAGA

CTATGCCCACTAGATAATACAAGATCTCAGATCCTTAACTTCCATCACATCTGCAAAGTCGCTTTTGCCTCATAA

AAGAGTCTGAGGTTTAGACGGGAGATCTTAAGGGGGCTATTAATATGCCTACCATAATCACTGAGAATAAGTACA

AGTTAAGATTATAATAGCAATAGAATATACAAACGTGAAGCTCCAAAAGAACAACAACAACAAAAAAGGTGAACA

GGAAAAAGAAACTGAAAATCTTTAAAAAGGCAGTCTGTTTAAATCTATAAAAACTGGAAAAAAATGAGAGTGGAC

AAATATCTGGTAAGCATGATGGACTTAAAATTTGTGACTAGGGCATTACATTTTTTATATTAATATAATGAAGAT

TGAATTACTGATCAAAACAATTAAAAAGCAAGAGAACTATTCTCATCAAATCTGCAACACGAAAAGTTCAGACAA

AATTCCAACAACTTCACATTCTGAACTAAATGAGGACTAATTACCAGTTCGAGCAATGAGAATATATGAGGTCCT

CCGTTTGCACTTTGCCAGGGATCTGAAAACGTTGGGAGTAGGTCGGCTTCACCCTGAAGCCAGACCATCGACAGC

CAGTTTTCCCTCCCTTCTCCACCCACAGGTCTTAGGCCCTCATCCTTCCCAGCCTCAGAACTAGTCTCCAAAGAA

GAGGAAAGTTAGAGGAGAGAGTAAATCGTTGAATAGGATGAAGGAGATGTGGGAAAAAGAAAAAGAGAGGCTGCA

AGAGAGAGGGTCCCAGGGATAACTCTGCTCTTGGAAGGGTGGCCACAGTCATGTGGTCCCAAGAGGCAACAACAA

GCTTAGGAAGCCAGAGAAACCAGTTACAATCACTGCTACTCTTTTCGATTCTGTGTTGTTTAAGAAATATCACCC

GCCAGGAGTTCTCCAGAAACATTTTCCCTGATTCCATGTAAGTGCTCAACCAGTGAATGGTAATCCCATTTTGGT
```

-continued
TTAGTCTGTACCATCCCCTATTCCAAAATAAAGGGAAAAATGGTGGGTTTATATCTTAAATTTTCTACTTTACTA
AACTCAAGGGAAATAGCCAAGCAAAAACGAAAGCTGAGACTCTTGCTAATTATCCTTTCCATAGAATGTTTGCTA
AAATTCCTTGTCAAGGAAGGAATAACAAAGCTAGTCCACGCTCTGTATAGGGTGTTTCCAATTAGTTATACTTTA
AAGTATAAGTATTTAACAAAATCTATAAATTTTGTTAATTATTTACTTGTAGTGAAAAATGAGCCATTCTCAAGC
AAATCACTTTTTATTACACATTCCAGAGAATAACCATAAAAGGACATTTATTATAGCAAAAATAACCACATCTGG
ATGGAACTTCAATCACCAGTATTTACTAAATAAATGCCCAGAAAAAAAATAGTTCATCTTTAATTTCAGTCATCA
TTAATAAAAGCTGAAGTACCTCTTCAGATCTTTTGATCATTTTCTGTTGGATTGTTTTCTTTTTACTGAGTTGCA
AATGCTCTTTATATATTTGGATACAAAGCTTTATCACATAGGCATTTTGCAAGTATTTTTTCCAAGTTTTTTA
TCTTTTCATTTATTTAATAATATCTTTCAAAGAACGGGAATTTTATAATTTTTATGAAGTCCATTTATAATTTTT
TCTTTTATGGGTTGGTGGGGGTTGGGGGTTGTGTTGTCCTAAGAAATCTTGGCTCAACACAAAAAGATTAGTTTC
TATATTTTCTTCTAGAAGTTTTATAGTACGATCTCAGATCCATTTCAGATGATGAATAAGCACATAAAAAAAGGA
TACTCATCGTTAGTCATTAGAGAAATGCATATTAAAACCATAAGGAAATACTACTATATACATATATTAGATAGG
ATGAAGAGCAACTGGAATCTCATACAGTGCTGATTGAAATGCAAAATGGCAAAACAACTTTAGAAACCAATTTGG
AAGCAGCTGTACTGACATGGAATTTTGAGCTGGAAGAATCTTAGAAAAAGAATACTTTACCACCTCCCCCATTCT
CTTCACCCTGGGGAACTGTTAAATGAGGAAATTGTGGTTCAAGGAGGAACTTGTCTATATGCTTTCTCAGCTTTC
CCGTGGTAATTACCATCTTGATAATATAACGTAATGTATGTATATGTTATCAAATAATATAATATCTTCATCATA
TATTTATCATCTTCATAATGTTAGCTGTCTAGTGGTAACTTTTTTTTGCTCTTTATTGCCTCCCTCTTTTTTCCC
TCTTTGTTGTTTTTTGTCATACAATTATGATATATGTGTATATATTCTCACTGTAAAGATGTAAACAACACAAAG
ATTATTGAACAAATCACGAAAGTAACCCTTCCTTCATTCTTACCCTATCCAACCCTCATCTCCTCAGAAGAATAC
ACCATTTTAGTTGTAAATGTTTTTCTAGCTCTTTTTCAATGTTTCTACCTATATGCATGTATGTATAATGTATAT
ACATACATATATACATACATATTGATATATACATATATAGAGGTATGGTTTTTTAACTTAAATGGAATTGCATTG
TGGATATTGTCCTATGACTTGCTTTCAACCAAATTATATGTCTTGGAAATACATACATATATTTAAAAAATATGT
TATGTATATGTAACATACTATATGTGCATAATATATATTACATAGATATAATAAGGCCTAGGAAGAAATTGTGTG
CAACCTCTAGTACATCTTCCTCTATATCTACTGTACATACATACAACCCATTCTTTTTTTAATTTTTTTATTTTT
TTAGACAGAATCTTGCTCTGTCGCCCAGGCTGGAGTGCAGTGGCACAATCTCGGCTCACTGCAAGCTCCACCTCC
TGGGTTCACGCCATTCTCCTGCCTCAGCCTCCCAAGTAGCTGGGAATACAGGCACCTGCCATCAGGCCCAGCTAA
TTTTTTTTTGTATTTTTAGTACAGATGGGGTTTCACCGTGTTAGCCAGGATGGTCTCCATCTCCTGACCTCGTGA
TCCGCCCACCTCATCCTCCCAAAGTGCTGGGATTTACAGGCGTGAGCCACCGCGCCCAGCCACAACTCATTGCAG
AGTAGTCCAAAATATGGATGGACTGTAGCTTAATTACTTATTCTCCCATTGATAGACACTTAGGACTTTTCTAAT
TTTTATAATTTAAAAATATGCTGCAATTAACAAACATTCTTGTGTATCTTTTTGCTGTATGTATGCATATTTCTT
TAGTATGGGTTTTGGAAGAGGAATCACAAAGGAGGCATAGAATATAAATATTTTTATTTTGAAAAATACAGTTGT
AATTTAATAACCCACCAAAAGACTCTAACAGTTTAGATTCACATCAACAGTGTAAGAACATGTCTGTTTTACTGC
ATCCTTACCCCCACTGGTTATAATACTTTTAATTAACAATCTTATGGATGAAGAATACTATCGCAATGTTGTTTT
AATGCATTTTTCCAATTACTAGTGAGATTGAACATTAATTCTTTTATTTTATGGATCACTGGCTTTTCTCCTTCT
GTGAACTACCTGTTCACATCCTCTGCTTTTCAGCTCTTGAGCTGTTATCTTTTTCTTATTGATTTATATGAGCTC
TTTATATATTCAAGATGTTAATCATTTGTATTTTATGTATATGGCAATGATTTTCTTCCAAACCAATGCTTGTCT
TTTATTTATTTATTTATTTATTTATTTATTTGAGACCGAGTCTCGCTCTGTCGCCCAGGCTGGAGTGCAGTGGCG
CGATCTCGGCTCACTGCAAGCTCCGCCTCCCGGGTTCACGCCATTCTCCTGCCTCAGCCTCCTGAGTAGGTGGGA
CTACAGGCGCCCGCTGCCACACCCGGCTAATTTTTTGTATTTTTAGTAGAGACAGGGTTTCACCGTGTTAGCCAG
GATGCTCTCTATCTCCTGACCTCGTGATCCGCCCGCCTCGGCCTTCCAAAGTGGTCGGATTACAGGCATGAGCCA
CCACGCCTGGCCAATGCTTGTCTTTTTATCTCTGTTTATGGCATCTTTCATACTATGGACATTTTTATTTTTATT -continued

TTTTATGTTGATTTATTCTTGAATTGTATACATGTTAATTATACCTAAGTTATTGTAATACCCTTAAAGCCAAGT

TCTACACATATATTTAATTTGCTTTCCCAATAGGTCTCTGAGGGAACACATTTTTTCAAATCACTTTGTTTCATC

TTTTTTAGGTGTTGATCAATTATTAAGGAGTTTGAAATAATCATTTAAACGGAATTCTTCAGATGAAAACATAAA

GACATTTATCGGGTCAGAGCATTGGTCGGTTCACATACTCAGGATCAGTGGCCTGGGTGGGCAGGCACTGGGTGA

ATGGAGAGCTGCAGGTATTGGAAGAGAGCCCAGTTGGATATGTAGTTTCCAAAGATCATCAAGGCAGACAACCAA

AGGGAAACCGTGGGAAACACCTGCTTTGGGCCATCTAAGATGAGATGATAAAGTAAGGAAAGAGTTGAGCCCAAC

ACAGTGATAGCCAATCTGAAAGCGGGCAGAACTGACAAGACCAAACAAGTAGGTGAACTGGCTGCAGGCAGCCAG

CCACCACAGGGACAGCGTGTACTCCAGGGACAAGCTCAAGGCTATAGGTAGTTAGTTCAAGGCTACTAGGGTGAG

AAGAGCAGGAACTGAGTTCTATACCAGTGCTTCTCAAAACTAATGTGCATCCTAATCACCTGGAAATCTTGTAAA

AATGTAGATTCTGATTCAGTGAGTCTGAAGCAGAGCTTAAGATACTACATGCTTAACAAGAGCCTAGTTGATGCT

GACACTGCTGGTCCCTGGAGCTCTCTTTGAGTAGCAGGCTTCTGGAAGGCTTGTGTCACTAAGCACAGAGAAGCC

TCACTTATCAAATCTGCACCAAAACAGGAAAACTAATGTGAAGAATAATGTGATGCACACGTCAGAGCATGAGGC

AGTTGCTTTGTCCCTGAGGTTGCGCTCCAGATGGCTTCCTAAGATGCGACAGGCTGATCTTGTGCGTGGGGGTCC

CGGAGGCTTGGGCCACGGGAGAGACAGGACCTCAGAGGCTGGGAGACAGGCAGAGACAGAAGAGTGACATCCTGC

TGCTTTTGAATTTGCACATTCTGTAGAATAATAACAGCAGTAAACTGTTACACAATATCTATTCTCAGCATCTTG

AAGCCCTTTCACATATTGTTACTTCCATTAATGGGGCCCTTTGCTGCTATTTCTACTTTTCTCTTCAGCTATCAA

CAATATGGCTTTCCACACCTCCATCAGACAGTAGCCAGATGAAATAAAATGTGCCAGAATGAAAACTTGTTCATT

TGTCTACTTTTTGCCAAGACTAGACAGGCAGGAAATTGAATGTATTTTTACAGAAAAGGTTTTCAAAACTTTTTC

CCCTCTGTGGCTCATTTAGGTAAACTAAAAGGCATAAGACCCACCTAAAACATGGGTTCCCGCTTTTTATTGGAG

AAAGAACATAGTACTTTAAAAAAATACATAAAATAATAAAAAGGAAAGACAAAGATAATGAAGGTTGTACATGGT

ACCAAATTTTTGTATCCCATAATAACACATGAGTAGATCACTACTAAGTAGGTTTTAGTGACATATAGGAAACAT

TAAAATCTACAGAAATTTGCATTATTTTCTGTCAAAAAGGATCATTTCACAGCCTTTCAGGGGGAACCCATTGCC

CACAGGAACTCATGCATTCCATGCTTTGAGGATCACTAGATCTAAGAAGCCTTCCTTGGAGGTTCTAGCCTCCAA

CCCTTATTTTAGTAAAAGAAGCTCCAGTTTTATCTGTTTCTAAGTCAGACTACCACACAACATTGGGCTTAAAGA

AAGGTTTCCAGGGCTAAAGCAGACTTTGAGGATTACTAATTCCGAGTTAAATTTCTGTGTATTATCTCTGGATTT

GACTTATTCACACTGGACTATCACTCATAAATATACATAATACAGAGTTAACTATTTAAATTTATAAAGAGAGTA

TTTTCCTTTTTTATGAGCAAAACATGCTGCCAACTACTTGGACCACATACTGATCCATAAATACTGACAGCTTTG

TAATTGGAAATAATAAATACACACTAATGAAGCATCTCAAAAGGGAAGAGCCACAGGTAATCTGAGTGATTAGGC

ATTCATGTTAGGTTAGGCTTTGATCATTGTTTTTAATCGCAATTTCATTGCAGTGCATCTATAAATCCATGTCCA

GAAGTATGAAGTGGTTCTATAGTAAGAATAAGATGCTACAGATAATGCGACTAAATAAGACACTATAGGTAATGA

CACAGATTCAAGTCTTATTGTTGATGGGAAGAGGTCAATAATGGATGATATAATATACTACAGCAATGAGAATTA

TTGAATGTTTTCCAGACTCACTTGTATAATTGGCCATAACAGCAAACAAAAAACAGGTTCTGATAGCAAAATGAT

ATACAGTACTAACAAAGGTGAATCTTGAGGTGAACCTTCTCTTTATAAGTTTAAATAGTTTACCCCCGACCTTTT

CCCATAGTAGAACAGCCTAAAAAGTATCTTTCAGTAGAATGCTAGTGCTTATGAGGTTTTCTTAAGATATCATTT

TTCAATTAAAATTTATTTCACAAAAGACTCACATCCTTGCCAGCCTTCAGGGTGAGTGTTGATTCAGGCTGTGTC

CAACGGCAACGATGAGTGAACTTCTCACCCTCAGAATCACATGAGCATTCCTGAGATGTTTTATCAGAGTGATAC

CAACTTCATTATTAGAATATTGAGTCCCTATTTCCTATATTCAATGTCCTTTCAAGCCCTAACTTTGTCCGGGTT

GAAGGCAAAGATCCAAATAATCACATTTGTCTTTGATAACTGAAACTGGGAGAACTGGGACTGTCTCAAGAGTTC

TACGTGACTGTAGGTTGCAAGTACTGTGGTTGCATCTCCAAATATTAACCAATCCCAGTGACAATTCAATGGGGT

CTCCTGAACCATGATCCTCATGTCTCCAGTGAAGGAAATGGGCAAAGGGGATTCAAAAATCCCTTTTGGAGGAAT

-continued

AGGAAACTTCTGCTTTCCTTCATTTCATAACATTTGCGATGGAACAAAGGCTTTTTTAGAATGGAGCAACCAGAT

CCTTTTTTGGGGGAATCAGCTTAAATGTCCCTTCTTCTCATACTACTTTTATCTATGTGATCCTATTCTTTTCTG

TTGTGGATTGAATCATGTCCCTCAAAAAGATTGAATTTAGAGTGTGCTCTAAATTCAATGTGGAGAAATTTGGAC

ACAGAGGCAGACACACAGGGAGAACCCCGTGTGACAATGGAGGAAGAGGATGCATTTATGCTGCCACAAGCCAAG

GAACACCAAAGATTGTCAGCAGCCACCAGAAGCTAGGATAAAGGCATGGCACATCACTCCCTCTGAGCCCCCAAA

AGGAGCCAAGACTGCTAATACTCTGATCTCGGACTTCTGGCCTGAAACAGTGAGAGAATAAGGTTCTGTTGTTTC

AAGCTACCCAGCTTGCGGTATTTTGTCACAGAAGCACAAGGAATCAAGTACATTTTCTTTCTCAGCACTTGTGAT

AATTTGATTTTTTCTTTACTCAGTGGTTGTTTCACACCTATGTCCCCATCAGACTGTAAGCTTAAAGAGACCTGG

ATCTGGTCTGTCTTCACCACTGTTGATTCATTACCAGCACAGTGCCTGGCCCATGGTCACTGAATAAACGTTTGT

TGAGAGAATGAATGTGCTTAACCAGAAGTACTATTGACCTATTAGGCCAAGTTCAAGGTGCCTAACAGCTCAGCT

GTGAAGGATACCTCTCCTTTCAGTCCTCTGTTACATATGTCCCTGATAGATGTGTTATTTGTATCTCCTCCTGGC

CCTCAAGTTTGTTTGAGGGCAGGACCCTTTTTTGTATATCTGTAGAGCTTCGTAGTACCTAAATACTACTTTGCA

TATATAATAAAGTTTCGATAAATATTCATTAAATAAAGAAATAAATGAAATGACTAAGTTTTCTAAGATGTTACA

ACTAGATTGAAGATATTTAGCTCATTATTTAACAAGAAAACTATGGTTAATTATGGTGTCCTGTGTGAAAATGGT

TATAGTTTGTTTTTTAATTAATATAAGCATGTATGTGCATTATCAGTATACACAATTTGTGGTATGAGTGTTTTG

TGTCCCTGCACACAGACCACGGAAATCCTGAGAAACAAACTGCCACCCCAGAGCAGGTGCCTAACACAGAGACTT

TTAATCCTTAAAGTTTTTCTATAACTAAGCAATGTTTTTTCAAATGCAATAACACTGATATGCAGACATATTGAT

TGTCCACTCACAAAGCCATTCCTCAATATCATTACAACATGCCTCTTTGAATGTCATTAAAAATAGATGTCTCAT

TTTTCTAGGACAAGTTGGCTGAAGTTCTGCTTGAAAACTGGTAATAGAAAATACAATTTCTCAACCCGCTTTGGC

CTTTTAATTCTGTTCTACAACCTTGCCAGTTCACTTTCAAAGTCAAGGGATGCATCTTGCAAAACCATGACATCT

TTTGAGTAACTCCTTCTGTTCTTAACACATATTCCCAGGAGCTTAATAAATATTGTTTTTGCAACTTGTTTAGTG

GCAAAATAATGAGTCCTTGGTGTATGCTTATCCTCTGCTTTGCTATTAGAGAAGATATATTCAGACTGTTTTAAA

CAAATTAATTCAAGGGCAGGGAACAGTCCTAAAACCTGTTAAAATTCAAATACTTGGTCACTGTATGTGCAGCAT

GTGTGTTCTAGAAAGTCCTATTATTTTAAAATATAAATTGAATCTTGTTGAGAAATTAATGTCATATGAATATAT

TAATAACTGAAATGCTGCCAAGTTTACAAAAAGCCCTCAATGAAACTGTGACCTTGTATAGACAAGGGCCTGTGG

AGGGACATTTTTAAACCATCTCTTTTTTTATTTCCTCATGAGATCTACAATGTAAGTGCATTAAAGTTGATGAAT

GAATTGCAGTGCAACTTTTCCTGCCTCTTTTGCCTTTCATTTGTCTATATTTCAAGCTTCACTGAAGTGATAGAT

TTTGGGCTTTGCCACATTGTCCTCTGATTGCTTCCCTCTGCTCCTCCTTTTCCTAGTGAATCTTTGTTTTACTGG

TGGAAAAATCTACATCTTTGTATCTTGGCATTTTACTTTCACATTATCTCATAGATTTTATTTCAAGTTGCTATA

AAGTTATCAACTTTTATTTTTAACTAATATTATTTTTAACAATTAGAAAATTGTTGACCAGGTAATTCCAGCACT

TTGGGAAGCTGAAGCGGGAGGATCACGTGAGCCCAGGAGCTCGAGACCAGCCTGGGCAATGCAAGGAGACTGTCT

CTACAAAATATAAAAATACATTAGCCAGGTTTGGCGGTGCATGCCTGGGGTCCAGCTATTCAGGAAGCTGAGGTG

GGAGGATCACTTGAGCTGGAGAGGTTGAGGCTGCAGTGAGCAGTGATCGCACCACTGCACTCCAGTCTGGGTGAC

AGAGGGAGACCCTATCTCGAAAAAAAGGAAAAGAAGAGGATTTTGCTGGCAAGATGGCTGAATAGGAATAGCTCC

GTTCTGCAGCTCCCAGTGAGATCAATGCAGAAGGCAGGTGATTTCTGCATTTCCAACAGAGGTACCTGGTTCATC

TCACTGGGACTGGTTGGACGGTGGGTGCAGCCCATGGAGGGTGAGCAGAAGTAGGGTGGGGCGTTGCCTCACTCA

GGAAGTGCAAGGGGTCCCTCTTCTAGCCAAGTGAAGCCGTCAGGGACTGTGCCATAAGAACAGTGCACTCTGGTC

CAGGCTTTTCCCACAGTCTTTGCAACCCACAGACCAGGAGATAACAAGCGGTGCCTATGCCACCAGGGCCCGGGG

TTTCAAGCACAAAACTGGGTGGCCATTTGGGCAGACATCAAGCTAGCTGCAGGAGTTTTTATTTTCATACCCCAG

TGGTGCCTGGAACGCCAGTGAGACAGAACCGTTCACTCCCCTGGATAAGGGGCAGAATCCAGGGAGCCAAGTGGT

CTGGCTTGGCGGGTCCCACACCCACGGCGCCCAGCAAGCTAAGATCCACTGGCTTGAAACTCTCGCTTCCAGCAC

-continued

AGCAGTCTGAGGTCCACCTGAGACGCCCGGGCTTGGTGTGGGGAGGGGCATCCACCATTGCTGAGGCTTGAGTAG

GCGGTTTTACCCTCACGGTGTAAACAAAGCTGCCTGGAAGGTCCAGCTGGGCACAGCCCACCACAGCTCACCAAG

GCCGCTGTGGCCAGAGTGCCCCTCTGGATTCCTCCTCTCTGGGCAAGGCATCTCTGAAAAAAAGGCAGCAGCGCC

AGTCAGAGACTTATAGATAAAACCCCCATCACCCTGGGACAGAGCACCTCAGGGAAGGAGTGGCTGTGGGTGCAG

TTTCAGCAGATTTAAACGTTCCTGCCTGACAGCTCTGAGAGAGCAACAGATCTCCCAGCACAGCGTTCAAGCTCT

GTTAAAGATCAGACTGCCTCCTCAAGTGGGTCCCTGACTCCCATGTCTCCTGATTGAGAGACACCTCCCAGTAGG

GGCTGACAAACACCTCATAAAGGAGAGCTCCAGCTGGCATCTGGCAGGTGCCCCTCTGGGACGAAGCTTCCAGAG

GAAGGAACAGGCAGCAATCTTTGCTGTTCTGCAGTCTCAGCTGATGATACCCAGTCAAACAGGTCCTGGAGTGGA

CCTCCAGCAAACTCCAGCAGACCTGCAGCAGAGGGGCCTGACCGTTAGAAGGAAAATTAACAAATAGAAAGGAAT

AGTATCAACATCAACAAAAAGGACGTCCACTCAGAGACCCCATCCAAAAGTCACCAACATCAAAGACCAAAGGTA

GATAAATCCACAAAGATGGGGAGAAACCAGTGCAAAAAAGTCTGAAAATTCCAAAAACCAGAACGCCTCTTCTCC

TCCAAAGAATCACCACTCCTCACTAGCAAGGTAACAAAACTGGACAGAGAATGAGTTTGACAAATTCACAGAATT

AGTGTTCAGAAGGTGGGCAATAACAAACTCCTCCAAGCTAACGGAGCATGCAAGGAAGCTAAGAACCTTGAAAAA

AGTTAGAGCAATTGCTAACTAGAATAACCAGTTTAGAGAAGAACATAAATGACCTGATGGAGCTGAAAAACACAG

CACGAGAACTTTGTGAAGCATACACAAGTATCAATAGCCAAATCGATCACGTGGAAGAAAGGATATCAGAGATTA

AAGATCAACTTAATGAAATAAATTGAGAAGACAAGATTAGAGAAAAAAGAATGAAAAGGAATGAACAAAGCCTCC

AAGCAATATAGGACTATGTGAAAAGACCAAATCTATGTTTGACTGGTGTACCAGAAAGTGACGGGGAGCATGGAA

CCAAGCTGGAAAACACTCTTCAGGATATTATCCAGGAGAACGTCCCCAACCTAGCAAAACAGGCCAACATTTAAA

TTCAAGAAATACAGACAACACCACAAAGATACTCCTCGAGAAGACCAACCCCAAGACACATAATCGTCAGATTCA

CCAAGGTTGAAATGAAGAAAAAAATGTTAAGGGCAGCCAGAGAGAAAGGTCAGGTTACCCACAAAGGAAGCCCAT

CAGACTAACAGCAGATCTCTCTGCAGAAACCCTACAAGCCAGAAGAGAGTGGGGGCCAATATTCAACATTTTTAA

AGAAAAGAATTTTCAACCCAGAATTTCATGTCCAGCCAAACTAAGCTTCATAAGTGAAGGAGAAATAAAATCCTT

TACAGACAACCAAATGCTGAGAGATTTTGTCAACAGCAAGCGTGCCTTACAAGAGCTCCTGAAGGAAGCACTAAA

CGTGGAAAGGAACAATCGGTACCAGCCACTGCAAAAGCACACCAAATTTTAAAGTCCATTGACACTATGAAAAAA

CTGCATCAACTAACAGGCAAAATAACCAGCTAGCATCATAATGACAGGATCAAATTAACCTTAATTAAGTTAGCC

TTAAATGTAAACGGGCTAAATGCCCCAGTTAAAAGACACAGACTGGCCACCTGTATAAAGAGTAAAGACCCATCA

GTGTGCTATATTCAGGAGACCCATCTCACATGAAAAGACACACATAGGCTCAAAATAAAGGGATGGAGGAATATT

TACTAAGCAAATGGGAAGCAAAGAAAACAAAAAGCAGGGGTTGCAATCCTAGTCTCTGATAAAACAGACTTTAAA

CCAACAAAGATCAAAATAGACAAACAAGGGCATTACATAATGGTAAAGGGATCAATGCAACAAGAACAGCTAACT

ATCCTAAATATATATGCACCCAATACAGGAGCACCCAGATTCATAAAGCAAGTTCTTAGAGACCTACAAAGAGAC

TTAGACTCCCACACAATAATAATGGGAGACTTTAACACTCCACTGTCAATATTAGACAGATCAATGAGATAGGAA

ATTAACAAGGATACTCAGGACTTGAACTCAGTTCTGGATCAAGTGGTCCTAATAGATACCTACAGAACTCTCCAC

CCCAAATCAACAGAATTTACATTCTTCTCAGCACCACATCGCACTTATTCTAAAATTCACCACATAGTTGGAAGT

AAAACACTCCTCAGCAAATGCAAAAGAACGGAAATCATAACAGTCTCTTAGACCACAGTGCAGTCAAATTAGAAC

TCAGGATTAAGAAACTCACTCAAAACCGCACAACTACATGGAAACTGAACCTGTTCCTGAATGACTACTGGGTAA

ATAATGAAATGAAGGGCAAAATAAAGAAGTTCTTTGAAACCAATGACAACAAACACACAATGTACCAGAATCTCT

GGGACACATTTAAAGCAGTGTTAAGAGGGAAATTTATAGCACTAGATGCCCAAAAAAGAAAGCAGAAAAGATCTA

AAATCGACACCCTAGCATCACAATTAAAAGAACTAGAGAAGCAAGAGCAAACAAATTCAAAAGCTAGCAGAAGAC

AATAAATAAGATCAGAGCAGAACTGAAGAGGAGAGAGACATGAAAAACCCTTCAAAAAAATCAATGAATCCAGGA

GCTGGTTTTTTGAAGAGATTGACAAAACAGATAGACCACTAGCCAGACAATAAAGAAGGAGAGAAGAATCAAATA

-continued

GATGCAATAAAAAATGATAAAGGGGGTATCACCACTGATCCCACAGAAATACAAACTACCATCAGAGAGAATACT

ATAAACAACTACACAAATAAACTAGAAAATCTAGAAGAAATGGATAAATTCCTGGACACATACACCCTCCCAAGT

CTAAACCAGGAAGAAGTTGAATCCCTGAATAGACCAATAACAAGTTCTGAAATTCAGGTAGTAATTAATAGCCTA

CCAACCAAAAAAAGTCCAGGACCAGACAGATTCACAGCCGAATTCTATCAGAGGTACAAACAGGAGCTGGTACCA

TTCCTTCTGAAACTATTCCAATAGAAAAAGAGGGAATCCTCCCTAACTGATTGTATGAAGCCAGCATCATCGTGA

TACCAAAACCTGGCAGAGACACAACAAAAAAAAGAAATTTTCAGGCCAATATCCCTGATGAACATTGATGCGAAA

ATCCTCAATAAAATACTGGCAAGCGGAATCCAGCAGCGCATCAAAAAGCTTATCCGCCAGGATCAAGTCGGCTTC

ATCTCTGGGATGCAAGGCTGGTTCAACATACGCAAATCAATAAACCCATCATTCTCAGCAAATTATCACAAGAACA

GAAAACCAAACACCGCATGTTCTCACTCATAAGAGGGAGTTGAACAATGAGAACACGTGGACCCAAGGAGGGGAA

CATCACATACTGCGGCCTGTCGAGGGATTTGGGGTTGAGGGAGTGATAGCATTAGGAGAAATACCTAATGTAGGT

AACAGGTTGATGGGTGCAGCAAACCACAATGCGATGTGTATACCTACCTAACAAACCTGCACGTTCTGCACATGC

ACTCCAGAACTTAAAGTATAATAATAAAAGGCGCTGCCTCAGGATGTAAAGTGTAACAAGGGGGCTGGGGTGGGC

AGCGTGGGCCTCTGAGACCTTTGGTTGCCCGTGTCCGCAGCTCGCCCCGCAGCCGGCTCCACAATGGTCCGCTCC

GTTTGCCACGTGCGGATTCGGGTTCCAGACTGAAGGCTGCGTGTTCTCTGCCGCCCACAGCCCAAGTTTATTGTG

GCAACCGCCGGAGCAGCCTTCCCCGCTGTGGAGGAGCCTGGGGCTACCCCTCAGCGGTATTTGGGGCTGGTCCTG

GGGGAGCTAAGCAGGGTTGTGGCAGCACTGCCTGAAAGTGTGAGACCAGACTCTAATCCTTATGGTTTTCCATGG

GAGTTGGTGATATGTGCAGCTGTACATGGATTTTTTGCTGTTCTCTTTTTTTGTGTGGAGAAGTTTTAGATCGGT

TGGGAGTCGGCTTTATGTGGGAAGAGAAAAAAAGCTTGCTGTAATGCTTTCTGGACTAATTGAAGAAAAGCATAA

ACTACTTGAAAAATTTAGCCATGTTCAAAAAGAGTATGAAGGCTATGAAGTAGAGTCATCTTTAAAGAATGCCAG

CTTTGAGAAGGAGGCAACCTGTGAAAAGCTAAACAGGTCCAATTCTGAACTTGAGGATGAAATACTCTGTCTAGA

AAAAGAGTTAAAATAAGAGAAATCTAAACATTCTGAACAAGGTGAATTGATGGTGGATATTTGCAAAAGGATACA

GTCTCTAGAAGATGAGTCAAAATCCCTCAAATGACAAGTAGCTGAAGCCAAAATGAACTTGACGATATTTCAAAT

GAATGAAGAACGACTGAAGATAGCAATAAAAGATGCTTTGAATGAAAATTCTCAACTCCAGGAAAACGAGAGACA

GCTTTTGCAAGAAGCTGAGGTATGGAAAGAACAAGTGAGTGAACTTAATAAACAGAAAATAACATTTGAAGACTC

CAAAGTACATGCAGAACAAGTTCTAAATGATAAAGAAAATCACATCAAGACTCTGAACGCTTGCTAAAAATGAAA

GATCAGGCTGCTATGCTTGGAGAAGACATAACGGATGATGGTAACTTGGAATTAGAAATGAACAGTGAATCGGAA

AATGGTGCTTACTTAGATAATCCTCCGAAAGGAGCTCTGAAGAAACTGATTTATGCTGCTAAGTTAAATGCTTCT

TTAAAAACCTTACAAGGAGAAAGAAACCAAATTTATAGTCAGTTATCTGAAGTTGATAAAGGAAGAGCTTACAGA

GCATATTAAAAATCTTCAGACTGAACAAGCATCTTTGCAGTCAGAAAACACACATTTTGAAAGTGAGAATCAGAA

GCTTCAACAAAAACTTAAAGTAATGATTGAATTTTATCAAGAAAATGAAATGAAACTCCAGAGGAAATTAACAGT

AGATGAAATTACCGGTTAGAAAAGGAAGAAAAACTTTCTAAAGTACACGAAAAGATCAGCCGTGCCACTGAAGAG

TTGGAGACCTATAGAAAGTGAGCCAAAGATCTTGAAGAAGAGTTGGCGAGAACTATTCATTCTTATCAAGGATGG

ATTATTTCCCACGAGAAAAAAGCACATAATAATTGGTTGGCAGCTTGGACTGCTGAAAGAAACCTCAATGGTTTA

AGGAAAGAAAGTGCTCACAACAGACAAAAATTAACTGAAGCAGAGTTTAAATTTGAACTTTTAGAAAAAGATCCT

TATGCACTTCATGTTCCAAATACAGCATTTGGCAGAGAGCATTCCCCATATGGTCCCTCACCACTGGGTCGGCCT

TCATCCTAAACAAGAGCTTTTCTCTGAGGGCCCACTGAGACTCTCATCTTTGCTAACAGGAGGAGGAGGAAGAGG

CTCAAGAGGTCCAGGGAATCCTCTGGACCATCAGATTACCAATGAAAGAGGAGAATCAAGATGTGACAGGTTAAC

CAATCCTCACAGGGCTTCTCTGACACTGGGTCCCTGTCACCTCCATGGGAACAGGACCGTAGGATGATGTTTCTT

CCACCAGGACAATCATATCCTGATTCAGCTCTTCCTCCACAAAGGCAAGACAGATTTTATTCTAATTCTGGCACA

CTGTCTGGACCAGCAGAACTCAGAAGGTTTAATATGACTTCTTTGGATAAAGTGGATGGGTCAATGCTTTCAGAA

ATGGAATCCAGCAGAAATGATACCAAAGATGACCTTGGTAATTTAAATGTGCCTGATTCATCTCTCCCTGCTGAA

-continued

AATGAAGCAACTGGCCCTTACTTTTCTCCTCCACCTCTTGCTCCAATCAGAGGTCCATTGTTTCCGGGGGATACA

AGGAGCCTGTTCATGAGAAGAGGACCTCCTTTCCCCCCACCTCCTCCAGGAACCATGTTTGGAGCTTCTCAAGAT

TATTTTCCACCAAGGGATTTCCCAGATCCACCACATGCTCCATTTGCAATGAGAAATGTCTATCCAGCGAGGCGT

TTCCTCCTTACCTTCCCCCAAAACCTGGATTTTTCCCCATAAACCCCACATTCTGAAGGTAGAAGTGAGTTCCCT

GCAGGGCTGATTCTGCCTTCAAATGAGCCTGCTACTGAACATCCAGAACCACAGCAAGAAACCTGACAATATTTT

TGCTCTCTTCAAAAGTAATTTTGACTGATCTCATTTTCAGTTTAAGTAACTGCTGTTACTTAAGTGATTACACTT

TTGCTCCCACTGAAGCTTAATGGAATTATAATTCTCAGGATAGTGTTTTCTAAATAAAGATGATTTAAATATGAA

TCTTATGAGTAAATTATTTCCATTTTATGTTATTCTGGATAGTATAACTATTTTAATTTGATAAACTAATCCACG

ATTATATAAACAATAATGGGAGTTTTATATATGTAATCTTGCAGGTAGGGAGGCTTTAAATTATAAAGGTTGTGT

CTTTATGCCAAGAACTGTATTAACTGTGGTTGTAGACAAATGTGAAAGTAATTTTATGCTTCATTAAATAAATTT

TAGTTGATTTTTTTTTAAAAAAAGAAAATGGTTAATCTATCATTTAGGTGCATCATCAGTTGTTTAACCATTCTC

TCTTACTGAACATTGGGTTGTTTAAAAAGTGTTGTTATTTTTGAATCATGGTTCAGTGAACAATTTTGGACACAT

AACTTTTTATCTGATGAGTTATTTCCTAAGGATCCAGCTCAGAAACTCAGCACATAAACCTAATAAGAAAAAAAC

AATTTGAAGTGGCTAACCTCTTATCCCAATAAAAATGTTGTATTTATGTTTGGATTTAGATGCCTTTCAGTGGTC

ATACCTTCACCTAACTTTTATGGATTCTACTTTTAACATGTAGAGTGACTGTTTAAATCACCTAAACTCACTGAG

TTTTAAGTTCCTTTTTATTCAACAAGACTGGATTGTATGTTCCAGCTCCTCAAACTTAGTTACCAACCACCATCC

TAGAGAAGTGAATTCACATGAGGCCTGTCCAGAAGAACAATCTCCCTTTCAGTGTCCTCATGCATGCAGTGACCA

GAGACCAACCTTGATAAATTATGGAAAAAGTACAGCACATTCTGGAAGAGCCATGAAAGATCCAGATCATCTGGT

GCTGGATAAGAATATTAATGGACAGGCTGGGCGCGGTGGCTCACGCCTGTAATCCTAGCACTTTGGGAGGCCGAG

GCGGGCGGAACATGAGGTCAGGAGATCGAGACCATCCTGGCTAACACGGTGAAACCCCGTCTCTACTGAAAATAC

AAAAAATTAGCCGGGCATGGTGGCGGGCGCCTGTAGTCCCAGCTACACGAGAGGCTGAGGCAGGAGAATGGCGTG

AACCCGGGAGGCAGAGCTTGTAGTGAGCCCAGATGGCGCCATTGCACTTCAGCCTGGGCGACAGAGTGAGACTCC

GTTTCAAAAAAAAAAAAAAAAGAATATTAATGGACAAAAAGATTAATGAAAGAACATATTGAAGCATCCAATTAC

CTGGTGTCTGCTCAAATGAGGAATCGGTGAGATAGGTCAGTTAGCAGTCAAGATTTATAAAAGAGACGATGGCCT

TGGGAGGGGCTGCCCTACTCGACTTTTTAATGGCTAGAAGCTATTAAGGGCTAAGCCAGAACCCTTCAGTATGGT

TCAGTGAGGATCCCAATTTGGGGTCCAAAAGTAAATGACAACTCCCAGGAACCATTAAGAATAAAAATCATGGAG

CATTACTGAGAATTTATGTTATCTAAGTCTGAGGAAAATTAATGTTAAGGAAGCTTTCAAAAGTCTAATATTTAC

ACCGAATTCCAGGGCACCATGCTCTAAGACAAAGCACTCTGGTCCTGCCCCTCTCCTTTCCTCATGTTTTTTGGT

TCTTGGGATCCTTAAGGGTCAATGTTATTCTTAAAATACAGAGCATCCTGGAAACTAAAAAAGTGGAAGATATTC

AAATTCTAATGAATGTACTGGCAGTATTGTAGATCATGGAGTATAACATAAAGACAAGAATCCCTAGCCTCTTCC

ACCATACTTTGTAATGGTAAGGAGAAAGGATAGAATTTTGAGAAGTCTGGGAAGACAATGTATGATAACATCTGG

AGAAGCTCTGCATAAGTTACTTTTGTTCAGGCTTAAGAAAAATTCTAGCTTGCCCCTGCACTGTCATCAGGTATC

ATGAAAGTAAATAAAACCTTTAAAGATTCTTCAAGCCAGCAGACTTCTATCTTCTCTATACTATCCTGTGATCCT

AAACTCTTAACAGTTACTACGTATAATTTCCCTACATTTGCTACTAGTATTTTATCATACACAATATTACACTCA

ATATTTCAAAAGTGGATGATTCATCTCCCGAAGAGACTGCAAAATTCATGAGTTAAGATTTGAGAATACTATTTT

AGACAAGATTTAGTCAGATTTTAGAGAGTTAGAAACCTGTAACAATTCTCTAACAATACTGCTTCTCCTTTTGTG

TATTAAGGAATTTTTGTCTATCAAAGATAGTACGAGGTAGACCAGAAGATAACTTGCCTTCAAAATGTCTGGAAT

GTAAAATGGCAACAGTAGTATTTGGGGACTTCGTAGGGGATGGCCAATATACACCCATTCTTAGAGGTACTGATG

ATATAATGTATAAGACAAAATCAAGTGGTCTCCATCACCATATAATGTTTAAAATGGCAAAGAGGGAGCAGAACA

AACACCCTTTGCAAATCTCTTCATAGAATCTACCGTAATAAACTTGTACTTGCTTAAAGTGTGTCTCTTCAGTGG

-continued
```
TCTTATTACCACTACTTTGGGGAAAATGAGGCTGCTTAAAAGATTAACAGACATTACATTTTACATATCTGTGGC

AGAGAAAACACTATGTATTCACCAAACCACTTCTTTTCCTTCCCAGTCACTCGGGAAGAGGTCATTTCTTTGTCC

CCTTTCATCTAATTGAGGTGCCGTGACTACTTCTAGACAGGCAATGTGAGCAGAAGGTATGCACGCCACGTATAG

GCCTGGTCTTCAAAAATCCCTCAGATATGATCTTCTTCTCTCGTCTCTTTCATGGACAAACTACAGGCCATGTAA

TAAGGATGGTGGGGTTCCAAACTGAAAGAGCCTGGATTTCTGATTTACTGTTTTGAGAAGAGTTCACCAGGGAAA

CAGCCTGGAAATACGCACAGGAAAATATGCACAGGACCCTGTGTGAGCAAGATATAAAGATCTATTACATGGTGC

CATTAAGGTGAGAGTATTGTGCTTATAGTATCCAGCATTAATTATCCTCACTACTACAACTTCTTTGTATCCATC

ATGTGGAAAAGTAGAGTATTTAATAAATGATTATTGAGTTTATTACCTTTTTTATATTCCAATCATTGCTAATTG

TACGTTACCTCATTTCAAGGTAAAGGTGACCAAGGGCTAAAGCAGTGCTATCCAAACCAAGCCAGACATCAAAAT

CACACAAAACCTTTTGAAAATACAACTTTGAAGATGCCATTCACATAGATATTTATTCAGTGGGTTTTCAAATGG

AACCCTGGAATCTACAGTCTTTAACAAGGCTTCCCAAGTTATTCTGATATACAGCAGGCAAATCTGAGAACCACT

GGACAAGAAGAAAATAAAGGCTATATCTTTCGACAACAAAGACAATGCCTTAAACATAGAATGTATTCAATTAAA

GCTTGTAGAAAGATAGGTTTGTGAACAGGCACAGGGACTAGCCTCGAGCAAATTAATAAGGGCAGCAATGTTTTT

CACTGAAACCATTATTCCCCCTATTTTATTTCTTCTGGGGCTCTGTGTTTCCTTTCTCCTATCAAAATCCATTCT

AAGGTTGGAGGTTGGGGGTATCTCTTGCCTACTCCATACAGCAAGGAATAAAATTAGTATTTCTCGAACTATCTG

TGACAGCAGACCCATTGTAGGCCAGTACTTTTGTAAAATGCAATAAAAATTAACTTCTAGAGAATGAAATTTTAA

AATCACAGACATTCAAAATACAAATTCCAATTTTTTTATTATTAACTGTAAGAAATTTAAAATTAAAYCTCAATA

AATAAAATTAAAGCAAACATAAGATAGAAAAAAATAAGCATTATGGATTGGCCCAGTCTGCAAACTGTATACACT

TTGCCAAACATGGGCATAAATTACTAAGAAGCAAAATCTTCCATCTGTAAACATTTCCATTTCCATTGACAATAT

GTGTGAGGGAAAGGAGGGATGCTTCTGTTTTAGAATGCCAGGCGTCAGCTAACAAGTGACAAATACGTATTGAGA

CTGAGATCTCCCCAGCCTCTCAGTAGTCAGCAAGAACATGTTGAGGCCTCTGTTTTTGACTAAAAAATTGGCCAG

TGCATGGGCAACATGCATAGGTCCTGAATGAAAAAAATAGCAGCAGCAGAAATTTAAAAGAATTTTCACAGCTAG

GCCACAGTAAATTCTCAAGCCCTTCATCAGAAGCCACTGTGGGGCCTCATTTATGCCTTTGTTTTTATTAAATTG

GATGTGATCTTAAGATTCTTCTGTCAAAATTCCACTAGCATGTGAAGGCACCAAAAGTTTAAAATGTAAAATTAA

CCCAAGTTAAGCTATTCCATTATTAAGCAATAGCAGATATATTTGTTATTATATGAGAAGAAAGTTAACAGGGAG

CTAAGATTGATGTTACTGATAAGAAACAGAAACAAGACTTTAAAATTAAATAAATGAATTATTTATTTAATAAGA

ACCAATTGACAGATTCTCGATAAAGACTGTAAGATGTCTTAAAACATTAGGTGTATGGAGATAACATTTGTAACT

TTGACAATTTATATGATGAGAAAAATCAAGGAATGTTATTGTTTATTGGCAGAGTTCTAGAATTACAATTCCATC

ATTCTGTTTTGGGGAAGTTTCCCTTGAAGTAAATGATAACAGGGCTTGAAATAGTACACCTCAGCATTTTGTTTA

TAAAACTGTGGAATAGGTAAGGTTTGTATTGTAACTGAACCCAGGTTCAGCTGCTTGCTGCTCTAAAGCTAGACA

TAAGAGAGGAAGGTTGGTGGGAGGAAAAGCGATTTTAATCGGAGAAGCAGCAAACCAAGAAGATGGTGAACAATA

GTCACAGAACCATCTTAAATTTTAAAATTTACCATAGAGTGTTCAAAGGAAAACTTGGTATGGGAGGCATGCAGG

AGGGGTGCAGGGGGCGGGGTCTGTGTGTCTTGTTCCAATGGCTATCTCAGATAGTCACCCATCTGGAGGTCTAGT

TGGTATTATTTTGAATTCAGCCCAGTGGTGGTGGACTGTCAGTGACTCCTCGCTAAGCAGGAGGATTCTGCACTC

AGGGCTCCATGCATGGTTTGTTTCAAGATTGGCCTCTGGAATTTCTCAAGCAAGAACATAATTAAATAAGCAGGC

ATTGCCAGAGGGGAGTGTCTGGAAAGGAAAGGAATGAAGAGATGAAAGGAAAGTGGGTGGTTAAACTATATTTTT

AAAACTGAGGTTCCCAGTTATAGTATGTTTCGCACGCTCCCCCCATTTTAGCACCCCTGACAGAATTTAGTAATC

TCCTCATCTTGTCCTCTACTTCAGGTCCCCTATCTGTCCTTGTACTCTCCAGGGTTTCCTTTTCTTCTTCACGAC

CTTCCTTCCCTGCAATTTTATAAGCTATTCCTATCCCAGTGATTTAGTTTCAGCTTATAAAACTGTGTCTTTGCC

ATTGTAATCAAATTGAAGGGCCTCTGCTTCATGGTTGGATTCTGTGACCAGGAGACTCTTACGAGGAGTTGGCCA

GGTCTCTGTTAGGAAAGCAAAAAAGAACAATGGAGGCAATTATCCCATTGATTTCAGCTATAAATCCTATTTTGC
```

-continued

CTGAATTGTCTGAACGATGAGTATTCTGTGAAAATGCTGCTCTCTAGTGCAATAGAACTGCAAATAATGCACATC

TATTTCTTATAATCTCATCCAACATACCCACAGAGATTCAGATCTAACAAAACAGAGGTGATTTGGTTATTGAAT

CATAATATAAATATGGGGAAGAGGAGGGAAATTTCAAGCCTGAGGAAACTGTAGTAGGAGTAAGTATGCTGTGTT

TAAGAGGTCACAGATAAAATTAATATTACCAATCCATCAATAGGCAATTACTAATAGCTTACTACACACACAGGA

ATAAAATGTGAAGACAGAGGAAGTGTAAAATGGAGCCGCCAACTCTACGGAGTTGTTTGCAATTTGGTCTGGTAG

AAAGCTATGAAATAAGGAAGTACATGATTGAGAGCTAGAGAATGTGGCACAGGCTCTGAACCCCGGACCGTTCAAT

GTAGTAAGCTCTAGCCACACTGGACACTTGCAATGTGGCTTGTCCAAACTGACATGTGCTTTAAGTATAAAATAT

AATCCAGATTTCTAAGACTTCAAAAAAAATGGAAATATCTCATTAATAATCTTAAGTTTATTACAGGTAGAAATG

ATAGATTAAATAAACTATATTGTCAAAATTCATTTGATCTGTTTCTACAGTATAACAAACTTACTTGTGTGGTTT

GCATTTTATTTCTACTGGATAACATGGCTTTAAAAATGGTATTTTAGAGGAAGGAAAGCTTGGTAGAGAATGGAC

TAATCCGGATCCCTGGAAGAAATGGACCTTGAATGGGTCTTGATGACTTGGAGAGGCAGAGAGAGAAAAAGAAAA

GTCAAACATAGGGAATTGGTTGATAAAATGAAGGTGAGGGGAGAAGGAACAGAGGGAGGAGAAGATCCAGTTTGA

GGGATATTACAGCGAGCAGCCTGAGAAAGAAGGATAAGAAAGGAGAGAAAAAATGCAAGGGAAGTAACCCTTCAA

AGCCAGTCAGAAGTTTCTGGGTTCCTCAGCAGCCAGAAAAGAAGCCGTTGAAAAGATCTGAGTAACGGAGATTCT

GGACGAAAACTGAAGTTATGGAAGGGAAGTTTAGACATGGGTTATTAAACGCTTTAGCGCATTAGAAGTTTCTTA

TGTAATCACTAAATTCAGATCCTGAAATAATGCCACAAGAACTATACAGCTCAGCCACCCAATTCAATAAGAAGT

TACAGCACAGTCTCACACATATCCAATTAACCTTGGCCTTTAGTCAACATCTGGGTTCTTTTTGTCATTTTCAAA

TACTATCACCCAGAGGTGCTATGATTTATATTGGGGAGGGGATTAAAAGAAAATAAGTAAGTTGGTGATAAGAAA

AAGCTTTCAGATGATTCCATCTGAATTAACAGCCCTCTTTAGTTGTCTAGGAAAGAGGATGCTTTTTCTTGAAAG

TGCTTTGAAATGATGATGTGCTTGTTAGTAAACATCAATTATTTTCAAATCGTAATGTTTGCAAGTTTGTCTTCC

TGTAGCTCACCCTTTATGTAGGTCCAGAATATGATTGTCACAAATATCTGGGTGAGCAAGACTATGAAATGTGGT

CATAAAGTAAGTGATTATTTCTAAACTCATCTTTGTCACTCGTAGTGCTTCACAAAGCACCTTTTCCTGGACTAC

AATTCATTTTAATTGATCCCATCAGCACTATATCTGTATCCTGAGTGACTTCACAATACCCTCTATTTCAAGAGA

AACCAATCAGGTTATGGGTTTGTTAGTAATAAAAATTACCAAGGAGCAGTTTGTGGATGGTAAAAGCAATGCAAA

TTCTAAAGAGAAGTCATAAGAGCAATAATAAGCATCCTCCTCACTTCTTGGAAGTGAACAATTCCAAGCTCCCTG

AAGCAACACTTAACCTATCATATTAAACAGTAATGGACAAATATTAGAAATGTTGATGTCAGCTTTCAGAATCTG

TGGGCATCAAAACATCACTTAAGTTCTCCGAAGTATTCTCTGTCAAGTTTCCTTCTACAGTATTCTTTTCCTACT

AGGACAGAGCCTTAAGCCCTAGAAGAATAATTTTGCTTGTGTGTTAATTATTTGTTTACTGGTTCATTCCAGAGT

GTGAGCTGGAAAAAGGGGGAAGTGTCATAAATAGTTTTTTATGGCCCATGGTTTTTCAACTACGTCACTATTGGT

AGCAGTTTCCACTGCAGGATCTATTTGCAAAGCCTAGGAAATTAGCATTAAGCAAGCTGCTAGGAAGACTTCAAC

AGTAACTAGGCCACAGGCCTCACACATTTTTCCTCCACCCCAGCCTCCTCTGGAGAGTACTTGCTAAACCTCTGT

GACACATAATGAAGCAAAGAAAGTGATAGAACAACAGAATTACACGGGCAGATCCTTGTTTCTTCTTCTCTCTCT

AAAGAATTCCTTGGACTGAAAAGCAGTTTATTTTGGAGGAGTGAGAAAGTGGTGACAGAATTAGAAGGGCCTGGG

AGGGCTTCATTTTAGGAGACAGTTTTAGGCTGAAAAGAGATTTCATGAGTGTGATTTACCTGAGGTGACTTTTGG

GGGCTCTTATAAAAAGGAAGTTCATGCTGAATGGGAGGTGGCTTCTGAGATGCAGATTCTGGTGAGCTAAGAGGG

CTCGGTAAAGAGGAGGCAGGAGTTAAGTAGCGTGAACTATGCAGTAGCAGCCTTCTTCCCCCCTTGCTTGGGGCA

GGTCATCACAACCCTTCTCAATAAAGGGGTCCAGGAACCACTAGGAATAAATGGGCATTTGCACTTCAGGTGAAA

CCCATTTGTCATAACTGCTTGGACTTTAAGCTTACAAATAAAAAGAACCACATATTTCCCTTTGCAGCTTGATTT

AGTTAATGTCATTTTGAGAAAGAAAGAAGACATTGTTATCCCGTCCCTTTTTTTTTTTTTTTTTTTTTTTTATGA

AGAGACTGGGACTCAGAGAAGTCAAGTGATTTTCCCAGAACCAGAAAACACAGAAGTAGCAGAGCTGAGATGACT

-continued

ACTCCGGTCTTCTGATTCCAAATTCCAAATTCATTCTTCTAAGCGATTTCCCAAAACGGGAAATGGGTTTATCTT

CTATTTATGGGAAGTGATAGTGGTATTCTATTTAGAGAACTTATATAAAATCTTACTTTAAAATAAATAATATTT

CAAAAAGTAAGCTTAATTTAAAGAAAATAATCAAGAAAGTCTGGTATATTTTTACAAATATACCAAATGACCTTG

CTCTAAAATACATCTACTTTCCAGCAAGCCAAAGTGAAACAATTTGAAATAAGTGGCATTTACTGACCACTCCCT

AAAGTTCACACAAAAGAGGTAGTACTCTAACTTAAATATACAAGGTGAAGAAATAGCTTACTCAGCCTGTTGGGC

TTCCTCTTCTACACTCTTGGGAAATGCCCTCCGTGTTAACCAAGAATTCTCAGGCCTTGGAGGGAGTTTTCCATT

CTCAGTAAACTGAGATTGCAGTTGCGGAAATTAAGAGGTATCTGTCCAGCACTTCATTCCCTTAAGGTCAGGATC

TGTGCTTTTAATAATGACAATTAGCTAACATATACAATTAAGCCATGCAAATGAAGTAAGAGAAAGCTAGAGGAG

AAATTCAGGAGCCAGTTGCCTTTTCCAGACATCTTGTACAAATAGTGTTCAAAGGACTAATTCAAAAGATGGGAT

TCTTCGCTTGAACCCAGGAGGTGGAGTTTGCAGTGAGCGGAGATCGCTCCACTGCACTCCAGCCTGGGTGACAAA

GTGAGACCCCATCCAAAAAAAAAAAAAAAAAAAAAAAAAAAAAGATGGGATTCTTTTTTAAAAAATAAATTTTACT

GCGTATTTTTAAGGTATACAACGTGATGTTATAAGATGGATATAGATAGTGAAAAGGTAACTGTAGTGAAGCAAA

TTAACATATTCATCATCTCACATAGTTATCTTTTATTTGTTTTGTTTTGATGGGATTTTTAAGATAGTAGAAAGG

AATGGTAGACAATAAACATTTGAGGGAAAGTGGGGCTTTGTAGAACTCCTAAAATGACAGCACGCACAAATGTCC

CCATTATGTCTAAAGGGTAACTCGTTCCTACTTCTAGGGACAGCTGAGGGACATCAATGTAAATTTCTAAATGAC

TTCCTGAACTTTTTATTTTTATTTTTTGTATTTTTAGAGGAAATTATAATAACATCAAGCCACCTCTGGACCATA

TCGCTGCTGATATCATCAGCAAATGGCACTATTCCTAAATCCTAAGATGCACTTTTCCCTTCACATTTCAACATT

TGTGAAACTCGATTGTACCTACACCTGATTTTATATACAATGCAGCCTTTCCTTTTCTTTTGTCATTGCATCTTA

CGCCTGATTTCTCCTTGGAATTGAGTAAATATAATGCTTACATGTGTTAATAAGAATTGAGGTCACTCATAATTT

TTGAAATATGCCACCAAATATAAGCCTTTCTACATATTGTTGACTTTGAAGTCATTTCTTTTTTTAACTACTAAA

CAATAACACTTTTTGTTGAGAAAAAATTGCATATGAACAAGAGACCAAGCAGGTAGAGAGAAAAAAACTTTTAATA

ATCAAGAGAATGTTACTGTGTCCCAAAGGCTAAAGTCACCTTACTATCAAGAGAGAAGGACAGGAACAGAGAGAA

CCAGGTAAATTACGAATTGAAAATTCCATGGTTCATTTATCTTTATTTTTAATAATTCCATTTGTGTGATTGTGT

TGACCACAAGGTCATAATGTTACTCTTCATACTGACTTCTCATGTAAATTATAAATAAGTTTTTATGCTAATGAT

TTATGGAGTAAGCTATTCATCTTTCCGACAGAGAGTTACCTACAAAGAAATAATTATTCTACCTCTGAGATGAAA

TATCATGAAAGGAGTGGTTTCCAGATATTTTGACTTTTAAAAGCTTAAAGAATATATGTAGTATAAAATTCTAAA

GCAGGCAAAATTAATCCTTTTAGCAATCAAGATAGCGGCTACTTTTGGTGAGAAGGACAAGGTAGTGATAGAGAA

GGGGCTCAGGGGTCTTTCCTGAAGACAGTGAGGTGGGCAATGGTATTTTCCTTGACCTGGATGGTGATTAAACAG

ATGTGTTTACTTTGTGATAATTGACTAGGCTGTGCACCTATGAACTGCATACTTTTCCATATATGTACTGTATTC

TTATACTTAAAAAGAAGTTTAAAAATAAATGCAACAGATATAGGACTTCCTATATTACTCGTTGACCAAAAAAAT

GGATTCATTTTTCTTTCAGGTAAAACGTACTAGTGGTTTTAATATTATATTGACCAGGGAGTAAATGTTTACCTT

AGGAACCTTAATCTTGATGTTCTCCAAAGTCATTATCTGTTCTTTCTGATTATCAGAATAGAGTATATCTCTATA

TAAATGAAAATTTCTGGTCATTCTCAAAAAATAACACTAAGCATGAAAATCAGAAATATTGATCTTGTTTTGTAA

TGATGTTTCTATTGATGTGAAGTAGTTTCTAGTAGAGTTGCTGTCCTAACACACAAATGAAATTGCACTGTTTGG

AAGACACAACTGTGAATGACTTGCTTCAGTAAGGAATTTCCAACATGATGGTTTAGGGATAGAGGTGCTCGATTC

CTCTGTCTCCGGTTACCCAGGTTATTGAGGACAGGGAGGTCAATAAGTAATGCCCTCCTCCCACCCATAGCACAA

AACAGAGCGGGGTTCAGAGAATAGGTAAGGCTTTGGCCAGGGTGTTGAGGAGACTTACATCCCTGGGAACCAGTC

AGAATGGGGGCGCTGAAAACAATGTTTTAAATTCTAGCACCCAGCAACATATGTGTGAAGATTAAATGTACTCGT

GCTAAATTCACTTGCTCCATTACTGAATTTGGGTGGTGTCTGTTAAAGATGGGAACAAAGGCATTCAGGTCCTGG

TATCTTCTACCACTCCCAGCATGAACAGACTCATGTCAGTGGGTAAGGGATGGTATTTCCCGAGAAGGCTTTGAA

CTCTTGTAGTGGGTCAAATAATGGCCCCCCACTTAAAAATGTTCATGTCCAAATCCCTGGAAGCTGTGAAAAGGG

-continued

GTTTTTGCACATGTAATTAAGTCAAAGATATTGAAATTAGATCATCCTGGATTACATAGGTGGGCCCTACATTTA

ATGACAAGTATCCTCATAACAGAAGAGGAGAAGGTGATGTGAGATTTGGAGCAGCAGAGATTGGAGTGATGTGGC

CACCAATCAAGGAAACCAAGGACTTCCAGCAGCCACCAGAAGCTGGAAGAGGCAAGGAAGGACTCTTCCCTAAAG

CCTTTAAAGGAGCACAGCCCTACTAACACCTTGCTTTTGGGCTCTGGCCCGCAAAACTGTGAAAGGATACATTGC

TGTTATTTGAAGCCACAGTTCGTAGTAAATTTATTACAGCAGCCCTAGAAACTGATACAACTCCTAAATACACCC

TTAGCAACACTGCTCAACAAGAAGTAGGCAATTTCCTCCTGACTGAAAAATACTGATACTGTTATGGGATCCTTG

GGGGTGTTGCTTTTCTGTCCAGAAACCTCTGTGGCGGTGGCACCTTTGCATGAGTTTTGCTCGGGTCCACTGGGC

CCACTCATCCTGGCAGGCTGCGCTCAGCTGACACTACTGGCGTGGATCCCATGCCTCCAAAGAGACTGGAGCGAA

GCGGTGAGGGATGTGTGAGGAAGTGAGCGTGGGGTCTGGCACACAGTCAGGCTCAATGGCTGCTACAGCGGGATG

GGCAGCTTCAGGTGCTGGCACGGGTGCTGGCTCACTGCAAGGCTGTGGCTGCACCAAGCAGCGCAGCAACGGAAC

GCATTGGTGCCTGGAAACTTGGAGACTCCAGGAACCTCAGGGCTCCAAAAGGCAAATCACAGCCCTAGCTTCGGG

AGCTCCCAGGTCTGGGCTGCCAAAGGGCTGCAGCTCTTCTCTCCTCTCTCTCTCTTCGCTCCTCTCCCTTTCTCT

CTTCACTCCTCCCTCTTTCTCTCTTCACTCCTCCTGTCGCCTATGAACAGCGAATTCAACCTTCCAGTTTTCAGA

CTAGGAATGCTGGAGTTGTCCTTGATTACTCTGAATTGTTCACTCCGCATATGGGCACTGAGGATACGTTGATGA

ACTACACAGACAAAAAGGATAGAAATTCCTGTCAAGACTACATTCAATAGGGATGAAGCAGGCAATAATGAATAA

ACATACTAAGTTGAATATGACTATTTAAATATATATAACACATATGACTTGTATAATGTTAAATATTTTAAGTTT

TTTAAATTCTTCCCTTCATAGATTTTACATTATAGTAGAAGAGGCATTTTTGTTGTTGTTCTTTTTGTTTTGGAT

TCAGAGGGTAAATGTGCGGGGTTGTTACATGGGTATATTGCATAATGCTGATGATGGTCCCATCACCCAGGTGGT

AAACATAGTACGTAATAGGTGAATTTTTAGCCCGTGCTTCCCTCTCCCATCTAGTCGTCCTGAGTGTTTATCGTT

GCTACGTTTATGTCAATGTGTATTCAATATTTAGCTCCCACTTATAATTGAGAATATGCAGTATTTCGTTTTTTG

TTCTCGTGTTAATTTGTTTAGGATAATGGCCTACAAAGAACATGATTTCATTATTTTTATGGACATGTAGTATTT

CATGGTGTATATGTACCACGGTTTCTTTATACAATCCCACTGTTGATGGGCACCTAGGTTGATTCTATTGCTGTT

GTGAATAGGGCTGCAATGAACATACAAGTGCATGTATCTTTTTGGTAACAAAAATTTTATATTTGGATTACCCAG

TAGAATTGCTGGGTTGAATAATAGTTTTGGTTTAAGTTCTCTGAGAAATCTCCAAACTGCTTTCCACAGTAGCTG

AACTAATTTACATTTCCACTAGCAGTGTATAAGCGTTCTCTTTTCTCCACAATCTTTTCACCAGCATCTGTTATG

TTTTGGCTTTTTAATAGCCTTTTGATGACTGTGAAATGGTATCTCACTGTGGTTTGGATTTCCATTTCTCTAATG

ATTAGTGAATGTTGAGCATTTTTTTCATATGTTTATTGGCCGTTTGTATGTCTTCTTTTGATAAGCGTCTGTTCA

TGTCCTTTACACATTTTCAATTAAAATATTTGTTTTTTGCTTGCTGATTTAAGTTCTTTGTATATTCTGGAAATT

AGATCTTTGTCAGATGCATAGTTTGCAAATATTTTCTCCCATTCTGTAGCCTGTTTACTCTGTTGGTAATTTCTT

TTGCTGTACAGAAACTCTTTAATTAGGTCCCACTTGCCTATTTTTAGTTTTGTTGCAATTATTCTCTGGAACTTA

GCCATAAATTGTTTGCCAAAGCCAACGTGGAGAAGGATATTTTCTAGGTTTTCTTCTAGGATTTTATAGTTTAAG

TTTTACATTTAAATCTTTAATCCATCTTGAGTTAATTTTTGTATATGTTGAGAAGCAGGAGTCTAATTTCATTCT

TCTGCATAGGGCTAGCCATTATCTTGGCACCATTTATTGAATAGAGAGTCCTTTCCTTATTGCTTATTTCTGTCA

ATTTTGTTGAATATCAGATCGTCGTAGGTGTATGGGTCCATTTCTGGGTTTTCTATTCTGTTCTATTTGTCTCTG

TGTCTGTTTTTGTACCAGAACCATGCTGCTTGGTTACTGTAGCCTTTTAGTATAGTTTGAAGTTGGGTAATGTGA

TGTCTCTGGCTTCGTTCTTTTTGCTTAGGATTGCTTTGGCTATTCAGGCTCCTTTTTGGTTCCATATGAATTTTA

GAATATTTTTCTGATTCTGTGAAAAATGACTTGATATTTTGCTAGGGATAGCATTGGAGTGGTAACTTGCTTTGG

ACAGTGTGGCCATTTTAATGATATTGATTATTCCAATCCATGAGCATGGAGTATTTTTATATTTATTCAGTCATC

TTGATTTCTTTCAGCAGTGTTTTGTAGTTCACCCTGTAGAACATTTCACTTCCATGGTTAGATGTATTCCTATTT

TGTGGCTATTGTAAATGGCATTGTATTTTTTTTTATTTGGCCCTAAACTAGAATGTTATTGGTGTATAGAATTGC

-continued

TACTGATTTTTGTACATTGATTTTGTATCCTTAAACTTTACTGAAGTTATTTATCAGTTCTAGGAGACTTTTGGA

GAAGTCTTTAGGGTTTTCTATGTATGAAATCATATCATCAGCAAAGAGAGACAGTTTGACTTCTTCTTCTTTTTG

GATGCCATTTATTTCTTTCTCTTGCCTAGTTGCTCTGACTAGGACTTCCAGGGCAATGCTGAATAGGAGTGGTGA

GAGTGGGCATCCTTGTCTTGTTCCAGTACTCAAGAGAAATGCTTCCAGCATTTACCTGTTTAGTATGATGTTGGC

TGTGGTTTGTCATAGGTGGATCTTATTATTCTAAGGTATATTCCTTTGATGCCTAGCCTGTCGAGGGTTTTTAAT

CATGAATGGATATTGAATTTTATTGAAGGTTTTTTCTGAAACTATTGAGATGATCATATGGTTTTTGTTTTTTCA

TTCTGTTTATGTGGTGAATCACACTTATTGATTTGTTATGTTGAACCAGCCTTGCATCCCAGGAATAAAGCCTAC

TTGATTGTTGTGAATTAACTTTTTGATGTGCTTCTTGATTTAGTTTGCTCATATTTTGTTGAGGATTTTCGTGTT

TATGTTAATCAGAGATATTGTCCTGAAGTTTTCTTTTTTCATTGTGTCTCTGGCAGATTTTGATATCAGGATGAT

GCTGGCATTGTAGAATGAGTTAGGGAGGAGCCCCTCTCCTTAATATTATGGAATAGTTTCAGTAAGATTACTATC

AGTTCTTCTTTGTATGCTTGGTAGAATTCAGTTGTGAATCCATCTGGTCCAGGGCTAAATTTGGTTGGTAGGTTT

TTTATTACTGATTCAATTTTGGAACTTGTTATAGGTCTGTTCAAGTTTTCACTTCCGTCCTGGTTCAATCTTGGG

AGGTTGTATGTTTCCAGGAATTTATCCATTTCCTCTAGATTTCCTACTTTGTGTGCATAGAGGTGTTCATAACGG

TCTCTGAAAATCTTTGGCATTTCTGTGGGATTGGTCGTAATGTCATTTTTGTCATTTCTTGTGCTTTTTGGAACT

TCTGTCTGTTTTTCCTCGTTTTTCTAGCTAGCAGTCTATTAGTCTTGTTTATTCTTATGAAAAACCAACTCTTTG

TTTCACTAACATTTTATGGACTTTTGCATCTCAATTTTATTTAGTCATTATCTGATTTTAGTTATGTCTTTTCCT

CTGCTAGCTGTGAGATTGAATTGTGCTCTTTTTTTCTAGTTCCTCTAGTGTTATGTTAGATTGTTTAGTTGAGAT

CTTTCTAACCTCTTGATGAAGGCATTTTAGCACTATAAACTTTCCTCTTAACACTGCTTTTGCTACATCCCAAAG

ATTTTGGAAAGTTGTGTCTCTATTTTCATTAATTTCAAATAATTTTTTGATTTCTGCCTTAATTTCATTGTTCAC

CCAACAGTTATTCGGGAGCATGTGGCTTAATTTCCATGCTTTTGTGTAGTTTTGAGAGATCTTCTTGGTATTGAT

TTCTATTGTTATTTCACTATGATTTGAGAGTGGCCTTTGTATGATTTTAATTTTTTTTAATTTATTGAGACTTGC

TTTATGACTGAGCATGTGGGGCAATCTTAGAATACGTTCCATGTGCATATGAGAAGAATGTGTGTTCTGTCATTG

TTGGCTTGAGTATCCTAGAGAGGTCTATTAGGTCCAACTGGTCAAGTGTCAAGTTTAATTCCAGAATTCCTTCGT

CAGTTTTCTGCCTCAGTGATCTGTCTAATGCTATCAGTGGAGTGATAAAGCCCCCACTAATATTGTGCTGCCATC

TACGTTTTATTGTAGGCCAATAATTTGTTTTATGAATCTGAGTGCTCCAGTGTTGGGTGCATATATGTTTAGAAT

AGTTAAGTCTTTTTGTTCAATTGAACCTTTTATCATTTTATAATGCCCTTCTTTGTCCTTCCTGATTGTTGTTGG

TTTAAAGTATGTTTTAATCTGATTTAAGGGTAGCAACTCCTGCTCTTTTTTGTTTTTCATTTGCATGGTAGATCT

TTCTTCATTCTTTCACTTTGAGCCTGTGAGTGTCATTCATGTAGGATGCATCTTCTGAAAACAGCAGACAGTTGT

GTCTTGTCTTTTTATCCAGCTTACCACTTTATGCATTTTAAAGGGAGAGTGTAGACTGTTTACATTTAGGGTTAG

CATTGACATGTGAGATTTTGCTCCTGTCATTGTGTTGTTTAGCTGGTTGTTTTGTAGACTTCATTGTGTAATAAG

TGTATTTTTATTGGTAGCAGGTTTCGTCTTTCATTTCCATGTTTAGCAATCACTTACGGATTTCCTGTAAGAATC

ATCTGGTGGTAATGAATCTCCTTGGTGCTTGCTTGTCTGAGAAGGATTGTATTTCTCCTTCACTTATGAAACTCA

GTTTGGTGGGATATGAGTTCTTGGTTGAAATTTATTTTCTTTAATAATGCTGAAAATATAGGCCCCCCCATATCT

TCTGGCTTGTAAGGTTTCTGCTGACAGAACTGTTGCTGGCCTGATGAGGTTCTTTTTGTAGGTGACCTGACCTTT

CTCACTAGCTGCCTTAACAATTTTTTCTTTTGCATTGACCTTGGTGAATCTGATGACTATGTGACTTGGCAATGG

TTGTCTTGTATAGTGTCTCACAGGAGTTCTCTGTATTTCTTGAATTTGTATGCCCACCTCTCTGGTGAGATAGGG

GAAATTTTCATGGACTGCATCCTCAGATGTATGTTCTAAGTTGCTTACTCTCTTTCTCAGGAATGACTGTGAGTC

ATAGACTTGGTCTCTTTACATAACCTCATAAATCTTGAAGGTTTTGTTCATGTTTTAAATTCTTTTTTCTTTATT

TTTGTCCAACCAAGTTGATTCAAATAACTGGTCTTCAAACTCTGAGATTCTTTCCTCAGCTTGGTCTGTTCTGCT

GTTAATGCCTCTGACTATATTATGAAATTTTTGAAGTTGATCCCTCAATTTCTGAAGTTCAGTTTTGTTCTTTCT

TAAAATAGCTATTTCATCTTTAAGCTCTTTGATCATTTTTCTGGATTCCTTGAGTTCCTTGTATTGGGTTTCAAT

-continued

GATCTCCTGGATCTTGATGTACTTCCTTGCCATCCAGATTCTGAATTCTATGTATGTCATTTGAGTCATTTTAAT

CTGGTTAAAATCCTTTGCTGGAGGACTTGTGTGTTTGTCTGGAGGTAAGGAGACACCAGCTTTTTTGAATTGCTA

GAGTTCTTGAGATGACTCTTTAACATATGAGGGCTGGTGTTCCATTAACAATAGTGTACATTGAGTATAGTCAGT

TGGCTTCATTCTGAGTGCTTTCAAAGGGCCAAAGCTCTGTACAGCATCTTTATTTGTGGCTAGATTTTTGCTTTA

GGTTTCACAGGTGCTGTATATTGGAAAAATGTTTTTGGTGTTGTCATTTGGGGTGCAATCCAGTAGGTGATGCTT

AAGAGTGGTAGCTGGCAGATAGGCTCTTACTCAGTCCACAGCTCTTTTGTATTTTGGTGCAGTCCTCAGTAGTGC

TCTGTGGTGGTAGGGAGAGATGACCCCCTCACCAGATACATTCCTGGGCCTTGGGGGAGCCCTCTCTTATTACTG

GCACTGCACCTGCATTTCATTTATTAGGTGTCCTGGGCTGCAGGGTGCCCTCAGGCAGAGGCTGCGGCTGGAAAA

TAGACCATACCCTTCCCTGGCTGGCCCTGCACAAGGAGGCACACCCTGTTCCTGAGCCAGTCCATGAACCCAGCT

GTCTCACCCCTCTCAGTGTTCTGAGAGTAGGGGATCCCCCACTGCTTGAGCACCATGAGCCCCTCCTGGCTACAG

GCAGTGGGGGTAGGTATAGTCTCTCAACCCACTGTCCAACTGATTTCCAGGGTAACAGAGAGCTGTGCCTGCCCA

CAGAGTTCAGGCAGAGGCCAGGCCATTGTGCTGGAAGCTGATGCTAAGCCTTGTCTGATGATGGGGAGTGAAGCA

ATGTAACGGCTCCCTAACTGTGGCTTCTCTCAGGGCTATGGCAGCTGGCATGAGACTGCTCCAGGTCCAAGGCCT

GTGGGACTTCCTGTGGACTTGAGTTTTGCCTCTGCAAACACTCCAGCAACTCTCTATGTCAGTCTAGAGGCCCAG

GGACACGGATCAGGTATTGGGATGAAGGGGTTCTCCAGTTCCCAGGATTTCACAGGTCCCTGTGGAAAGTGAGGA

TCCCCCAGGGGCTCTCACTCACTCACCCTTTCTCTATGTTGGGGAGCTTCCCCTGGCTCCATGCCCATCTTGGGT

GGCCAGCTGCCCAGCTTCACTCTTCCCTGTTCTCTGTGTCCCCTCACTCCCTTAATTGTCCTGATATCGTTCCTT

AGGTGATCTACTTGCAGAGGCAGTGTTTACTCGCCACTTGTTTTCTCTCTGTGAGAGTAGCACACACTAGCTGCT

ACTCATCTAGCATCTTGAATTCTTCCCATCTGAAAAAGTTTCAACTGCAATCACAGTTAAAGAAATACAAAAACA

ATAGCACTCTAAGTTACAACTTCTCACCTATAGAATTCAAAAACATCCAAATGATTAACTAAACATTTGTTTGGT

AGATCTGTGGGAAAACATGAATTCCTTGTGAATTACTGGAGAAAATGAAAATGATGCAACACTTATGGAAGAAAA

TTTGGGGATTTTTGGGGGGGAGGGGAACAATATATTTAAAACTATAAATGCATTTATCCTAGCAATTCTATGAAT

GGGGATTTATCTTAGGGTACACCTGCACACTTAGGAAATAATGTATGCAGTCATTCATTACAGAATTGTTTGTAA

TAGCAACAACCTGAAAAGCAACTCATATATCCATCCATCACACAGGGACTGGTTTCATGACTACGGTTCATGAAT

ACTCTGCAGCCCTTAGAAAGAATGAGGAAGTGGCCGGGCACGGTGGCTCATGCCTGTAATCCCAGCACTTTGGGA

GGCCGAGGCGGGTGGATCACGAGGTCAGGAGATCAAGACCATCCTGGCTAACACGGTGAAACCCCGTCTCTACTA

AAAACAATACAAAAAAATTAGCCAGGCAGGCGCCTATAGTCCCAGCTATTCGGGAGGCTGAGGCCGGAGAATGGC

ATGAACCCGGGAGGCAGAGCTTGCAGTGAGCCGAGATAACGCCACTGCACTCCATCCAGCCTGGGCGACAGAGCG

AGACTCCGTCAAAAAAAAAAAAAAAGAGGAAGTTCTCTATGCGCTGACATGGAAGGAAGACAGATGGTTGAATGA

AAAAAGTACATAATTAGCCATAAAGTGTAAGACTTTTTGTCTAAAAAAGAAGGGTGATATAATTGCATATTTATA

TTTTCTTCCATTTATATTAAGAGATAATAAAGGTACACAAATTGGCTAGAATAAAGTGGTTTCCTATAAAGGGTA

AGAGTAATTGAGTGGATGAAGACTAGGGTTAGGGATAGATTTCTCAGTGTATTCATTTTAATATATGTATTCATT

TTATATATGTACTAATTTTTATATATGTATTTATTTTATATTTGATTTTCTTAACATAAATATATTATTCCTTC

ATAAAATTAAACTTGATACATTTTTGATTACTAGATATGTAGAAAGCATTATGTTCAGTACCACAGTAATACTTT

CAAACCAGCTACAATTAGTATTTATGAGCATCTATGTGCCAGACATTGTGTTCTGCTTTGGTTGGTGGGGGTAGA

GGAGGAAAGGAAACCATGGCTTACATAGGAGTGGAAGTCTTGTCTTTCACTTTGCACCTCTCTCCTTCAGACCTA

GCATAAATATGACCTTAGGGGAGGCAGAACACATATGATAAAGAGATAACTAGCAAGAGACATAATAGTAGCTAA

ATAAATACTGAAGGAAAAATTCAGGAAGAGGTAGGAAGGATATGCCTCATCACTTCCACCTGTTAAGAAAAACTT

TAGACATTCTTGCCAATATTCCTTATTGCCTGTCTTTTGAACAAATGCCATTATCACTAGAGTGAAATGATATTT

CATTGTAGTTTTGATTTGCATTTCTCTCATGATCGGTGATGTTGAGCACCTTTTTATATACCTGTTTGCCATTTG

-continued

TATGTCTTCTCTTGAAAAATGTCTATTCAGATCTTTGCCCATTTTTAAATGGCGTAATACATTTTTTCCTATTGA

GTTGTTTGAGTTCTTTATATATTCTGGTTATTAATCCCTTGTCAGATGAATAATTTGCAAATATTTTCTCCCATT

CTGAGGATTACCAGAGGCTCAGAGGGGTAATGGTGGTGGGGGAGAATAAAAATGGTTAATGAGTACAAAAATATA

GATAGGAGTAATAAGATCTAGTATCTGATAGCACAACAGGGTAATTACAGCCAACAAAAATTTATTGTGCATTTC

AAAATAACTAAGAGTATAATTGGAATGTCTGTAACACAAAGAAGCAATAAATGCTTGAGGTGATGTGAGGGGATG

GATATCTAATTTACCTTGATGTGATTATTACATATTGTATGCCTGCATCAAAATAGCTCATGTATCTTATAAGTA

TATACACCTATTATGTACCCATTAAATTTTTTAAGAACTTTAAACAAATCAAATTTAACAGAGTTTAATTGGGCA

AAGAATGATTTGAGGATCAGGCAACCCCCAGAAACAGAAGAGGTTCAAAGCAACTCAGTGCTGTCACATGGTTGG

AGAGGATTTATGGGCAGAAAAGGGAAAGAGAGATACAGAAAATGGAAGTGAGGTACACAAACAGCTGGATTGGTT

ACAGCTTGCCATTTGCGTTATTTGAACATAATCTGAACAGTTGGCTGTCTTTGCTTGACCAAAACTTGGTGTTTG

GTACAAGAGCAGATTACAGTCTATTTACACATCCAGTTAGTTTACAGTTCACTATACACGAAGAAGAAACCTTTA

AGCAGAACTTAAAATATGCAAAGAGGAAGCTTTAAGTTAAACTTAATTTAACACACCCAATTATCAAAAAATGAG

TAGCTCTGCAAAAGTGGATTTTCCTGGTCATCTTTGGTACTTCCTTAAAAAAGAGAAAAGTAGTACTCACGATAA

AAAAAAAAAAGTCCTCAAGTCTTTATTTTATTCCTTTCCAATTTAAAATGTTACATCATCTGAGGAAGGTTTTTC

CCTTTGACCGCTTTCATAGACATTTCTTCTGCATGGGTTGGCCAGAATCAGAAGAGTAATTGTAACTTTCTGTTC

TTGTCCTACAGTTACAAAGCGGTTTCACTTTGTAAATGCTCTTTGGATGGCAGGAACCAAGCAGCCATGAAAAGA

GGAGTTACACCTTTAAAGGAGTCATTCCATCATGACTCTCAGGACTGGAACATGGAATACCTGAATGGCCTCTTT

GGCACAGATAGGCCACCCTTGAAAGGTGTTCCAAGCTAGGAACTCACTACCACTGTTACATCGATGCAACTCTGT

GAGAAGTTTTTATCTGGTGATGGAAAATCTCATCTCTTCAACACACTGACTACTACCAGTCTCAGAACCCTGTAA

ACAAGATTCATTCATCTCAAATTGGGTTAAAGCAGTCACCCTGCCTTACATTAGTTTGGAATAAGGATGTGGGGA

TGGTGGTAGAGGAGGGGAGTGGATGATGATTTTTTTATTGTTATTTGATTCTAAAGAAACTTCTATACATTTTGC

ATTTAAAATAATTATGTTTTTAACAATGTTTGGATTAATTCAAAATAGGATATTATATCCTATTATATTAAATAT

ACTATTTAATCATCTTGTTGACCAAATGCAACTTAAACATGTAAAATGGTAAATAGCATAATAATTGTCTTCTAA

GCCTGCACTATAAAGTATTTCAGTGGCCTCATTATTAAAGGACCAAGGTGCCCAAAGAAACAAAATTTAGTAATC

ATAAACAAGAGACAAACCTACTTCTTTTCCCCCAGAGTTCTGGCCACATTGAAATAAGGTGTTTGAATGCTTAAT

AAGAATTATTTTGGCCCACACAGTGGCTCATGCCTGTAATCTCAGCACTTTGGGATGCCAAGGTGAGCAGATCAC

TTGAGGCCAGGAGTTCAAGACCAGCGTGGCCAACGTGGTGAAACCCCATCTCTACTAAAAATACAAAAATTAGCC

CGGTGTGGTGGTACACGCCTATAGTCCCAGCTACTCGGGAGACTGAGGTGGGAGAATCACTTGAACCCGGGAGGC

CAAGGCTGCAATATCGAGATCACACCACTGCACTCTAGCCTGGGCAACAGAGTGAGAGTGAGACTCTTTCTCGGA

AAAAAAAAAAAAGAATTATTTTGAACAAAGTGCTGTCACCTAAGTTAGCAAAACTCCAAGCAAGGTTTTTGGCTC

TGTAAGGAAAGAATTAGCCTACTCATTTGGAAATTTAGTGGTGTTTGTAATGCAGAAAGTGACAGTGAGACTGGA

AAGGGATTGGCTTTGGGGCTTGTTCTGCTTTATAAATAATAATGAATCTTCTCCAACATGAAGTAATGTGAATTA

AAAAAAAAAAATCTGTCCTTAGAGTACAAAATTACTTCATAACCCAATCTGCATTTCTCCACTCCAAGCATATTT

TCTGGGAGTTCTACTTAGAGAGTGAAAGCTGCTGTGTGTGTGATAATTAATTTTAACAAACACTTGGCAAACTGA

GCTGGACTATGTATAAGCTACCCTAGACTAAGCATGAATTTGAACTGCACTTTTTATGGTGTTTTTTCCACAATG

ACATTATTTAGGCATTTAAAGTTATCTGAACTGCAATTTTTTGTTCTTTTTTTTTTAATTTGACTTTTTAAAAAA

AATTATTCCTGAATAAAGAGGCAGTTTGTAAAAACTCGAGAACTGTGAGAGATAATTGGATCTTTGTGTAGCAAA

ACTAGAAGGGTGTTGGGTATCTGCTCTTTATCAAATGGACCACTTACTTTTCTTTTCTTTTTTGCCCTGTGTTCA

GAAAACAAATGTGCGTGTCTCCTGATTTATAATGTATAGTTCATTAATGGAGAAAGTGCTTGAGAATTAGATCCT

AATGTCATTTCCCATGCAGCATCTTCATTCTTTTCTAAAGCACTATTTGGTAAAAACAACTGATAGTCGTCAGAG

GTGATCAGCAATGTTTGAGCACTATTTCCTTTTTATATCCTGCACATGGAATATGGACAGGCAAACAAATCATTT

-continued

CCAAGTAAGAAAATAAATTTTGAGGGAGTTAATACTATAATTTGAAAGTAATAACCTCCTATTTATCCATCTAGT
TTGTTGTTCTGTACTAAATTATTTGTGCATGTCTCTGTGTCTATAATTTATGTGAAACTTTGCACAATCTTAAAT
AGGACAAAATAGACATTCTGTAATTTCCCAGGCAAGCTATTTAAGGTGACTATCTCTCTACATATTTGAGATGAA
AAACAATAACATGACAATCCATCCCTTCTTAGGTTTTTGTAAGCAGACTTACTACCTGTGACTCAGTTTTGTTCT
CACAGGGTACTAATTAATCCTTCACGATAATAACTTGTCAAATTCCATTACTTCTGTAAAGGCAATACTTTATAT
TTGTTTGTATTCAAATTTTAAACTGATGTTAAATGCCGTGGGTGCAACTGCAGGTTAAAAATATGTGTTTGAATC
TCTTATTCTTTTTGCTTGGCAATGTATGAAATAACTGCTCTTTCTAGAAATCTTGATGATGAAGTGGCCTGTTGT
TTTGTCACCTAAAAATGCAATAATGTTCAAATTAAGCTTTTCTTTATTAACATCACTTGATTGTGTGCCATATTT
AGAGCTTAGTGAAATTTTAATCTACACATTGATTAAATACATTTTATTTATTCTTGTTTCTAATGGGAACTTTCT
TTGTTTCTAATGGGAACTTTCTTAAATTAAATTACATCCAACATTTATTAAAGACCTAAAACATAGGCAATTACT
GTGCTTAGAGGAAAAGCGCAGACGAAAGTGAATCAGACAAGTTCCCTGCCCTCCGGAAGCTTTCAGTCTAGTGAT
GAGAAAGACGTATACACACCTTATGTTGATTTAAAAAAAAAAAAAGCTCTTACCTGGTTGCTGGCATATGAAAGT
GTTAGTTACAGATCTGCCCCAAACTAAAGGTGTCACCTCGAGTAAATCTCTTTCCCTTTCCCTTTCAATCTCTTC
ATCTATAAACTAGGGGTTGGGAATACATTTATTAACAAACACAAATTGAGCGTCTACCATGTGATAATAGTAGCT
AAACTTACTGAGCAATTACCATGGGGCAGGTATCAAGATAAACCCTTTATGATGGTAACCTCATTTAATCCTCAA
AGCAATTCCATTTTCAAGAGGAGGAAATTGAGGCTCAAAAATGTTAAGTAACTCCCCCAAGGATGCAAAGTGATT
GAGCCAGAATTCAAGACTAGGTTGGTTTGACTCCAAAACTCATGCCATTAAACCCTATTGTGTCACTGCAAACAA
CTCTAATAGTTTCAAATTATTAGTTCTATTAATATTATATTACCATTATTTGCCCCCAAAATGTAAAATGTAAAT
ACAAAGAGTTTGGTTTTTGTATTACTAGTGGAGGTTAAAGGTGCACAATGGAATTATTCAAACTGGGAAAATCCA
GGAAGACTTCATGGAGGAGGCAGCATATGGCTGCAGTTAATAAGGTTTGCTCACACAAAATGGAGAGGTGAGGAC
ATTTCAGGCAGAGAGAATTATATGAGAGGTTACAGAGCAGTAAACAGTCATGCGTCTGCAAGATCAAAGGGAAAG
GGCGGTAAGAGAGAAGCTTGAAAGTCAAGTGGAGCCAGATTGTGGAAAAACTAGAGAGTCATGCCAAGGACCTTG
ACATATAGAAAATGGGAAGCCCCTGAAAGGTGAAGAACATGAGAGTGAAATGATTAGTAACTTTTTGGTTTAGGA
CTTGTTTCTTTTGTGTTTTGGTTGCTTTCTTGTTTTGTTTTGTTTGTGGTTTTTAAATTTACAACCAATAAGAAT
ATTTAGTAAGGTTTCCAAATACATCATGAATATATAAAACTAGCCTGACTCAAGGATAATAATTCTGGGTAGTTG
GAGTGAAGTTTCAATCAGCTACGTGGCATTTGCTAATCATCTGATATGAGCTAACAATAAAGGAGTTAACAAATA
AACTGTCAGCCTACAGTCCAGGGTCTCAAATAGCATGTGACATAGTTGAGAAGCAGTTTTCCATATCATACATGA
AATAACTAAAGAAACTACTTACAAAGCACTATACCAGTAACTACAATAAAATACAACTATACATGCAAAATAATG
CTGAAAGCTGCAAGTAGAGGGGTAAAGCTAGGCCAGTTGCTCAGGGAACCATTCTGAAGTGGATTTGGGAAGTAT
GTCTAGAAGGGGAGCCATTGCTGTGAGAGTGCTGAGGCTCATCTGCTACTAGTCCCCCACTACTCAGGCATATGG
TAGGTCAGTAACAAAACCATCATTGTGCACTGTTCTTTCCATCTAAATTCCATCAAATTATGACCAACCTATCAA
GGTACTAGTTCAAATTCTCTCTTCCTCTATAAGCTAGTGGTCTTCTCTAAAATTTAAGAAGATCGTGCTCATCTT
CCTACTTCTTGTTCTCTTTCTTCTGTGTTTTCTGAGGCTGCAATGAACTAGGAACTTCCTCTCCCCAGAACTCTG
TATTCCAGGCCTTAGATCACTCAAAACTGTTGCTTATAAAGTGCAGAGAATCAACAGAGAAGGAATAGAGGTTAA
TGTCTGGTCAAAGATGTGATTCTCTTGTTGAAAAGTTCATTAGCTTATTATTTATAGAATCATAAGTCCCAGGAA
AAACCAAAAGGAAATATATATTGGATCCTAATGATATTCTCTTTTTTTCTTTTTTCTTTTCCCCCACTCCATTGC
CCAGGCTGGAGTGCAGTGGCATAATCTCAGCTCACTGCAACCTCCACCTCCCGGGTTCAAGGGACTCTCCTGCCT
CAGCCTTCCAAGTAGATGGGATTACAGGCATGTGCCACCACATCTGGCTAATTTTTTTTTGTATTTTTAGTAGAG
ATGGGGTTTCACCATGTTAGTCAGGCTGGTGTTGAACTCCTGACCTCAAATGATCCACCAGCCTCGGCCTCCCAG
TGTGCTGGGATTGCAGGCGTGAGCCACCACACCCGGCCTGATATTCTCTTGCAAGGGCATTGTTTACATTGTCTA

-continued

TCATCAGAACTGTAGAGTGTTGGCTCCAGGCACAGAACCCCTAGAGTTTTGTAAACCATTTATATCACACTGGCA

ACCAGAAGTAACTTTATATACTCAAGAATCAAGATTTCACCTAGAAGTACCTCAGGTAGGTGTTGGTTCATTCAC

ATTCCAACCAAAAGATAATGTACCATAAAGTGCATACCGCCTAGTCCGTAATGATTAAGGCAACCACATAAAATC

TCATTATTTAAAAGAAATTAAGTCCAGGCACGGTGGCTCACACCTGTAATCTCAGCACTTCGGGAGGCCAAGGAG

GGCAGATCACCTGAGGTTGGGAGTTTGAGACCAGCCTGATCAACATGGAGAAATCCCATCTCTACTAAAAATACA

AAATTAGCGGGGCATGGTGGTGCATGCCTATAATCCCAGCTACTCAGGAGGCTGAGGCAGGAGAATCACTTGAAC

CCAGGAGGTGGAGGTTGAGATCGTGCCATTGCACTCCAGCCTGGACAACAAGAGTGAAACTCTGTCTCAAAAAAG

AAAAAAAGAAAAAGAAATTAAATGCACTATGGTTTATGGAGCGGTATTCCTCCTCCATGTCCTACATAAGATCTT

TCACATGCCAGTCACAGTTAAATCTAATTTGCTGTAATCTGGATAAATGGGAGCTAATCAACAAGCTCTCAGCTC

TAGCTCTGAATCAGCAGCAGATATTGCATTTTTGAAATACACTAATAGCAAGAATGCCTTCCTGACAACAACTGG

CATTTTTGACACAGCAGGAAGTTTATCTGGATTCTGATATAATAGTTATTGGAATCATACATAGGTACATAGTTT

AAAAGGCTAATAAGTCATTTGTTATTGCTTTTATTATCTCTGCATAGTTAGTAAAATTGAGATTAGAACCACTTC

TCGAATGTACTGTTCTAAATCCTTAGCTTGCTTGATCACACATGACCCTCACAATGATCCTAGGAGAAATTATTC

TGCATGCCATTTTGTAGCTGGGGAAACTGAGGCACAGAGAAATACAGTACTGCCCAAAATGTCATAACTAATCAA

AGGCAAAGACAATACTCACACCAGCTCTGATTCCAGAGCCCACTCTCTTAACCATATGCTTTTCTGCTTCCCTAG

TTGTAGAGTCTTTTTGTATGACTGCATTAATTATATGTGAAGAGTTCAAAAATTTCTATATAAGGTCTTTTAAGG

GTGTCATTCTGGTTGAAAATGGAGGACTAGGCTTCTCACTTGAAGACATATTTCTGTAGAAAAACCTATTTTCAT

TTAGATGCTACAGTTACTTGATGTGGTTAATAAACCAGTTAACAGAGTATGAAAAGGATAAGGGTTAAAGCCCTC

CCAAGCCATCTTTCATGCTGCTAATATGAATCACATTACTAGATACTTAAATATCATTTTCTCTTTGGTTCCCAG

AAGACTGCATATATGCTAGAATATTTGTCCTCCTCTTTTACCCTTTCAGGCAATAAAGTATTTTGGACCACTGTA

CTATGTTATAATTATTGTTTCTCTCCTGATTTTTTTGCTCCAATCTAATGAAAGACATACAAGCTACTATACTGC

TACACAATGACTAAATACCTGTTGGATTAGGTGGGGGGAAGATACACAGTCACTGGCTAGAAAGCATCATGCATA

CAGAGCCATTTTCACCATATATTTTATTTCTCATGATCATGTAGAATTTAGGCTTTGGTGTTGATTATTTCTCTC

TTAGGAAACATAGTTGTTTCAGGGTTGATATCACAAAAAAACAGAAAAACCTATTCGAGAAAAGGAAAATTATTT

GTCTGTAGGCCAAATTTTGAAGTAGGAAAACCTGCTTTTGGAGTTGTATTCCCCTCCCAGGCACTTAATCCAAGT

TCCAGTCTTATTCTAAACTGGGGATGCTAGTATTAACCACCATAGGAGTTATCTGAGATGAGTTATCATCAACTT

GGTACCAGGTTGTTGTCCTCTGGACTCAGTGAGCTCTAGAATTGCATGAAACTGGCCTAATTTATCAAAGTATGT

AGCCTTGGGTAAATAATTCAAGCTCTCAGAGGTCCAGTTATCTCCTCTGTAAAACATATCTACATCCTAGGGATG

ACAATATCTACATCCTAGAGATGTCAGGAGGATTAAGTGTAATTTTTTTAATTGTATGTATTTAAAATGGGCAA

CATAATGTTTTGATATACACGTGTATAGTGATTACTACAGTCAAGCAAATTAACATATCCATCATTTCATAGCTA

CCTTTTATGTATGTGATAAGATTATCTAAAATCTATTCTCTTACCAAATTTCCAGTATACAATATTGATATGGTT

TGATCCATATCCCCATCCAAATCTCATGTTCAGTTGCAATCCCCAACGTTGGAGATGGAGCCTGGTTGGAGGTGA

TTGGATCACAGGGGTGGCTTCTAATGGTTCAGCACCATCCTTTCTTGGTACTGTATAGTGAGTAAGTTCTCACGA

GATCTGGTTGTTTAAAAGTGTGTAACACCTCCCCCACTTTCCCTCTCTCTGTTCCTCCTGCTCCCGCTATGTGAA

GTGCCAGCTCCCTCTTTGCCTTCCGCCATGATTGTAAGTTCTCTGAGGCATCCCCAGAAGCTGATGCTGCCATGC

TTCCTATACAGCCTGCAGAACCATGAGTCAATTAAACCTCTTTTCTTTGTAAATTACCCAGTCTCAAGTATTTCT

TTATAGCAATGCAAGAATGGACTAATACAGAAAATTGTTACTGAGAAGAAGGGCATTGCTATAAAGATACCTGAA

AATGTAGAAGTGACTTTGGAACCGGCTAACAGGCAGAAGTTGAAACATTTTAGAGGGCTCAGAAGAAGACAGAAA

GATGAGAGAAAGTTTGGAACTCGCTAGGAACTTGTTGAGTGGTTGTAACCAAAATACTGATAGTGATATAGACAG

TGAAGTCCAGGCTGAGGAGGTCTCAGATGGAAATGAGAAATTTATTGGGAATGAGTAAAGGTCAGGTTTGCTATG

CTTTAGCAAAGAGCTTAGCTGCATTGTTCCTCTGTTCTAGGGATCTGTGAAATCTTAGACTTAAGAATGATGATT

-continued

TAGGGTATCTGGCAGAAGAAATTTCTAAGCAGCAGAGTGTTCAAGAAGTAACCTAGCTGCTTCTAATAGCCTATG

CTCATAGGCATGAGCACAGAAATGACCTGAAATTGGAACTTACACTTAAAAGGGAAGCAGAGCATAAAAGTTTGT

AAATTTTGCAGCCTGGCCATGTGGTAGTAAAGAAAAGCTCGTTCTCAGGAGAGGAAGTCAAGCAGGCTGCATAAA

TTTGCATAACTAAAAGGAAGGCAAGGGCTGATAACCAAAACAATGGGGAGAAAGACTCATAGGACTAACAGGCAT

TTTATTTTATTTTATTTTTATTTTATTATTATTATACTTTAAGTTTTAGGGTACATGTGCACAATGTGCAGGTTA

GTTGCATATGTATACATGTGCCATGCTGGTGTGCTGCACCCATTAACTCGTCATTTAGCATTAGGTATATCTCCT

AATGCTATCCCTCCCCCCTCCCCCACCCCACAACAGTCCCCAGAGTGTGATGTTCCCCTTCCTGTGTCCATGTGT

TCTCATTGTTCAATTCCCACCTATGAGTGAGAACATGTGGTGTTTGGTTTTTTGACCTTGCAATAGTTTACTGAG

AATGACGATTTCCAATTTCATCCATGTCCCTACAAAGGACATGAACTCATCATTTTTTATGGCTGCATAGTATTC

CATGGTGTATATGTGCCACATTTTCTTAATCCAGTCTATCACTGTTGGACATTTGGGTTGGTTCCAAGTCTTTGC

TATTGTGAATAGTGCCACAATAAACATAGTGTGCATGTGTCTTTATAGCAGCAGGATTTATAGTCCTTTGGGTAT

ATACCCAGTGATGGGATGGCTGGGTCAAATGGTATTTCTAGTTCTAGATCCCTGAGGAATCGCCACACTGACTTC

CACAATGGTTGAACTAGTTTACAGTCCCACCAACAGTGTAAAAGTGTTCCTAATAGGCATTTTAGGCTTTCATGG

TGGTCCCTCTCATCACAGGCCCCGAGGCCTAGGAGGACTGAATCATTTCCTGGGCCAGGCCTAGGGCCCCTGCTC

CCTCTTACAGCCTTGGGACTCTGCTCCCTGAATCCCAGCTGCTCAAAGGGGCCCAGGTACTGTTACAGTAGGTAG

CTAATCAGGCATGAGTGGGGTAAGAGAGAAGTCCCCACCACCCACCAGGAATGTCAGGCAACCATCAGATGATGG

TCAGGCAGTTGTCATACTGCCTCTCTAAAATAGTAATTGGTTGCAGCCAGCACCAGGGAGAGGCAACTTCTCAAT

AGATAGAAACACCTGAAATTGGTAACTGGGCGCTTCCAATAAGATCTCAGGAACTGAGAGAGTGGGCTTAACATG

CACATTAAGAGGCAAAATGGTGAAGTATGACCTTTGGGGGCATTCCACCGGAAAAGGGAAGAAAGCCTCAGGTAA

GCATGTATACAACTCCAGTAAACACACTGCACACGCTCACCTTCCAAGTGCAAGCAGGGCACCATGCATGCGGCA

AGCTCACCCTTAGGGAAGGACCAAGGGAAAGGGGCACAAGATGTCAGAAGTAGGCCAGTGTATAAGATCCTAGGT

TCAAGGTCAAACAGGGCACTTGACCTCCAAGGTGCCCACTTGGGCCTCTTCCAAATGTACTTTCCTTTCATTCCT

GTTCTAAAGCTTTTTAATAAACTTTTACTCCTGCTCTGAAACTTGTCGCAGTCTCTTTTTCTGCCTTATGCCTCT

TGGTCAAATTCTTTCTTCTGAGGAGGCAAGAATTGAGGTTGCTGCAGACCCACATGGATTTGCAGCTGGTAACTC

AGATAACTTTCACCAGTAAGAATACAGTTCAGGCTGCTGCTTCACAGGGTGCCAGGCATAAGCCTTGGTGGCTTC

CATAAGCTGTGAAGCCGGGGGGCGCACATAATGCAAGAGTTGAGGCTTAAGAAGCTCTGCCTAGATTTTAGAGGA

TGTATGAAAAAGCCTGGATGTCCAGACAGAAGCCTGTTACTGGGGTGGAATCCTCATGGAGAACATCTACTAGGG

AAGCAAGGAGAAGAAATGTGGGGTTGCAGCCCCCACAGAGAGTCCCCTGGGGCACTGCCTAGCAGAGCTATGACA

AGACAGCCACCGTCCTCCAGACCCCAGAATGGTAGATCCACCAACAACTTGCACCCTGCAGCCTGGAAAAGCTGC

AAGCACTCAATGCTAGCCCATGAGAGCAGCTGTGGGAGATGAACCCTGGAAAACCACAGGGGTGGTTCTGCCCAA

GGTTTTGGGAGCCCACTCATTGCATCAGTGTTCCCTGGGTGTGAGTCAAAGGAGATTATTTCAGAGCTTTAACAT

TTAATGACTGCCCGGCTGGCTTTCAGACTTGCAATGGGGCCCTATAGCCTCTTTCTTTTGGCAGATTTCTCCCTT

TCGGAATGGCAGTATCTGCCCAATGCCTATACCCCCATTGTATCTTTGAAGCAATTACCTTGTTTTTGATTTTAC

AGGTTCATAGGTAGAAGGGACTAGCTTCGTCTCAGGTGAGACTTGGGACTTTGGACTTTTGAATGAATGCTGGAT

CGAGTTAAGACTTTGGGGAACTGTTGGTAAGGCACGACAGTATTTTGCAATATGAGAAGGACATTAGATTTGGGA

GGGGCCAGAGTTGGAATAACATGGTTTGGATCTCTGTCCCCACCCAAATCTCATGTTCAACTGTAATCCCCAGTG

TTGGAGGTTGGGCCTGGTGGGAGGTGAGTGGATTATGGGGTGGCTTCTAATGGTTTTGTACAGTCCCCTCTTGGT

ACTATATAGTGAGTTCTGACAAGATCTAGTTGTTTAAACGTATGTAGCACCTCCCATTTCTCTCTTCCCCCAGTT

CCTGCCATGTGAAGTCTGGGGTCTCCCTATGCCTTCCATCATGATTTTAAGTTCCCTATGGCCTGCCCAGAAGCT

GATCCAGCCATGCTTCTTGTACAGCCTGCAGAACTGTGAGCCATTAAACTTTTCTTTATAAATTACCCAGTTTCA

-continued

GTTATTTCTTTATAGCAGTGTAAGAATGGACTAACACAATTATTAACGCTAGTCCTCATGTTGTACATTAAATCT

CTAGATGTATTAGACGTAACTGCAACTTTGTACCCTACCCTACAATTTTCTTTCCCCCCAAGCCCCCCAACCAAG

GGTCTACTCTGTTTCTATAAATTCAGTTGTTTTTAATTCCACGTATAAGTGAAGTACAACTCAGTGTAGAAACT

TGGTAAATGCTAGCTACTTGTTATAAGCTGTCAGTCAAAATAAAAATACAGAGATGAATCTCTAAATTAAGTGAT

TTATTTGGGAAGAAAGAATTGCAATTAGGGCATACATGTAGATCAGATGGTCTTCGGTATATCCACACAACAAAG

AAAAGGGGGAGGTTTTGTTAAAAAAGAGAAATGTTACATAGTGCTCTTTGAGAAAATTCATTGGCACTATTAAGG

ATCTGAGGAGCTGGTGAGTTTCAACTGGTGAGTGATGGTGGTAGATAAAATTAGAGCTGCAGCAGGTCATTTTAG

CAACTATTAGATAAAACTGGTCTCAGGTCACAACGGGCAGTTGCAGCAGCTGGACTTGGAGAGAATTACACTGTG

GGAGCAGTGTCATTTGTCCTAAGTGCTTTTCTACCCCCTACCCCCACTATTTTAGTTGGGTATAAAAAGAATGAC

CCAATTTGTATGATCAACTTTCACAAAGCATAGAACAGTAGGAAAAGGGTCTGTTTCTGCAGAAGGTGTAGACGT

TGAGAGCCATTTTGTGTATTTATTCCTCCCTTTCTTCCTCGGTGAATGATTAAAACGTTCTGTGTGATTTTTAGT

GATGAAAAAGATTAAATGCTACTCACTGTAGTAAGTGCCATCTCACACTTGCAGATCAAAAGGCACACAGTTTAA

AAAACCTTTGTTTTTTTACACATCTGAGTGGTGTAAATGCTACTCATCTGTAGTAAGTGGAATCTATACACCTGC

AGACCAAAAGACGCAAGGTTTCAAAAATCTTTGTGTTTTTTACACATCAAACAGAATGGTACGTTTTTCAAAAGT

TAAAAAAAAACAACTCATCCACATATTGCAACTAGCAAAAATGACATTCCCCAGTGTGAAAATCATGCTTGAGAG

AATTCTTACATGTAAAGGCAAAATTGCGATGACTTTGCAGGGGACCGTGGGATTCCCGCCCGCAGTGCCGGAGCT

GTCCCCTACCAGGGTTTGCAGTGGAGTTTTGAATGCACTTAACAGTGTCTTACGGTAAAAACAAAATTTCATCCA

CCAATTATGTGTTGAGCGCCCACTGCCTACCAAGCACAAACAAAACCATTCAAAACCACGAAATCGTCTTCACTT

TCTCCAGATCCAGCAGCCTCCCCTATTAAGGTTCGCACACGCTATTGCGCCAACGCTCCTCCAGAGCGGGTCTTA

AGATAAAAGAACAGGACAAGTTGCCCCGCCCCATTTCGCTAGCCTCGTGAGAAAACGTCATCGCACATAGAAAAC

AGACAGACGTAACCTACGGTGTCCCGCTAGGAAAGAGAGGTGCGTCAAACAGCGACAAGTTCCGCCCACGTAAAA

GATGACGCTTGGTGTGTCAGCCGTCCCTGCTGCCCGGTTGCTTCTCTTTTGGGGGGGGGGTCTAGCAAGAGCAGG

TGTGGGTTTAGGAGGTGTGTGTTTTTGTTTTTCCCACCCTCTCTCCCCACTACTTGCTCTCACAGTACTCGCTGA

GGGTGAACAAGAAAAGACCTGATAAAGATTAACCAGAAGAAAACAAGGAGGGAAACAACCGCAGCCTGTAGCAAG

CTCTGGAACTCAGGAGTCGCGCGCTAGGGGCC(GGGGCC)$_n$

GGGGCCGGGGCGTGGTCGGGGGGGGCCCGGGGGGGGG

CCCGGGGCGGGGCTGCGGTTGCGGTGCCTGCGCCCGCGGCGGCGGAGGCGCAGGCGGTGGCGAGTGGGTGAGTGA

GGAGGCGGCATCCTGGCGGGTGGCTGTTTGGGGTTCGGCTGCCGGGAAGAGGCGCGGGTAGAAGCGGGGGCTCTC

CTCAGAGCTCGACGCATTTTTACTTTCCCTCTCATTTCTCTGACCGAAGCTGGGTGTCGGGCTTTCGCCTCTAGC

GACTGGTGGAATTGCCTGCATCCGGGCCCCGGGCTTCCCGGCGGCGGCGGCGGCGGCGGCGGCGCAGGGACAAGG

GATGGGGATCTGGCCTCTTCCTTGCTTTCCCGCCCTCAGTACCCGAGCTGTCTCCTTCCCGGGGACCCGCTGGGA

GCGCTGCCGCTGCGGGCTCGAGAAAAGGGAGCCTCGGGTACTGAGAGGCCTCGCCTGGGGGAAGGCCGGAGGGTG

GGCGGCGCGCGGCTTCTGCGGACCAAGTCGGGGTTCGCTAGGAACCCGAGACGGTCCCTGCCGGCGAGGAGATCA

TGCGGGATGAGATGGGGGTGTGGAGACGCCTGCACAATTTCAGCCCAAGCTTCTAGAGAGTGGTGATGACTTGCA

TATGAGGGCAGCAATGCAAGTCGGTGTGCTCCCCATTCTGTGGGACATGACCTGGTTGCTTCACAGCTCCGAGAT

GACACAGACTTGCTTAAAGGAAGTGACTATTGTGACTTGGGCATCACTTGACTGATGGTAATCAGTTGTCTAAAG

AAGTGCACAGATTACATGTCCGTGTGCTCATTGGGTCTATCTGGCCGCGTTGAACACCACCAGGCTTTGTATTCA

GAAACAGGAGGGAGGTCCTGCACTTTCCCAGGAGGGGTGGCCCTTTCAGATGCAATCGAGATTGTTAGGCTCTGG

GAGAGTAGTTGCCTGGTTGTGGCAGTTGGTAAATTTCTATTCAAACAGTTGCCATGCACCAGTTGTTCACAACAA

GGGTACGTAATCTGTCTGGCATTACTTCTACTTTTGTACAAAGGATCAAAAAAAAAAAAGATACTGTTAAGATAT

GATTTTTCTCAGACTTTGGGAAACTTTTAACATAATCTGTGAATATCACAGAAACAAGACTATCATATAGGGGAT

-continued

ATTAATAACCTGGAGTCAGAATACTTGAAATACGGTGTCATTTGACACGGGCATTGTTGTCACCACCTCTGCCAA

GGCCTGCCACTTTAGGAAAACCCTGAATCAGTTGGAAACTGCTACATGCTGATAGTACATCTGAAACAAGAACGA

GAGTAATTACCACATTCCAGATTGTTCACTAAGCCAGCATTTACCTGCTCCAGGAAAAAATTACAAGCACCTTAT

GAAGTTGATAAAATATTTTGTTTGGCTATGTTGGCACTCCACAATTTGCTTTCAGAGAAACAAAGTAAACCAAGG

AGGACTTCTGTTTTTCAAGTCTGCCCTCGGGTTCTATTCTACGTTAATTAGATAGTTCCCAGGAGGACTAGGTTA

GCCTACCTATTGTCTGAGAAACTTGGAACTGTGAGAAATGGCCAGATAGTGATATGAACTTCACCTTCCAGTCTT

CCCTGATGTTGAAGATTGAGAAAGTGTTGTGAACTTTCTGGTACTGTAAACAGTTCACTGTCCTTGAAGTGGTCC

TGGGCAGCTCCTGTTGTGGAAAGTGGACGGTTTAGGATCCTGCTTCTCTTTGGGCTGGGAGAAAATAAACAGCAT

GGTTACAAGTATTGAGAGCCAGGTTGGAGAAGGTGGCTTACACCTGTAATGCCAGAGCTTTGGGAGGCGGAGGCA

AGAGGATCACTTGAAGCCAGGAGTTCAAGCTCAACCTGGGCAACGTAGACCCTGTCTCTACAAAAAATTAAAAAC

TTAGCCGGGCGTGGTGATGTGCACCTGTAGTCCTAGCTACTTGGGAGGCTGAGGCAGGAGGGTCATTTGAGCCCA

AGAGTTTGAAGTTACCGAGAGCTATGATCCTGCCAGTGCATTCCAGCCTGGATGACAAAACGAGACCCTGTCTCT

AAAAAACAAGAAGTGAGGGCTTTATGATTGTAGAATTTTCACTACAATAGCAGTGGACCAACCACCTTTCTAAAT

ACCAATCAGGGAAGAGATGGTTGATTTTTTAACAGACGTTTAAAGAAAAAGCAAAACCTCAAACTTAGCACTCTA

CTAACAGTTTTAGCAGATGTTAATTAATGTAATCATGTCTGCATGTATGGGATTATTTCCAGAAAGTGTATTGGG

AAACCTCTCATGAACCCTGTGAGCAAGCCACCGTCTCACTCAATTTGAATCTTGGCTTCCCTCAAAAGACTGGCT

AATGTTTGGTAACTCTCTGGAGTAGACAGCACTACATGTACGTAAGATAGGTACATAAACAACTATTGGTTTTGA

GCTGATTTTTTTCAGCTGCATTTGCATGTATGGATTTTTCTCACCAAAGACGATGACTTCAAGTATTAGTAAAAT

AATTGTACAGCTCTCCTGATTATACTTCTCTGTGACATTTCATTTCCCAGGCTATTTCTTTTGGTAGGATTTAAA

ACTAAGCAATTCAGTATGATCTTTGTCCTTCATTTTCTTTCTTATTCTTTTTGTTTGTTTGTTTGTTTGTTTTTT

TCTTGAGGCAGAGTCTCTCTCTGTCGCCCAGGCTGGAGTGCAGTGGCGCCATCTCAGCTCATTGCAACCTCTGCC

ACCTCCGGGTTCAAGAGATTCTCCTGCCTCAGCCTCCCGAGTAGCTGGGATTACAGGTGTCCACCACCACACCCG

GCTAATTTTTTGTATTTTTAGTAGAGGTGGGGTTTCACCATGTTGGCCAGGCTGGTCTTGAGCTCCTGACCTCAG

GTGATCCACCTGCCTCGGCCTACCAAAGAGCTGGGATAACAGGTGTGACCCACCATGCCCGGCCCATTTTTTTTT

TCTTATTCTGTTAGGAGTGAGAGTGTAACTAGCAGTATAATAGTTCAATTTTCACAACGTGGTAAAAGTTTCCCT

ATAATTCAATCAGATTTTGCTCCAGGGTTCAGTTCTGTTTTAGGAAATACTTTTATTTTCAGTTTAATGATGAAA

TATTAGAGTTGTAATATTGCCTTTATGATTATCCACCTTTTTAACCTAAAAGAATGAAAGAAAAATATGTTTGCA

ATATAATTTTATGGTTGTATGTTAACTTAATTCATTATGTTGGCCTCCAGTTTGCTGTTGTTAGTTATGACAGCA

GTAGTGTCATTACCATTTCAATTCAGATTACATTCCTATATTTGATCATTGTAAACTGACTGCTTACATTGTATT

AAAAACAGTGGATATTTTAAAGAAGCTGTACGGCTTATATCTAGTGCTGTCTCTTAAGACTATTAAATTGATACA

ACATATTTAAAAGTAAATATTACCTAAATGAATTTTTGAAATTACAAATACACGTGTTAAAACTGTCGTTGTGTT

CAACCATTTCTGTACATACTTAGAGTTAACTGTTTTGCCAGGCTCTGTATGCCTACTCATAATATGATAAAAGCA

CTCATCTAATGCTCTGTAAATAGAAGTCAGTGCTTTCCATCAGACTGAACTCTCTTGACAAGATGTGGATGAAAT

TCTTTAAGTAAAATTGTTTACTTTGTCATACATTTACAGATCAAATGTTAGCTCCCAAAGCAATCATATGGCAAA

GATAGGTATATCATAGTTTGCCTATTAGCTGCTTTGTATTGCTATTATTATAAATAGACTTCACAGTTTTAGACT

TGCTTAGGTGAAATTGCAATTCTTTTTACTTTCAGTCTTAGATAACAAGTCTTCAATTATAGTACAATCACACAT

TGCTTAGGAATGCATCATTAGGCGATTTTGTCATTATGCAAACATCATAGAGTGTACTTACACAAACCTAGATAG

TATAGCCTTTATGTACCTAGGCCGTATGGTATAGTCTGTTGCTCCTAGGCCACAAACCTGTACAACTGTTACTGT

ACTGAATACTATAGACAGTTGTAACACAGTGGTAAATATTTATCTAAATATATGCAAACAGAGAAAAGGTACAGT

AAAAGTATGGTATAAAAGATAATGGTATACCTGTGTAGGCCACTTACCACGAATGGAGCTTGCAGGACTAGAAGT

-continued

TGCTCTGGGTGAGTCAGTGAGTGAGTGGTGAATTAATGTGAAGGCCTAGAACACTGTACACCACTGTAGACTATA

AACACAGTACGCTGAAGCTACACCAAATTTATCTTAACAGTTTTCTTCAATAAAAAATTATAACTTTTTAACTT

TGTAAACTTTTTAATTTTTTAACTTTTAAAATACTTAGCTTGAAACACAAATACATTGTATAGCTATACAAAAAT

ATTTTTTCTTTGTATCCTTATTCTAGAAGCTTTTTTCTATTTTCTATTTTAAATTTTTTTTTTTACTTGTTAGTC

GTTTTTGTTAAAAACTAAAACACACACACTTTCACCTAGGCATAGACAGGATTAGGATCATCAGTATCACTCCCT

TCCACCTCACTGCCTTCCACCTCCACATCTTGTCCCACTGGAAGGTTTTTAGGGGCAATAACACACATGTAGCTG

TCACCTATGATAACAGTGCTTTCTGTTGAATACCTCCTGAAGGACTTGCCTGAGGCTGTTTTACATTTAACTTAA

AAAAAAAAAAAGTAGAAGGAGTGCACTCTAAAATAACAATAAAAGGCATAGTATAGTGAATACATAAACCAGCAA

TGTAGTAGTTTATTATCAAGTGTTGTACACTGTAATAATTGTATGTGCTATACTTTAAATAACTTGCAAAATAGT

ACTAAGACCTTATGATGGTTACAGTGTCACTAAGGCAATAGCATATTTTCAGGTCCATTGTAATCTAATGGGACT

ACCATCATATATGCAGTCTACCATTGACTGAAACGTTACATGGCACATAACTGTATTTGCAAGAATGATTTGTTT

TACATTAATATCACATAGGATGTACCTTTTTAGAGTGGTATGTTTATGTGGATTAAGATGTACAAGTTGAGCAAG

GGGACCAAGAGCCCTGGGTTCTGTCTTGGATGTGAGCGTTTATGTTCTTCTCCTCATGTCTGTTTTCTCATTAAA

TTCAAAGGCTTGAACGGGCCCTATTTAGCCCTTCTGTTTTCTACGTGTTCTAAATAACTAAAGCTTTTAAATTCT

AGCCATTTAGTGTAGAACTCTCTTTGCAGTGATGAAATGCTGTATTGGTTTCTTGGCTAGCATATTAAATATTTT

TATCTTTGTCTTGATACTTCAATGTCGTTTTAAACATCAGGATCGGGCTTCAGTATTCTCATAACCAGAGAGTTC

ACTGAGGATACAGGACTGTTTGCCCATTTTTTGTTATGGCTCCAGACTTGTGGTATTTCCATGTCTTTTTTTTTT

TTTTTTTTTTTGACCTTTTAGCGGCTTTAAAGTATTTCTGTTGTTAGGTGTTGTATTACTTTTCTAAGATTACTT

AACAAAGCACCACAAACTGAGTGGCTTTAAACAACAGCAATTTATTCTCTCACAATTCTAGAAGCTAGAAGTCCG

AAATCAAAGTGTTGACAGGGGCATGATCTTCAAGAGAGAAGACTCTTTCCTTGCCTCTTCCTGGCTTCTGGTGGT

TACCAGCAATCCTGAGTGTTCCTTTCTTGCCTTGTAGTTTCAACAATCCAGTATCTGCCTTTTGTCTTCACATGG

CTGTCTACCATTTGTCTCTGTGTCTCCAAATCTCTCTCCTTATAAACACAGCAGTTATTGGATTAGGCCCCACTC

TAATCCAGTATGACCCCATTTTAACATGATTACACTTATTTCTAGATAAGGTCACATTCACGTACACCAAGGGTT

AGGAATTGAACATATCTTTTTGGGGGACACAATTCAACCCACAAGTGTCAGTCTCTAGCTGAGCCTTTCCCTTCC

TGTTTTTCTCCTTTTTAGTTGCTATGGGTTAGGGGCCAAATCTCCAGTCATACTAGAATTGCACATGGACTGGAT

ATTTGGGAATACTGCGGGTCTATTCTATGAGCTTTAGTATGTAACATTTAATATCAGTGTAAAGAAGCCCTTTTT

TAAGTTATTTCTTTGAATTTCTAAATGTATGCCCTGAATATAAGTAACAAGTTACCATGTCTTGTAAAATGATCA

TATCAACAAACATTTAATGTGCACCTACTGTGCTAGTTGAATGTCTTTATCCTGATAGGAGATAACAGGATTCCA

CATCTTTGACTTAAGAGGACAAACCAAATATGTCTAAATCATTTGGGGTTTTGATGGATATCTTTAAATTGCTGA

ACCTAATCATTGGTTTCATATGTCATTGTTTAGATATCTCCGGAGCATTTGGATAATGTGACAGTTGGAATGCAG

TGATGTCGACTCTTTGCCCACCGCCATCTCCAGCTGTTGCCAAGACAGAGATTGCTTTAAGTGGCAAATCACCTT

TATTAGCAGCTACTTTTGCTTACTGGGACAATATTCTTGGTCCTAGAGTAAGGCACATTTGGGCTCCAAAGACAG

AACAGGTACTTCTCAGTGATGGAGAAATAACTTTTCTTGCCAACCACACTCTAAATGGAGAAATCCTTCGAAATG

CAGAGAGTGGTGCTATAGATGTAAAGTTTTTTGTCTTGTCTGAAAAGGGAGTGATTATTGTTTCATTAATCTTTG

ATGGAAACTGGAATGGGGATCGCAGCACATATGGACTATCAATTATACTTCCACAGACAGAACTTAGTTTCTACC

TCCCACTTCATAGAGTGTGTGTTGATAGATTAACACATATAATCCGGAAAGGAAGAATATGGATGCATAAGGTAA

GTGATTTTTCAGCTTATTAATCATGTTAACCTATCTGTTGAAAGCTTATTTTCTGGTACATATAAATCTTATTTT

TTTAATTATATGCAGTGAACATCAAACAATAAATGTTATTTATTTTGCATTTACCCTATTAGATACAAATACATC

TGGTCTGATACCTGTCATCTTCATATTAACTGTGGAAGGTACGAAATGGTAGCTCCACATTATAGATGAAAAGCT

AAAGCTTAGACAAATAAAGAAACTTTTAGACCCTGGATTCTTCTTGGGAGCCTTTGACTCTAATACCTTTTGTTT

CCCTTTCATTGCACAATTCTGTCTTTTGCTTACTACTATGTGTAAGTATAACAGTTCAAAGTAATAGTTTCATAA

-continued

GCTGTTGGTCATGTAGCCTTTGGTCTCTTTAACCTCTTTGCCAAGTTCCCAGGTTCATAAAATGAGGAGGTTGAA

TGGAATGGTTCCCAAGAGAATTCCTTTTAATCTTACAGAAATTATTGTTTTCCTAAATCCTGTAGTTGAATATAT

AATGCTATTTACATTTCAGTATAGTTTTGATGTATCTAAAGAACACATTGAATTCTCCTTCCTGTGTTCCAGTTT

GATACTAACCTGAAAGTCCATTAAGCATTACCAGTTTTAAAAGGCTTTTGCCCAATAGTAAGGAAAAATAATATC

TTTTAAAAGAATAATTTTTTACTATGTTTGCAGGCTTACTTCCTTTTTTCTCACATTATGAAACTCTTAAAATCA

GGAGAATCTTTTAAACAACATCATAATGTTTAATTTGAAAAGTGCAAGTCATTCTTTTCCTTTTTGAAACTATGC

AGATGTTACATTGACTGTTTTCTGTGAAGTTATCTTTTTTTCACTGCAGAATAAAGGTTGTTTTGATTTTATTTT

GTATTGTTTATGAGAACATGCATTTGTTGGGTTAATTTCCTACCCCTGCCCCCATTTTTTCCCTAAAGTAGAAAG

TATTTTTCTTGTGAACTAAATTACTACACAAGAACATGTCTATTGAAAAATAAGCAAGTATCAAAATGTTGTGGG

TTGTTTTTTTAAATAAATTTTCTCTTGCTCAGGAAAGACAAGAAAATGTCCAGAAGATTATCTTAGAAGGCACAG

AGAGAATGGAAGATCAGGTATATGCAAATTGCATACTGTCAAATGTTTTTCTCACAGCATGTATCTGTATAAGGT

TGATGGCTACATTTGTCAAGGCCTTGGAGACATACGAATAAGCCTTTAATGGAGCTTTTATGGAGGTGTACAGAA

TAAACTGGAGGAAGATTTCCATATCTTAAACCCAAAGAGTTAAATCAGTAAACAAAGGAAAATAGTAATTGCATC

TACAAATTAATATTTGCTCCCTTTTTTTTTCTGTTTGCCCAGAATAAATTTTGGATAACTTGTTCATAGTAAAAA

TAAAAAAAATTGTCTCTGATATGTTCTTTAAGGTACTACTTCTCGAACCTTTCCCTAGAAGTAGCTGTAACAGAA

GGAGAGCATATGTACCCCTGAGGTATCTGTCTGGGGTGTAGGCCCAGGTCCACACAATATTTCTTCTAAGTCTTA

TGTTGTATCGTTAAGACTCATGCAATTTACATTTTATTCCATAACTATTTTAGTATTAAAATTTGTCAGTGATAT

TTCTTACCCTCTCCTCTAGGAAAATGTGCCATGTTTATCCCTTGGCTTTGAATGCCCCTCAGGAACAGACACTAA

GAGTTTGAGAAGCATGGTTACAAGGGTGTGGCTTCCCCTGCGGAAACTAAGTACAGACTATTTCACTGTAAAGCA

GAGAAGTTCTTTTGAAGGAGAATCTCCAGTGAAGAAAGAGTTCTTCACTTTTACTTCCATTTCCTCTTGTGGGTG

ACCCTCAATGCTCCTTGTAAAACTCCAATATTTTAAACATGGCTGTTTTGCCTTTCTTTGCTTCTTTTTAGCATG

AATGAGACAGATGATACTTTAAAAAAGTAATTAAAAAAAAAAAACTTGTGAAAATACATGGCCATAATACAGAACC

CAATACAATGATCTCCTTTACCAAATTGTTATGTTTGTACTTTTGTAGATAGCTTTCCAATTCAGAGACAGTTAT

TCTGTGTAAAGGTCTGACTTAACAAGAAAAGATTTCCCTTTACCCAAAGAATCCCAGTCCTTATTTGCTGGTCAA

TAAGCAGGGTCCCCAGGAATGGGGTAACTTTCAGCACCCTCTAACCCACTAGTTATTAGTAGACTAATTAAGTAA

ACTTATCGCAAGTTGAGGAAACTTAGAACCAACTAAAATTCTGCTTTTACTGGGATTTTGTTTTTTCAAACCAGA

AACCTTTACTTAAGTTGACTACTATTAATGAATTTTGGTCTCTCTTTTAAGTGCTCTTCTTAAAAATGTTATCTT

ACTGCTGAGAAGTTCAAGTTTGGGAAGTACAAGGAGGAATAGAAACTTAAGAGATTTTCTTTTAGAGCCTCTTCT

GTATTTAGCCCTGTAGGATTTTTTTTTTTTTTTTTTTTTTGGTGTTGTTGAGCTTCAGTGAGGCTATTCATTCA

CTTATACTGATAATGTCTGAGATACTGTGAATGAAATACTATGTATGCTTAAACCTAAGAGGAAATATTTTCCCA

AAATTATTCTTCCCGAAAAGGAGGAGTTGCCTTTTGATTGAGTTCTTGCAAATCTCACAACGACTTTATTTTGAA

CAATACTGTTTGGGGATGATGCATTAGTTTGAAACAACTTCAGTTGTAGCTGTCATCTGATAAAATTGCTTCACA

GGGAAGGAAATTTAACACGGATCTAGTCATTATTCTTGTTAGATTGAATGTGTGAATTGTAATTGTAAACAGGCA

TGATAATTATTACTTTAAAAACTAAAAACAGTGAATAGTTAGTTGTGGAGGTTACTAAAGGATGGTTTTTTTTA

AATAAAACTTTCAGCATTATGCAAATGGGCATATGGCTTAGGATAAAACTTCCAGAAGTAGCATCACATTTAAAT

TCTCAAGCAACTTAATAATATGGGGCTCTGAAAAACTGGTTAAGGTTACTCCAAAAATGGCCCTGGGTCTGACAA

AGATTCTAACTTAAAGATGCTTATGAAGACTTTGAGTAAAATCATTTCATAAAATAAGTGAGGAAAAACAACTAG

TATTAAATTCATCTTAAATAATGTATGATTTAAAAAATATGTTTAGCTAAAAATGCATAGTCATTTGACAATTTC

ATTTATATCTCAAAAAATTTACTTAACCAAGTTGGTCACAAAACTGATGAGACTGGTGGTGGTAGTGAATAAATG

AGGGACCATCCATATTTGAGACACTTTACATTTGTGATGTGTTATACTGAATTTTCAGTTTGATTCTATAGACTA

-continued

CAAATTTCAAAATTACAATTTCAAGATGTAATAAGTAGTAATATCTTGAAATAGCTCTAAAGGGAATTTTTCTGT

TTTATTGATTCTTAAAATATATGTGCTGATTTTGATTTGCATTTGGGTAGATTATACTTTTATGAGTATGGAGGT

TAGGTATTGATTCAAGTTTTCCTTACCTATTTGGTAAGGATTTCAAAGTCTTTTTGTGCTTGGTTTTCCTCATTT

TTAAATATGAAATATATTGATGACCTTTAACAAATTTTTTTATCTCAAATTTTAAAGGAGATCTTTTCTAAAAG

AGGCATGATGACTTAATCATTGCATGTAACAGTAAACGATAAACCAATGATTCCATACTCTCTAAAGAATAAAAG

TGAGCTTTAGGGCCGGGCATGGTCAGAAATTTGACACCAACCTGGCCAACATGGCGAAACCCCGTCTCTACTAAA

AATACAAAAATCAGCCGGGCATGGTGGCGGCACCTATAGTCCCAGCTACTTGGGAGGATGAGACAGGAGAGTCAC

TTGAACCTGGGAGGAGAGGTTGCAGTGAGCTGAGATCACGCCATTGCACTCCAGCCTGAGCAATGAAAGCAAAAC

TCCATCTCAAAAAAAAAAAAAGAAAAGAAAGAATAAAAGTGAGCTTTGGATTGCATATAAATCCTTTAGACATGT

AGTAGACTTGTTTGATACTGTGTTTGAACAAATTACGAAGTATTTTCATCAAAGAATGTTATTGTTTGATGTTAT

TTTTATTTTTTATTGCCCAGCTTCTCTCATATTACGTGATTTTCTTCACTTCATGTCACTTTATTGTGCAGGGTC

AGAGTATTATTCCAATGCTTACTGGAGAAGTGATTCCTGTAATGGAACTGCTTTCATCTATGAAATCACACAGTG

TTCCTGAAGAAATAGATGTAAGTTTAAATGAGAGCAATTATACACTTTATGAGTTETTTGGGGTTATAGTATTAT

TATGTATATTATTAATATTCTAATTTTAATAGTAAGGACTTTGTCATACATACTATTCACATACAGTATTAGCCA

CTTTAGCAAATAAGCACACACAAAATCCTGGATTTTATGGCAAAACAGAGGCATTTTTGATCAGTGATGACAAAA

TTAAATTCATTTTGTTTATTTCATTACTTTTATAATTCCTAAAAGTGGGAGGATCCCAGCTCTTATAGGAGCAAT

TAATATTTAATGTAGTGTCTTTTGAAACAAAACTGTGTGCCAAAGTAGTAACCATTAATGGAAGTTTACTTGTAG

TCACAAATTTAGTTTCCTTAATCATTTGTTGAGGACGTTTTGAATCACACACTATGAGTGTTAAGAGATACCTTT

AGGAAACTATTCTTGTTGTTTTCTGATTTTGTCATTTAGGTTAGTCTCCTGATTCTGACAGCTCAGAAGAGGAAG

TTGTTCTTGTAAAAATTGTTTAACCTGCTTGACCAGCTTTCACATTTGTTCTTCTGAAGTTTATGGTAGTGCACA

GAGATTGTTTTTTGGGGAGTCTTGATTCTCGGAAATGAAGGCAGTGTGTTATATTGAATCCAGACTTCCGAAAAC

TTGTATATTAAAAGTGTTATTTCAACACTATGTTACAGCCAGACTAATTTTTTTATTTTTTGATGCATTTTAGAT

AGCTGATACAGTACTCAATGATGATGATATTGGTGACAGCTGTCATGAAGGCTTTCTTCTCAAGTAAGAATTTTT

CTTTTCATAAAAGCTGGATGAAGCAGATACCATCTTATGCTCACCTATGACAAGATTTGGAAGAAAGAAAATAAC

AGACTGTCTACTTAGATTGTTCTAGGGACATTACGTATTTGAACTGTTGCTTAAATTTGTGTTATTTTTCACTCA

TTATATTTCTATATATATTTGGTGTTATTCCATTTGCTATTTAAAGAAACCGAGTTTCCATCCCAGACAAGAAAT

CATGGCCCCTTGCTTGATTCTGGTTTCTTGTTTTACTTCTCATTAAAGCTAACAGAATCCTTTCATATTAAGTTG

TACTGTAGATGAACTTAAGTTATTTAGGCGTAGAACAAAATTATTCATATTTATACTGATCTTTTTCCATCCAGC

AGTGGAGTTTAGTACTTAAGAGTTTGTGCCCTTAAACCAGACTCCCTGGATTAATGCTGTGTACCCGTGGGCAAG

GTGCCTGAATTCTCTATACACCTATTTCCTCATCTGTAAAATGGCAATAATAGTAATAGTACCTAATGTGTAGGG

TTGTTATAAGCATTGAGTAAGATAAATAATATAAAGCACTTAGAACAGTGCCTGGAACATAAAAACACTTAATAA

TAGCTCATAGCTAACATTTCCTATTTACATTTCTTCTAGAAATAGCCAGTATTTGTTGAGTGCCTACATGTTAGT

TCCTTTACTAGTTGCTTTACATGTATTATCTTATATTCTGTTTTAAAGTTTCTTCACAGTTACAGATTTTCATGA

AATTTTACTTTTAATAAAAGAGAAGTAAAAGTATAAAGTATTCACTTTTATGTTCACAGTCTTTTCCTTTAGGCT

CATGATGGAGTATCAGAGGCATGAGTGTGTTTAACCTAAGAGCCTTAATGGCTTGAATCAGAAGCACTTTAGTCC

TGTATCTGTTCAGTGTCAGCCTTTCATACATCATTTTAAATCCCATTTGACTTTAAGTAAGTCACTTAATCTCTC

TACATGTCAATTTCTTCAGCTATAAAATGATGGTATTTCAATAAATAAATACATTAATTAAATGATATTATACTG

ACTAATTGGGCTGTTTTAAGGCTCAATAAGAAAATTTCTGTGAAAGGTCTCTAGAAAATGTAGGTTCCTATACAA

ATAAAAGATAACATTGTGCTTATAGCTTCGGTGTTTATCATATAAAGCTATTCTGAGTTATTTGAAGAGCTCACC

TACTTTTTTTTGTTTTTAGTTTGTTAAATTGTTTTATAGGCAATGTTTTTAATCTGTTTTCTTTAACTTACAGTG

CCATCAGCTCACACTTGCAAACCTGTGGCTGTTCCGTTGTAGTAGGTAGCAGTGCAGAGAAAGTAAATAAGGTAG

-continued

TTTATTTTATAATCTAGCAAATGATTTGACTCTTTAAGACTGATGATATATCATGGATTGTCATTTAAATGGTAG

GTTGCAATTAAAATGATCTAGTAGTATAAGGAGGCAATGTAATCTCATCAAATTGCTAAGACACCTTGTGGCAAC

AGTGAGTTTGAAATAAACTGAGTAAGAATCATTTATCAGTTTATTTTGATAGCTCGGAAATACCAGTGTCAGTAG

TGTATAAATGGTTTTGAGAATATATTAAAATCAGATATATAAAAAAAATTACTCTTCTATTTCCCAATGTTATCT

TTAACAAATCTGAAGATAGTCATGTACTTTTGGTAGTAGTTCCAAAGAAATGTTATTTGTTTATTCATCTTGATT

TCATTGTCTTCGCTTTCCTTCTAAATCTGTCCCTTCTAGGGAGCTATTGGGATTAAGTGGTCATTGATTATTATA

CTTTATTCAGTAATGTTTCTGACCCTTTCCTTCAGTGCTACTTGAGTTAATTAAGGATTAATGAACAGTTACATT

TCCAAGCATTAGCTAATAAACTAAAGGATTTTGCACTTTTCTTCACTGACCATTAGTTAGAAAGAGTTCAGAGAT

AAGTATGTGTATCTTTCAATTTCAGCAAACCTAATTTTTTAAAAAAAGTTTTACATAGGAAATATGTTGGAAATG

ATACTTTACAAAGATATTCATAATTTTTTTTTGTAATCAGCTACTTTGTATATTTACATGAGCCTTAATTTATAT

TTCTCATATAACCATTTATGAGAGCTTAGTATACCTGTGTCATTATATTGCATCTACGAACTAGTGACCTTATTC

CTTCTGTTACCTCAAACAGGTGGCTTTCCATCTGTGATCTCCAAAGCCTTAGGTTGCACAGAGTGACTGCCGAGC

TGCTTTATGAAGGGAGAAAGGCTCCATAGTTGGAGTGTTTTTTTTTTTTTTTTTAAACATTTTTCCCATCCTCCA

TCCTCTTGAGGGAGAATAGCTTACCTTTTATCTTGTTTTAATTTGAGAAAGAAGTTGCCACCACTCTAGGTTGAA

AACCACTCCTTTAACATAATAACTGTGGATATGGTTTGAATTTCAAGATAGTTACATGCCTTTTTATTTTTCCTA

ATAGAGCTGTAGGTCAAATATTATTAGAATCAGATTTCTAAATCCCACCCAATGACCTGCTTATTTTAAATCAAA

TTCAATAATTAATTCTCTTCTTTTTGGAGGATCTGGACATTCTTTGATATTTCTTACAACGAATTTCATGTGTAG

ACCCACTAAACAGAAGCTATAAAAGTTGCATGGTCAAATAAGTCTGAGAAAGTCTGCAGATGATATAATTCACCT

GAAGAGTCACAGTATGTAGCCAAATGTTAAAGGTTTTGAGATGCCATACAGTAAATTTACCAAGCATTTTCTAAA

TTTATTTGACCACAGAATCCCTATTTTAAGCAACAACTGTTACATCCCATGGATTCCAGGTGACTAAAGAATACT

TATTTCTTAGGATATGTTTTATTGATAATAACAATTAAAATTTCAGATATCTTTCATAAGCAAATCAGTGGTCTT

TTTACTTCATGTTTTAATGCTAAAATATTTTCTTTTATAGATAGTCAGAACATTATGCCTTTTTCTGACTCCAGC

AGAGAGAAAATGCTCCAGGTTATGTGAAGCAGAATCATCATTTAAATATGAGTCAGGGCTCTTTGTACAAGGCCT

GCTAAAGGTATAGTTTCTAGTTATCACAAGTGAAACCACTTTTCTAAAATCATTTTTGAGACTCTTTATAGACAA

ATCTTAAATATTAGCATTTAATGTATCTCATATTGACATGCCCAGAGACTGACTTCCTTTACACAGTTCTGCACA

TAGACTATATGTCTTATGGATTTATAGTTAGTATCATCAGTGAAACACCATAGAATACCCCTTTGTGTTCCAGGTG

GGTCCCTGTTCCTACATGTCTAGCCTCAGGACTTTTTTTTTTTTAACACATGCTTAAATCAGGTTGCACATCAAA

AATAAGATCATTTCTTTTTAACTAAATAGATTTGAATTTTATTGAAAAAAAATTTTAAACATCTTTAAGAAGCTT

ATAGGATTTAAGCAATTCCTATGTATGTGTACTAAAATATATATATTTCTATATATAATATATATTAGAAAAAAA

TTGTATTTTTCTTTTATTTGAGTCTACTGTCAAGGAGCAAAACAGAGAAATGTAAATTACCAATTATTTATAATA

CTTAAAGGGAAGAAAGTTGTTCACCTTGTTGAATCTATTATTGTTATTTCAATTATAGTCCCAAGACGTGAAGAA

ATAGCTTTCCTAATGGTTATGTGATTGTCTCATAGTGACTACTTTCTTGAGGATGTAGCCACGGCAAAATGAAAT

AAAAAAATTTAAAAATTGTTGCAAATACAAGTTATATTAGGCTTTTGTGCATTTTCAATAATGTGCTGCTATGAA

CTCAGAATGATAGTATTTAAATATAGAAACTAGTTAAAGGAAACGTAGTTTCTATTTGAGTTATACATATCTGTA

AATTAGAACTTCTCCTGTTAAAGGCATAATAAAGTGCTTAATACTTTTGTTTCCTCAGCACCCTCTCATTTAATT

ATATAATTTTAGTTCTGAAAGGGACCTATACCAGATGCCTAGAGGAAATTTCAAAACTATGATCTAATGAAAAAA

TATTTAATAGTTCTCCATGCAAATACAAATCATATAGTTTTCCAGAAAATACCTTTGACATTATACAAAGATGAT

TATCACAGCATTATAATAGTAAAAAAATGGAAATAGCCTCTTTCTTCTGTTCTGTTCATAGCACAGTGCCTCATA

CGCAGTAGGTTATTATTACATGGTAACTGGCTACCCCAACTGATTAGGAAAGAAGTAAATTTGTTTTATAAAAAT

ACATACTCATTGAGGTGCATAGAATAATTAAGAAATTAAAAGACACTTGTAATTTTGAATCCAGTGAATACCCAC

-continued

TGTTAATATTTGGTATATCTCTTTCTAGTCTTTTTTTCCCTTTTGCATGTATTTTCTTTAAGACTCCCACCCCCA

CTGGATCATCTCTGCATGTTCTAATCTGCTTTTTTCACAGCAGATTCTAAGCCTCTTTGAATATCAACACAAACT

TCAACAACTTCATCTATAGATGCCAAATAATAAATTCATTTTTATTTACTTAACCACTTCCTTTGGATGCTTAGG

TCATTCTGATGTTTTGCTATTGAAACCAATGCTATACTGAACACTTCTGTCACTAAAACTTTGCACACACTCATG

AATAGCTTCTTAGGATAAATTTTTAGAGATGGATTTGCTAAATCAGAGACCATTTTTTAAAATTAAAAAACAATT

ATTCATATCGTTTGGCATGTAAGACAGTAAATTTTCCTTTTATTTTGACAGGATTCAACTGGAAGCTTTGTGCTG

CCTTTCCGGCAAGTCATGTATGCTCCATATCCCACCACACACATAGATGTGGATGTCAATACTGTGAAGCAGATG

CCACCCTGTCATGAACATATTTATAATCAGCGTAGATACATGAGATCCGAGCTGACAGCCTTCTGGAGAGCCACT

TCAGAAGAAGACATGGCTCAGGATACGATCATCTACACTGACGAAAGCTTTACTCCTGATTTGTACGTAATGCTC

TGCCTGCTGGTACTGTAGTCAAGCAATATGAAATTGTGTCTTTTACGAATAAAAACAAAACAGAAGTTGCATTTA

AAAAGAAAGAAATATTACCAGCAGAATTATGCTTGAAGAAACATTTAATCAAGCATTTTTTTCTTAAATGTTCTT

CTTTTTCCATACAATTGTGTTTACCCTAAAATAGGTAAGATTAACCCTTAAAGTAAATATTTAACTATTTGTTTA

ATAAATATATATTGAGCTCCTAGGCACTGTTCTAGGTACCGGGCTTAATAGTGGCCAACCAGACAGCCCCAGCCC

CAGCCCCTACATTGTGTATAGTCTATTATGTAACAGTTATTGAATGGACTTATTAACAAAACCAAAGAAGTAATT

CTAAGTCTTTTTTTTCTTGACATATGAATATAAAATACAGCAAAACTGTTAAAATATATTAATGGAACATTTTTT

TACTTTGCATTTTATATTGTTATTCACTTCTTATTTTTTTTTAAAAAAAAAAGCCTGAACAGTAAATTCAAAAGG

AAAAGTAATGATAATTAATTGTTGAGCATGGACCCAACTTGAAAAAAAAAATGATGATGATAAATCTATAATCCT

AAAACCCTAAGTAAACACTTAAAAGATGTTCTGAAATCAGGAAAAGAATTATAGTATACTTTTGTGTTTCTCTTT

TATCAGTTGAAAAAAGGCACAGTAGCTCATGCCTGTAAGAACAGAGCTTTGGGAGTGCAAGGCAGGCGGATCACT

TGAGGCCAGGAGTTCCAGACCAGCCTGGGCAACATAGTGAAACCCCATCTCTACAAAAAATAAAAAAGAATTATT

GGAATGTGTTTCTGTGTGCCTGTAATCCTAGCTATTCCGAAAGCTGAGGCAGGAGGATCTTTTGAGCCCAGGAGT

TTGAGGTTACAGGGAGTTATGATGTGCCAGTGTACTCCAGCCTGGGGAACACCGAGACTCTGTCTTATTTAAAAA

AAAAAAAAAAAAAATGCTTGCAATAATGCCTGGCACATAGAAGGTAACAGTAAGTGTTAACTGTAATAACCCAGG

TCTAAGTGTGTAAGGCAATAGAAAAATTGGGGCAAATAAGCCTGACCTATGTATCTACAGAATCAGTTTGAGCTT

AGGTAACAGACCTGTGGAGCACCAGTAATTACACAGTAAGTGTTAACCAAAAGCATAGAATAGGAATATCTTGTT

CAAGGGACCCCCAGCCTTATACATCTCAAGGTGCAGAAAGATGACTTAATATAGGACCCATTTTTTCCTAGTTCT

CCAGAGTTTTTATTGGTTCTTGAGAAAGTAGTAGGGGAATGTTTTAGAAAATGAATTGGTCCAACTGAAATTACA

TGTCAGTAAGTTTTTATATATTGGTAAATTTTAGTAGACATGTAGAAGTTTTCTAATTAATCTGTGCCTTGAAAC

ATTTTCTTTTTTCCTAAAGTGCTTAGTATTTTTTCCGTTTTTTGATTGGTTACTTGGGAGCTTTTTTGAGGAAAT

TTAGTGAACTGCAGAATGGGTTTGCAACCATTTGGTATTTTTGTTTTGTTTTTTAGAGGATGTATGTGTATTTTA

ACATTTCTTAATCATTTTTAGCCAGCTATGTTTGTTTTGCTGATTTGACAAACTACAGTTAGACAGCTATTCTCA

TTTTGCTGATCATGACAAAATAATATCCTGAATTTTTAAATTTTGCATCCAGCTCTAAATTTTCTAAACATAAAA

TTGTCCAAAAAAATAGTATTTTCAGCCACTAGATTGTGTGTTAAGTCTATTGTCACAGAGTCATTTTACTTTTAAG

TATATGTTTTTACATGTTAATTATGTTTGTTATTTTTAATTTTAACTTTTTAAAATAATTCCAGTCACTGCCAAT

ACATGAAAAATTGGTCACTGGAATTTTTTTTTTGACTTTTATTTTAGGTTCATGTGTACATGTGCAGGTGTGTTA

TACAGGTAAATTGCGTGTCATGAGGGTTTGGTGTACAGGTGATTTCATTACCCAGGTAATAAGCATAGTACCCAA

TAGGTAGTTTTTTGATCCTCACCCTTCTCCCACCCTCAAGTAGGCCCTGGTGTTGCTGTTTCCTTCTTTGTGTCC

ATGTATACTCAGTGTTTAGCTCCCACTTAGAAGTGAGAACATGCGGTAGTTGGTTTTCTGTTCCTGGATTAGTTC

ACTTAGGATAATGACCTCTAGCTCCATCTGGTTTTTATGGCTGCATAGTATTCCATGGTGTATATGTATCACATT

TTCTTTATCCAGTCTACCATTGATAGGCATTTAGGTTGATTCCCTGTCTTTGTTATCATGAATAGTGCTGTGATG

AACATACACATGCATGTGTCTTTATGGTAGAAAAATTTGTATTCCTTTAGGTACATATAGAATAATGGGGTTGCT

-continued

AGGGTGAATGGTAGTTCTATTTTCAGTTATTTGAGAAATCTTCAAACTGCTTTTCATAATAGCTAAACTAATTTA

CAGTCCCGCCAGCAGTGTATAAGTGTTCCCTTTTCTCCACAACCTTGCCAACATCTGTGATTTTTTGACTTTTTA

ATAATAGCCATTCCTAGAGAATTGATTTGCAATTCTCTATTAGTGATATTAAGCATTTTTTCATATGCTTTTTAG

CTGTCTGTATATATTCTTCTGAAAAATTTTCATGTCCTTTGCCCAGTTTGTAGTGGGGTGGGTTGTTTTTTGCTT

GTTAATTAGTTTTAAGTTCCTTCCAGATTCTGCATATCCCTTTGTTGGATACATGGTTTGCAGATATTTTTCTCC

CATTGTGTAGGTTGTCTTTTACTCTGTTGATAGTTTCTTTTGCCATGCAGGAGCTCGTTAGGTCCCATTTGTGTT

TGTTTTTGTTGCAGTTGCTTTTGGCGTCTTCATCATAAAATCTGTGCCAGGGCCTATGTCCAGAATGGTATTTCC

TAGGTTGTCTTCCAGGGTTTTTACAATTTTAGATTTTACGTTTATGTCTTTAATCCATCTTGAGTTGATTTTTGT

ATATGGCACAAGGAAGGGGTCCAGTTTCACTCCAATTCCTATGGCTAGCAATTATCCCAGCACCATTTATTGAAT

ACGGAGTCCTTTCCCCATTGCTTGTTTTTTGTCAACTTTGTTGAAGATCAGATGGTTGTAAGTGTGTGGCTTTAT

TTCTTGGCTCTCTATTCTCCATTGGTCTATGTGTCTGTTTTTATAACAGTACCCTGCTGTTCAGGTTCCTATAGC

CTTTTAGTATAAAATCGGCTAATGTGATGCCTCCAGCTTTGTTCTTTTTGCTTAGGATTGCTTTGGCTATTTGGG

CTCCTTTTTGGGTCCATATTAATTTTAAAACAGTTTTTTCTGGTTTTGTGAAGGATATCATTGGTAGTTTATAGG

AATAGCATTGAATCTGTAGATTGCTTTGGGCAGTATGGCCATTTTAACAATATTAATTCTTCCTATCTATGAATA

TGGAATGTTTTTCCATGTGTTTGTGTCATCTCTTTATACCTGATGTATAAAGAAAAGCTGGTATTATTCCTACTC

AATCTGTTCCAAAAAATTGAGGAGGAGGAACTCTTCCCTAATGAGGCCAGCATCATTCTGATACCAAAACCTGGC

AGAGACACAACAGAAAAAAGAAAACTTCAGGCCAATATCCTTGATGAATATAGATGCAAAAATCCTCAACAAAAT

ACTAGCAAACCAAATCCAGCAGCACATCAAAAAGCTGATCTACTTTGATCAAGTAGGCTTTATCCCTGGGATGCA

AGGTTGGTTCAACATACACAAATCAATAAGTGTGATTCATCACATAAACAGAGCTAAAAACAAAAACCACAAGAT

TATCTCAATAGGTAGAGAAAAGGTTGTCAATAAAATTTAACATCCTCCATGTTAAAAACCTTCAGTAGGTCAGGT

GTAGTGACTCACACCTGTAATCCCAGCACTTTGGGAGGCCAAGGCGGGCATATCTCTTAAGCCCAGGAGTTCAAG

ACGAGCCTAGGCAGCATGGTGAAACCCCATCTCTACAAAAAAAAAAAAAAAAAAAAATTAGCTTGGTATGGTGAC

ATGCACCTATAGTCCCAGCTATTCAGGAGGTTGAGGTGGGAGGATTGTTTGAGCCCGGGAGGCAGAGGTTGGCAG

CGAGCTGAGATCATGCCACCGCACTCCAGCCTGGGCAACGGAGTGAGACCCTGTCTCAAAAAAGAAAAATCACAA

ACAATCCTAAACAAACTAGGCATTGAAGGAACATGCCTCAAAAAAATAAGAACCATCTATGACAGACCCATAGCC

AATATCTTACCAAATGGGCAAAAGCTGGAAGTATTCTCCTTGAGAACCGTAACAAGACAAGGATGTCCACTCTCA

CCACTCCTTTTCAGCATAGTTCTGGAAGTCCTAGCCAGAGCAATCAGGAAAGAGAAAGAAAGAAAGACATTCAGA

TAGGAAGAGAAGAAGTCAAACTATTTCTGTTTGCAGGCAGTATAATTCTGTACCTAGAAAATCTCATAGTCTCTG

CCCAGAAACTCCTAAATCTGTTAAAAATTTCAGCAAAGTTTTGGCATTCTCTATACTCCAACACCTTCCAAAGTG

AGAGCAAAATCAAGAACACAGTCCCATTCACAATAGCCGCAAAACGAATAAAATACCTAGGAATCCAGCTAACCA

GGGAGGTGAAAGATCTCTATGAGAATTACAAAACACTGCTGAAAGAAATCAGAGATGACACAAACAAATGGAAAT

GTTCTTTTTTAACACCTTGCTTTATCTAATTCACTTATGATGAAGATACTCATTCAGTGGAACAGGTATAATAAG

TCCACTCGATTAAATATAAGCCTTATTCTCTTTCCAGAGCCCAAGAAGGGGCACTATCAGTGCCCAGTCAATAAT

GACGAAATGCTAATATTTTTCCCCTTTACGGTTTCTTTCTTCTGTAGTGTGGTACACTCGTTTCTTAAGATAAGG

AAACTTGAACTACCTTCCTGTTTGCTTCTACACATACCCATTCTCTTTTTTTGCCACTCTGGTCAGGTATAGGAT

GATCCCTACCACTTTCAGTTAAAAACTCCTCCTCTTACTAAATGTTCTCTTACCCTCTGGCCTGAGTAGAACCTA

GGGAAAATGGAAGAGAAAAAGATGAAAGGGAGGTGGGGCCTGGGAAGGGAATAAGTAGTCCTGTTTGTTTGTGTG

TTTGCTTTAGCACCTGCTATATCCTAGGTGCTGTGTTAGGCACACATTATTTTAAGTGGCCATTATATTACTACT

ACTCACTCTGGTCGTTGCCAAGGTAGGTAGTACTTTCTTGGATAGTTGGTTCATGTTACTTACAGATGGTGGGCT

TGTTGAGGCAAACCCAGTGGATAATCATCGGAGTGTGTTCTCTAATCTCACTCAAATTTTTCTTCACATTTTTG

-continued

GTTTGTTTTGGTTTTTGATGGTAGTGGCTTATTTTTGTTGCTGGTTTGTTTTTTGTTTTTTTTTGAGATGGCAAG

AATTGGTAGTTTTATTTATTAATTGCCTAAGGGTCTCTACTTTTTTTAAAAGATGAGAGTAGTAAAATAGATTGA

TAGATACATACATACCCTTACTGGGGACTGCTTATATTCTTTAGAGAAAAAATTACATATTAGCCTGACAAACAC

CAGTAAAATGTAAATATATCCTTGAGTAAATAAATGAATGTATATTTTGTGTCTCCAAATATATATATCTATATT

CTTACAAATGTGTTTATATGTAATATCAATTTATAAGAACTTAAAATGTTGGCTCAAGTGAGGGATTGTGGAAGG

TAGCATTATATGGCCATTTCAACATTTGAACTTTTTTCTTTTCTTCATTTTCTTCTTTTCTTCAGGAATATTTTT

CAAGATGTCTTACACAGAGACACTCTAGTGAAAGCCTTCCTGGATCAGGTAAATGTTGAACTTGAGATTGTCAGA

GTGAATGATATGACATGTTTTCTTTTTTAATATATCCTACAATGCCTGTTCTATATATTTATATTCCCCTGGATC

ATGCCCCAGAGTTCTGCTCAGCAATTGCAGTTAAGTTAGTTACACTACAGTTCTCAGAAGAGTCTGTGAGGGCAT

GTCAAGTGCATCATTACATTGGTTGCCTCTTGTCCTAGATTTATGCTTCGGGAATTCAGACCTTTGTTTACAATA

TAATAAATATTATTGCTATCTTTTAAAGATATAATAATAAGATATAAAGTTGACCACAACTACTGTTTTTTGAAA

CATAGAATTCCTGGTTTACATGTATCAAAGTGAAATCTGACTTAGCTTTTACAGATATAATATATACATATATAT

ATCCTGCAATGCTTGTACTATATATGTAGTACAAGTATATATATATGTTTGTGTGTGTATATATATATAGTACGA

GCATATATACATATTACCAGCATTGTAGGATATATATATGTTTATATATTAAAAAAAAGTTATAAACTTAAAACC

CTATTATGTTATGTAGAGTATATGTTATATATGATATGTAAAATATATAACATATACTCTATGATAGAGTGTAAT

ATATTTTTTATATATATTTTAACATTTATAAAATGATAGAATTAAGAATTGAGTCCTAATCTGTTTTATTAGGTG

CTTTTTGTAGTGTCTGGTCTTTCTAAAGTGTCTAAATGATTTTTCCTTTTGACTTATTAATGGGGAAGAGCCTGT

ATATTAACAATTAAGAGTGCAGCATTCCATACGTCAAACAACAAACATTTTAATTCAAGCATTAACCTATAACAA

GTAAGTTTTTTTTTTTTTTTGAGAAAGGGAGGTTGTTTATTTGCCTGAAATGACTCAAAAATATTTTTGAAACA

TAGTGTACTTATTTAAATAACATCTTTATTGTTTCATTCTTTTAAAAAATATCTACTTAATTACACAGTTGAAGG

AAATCGTAGATTATATGGAACTTATTTCTTAATATATTACAGTTTGTTATAATAACATTCTGGGGATCAGGCCAG

GAAACTGTGTCATAGATAAAGCTTTGAAATAATGAGATCCTTATGTTTACTAGAAATTTTGGATTGAGATCTATG

AGGTCTGTGACATATTGCGAAGTTCAAGGAAAATTCGTAGGCCTGGAATTTCATGCTTCTCAAGCTGACATAAAA

TCCCTCCCACTCTCCACCTCATCATATGCACACATTCTACTCCTACCCACCCACTCCACCCCCTGCAAAAGTACA

GGTATATGAATGTCTCAAAACCATAGGCTCATCTTCTAGGAGCTTCAATGTTATTTGAAGATTTGGGCAGAAAAA

ATTAAGTAATACGAAATAACTTATGTATGAGTTTTAAAAGTGAAGTAAACATGGATGTATTCTGAAGTAGAATGC

AAAATTTGAATGCATTTTTAAAGATAAATTAGAAAACTTCTAAAAACTGTCAGATTGTCTGGGCCTGGTGGCTTA

TGCCTGTAATCCCAGCACTTTGGGAGTCCGAGGTGGGTGGATCACAAGGTCAGGAGATCGAGACCATCCTGCCAA

CATGGTGAAACCCCGTCTCTACTAAGTATACAAAAATTAGCTGGGCGTGGCAGCGTGTGCCTGTAATCCCAGCTA

CCTGGGAGGCTGAGGCAGGAGAATCGCTTGAACCCAGGAGGTGTAGGTTGCAGTGAGTCAAGATCGCGCCACTGC

ACTTTAGCCTGGTGACAGAGCTAGACTCCGTCTCAAAAAAAAAAAAAAAATATCAGATTGTTCCTACACCTAGTGC

TTCTATACCACACTCCTGTTAGGGGGCATCAGTGGAAATGGTTAAGGAGATGTTTAGTGTGTATTGTCTGCCAAG

CACTGTCAACACTGTCATAGAAACTTCTGTACGAGTAGAATGTGAGCAAATTATGTGTTGAAATGGTTCCTCTCC

CTGCAGGTCTTTCAGCTGAAACCTGGCTTATCTCTCAGAAGTACTTTCCTTGCACAGTTTCTACTTGTCCTTCAC

AGAAAAGCCTTGACACTAATAAAATATATAGAAGACGATACGTGAGTAAAACTCCTACACGGAAGAAAAACCTTT

GTACATTGTTTTTTTGTTTTGTTTCCTTTGTACATTTTCTATATCATAATTTTTGCGCTTCTTTTTTTTTTTTTT

TTTTTTTTTTTTCCATTATTTTTAGGCAGAAGGGAAAAAAGCCCTTTAAATCTCTTCGGAACCTGAAGATAGACC

TTGATTTAACAGCAGAGGGCGATCTTAACATAATAATGGCTCTGGCTGAGAAAATTAAACCAGGCCTACACTCTT

TTATCTTTGGAAGACCTTTCTACACTAGTGTGCAAGAACGAGATGTTCTAATGACTTTTTAAATGTGTAACTTAA

TAAGCCTATTCCATCACAATCATGATCGCTGGTAAAGTAGCTCAGTGGTGTGGGGAAACGTTCCCCTGGATCATA

CTCCAGAATTCTGCTCTCAGCAATTGCAGTTAAGTAAGTTACACTACAGTTCTCACAAGAGCCTGTGAGGGGATG

-continued

TCAGGTGCATCATTACATTGGGTGTCTCTTTTCCTAGATTTATGCTTTTGGGATACAGACCTATGTTTACAATAT

AATAAATATTATTGCTATCTTTTAAAGATATAATAATAGGATGTAAACTTGACCACAACTACTGTTTTTTTGAAA

TACATGATTCATGGTTTACATGTGTCAAGGTGAAATCTGAGTTGGCTTTTACAGATAGTTGACTTTCTATCTTTT

GGCATTCTTTGGTGTGTAGAATTACTGTAATACTTCTGCAATCAACTGAAAACTAGAGCCTTTAAATGATTTCAA

TTCCACAGAAAGAAAGTGAGCTTGAACATAGGATGAGCTTTAGAAAGAAAATTGATCAAGCAGATGTTTAATTGG

AATTGATTATTAGATCCTACTTTGTGGATTTAGTCCCTGGGATTCAGTCTGTAGAAATGTCTAATAGTTCTCTAT

AGTCCTTGTTCCTGGTGAACCACAGTTAGGGTGTTTTGTTTATTTTATTGTTCTTGCTATTGTTGATATTCTATG

TAGTTGAGCTCTGTAAAAGGAAATTGTATTTTATGTTTTAGTAATTGTTGCCAACTTTTTAAATTAATTTTCATT

ATTTTTGAGCCAAATTGAAATGTGCACCTCCTGTGCCTTTTTTCTCCTTAGAAAATCTAATTACTTGGAACAAGT

TCAGATTTCACTGGTCAGTCATTTTCATCTTGTTTTCTTCTTGCTAAGTCTTACCATGTACCTGCTTTGGCAATC

ATTGCAACTCTGAGATTATAAAATGCCTTAGAGAATATACTAACTAATAAGATCTTTTTTTCAGAAACAGAAAAT

AGTTCCTTGAGTACTTCCTTCTTGCATTTCTGCCTATGTTTTTGAAGTTGTTGCTGTTTGCCTGCAATAGGCTAT

AAGGAATAGCAGGAGAAATTTTACTGAAGTGCTGTTTTCCTAGGTGCTACTTTGGCAGAGCTAAGTTATCTTTTG

TTTTCTTAATGCGTTTGGACCATTTTGCTGGCTATAAAATAACTGATTAATATAATTCTAACACAATGTTGACAT

TGTAGTTACACAAACACAAATAAATATTTTATTTAAAATTCTGGAAGTAATATAAAAGGGAAAATATATTTATAA

GAAAGGGATAAAGGTAATAGAGCCCTTCTGCCCCCCACCCACCAAATTTACACAACAAAATGACATGTTCGAATG

TGAAAGGTCATAATAGCTTTCCCATCATGAATCAGAAAGATGTGGACAGCTTGATGTTTTAGACAACCACTGAAC

TAGATGACTGTTGTACTGTAGCTCAGTCATTTAAAAAAATATATAAATACTACCTTGTAGTGTCCCATACTGTGTT

TTTTACATGGTAGATTCTTATTTAAGTGCTAACTGGTTATTTTCTTTGGCTGGTTTATTGTACTGTTATACAGAA

TGTAAGTTGTACAGTGAAATAAGTTATTAAAGCATGTGTAAACATTGTTATATATCTTTTCTCCTAAATGGAGAA

TTTTGAATAAAATATATTTGAAATTTTGCCTCTTTCAGTTGTTCATTCAGAAAAAAATACTATGATATTTGAAGA

CTGATCAGCTTCTGTTCAGCTGACAGTCATGCTGGATCTAAACTTTTTTTAAAATTAATTTTGTCTTTTCAAAGA

AAAAATATTTAAAGAAGCTTTATAATATAATCTTATGTTAAAAAAACTTTCTGCTTAACTCTCTGGATTTCATTT

TGATTTTTCAAATTATATATTAATATTTCAAATGTAAAATACTATTTAGATAAATTGTTTTTAAACATTCTTATT

ATTATAATATTAATATAACCTAAACTGAAGTTATTCATCCCAGGTATCTAATACATGTATCCAAAGTAAAAATCC

AAGGAATCTGAACACTTTCATCTGCAAAGCTAGGAATAGGTTTGACATTTTCACTCCAAGAAAAAGTTTTTTTTT

GAAAATAGAATAGTTGGGATGAGAGGTTTCTTTAAAAGAAGACTAACTGATCACATTACTATGATTCTCAAAGAA

GAAACCAAAACTTCATATAATACTATAAAGTAAATATAAAATAGTTCCTTCTATAGTATATTTCTATAATGCTAC

AGTTTAAACAGATCACTCTTATATAATACTATTTTGATTTTGATGTAGAATTGCACAAATTGATATTTCTCCTAT

GATCTGCAGGGTATAGCTTAAAGTAACAAAAACAGTCAACCACCTCCATTTAACACACAGTAACACTATGGGACT

AGTTTTATTACTTCCATTTTACAAATGAGGAAACTAAAGCTTAAAGATGTGTAATACACCGCCCAAGGTCACACA

GCTGGTAAAGGTGGATTTCATCCCAGACAGTTACAGTCATTGCCATGGGCACAGCTCCTAACTTAGTAACTCCAT

GTAACTGGTACTCAGTGTAGCTGAATTGAAAGGAGAGTAAGGAAGCAGGTTTTACAGGTCTACTTGCACTATTCA

GAGCCCGAGTGTGAATCCCTGCTGTGCTGCTTGGAGAAGTTACTTAACCTATGCAAGGTTCATTTTGTAAATATT

GGAAATGGAGTGATAATACGTACTTCACCAGAGGATTTAATGAGACCTTATACGATCCTTAGTTCAGTACCTGAC

TAGTGCTTCATAAATGCTTTTTCATCCAATCTGACAATCTCCAGCTTGTAATTGGGGCATTTAGAACATTTAATA

TGATTATTGGCATGGTAGGTTAAAGCTGTCATCTTGCTGTTTTCTATTTGTTCTTTTTGTTTTCTCCTTACTTTT

GGATTTTTTTATTCTACTATGTCTTTTCTATTGTCTTATTAACTATACTCTTTGATTTATTTTAGTGGTTGTTTT

AGGGTTATACCTCTTTCTAATTTACCAGTTTATAACCAGTTTATATACTACTTGACATATAGCTTAAGAAACTTA

CTGTTGTTGTCTTTTTGCTGTTATGGTCTTAACGTTTTTATTTCTACAAACATTATAAACTCCACACTTTATTGT

-continued

TTTTTAATTTTACTTATACAGTCAATTATCTTTTAAAGATATTTAAATATAAACATTCAAAACACCCCAATTAAA

AGTCAGAGATTGTTAATACCACATGATCTCACTTACACACAGAATTGAAAAACTTGGAACTCATAGAAGCAGAGA

GTAAAAACATGGTTACCAGGTGCTGGGGAGAGGCGGTGGGCTGGGGAGATGTTGGTCAAAGTTAGACAGGAGGAA

TAAGTTCAAGAGATCTATTGTACAACTTATTCAGTTAGATAGGAGGAATAAGCTAAAGATCAAGAGATCTATTGT

ACAATGTGACTATAACCAACAACATATATTGTACACTTGAAAATTGCTAACAGTATCTTTTAAGTGTTCTCTCTA

CAAATAAATATGTGAGGTAATGTATATATTAATTAACTGTAGTCATTTCACAATGTATACTTATTTCAAAACATC

ATATTGTATGCTATAAATATATACAACTTTTATTTTTCAATTTTAGAAATGTCCTTAAAAAAATCAGATTTTCAGA

TCAGATAAAAAAGCAAGACCCAACTATATGCTGCCAACAGGAAACACACCTTAAAAATAAAGGACGAACAAACAG

ATTAAAAGTAAAAGGATGGAGAAAAGATACATCATATTGGTAATTAGAAGAAAACTGGAGTGACAATATGAAACA

AAATAGATTTCAGAGCAAAGAATATTACCAGGGGTAAAAATGATCATTTTATAATGATAAAAGAGTCAGTTCAGC

AAAAGGATATAACAGTCCTAAATGTTTTTCACCTCATAGCTGTGTCAAAATAGATGAAGCAAAAACTGATAGAA

CTGTAAGAAGTAGACAAGTCCACAATTATGTTTGGAGATTTTTTTTTTTTTTTTTTTGTCGCCCAGGCTGGAGT

GCAGTGGCAGGATCTCAGCTCACTGCAAGCTCCGCCTCCCAGGTTCACGCCATTCTCCTGCTTCAGCCTCCCCAG

TAGCTGGGACTACAGGCGGCCACCACCACGCCTGGCTAATTTTTTTGTATTTTTAGTAGAGACGGGGTTTCACCG

TGTTAGCCAGGATGGTCTCGATCTCCTGACCTCGTGATCTGCCTGCCTCGGCCTCCCAAAGTGCTGGGATTACAG

GCATGAGCCACTGCACGCAGCCTGGAGATTTTAATATCCTTTCAATGTTTAGTAGAACAAGAATACACAAAATCA

GTAAGGATATAGAAGATTAGAACAAGACTATCAAACAATTTGACTTAAATGACATTTGTAGAGCACAGCAGTCCC

CAACAACAATAAATCACACATTCTTTCCAAGAGTACATGAAACATGTACCAAGATAGACCGTATTTTGAGCCATG

AAACAAATCTTGATAAATTTAAAAGGATTCAAGTCATAGAAAATATGTTCTCTGACCACAATGGAATTAAATTAT

TAACCAATAACAAATATCTGGGAAAACCTCAAAAACTTGGACACCAGCGCTTTTAAAAGACTAAATAATTTCTAA

ATTATCTGTGTTGGGGGGAAAAGAGAAATGGATTAGAGAGCAAAAAGGGTATCAGAGTGCTGTGGTACGATTTTT

ATGAAGAGTGGAACAGAATCTGCCTTTGGCGTTTCCCCACTACAGCCCATTCTTCACATTGATAACAGCATGATC

CTTCTAAAATTAAATCTAACGATCACTTCTGCTTAATGGCTCTCCAACACTTACAGAATTAGGTCCAAAATTCTA

GCACAGTTTCTGTTCATCTTTCTAACCTTTCTTCCCACAGGTCTAGCTAGTACGTATTTCTTTTATTGCATTTAT

TACACTATTCCTTTGCTTATCTATCTCCCCACCTAGGCTAAAGAACAAGATTCTTGTCTTTTTCATTTTTGTGTC

TCAGTGCCTAGCATGGTGCCAGGCACACAGCATGCTTCCAGTAAATGTTAGCTGGATGGATGTAATGAGTATATT

AAATATTAATTTATTTGTTTTTCCCCAAAAAGAATTATTTCCTGCAAATCAAGGAAATTGCTTTCTTTATATAAT

CAAAAACTTATTTTCCCAGAAGATTCTTCATTAAAAATTAAGCCTATGCACAACCTAGCTCTAAAGTTTCAAAGA

TTTTAGGCAGCAATTTTTCAATCTTTTTGAAGTAATACATTTGAATCTTTTCAAATTTCTGTTTCTGCATTTGTG

CCACACCATCTCATCTCTTGCTGAAATGTTTTTGTTAAATTAATTGCTTGATAAATTGCTAAGTACTTTTCATCA

GACCAATTAGGACAATAGTAAGTATCCATCTGTGGAGCGCGGACATTCAAGAAATCTGATCCAGTATTTAGAAAG

TCATTCCTGAGCTGAGTTGGCTCAAACTGGCACCTTCTGGCATTTGCTTGTGGGTGGGGAATGTGGAATGCTTTG

AAAGCTGAATGAGTTTGTCAAGTTTTAAAATTCCCTTATGGCTAAAGGAAAACAACATTCATTGTTTAAAAACAC

CATTGTTTGTTTTTTCTGCTTTTTTGTTCTTTGGAGCCTGAATCTGCAAAAACACTCACACCCAGCATTTTGCTT

CATGTACCACTCCTAAGATGTTTTTAGAGACTTGAATAGTGTCTCCGCACTACTTTTTATTGTGATTGTTCAGAA

TGTTCATAACAAATGGTAAAAAGTCAGTTTTAGTGCTCAAATTGAGTTTTATGGAGAAAGACCATAATTTATGTT

TGTCATTGTAAATTGATAGGAGAATTTTTTGGAAGTTTGCGTCCTAGAACCAGATTTCCAAGGCTCAGATCCTTAT

TTTCTCACTTCCTAGCTGTGTGACCTTAGACAAGGTATTAAACCTGTCTGTGCTGCCTCAGTGTCCTCATCTATT

CTTTAAGAGTAAGAATAGAACCTACCCGATAGAGTCACTTGAAGATTAAGTGGGTTAGTAAATTCAGAATGCTTG

GAACAGTAACTAGCACAGAATAAGTGTCCAATAAAATTGGGTTGCAGCTATTATCAGTATTATTCCTGTCATAAT

CATCATCACCATTAAGCAATTAAATGTAGAGTTCCAAAATTTGATTATGAAACTACAGTTATACAGCCATGATTC

-continued

CCGGTGATACCACGTCAGTAACAAGATTATTTCCTTAGCTTGAGCCAGTCACTACCTCATTGCATGTGGCAGAGT
GTGTTGCCGTAGGCAAATGTCATTGTAGGGAATGAAAAAAAAATTGCCTGTGAGCTGCTCTCCAGAGGCCTCATC
CCATTTTCCCATCGTCCACTTTACTCCATCTCCACTGCCACTATTAGGACCTTATCATTTCTTGTCTAGATTAAT
TCAACAGCTTCCTTCCTTCTAGTCTCCATGATTTCACCCACTAGCCATCCCCTCCCCTTTGCCCAATTTTCTCCA
TTTATGGTAGAGTGATCTTTCTAATAGGAAACTCCTGACTTGCCTTAAAAAGCCCTCATTGAGGCCGGACGTGGT
GGCTCATGCCTGTAATCCCAGCACTTTGGGAGGCCGAGGCAGGTGGATCACGAGGTCAAGAGATTGAGACCATCG
TGACTAACACAGTGAAACCCCATCTGTACTAAAAATACAAGAAATTAGCCAGGCGTGGTGGGGGGTGCCTGTAGT
CGCAGCTACTTGGGAGGCTGAGGCAGGAGAATGGCGTGAACCCGGGAGGCAGAGCTTGCAGTGAGCCGAGATTGC
GCCACTGCACTCCAGCCTGGGCGACAGAGTGAGACTCCGTCTCAAAAAAAAAAAGCCCTCATTGACAACCTTCAA
CCCACAATCCATGGTGAAGCACAGGAGCCTTGGGGATCTGCCCCCAGCACACCTCTCCACCCTTGTCTCTCACTG
CTCCTGCCTTCATGGAGAGCCCTGATGAACTATTTGTAGTTTCCCCTGACTCACCTTGCTGTTACTGGGCCTGTG
TGCGTGTTGCTCCCACTACCTGCAATACGCTTACCCACTTCACCTGGGTGAACTTTACTTAGGATTCACCTTAGG
TGGGCATCATGTTCTTCCAGGCCCCTCCTCTAACTTTTAGTTGAGAGTATTCCAGACTTAAGGCTCCATGGGATA
GGGATCTTGTCTATGCACCAGCTTATTCCCAACTGCCTGGCACGTAATGCATTTATTAAATATATATTGAATTGA
TTACCCTACTTGGGGCTCTTGTTTGCTTCTACACTTACAGTTCTAGCATAGCACTTAACTCATTATCATGCATCA
TTATTATGGGTTTGTTTTGTCTCCCATTAGACTGTGAGCTCCACAAGGCTGTGTCCTTGTCTTATACATCATTGT
ATTTCCAGCTTCCAACATAGTGCTTGCCATGACACAGGAAGTCAGTAAGCTCTGAATGAATGAATAGTATCTACA
TACCATTAATCTGAGGTTTAAAGTTTCCCCAAATTCTGAAGCAAGGGGATTTACGGACTTCCCTGACAATTTTTG
GATGTCATCCCAATGATACCACTAACATTTTAAGGGACAGCTTGCATATATACATTTTTCTGGATGGCAGTTTTT
TTTCCCACAGGCTTCATCAGATATTTCTCCATAGCCTTCCTCAGATTCTCAAAGGGGTCTCTGATTCCCCCAAAA
GATAAGAAACTGTCATAAAAAATTATTTCTAAATATCAATTGTTAAATAAAATGTTTGCAAAGCAGCCTGATGAA
TCATTTCAGGCCACTTGACCCCGATGAGTTAGAGAGTTTGTGCTCTGCAATCTGACTGCTTCCAGCAGTCTCACT
GCTGCTGGACTGTGGCACTTCCAATTGGCAGCAGGGCAAGTTTCTTCTGGATGAATATTCTGTCATAGGGGTCCC
CCTTCCACACATACCTGTAGGAGCAGTTTGAAACTCATATGCATGGTCTTCCTGGTTCTAGGCACATGAGTCATT
TAAGCTGCTGGAGCCAGGACCAGCTAGTATGCTAGCCCGGCATTCAGAAAGTTAAAATTTGGGGTCAAAACTGAG
AACCTTCTTTGATCCACCTTGGCCAGACATTTTCTCTGGCTTCCATTAATAGCCTCAACATTTTTTTTTTTTCTG
GCCTAGACCCACACAGGCAAGAGACCAGAGCTTCTCTAAGGAGCTAAGGGAAAGCACATTTTAAAAATAACTTGA
GCAAATGAATTCATCTGGCAAAAGCAACCCCACTACGTAAAATAAACCTTTTTAGTTTCGCAATAGCAGTTCCTG
AAAATGTAAACAACCTCAGGGTCTACATGCACTGAATCATTTGCTGAACAGAAAGTCCCTGGTCCAAATTCTGCA
AGAATAAACACCTTACAAAACTAGGGGTCAATGACCTTCATATGGGAACAAGGAGGGTGTGGGGGGCAGCAACCC
ACCCTGAGGACAATGAGAAAGTCTTGAGACTTGATATTCAAAATGCTGGCTTTCTAAACCAAAAACTGGCATGAG
TGGAGGGAGAAGGGGAGGGTGGGCACAGTCTATGCCTCAGGCTCTTGCTCAGACCCTACCAGGCCCCTGCCTTCC
CTAGGGAAAGCGAGAGTCTACTCACTGTCATGAAGCCAGAGGAAGGCCCTGCAGGTTTCACTGTGTGTTCTGTTG
ACAAGATGATGGTTCCATTGAAACTGTAATAACATACTTGGCCAACTAAGCCCATACGATCGTAGTAACTTTGTA
CCCAGTCCTAGCTTTTCAAACATAATGATAATATGTTCTTTCTAATGTGGCCCATACTGTTCTAATGAACTTATG
CTGAGTTTTTCTGAGTACTAGAATAATATTCGCCATAAATAATAGATATAATTATTCTCATTTAATATTTGCGTA
GCTCTTCTTTAAAGCAGAAAGTATTTTCTCATTCCTTACTAGAACCTTTCTGTGTGAGGAGCACTGAGCTAGAAC
CCATATCTTAGAATGGTCAGAATTTGGAGAAATTCAGGGAAAAGGCACTGGACTCATTTTTAAAGACTAGAAAAT
GCAACCTCCAGAAAAAGATTCAAGAGTTTTTTACTCCCAGAGATGTAGGAAAGATTGGAGTAAATCTTAATATTA
TATTTCAGGTAAACAAAGGATCACTGTCAAAATAGCAGCATTTATTGAGTAATGGCTGTGTGCCAGGTACTTTAC

-continued

AGTTTCACATTTAACCCTCATAATAACCTTGTAAAGTGGATATCCCCTCAGTACATGATGAGAACACTGAAGCTT

AGGTTAAATGATTGTCCAAATCGGACAATCATTTTCAAAATCTCCCCCTTTTTTTCTCCTTTCTTATCTGCAAGG

CAGATTGCCCTTTCCCTTTCAGTGAAACTTGTGCATGACCACATGACTCTCTTTGGCCAATGAAACATGAACAAG

CAGCGTTTATCACTTTCAGATGGAAGGCTTTGCATGAGCTTTGCCTCCTTTTCACTCTGCCACAGTGGCCACTAA

CATTCCAGATAGTGGCGCTCTGCAGGCTAGGTCCTATAGTGGGAGCTATGGGCAGAGCCCCCTTTCCCACCCCCA

TCAAGATGTGCATGCTGCATAAGCCATGCATTAATCTTTGCAGTTTTAAGCCACTAAGTTTTGGAGTTATATTAA

TCATTAATCATGGTTCTCAAGAGAAACAGAGTGGGGGAGTGGTATTCATTATGGGAATTGGCTTACATGATTATG

GAAGCTGAGTAGTCCCCCAGTCTGCTGTTTTTGAGCTGGAGAACTAGAGGAGCCAGTGGTATAATTCAGCCCAAG

CCTGAAGGCCTGAGAAATGGGATGGGGGAATTGGGAGGGTGGGTGTGCTAGGGTAGGATAAGTCCTGAAGTTCAA

AGGCCAGCCAGAAGGTGGATGTTTCAGCACCAGAAGAGAGAGCAAATTCGCTTTTCTTCTGCCTTTTTGTCCTCT

CTGGGCCCTCAATGGATTGGATGATGCCCTCCCACATTGGTAAGGGTGGATCTTCTATACTCAGTCTGCTAATTT

CTTCCAGAAACATCTTCACAGACACATCCAGAAATAATGTTTTACCAGCTATCTCGGTATCCCTTAGCCTAGTCC

ATATTTAAAAATTAATGATCACAAGCAGTTGTTTGTTTCCACAGCAAAACCTGGGTGACAGACCAAGTGACCCAG

ATGACTAGAATTTGACCTTCTTTTGTTGCCCACACCATACTCTGAACTAACATGCTGTGCTGCCTTCCAAGTGGA

GAATGATGGCTAAGTATCTTCTACCTAATTTGAGTCACAGAAAAAAAAAAAAAAAGGTTATTAACTGCAGTGACAA

GAATTGTGATTCCCCAGGGGGCAGATCAAGACTGATAGATAAGAGAAGTGAGGAACATCTGGGGAATGTCCATTG

AAAATTTACTCAGAAGAGAAGAATAATTAATATAATAATATGATATATTGAATTATAATAAATAATATTTTGATG

TATTTCCTTCCAGGCATGTTTAAGTTATAGACTTTGAGTATATTTTCTCAAAGGGGGTTCTATGTAAGAGACTAT

TTCTTAATATAGTTCCTAGCTTGGAATTGCTCTTGCTGGTTTAAGCTGAGCTTATTTTATTACAGACTTCACAAC

AATAACGTTTTCCTTCACTAGTCAGTACACAAGATGGTCTTCATTTCCAGTTTGGAATCCCACACTATCAGAGCC

TGAGACAAGGACTAGTATGCAGTTAGTTTGTTTGGGAGGTGATTCCAGGAAGTGGGAATGAGAGATCAGTCAGCC

TGCAACACGAAGGAGGAAAAGTCAATATAAGGATGAATTTGGCAATTGGCCGTTTCATGCAACTGGGGCTAAATT

TTGCTTGGCTCTCTAAGAAATGTAAAGAATGCCTCCCGTAATTGCTCACCTCAAGTATTTATTCATTGGCTCTCA

TGCTCCATTGGTTGTCCATGAGAACTTTAGCCCTCCCTCGCTGCAGCACAGACACTGTGCTTTCTCCTAGGCTGA

GCAAGCTCCTGCATCTGTGGAAACCGTCCCGGGGCAGATAGTGAAATAATGACTGCTGCGTGCTTGAGATCTGGG

AAAGAGGCCACATCATAAGTGCACTGAAATCAGAGATGTGTCAAGAGATGTGACACAGGGCATCTGAGGTGTCTA

CTGCACCAGCTATAACTCCCTAAACGCTAATCTCAGTTCTTACAGAGGGGATGGATGCAAGGGAACAGTCATGAT

TGAGAGCACCGAAGAAGCTCTGTATGAACCTTAGGCAAGTTTCCTAATCTCCAAAATGAAGGTAATAATACCCAC

CATCCAAGATCTTCGGGAGGAATAGATGAACTAATGTATGTGAAAATGTCCAGCACAGGTCCTAACCCATAGTAG

GTGCTCACCAAATGTTAGTTCCCTGCCCTCCACGTTGTGTGTATCCGGAGCTGCACTAGATGCTGAGGCAAATGG

TCTCAAATGTACTTTAACACTTAATGACTGAGATTTTTTCTGAGCTGCCTACAGGTTATTGACTATATTCATTAT

TAATAATAATATATATGGCCACTTCAGGCAACTGGGGCTAAATTTTGCTTGGCTCTCTAAGAAATGTAAAGAATG

CCTCCTGTAATTGCTCACCTCAAGTATTTATTCATTGGCTCTCGTGCTTTATTGGTTGTCCCTGAGGACTTTAGC

CCTCTCTCACTGCAGCACAGACACTGTGCTTTCTCCTAGTTTCTGTGGCAAGTGACAGGAGCCCACCTCAAACTA

AAGCAAAAGGGACTTCATTGGCTCTTGTAGCTAGGAATTCCAGGGTTGGCACTGGCTTTGGGCACTACTGGATGC

AGGAATTCAAACAATGTCTTCAACTCTTTCTTTTGGTGTTTCTCTCAGCTGTGCTTCTCTTGTCGTTTCTTTTTC

CCATTTTACAGATAAGTTCATCCGTAACTGAGAGAGGTGAAAAGGGGATGGCTGCAGAGAACTCTGGCTTATATC

ATCCTTGCTTGCTGACCTCAAGGTCCATGTATAAATTCTCAGAGAAGAAGCCCTCTGGTTGGTGATGCTTGGAAC

ATGCCCTGGAGGGTGGGCCCCTTGAAGTGGAGCTTGCTGGAACCACATGGGCTGGAGCAAGGCGCTAGGGCCAGA

AGAGAGAGGTAGGCAGGGCTGCTGGCCAGGCACTCTTCACCAAGACAAGGCAAGAGGAGGGGCATGATTGAGGCA

GTGATACAGAAAGCAGACAGTAGAGGTCGTGGCAAGTGTGCCGTTACTTGCTACCTGTGGTTGATGGGAGAGTCA

-continued

CACCACATTTAGGAGGAGAGAATCCATTTGCCACTTCTGACAATGCCACAAGAATCACATATTTCATCCAGAGGT

TGAATTTGGCCCATGCTGAGCTTTAAAATACAGAGCTGTCTTGGAACAATGGCTCAGTACATTCATTTGGTGTCC

AACAAAGCCTGCCTCTGTTGCCTTCCCTCTCTCTGTGTGCCCTTCAAGATCTTCATTGTGCTTTGGGGAGAGAAA

GAGAAAATGTCATATCAGGGTAGCTCACCCCATGTGTCCTGGACTCAGGAAAAGAGTATCTTATCACCTTACTCT

TTTGTTATTATAAAAAATAAAGTTGAACGTCTTCAAATAAAATAAAGAAGTATAGAAAAAATTTTAAATTAACCT

GTTATGATTCTACCTAGAGAACCATTGTCAACATCTTGGTATATGTACTTCCAGATACTTTCCTATGAATATATA

CATTGTAGATTTTTTAATATTAAAAGGCTATCATGCTGCTTTGTATACAGGCTTTCTTTACTGATATGTAATATA

ATACACAGACAAATATACAAATCCTAAGCCATCAACTCATTGAATTTTTATTCATTGTTTTTAATACCTGCATTG

TGTTCCATTGTTAGGCTATGTCACAACATATTTAATTAAGCCCCTATTGATGAATATTAATTTACTCTATTTGCC

AGTTCATTCCAGTCCAACATTTATTGAGTGTCTACTTACGGGCCAGGCACTCTTGTATTCATCAAGATCACCACA

TTATCTGTATCAGTTATTTATTGCCACAATAAAACTGCATAACAAATCACTCCAAAATGTAGCACCTTAAAACTA

CAACTACTTATTATTTCTCAAGAGTCAATGGGTCAGCTGAGCAGTTCTGCCGATAGGGGTCAAGGTCAACACATT

TCAACTAGACTACTTGTAAAAAAGAATGAGTGTCTGGGTAGGTGTGTTCTTCTAAAAATAAAACAAGGAATGAGG

AAATTGCAGGTAGGATAAGAGGGGTGGTTGGCAACCAAACCCCACAAAAGGCAGACAAATTTTAAGGAAACATAA

TGCCAGACTCCTATGTCATCATCCAAGTAGATGCAGTGAAGTATAACCTGGGGCGTAGTAGGGTAGGAGTGGGGA

GAGCAGAGGAGAAGGAAGGGAGATTGCTTTTCATCACTTTTGGATTCCCTAATAACAGACATGACTGCCAGTATT

AAAATTTAACAAAGGATATCTGATCATTAATTTTCCTGTATAAGTCACTGGTGATCTTCAACATCTCTCCCTCCC

TTCCTCCCTTCCTTCCTCCCACCCTCCCTTCCTTCCTTCTTTCCTCTTTTGCTTTCAACTTCCTTTTCTCGTTTC

CTTTTGCTTTCTTTCTCTTCTCCCTTTTTTCTGTCACTCTGGGCGTATGTAGTAGTGTAAAAAGGTTGACAGAGA

AATCAAATATAACAGGAGCAGGGCCCTGAGAAAAGCACCTGGCATCCTGTAGGCAAACCATTGTTTCTAAAAGAA

GGGACTGAGAGATTGAGGAGCTCAGGACATTGCCAAATGAACAAGGCAAGCACATTTATTCAGTACCAAACAAAC

GGAAAACGGCCTTTCCAAATAACTGACCTATAAAACAGCCTTTTCACAAGAGTACCGTAATTACTGGCCAACAGC

AACAATGAAAAACAACTCCCAAACAAAGAAATATTTCTGGATTAAAAGCCATGAGATCTGGATTCTAACAAGCTG

TGCTCCTCAAACTACAAGTACAAAATCTGGCTCTAAACTAACAAGCTATGAGCCTCAAACTGATGACTGGCATGT

TTGGGTCTCCATCTCCTTCTTGGGGGTTGGGGTCTTAGAGACCCTTTTCCACGCCCTGATTCTCTTACTAGTGTG

TATGCTTTCCTTTTGACTTCTCATGCTGACCGTCTGAGCAGGAGTGAGAAGCAATTTCAAAGGAAAACATCGTTT

ATCATCTGCTGAAAGAAACCAAAAAGAACACAGGAAAACAAAAAGACAAGGAAAGGGAATGAAAATGTAATTCAT

TTTATTAAAAAGAAGAATTATTCTTCTGGGACACTGGATAGAAACCTTAATGAGTTACCTAGCTATCATAAATCC

TCTAACAGAGAAGAGAAGAGAAAGAAACAAAGACGGAAGAGGGCAGGATAAAAGAAAGAAAAAAGGAAGGGAAAA

ATGAAGGAAGGAAGTTATCTATTCATTTCTACAGAGACTCTGCTGAGCAGTAGACAAGAAGACTTGGGAAAAATT

TAACTGAAACTTTTCCAAAAATCTTTTCAGAGGGATTTTTTCCCTCTGAAAAGCATCATTAGAGGCTGTTCAATA

CCCAAGGCAAGCCTCTTTCATATTACTTACTGTACATGAAACACTCATGCAATTGAGGCTAGCCAGAGGCCATTT

AGAAATTCAATAATTATTCAACCCAAGGGGCTTTCCAAATGGTGAAGTAGCTTCTTAAGAGGAAATTAATATTGA

GCAGTATAGCAAACCTAATTGGAATCTTGAGAAAATAGTTCTGTGTCGTTAGAACAGCTAGAGGCTAAAGAAGAT

CAGGTTGGATGATACCTTCATTTTTGTCTCTTTCCTTAATTATGATGTAAAGGGAAAAATCTTGTTTATTTTCTA

TGCCAGGAGGGTAGAGGGTGATTTGGAGAGGTTCCAAGTTTATCAAAATCTACCTTCAGTCTGGCAGTAGAAAAG

TTTACTTCCTTCATTTCTTTCCTATAGACATTCAAAGAGAGCTAAGGAGATCCAAAAACCTTTTTTTCTATATTT

GCAATGCAAGGCAGTTGGGAATTAATGACTGATTTGTTGGTGAGGGCAGTGGGCATTGATCACAAAAGCAGTAAA

GCTGTGTTTCTCAAAGAGAGAAAGTCTCTTTGAGATCTTCATTATTTTACTATTTAGAAGAGAAAGGGGCGTTAT

ATCACGTTGGAAGCATCCATGAGTCACTAGTCTCTTCTCTATCTTTCTATGCCTTTCTGTATTAATTACTTTGAA

-continued

AGCACAACATTCCAAACCCATTGAGCACACAGTGGTCTGATTTCTCCACTTGTGAAAGGTGCTAAAGTCTCACTG

TAGGATTAATTTGGGGGTCCAGGCTATGGGCTTGTAGATATGACTACCTTAGACTTTGGTTCTCCTGGCAACTAA

CCCTTTTTGGATCGTATCTAAGTTGACCTGTTTCACAGTGAGAGAACTCCTCTCCATTACTCAGAATACTGAGGC

AGATCACAAGTGTACCACACCTGGCTAATGTTAAGCCAGACAGAAACATCAGGCTCATCTCTTGAGAAGAAGGGT

CGCTTATTAAGGATACAAACTATTTTTTTTTTTTTTTTTTGAGACAGGGTCTCATTGCCCAGGTTAGAGTGCAGT

GGTGCAATCATAGCTCACTGCAGCCTCAACCACATGGGTATTTTTAAATAAGAAAAAAATACCATCTGATAGATA

TGAAGGAGCATTGGGTCACTATAAACAAAACAGATTCTAAGAGCAGGAAGAAAGAGTACAGTCTCTTTTCAATAA

TTTTTTTTTAAACTTGGGAAAGAACACTCACTCTATTCCTATAGACCAGAAAGCAGATAATTGTCCATTATGATT

CCACATGACACTATCTTGTTCAGCTGTCACTGAAACAACTTTGAACACTGTCATATGTTCTTCCCAGCTCCTGAA

CTCTGACCTTTTTATGCCTTAGTTCCACTTTCACAAAAAGGGATTGATGTAATGTGCATTTCAGAGGAAACGACT

ATAGACATTTAGTGTCATTATAAATGTTGAGAAGTATGCTGGCAGAAATTATGCCTTAAGATCATATATGGATTC

TTGTATGGTTTGAAATTGCTTAAAAGATATATATGATCTCTAAAATGTGTGTGTATATATATATGATGTCTTCTT

ATATATCTATATGTGATATATTTATATATATATAAATCTGTGTATATCACATATATAAATTTGCTGTTATTTGAA

TTGCCATTACCTCAGTGCTTAGGGGAAGCCATGCACGTTTGTTTCTTTTCAGTACCCAGAGTTAATTAACATAAG

TTATCACAGAAGCTCCCATAAGCATTGAGACAATTTCTCTATACCTGTGACTATTTAAGGTTTTGAAAACAAAAC

AGAAGCAGGTAAGGAGGAAGTACGCTTTACTATTGAAGATTTATTAGGTACACATTTAGATTTGTGAACTCACAT

TGCTTAGGATGAAAGGGACTCTTGAGGATGTCTGCTGTTTGTTAGTGAACTGCCTGTAACAATTACAATTAGCAC

ACACATGAGCACAATGAACTGGGTAGTCAGACTCAGCCAAAATGAATAGAAATAGCCTCTTACCAAATTTACTTT

GAGTAGCCCTTGGACTCTGAGCACTGCTGCCCAGAGCAATATGACTGTAGGTCCAAGTTTGTCAATGACTATGCA

AATGTGCTTTCTTCGCTTTTACTCTATTGTCATCTGTCTATTACAATGTTGCTATGGTGACACCTTTCCAATATC

CCTGTGCTTCTTTGGTATCCTCTAAGGGGAAGCTGTAATGAAGTGGCTTGGCAAAAGAATCCTCTTGGAATTTTT

TTTTTTTCATATGCTACTGAAAACCAGCATGATTTTCCTCTTATGGGAAATGTATAAAGTATGAGTTGGAAATGA

TGGAAATTAATCTGTACTGACTTGGGCAAGGAATGTGAATGTTATTCATTCTGTTCCAAACTACCTGAAAATATT

CTCTTTCTGTTCCTACTTTCCAGGAGATAACATCTTAAGGGACACTGAAGCTTGTGCGTGTGTGAGTAGAACACG

TGCTGGGGGCTCTTGAGCTCATGAGGGAGGGGCTACATGTCGGTGGGGTGATAACTGTATGCTGGAAACAATGAT

AGGTGGTGACCCTGGAGCACTTACCATGTGACAGGTGTTATGCTAAGCATGTTGTATGCATTCCTTCATTGAATG

ACAGCTACCTATATTATCCTCATTTTATAAGATGAGGTAACAGAGCTTCAGAAAGGTTAGACTCAGCTGCTATGG

GTCTGTCTGACTCTGGTGTTCTTCCTCTTAAAAACTGGGGCACTTTGGAAATGAGATTCCTCGGTGATGAACAGA

AATATTGCTTAGCGGCTGTATTTTTGTATCTGGCAGTTTTCCCATATTTGAGTCTTATATTCACAATCGGTATCT

TTACATTACACAAAAGTGACACAGAATTAGAGTCATTTAATCCAGGGTTGATATCATTAAGTCATGACTATTTAT

TAAATGTTTCTTACAATATCTGAGATGATATTGCAAAAGATGTAAGTGATTTTAGAAGTTCTCACTTCGTAGTTA

GTTGCAGAAACCTCTTTTGGAGGAGGGATGTTTTCTCTATATATCCTAATTTCTACTTAATATATTTCCACACCT

CTTTGAAGTGTGTAGTAAGAATGGTAAAATGCAGTACTTCGTCATTTGGTACAGTTCAATCAATATGCATTAAGA

TGTGATCATATGGGTAATAGAAAAATGTGAAAGATCCAATTCTTTTTCTCCAGAAGGCAGGAAGCTCATATTTGA

TTTCTGTTACTATAAACTATAAAAACGTTTCAAATGTAGTTTACCCGTAACCATCACCCTGCAAGGGTGATATTG

CTCCCCGCCAATTTACGGAGGAGAATACTGAGGCTTTAAGGTTGTAGATAGACCAAGACCACACAAGTAGAGAGT

GGCGGGCTGTGGGTTGAGCTTTAAAATCCAGGTTCATCCATGACTCCCAGTGTGTTCTAGTAAATCCACTAGAAT

CTGAGTATTTTCCAATGATTTATGCTCCGCTCTGTGTCAGGCAGTTCATGGTATTTTTCAACAATCAGAAAATCC

TGGGGAAGGCAAACTGTTTCCCCCTCTCTAGGTGCCTTGGAAGTGGCCGTTGTGGACCCAGAGATCATCCTTTCT

GATCTGACACCTTCTTCACTGCCCTGGCCCAGTGTCTTTTCTGCAAGGCTGGAAGCCCCCTTAGACTGGTCATGT

CCCATCTCTTTCCGGAGGGAAGATGATCCCAAAGACGACTTTTCTCTCCACGGTGCTGCCATACCGCAGGCGGCC

-continued

GCCAGGGGTCCCCGCTCGGCGTCCCCGCGAGACAGTCGAGCCCCGGCCGGCTGCGCGGCGCGCTGGGTGCATGAG

GGGGCTGCTCCGGAGCGACGGCGGCTGCAGCTGGAGCCAGGCGCTCGCCCGTCCGCCGGTTGGCTCGCCGGGACC

TCGCGCACCGGCGGCAGAGTCCCTTGCGTGGATTGGCAAGCGACGCCCCACCTGCCCCGAGCTCACCATTTTCTT

TCGCGCTGGCTGCAGCTGACCCGGCGAAGGGAGCCGACCGGGCCCTGGGCTGGAGGTAAAACCCCACGGTGAGTA

AGAACCCGCTCCAAGCTAGGGGAGGCGGCGCAGCCCGGTGGCTGCTCGCTCCCGATCTCGCCCGGGGGGGGGGGG

AGGTTTGGGGCGCACCTGGGCGCGGGTGCAAGAAGGTGCGGGAGGCGGCGGACCGGTCTTCTGCCCGCCGGCCAC

GGGCTTCCGGGGCTGGAGTCCTCTTCAGACCCCTGCCGGCGCCTGGGTTTCTGGCCGGCTCCTCGTGTGCACTTC

CCGGCAGGAACAAGGGTCGCCCACTTTCCACCCCGGGATCTTGATTTGTCCTTGATTTGAAAAGATATAAATCAA

TAAGATCGTCCTTCTTTCGGGGTGCAAGACTCCGAGCCCATCCCCAGCCGCGGACGCCTGCAGGGTGCGTGTTGG

GCTGTGGGTGGCGGGAAGACAAACTTTTACAAAAGTGCGCCTGGGCTGGGGGACAACGCTTGGGCGTCCTGATCC

TGAGGGAGGAGTCTCGGCTTGGGGCAGCGTAGGGGAAGTCCGCACCGTCAGCCAGGTCGCCCCCGGGGCTGACGA

TGCCTCACGGAGGTGGGGAGCGTGTAAAGGCCGTACAAATCGCGCTTAACTTTGGGGCCAACAACTGTCAAACAT

CTGGAATCCCAGCCCCTCCCTTTCCCTGAACTGGGGAAGAAGGTGAAAACCCTTCAAGTTTTCTTTGATTGCCCC

TTCCCACCTTCAGACCCCTGCTGGGAGGGTAAAGCGCCGACCCCTGGTGCCTGGCAAGTACCAGAGACTCTAAAT

CTCTCGGGATCCCCCCCCTCGCGCTCTTTCCTGACCCTCTCCCCTAACCCTCCCCACAGAGATCTCTCTACGCAG

CCGACTGAGATCGTGGCGAATGGCCTTTTGTTTCTCCGCGTTTCCCCTATTGTTTGCCTTTCCAACATCTGGCGG

GGCTTGGGGAGAGAAGGAAGCCCCTCTGGTCCCCCTCCCCGGCCCCCACGCCAGCTCCGGCAGGGGATCCCAGCT

GGGAAAGTGGAGGAGCCCGACCCCAGCGAGGCCGCCCCACCCCGCCCTTGTGGTTAGAGGGCGGAGGGAAAGTTG

TTCCTTCCCCGCCTCCGCTGCTGCCTGTGGCCCAGGGCGCATTTCTCAGATCTCAGCCCAGGCGCGCCGCAAAGG

CTCAAATCCGAGAAGGTGCTGCTTTCGAGACAGTGGAAGCGCGTTCCGCCCCAATCCAGAGCGTCCAGTGGTTGG

TTCCAGAGGATTTCAATCTCTAGCCAAAGGCGTTGGGGCTGGGCCGCTGCTAGGGCAGTGGGAGGGGATCGGGGC

ACCTTTGGTAGGCGGAAAGCTGAGATTCTGGGGTCCACAAGTTTCCAAGGGCGGGAGGGCAGGCTAGTCGCCAAA

AAGAGAACGAAGATGCAAATAACGAGGAAGCCTTATGACGTTGCCTGGAAATAGTAGTGTGGTGGTTCACTCCGG

AATGAACGTGGAGTTCTGGCTTTGAGTACCGCTCCAAGTTTAAATCCCAAGTCCCCTTTCTTCATTGTAGAAAAA

GAGGACTCAGACGACGCAACACAGATACGGCTAGAGCACAGTTCCTGCTTCCACGTCCCAGAGAACAAGTGGCTT

AGGATGGTCCCGAGTTCCCCTGTGGGTGCGCTTGTTGGGTTGCAGGCGGCCCTGTTTCCCTGCACAAGTCAGATG

CTTACACATTGTGTTCATTCTTAGTGTGGATTATTGATTAAAGAACTGGGGCAAAAGCAAAGTAGCTACTCTGAG

AAGTCAGGGTCCCCAGATGGTGCCCAGCGAGTTGTCTTGCCTCTGAGGGGAGGCTGACTGAGACTGTGCACCTGT

TAGAACCTATGCTACCCCATAGCCTTGCAGTTGACTTGCTGTTGCCAGCTTTTCCTGTGGGATCCCCAATGAGTC

CCTCTTCCAAGGAAGCTCAATTACACTTTTGATTCCTCCTCAACCCAGGGGAAGAAAGAGGCTTCTGTAGGAACA

TTATGATCTATGTACCCACTCAGACATTGTCAGTGGATACCAGAAGCTTGGCTCTGCACAGCTCTGAGAGTTTTC

CCTTTGCGAACTCAACAGAACTTTTGAGTTTCCATTTAACATAAAAGAAGTGAGACTGCTAAGCCAGGAATGCGA

CACATAGAGCACTTTCTCTAGTGATTTCTGGGTATTATATCTCTTTACCTTCCCAACGGTGGAACCAGGAAAAGA

AAAAAAAGCAACATCTTTGAAGTACTGCAAGGCACTTTACAAACATTTCATTATGAAAATGATCCCCAAGGAAGG

ATTCCTTTGAAATTTAGCAGCAGCAACCCAGAAGCAACAAAAAAGACCAAAGTTACTCAAGAAGTACCCAAAGGC

ATCATTAACAAAATAAAAGAGCATTTCTTGTCTTGGCCTACCCCGCTAAGGAAAACAGGGTAATTATAGTGGAAG

TTAAGCTTG

In some embodiments, the human C9ORF72 gene and flanking sequences comprise a sequence that is, e.g., at least 75, 80, 85, 90, 95, 96, 97, 98, or 99% identical to the sequence above. As used herein, the term "percent sequence identity" or "percent identity" or "% identity" is the identity fraction times 100. The "identity fraction" for a sequence optimally aligned with a reference sequence is the number of nucleotide matches in the optimal alignment, divided by the total number of nucleotides in the reference sequence, e.g. the total number of nucleotides in the full length of the entire reference sequence.

In some embodiments, the number of GGGGCC hexanucleotide repeats (e.g., $(GGGGCC)_n$ in SEQ ID NO: 63) is 300-800, 300-700, 400-600, or 500-600. In some embodiments, the number of GGGGCC hexanucleotide repeats (e.g., $(GGGGCC)_n$ in SEQ ID NO: 63) is 500-600. In some embodiments, the number of GGGGCC hexanucleotide repeats (e.g., $(GGGGCC)_n$ in SEQ ID NO: 63) is greater than 300, 400, 500,600, 700 or 800. In some embodiments, the number of GGGGCC hexanucleotide repeats (e.g., $(GGGGCC)_n$ in SEQ ID NO: 63) is greater than 500. In some embodiments, the transgenic mouse is an FVB, balb-C or C57B/6 strain mouse. In some embodiments, the transgenic mouse is an FVB strain mouse. In some embodiments, the mouse can be used to screen for therapies for the treatment of ALS or FTD, e.g., a therapy described herein or a candidate therapeutic agent.

A transgenic mouse as described herein can be made using any method known in the art or described herein, e.g., Example 4 (see also, e.g., PCT Publication Number WO2001010199 and WO2013022715; and US Publication Number US20110113496 and 20060031954, each of which are incorporated by reference herein). For example, a transgenic mouse described herein may be produced by introducing transgenes (e.g., the human C9ORF72 gene, optionally with flanking sequences) into the germline of the mouse. Embryonal target cells at various developmental stages can be used to introduce transgenes. Different methods are used depending on the stage of development of the embryonal target cell. The specific line(s) of any animal used to practice this disclosure are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). The line(s) may themselves be transgenics, and/or may be knockouts (e.g., obtained from animals which have one or more genes partially or completely suppressed). The transgene construct may be introduced into a single stage embryo. The zygote is the preferred target for micro-injection. The use of zygotes as a target for gene transfer has a major advantage in that in most cases the injected DNA will be incorporated into the host gene before the first cleavage (Brinster et al. (1985) PNAS 82:4438-4442). Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote. Thus, the exogenous genetic material should be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane.

Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter. Any technique which allows for the addition of the exogenous genetic material into nucleic genetic material can be utilized so long as it is not destructive to the cell, nuclear membrane, or other existing cellular or genetic structures. Introduction of the transgene nucleotide sequence into the embryo may be accomplished by any means known in the art such as, for example, microinjection, electroporation, or lipofection. The exogenous genetic material is preferentially inserted into the nucleic genetic material by microinjection. Microinjection of cells and cellular structures is known and is used in the art. In the mouse, the male pronucleus reaches the size of approximately 20 micrometers in diameter which allows reproducible injection of 1-2 pl of DNA solution. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1-7 days, depending on the species, and then reimplant them into the surrogate host.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically. DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout: where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

Aspects of the disclosure also relate to polynucleotides, e.g., a bacterial artificial chromosome (BAC) vector, comprising SEQ ID NO: 63.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1

Figure 2A:
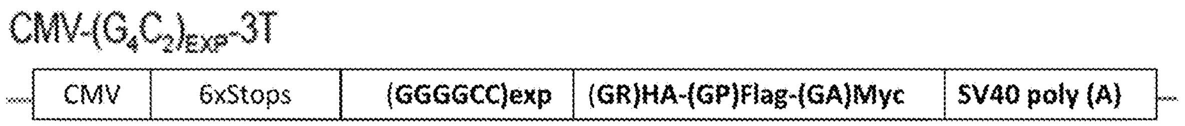
FIG. 2A is a diagram of an expression vector for expressing RAN translation proteins in cells. CMV=cytomegalovirus promoter. 6×Stop=6 stop codons, two in each frame. (GGGGCC)exp=a GGGGCC repeat sequence that extends for 4, 30, 60, or 120 repeats. (GR) HA-(GP)Flag-(GA)Myc=a HA, flag or myc tag that corresponds to the poly-(Gly-Arg), poly-(Gly-Pro), and poly- (Gly-Ala) repeat proteins, respectively. SV40 poly(a) =transcription terminator and poly A signal.
Figure 2B:
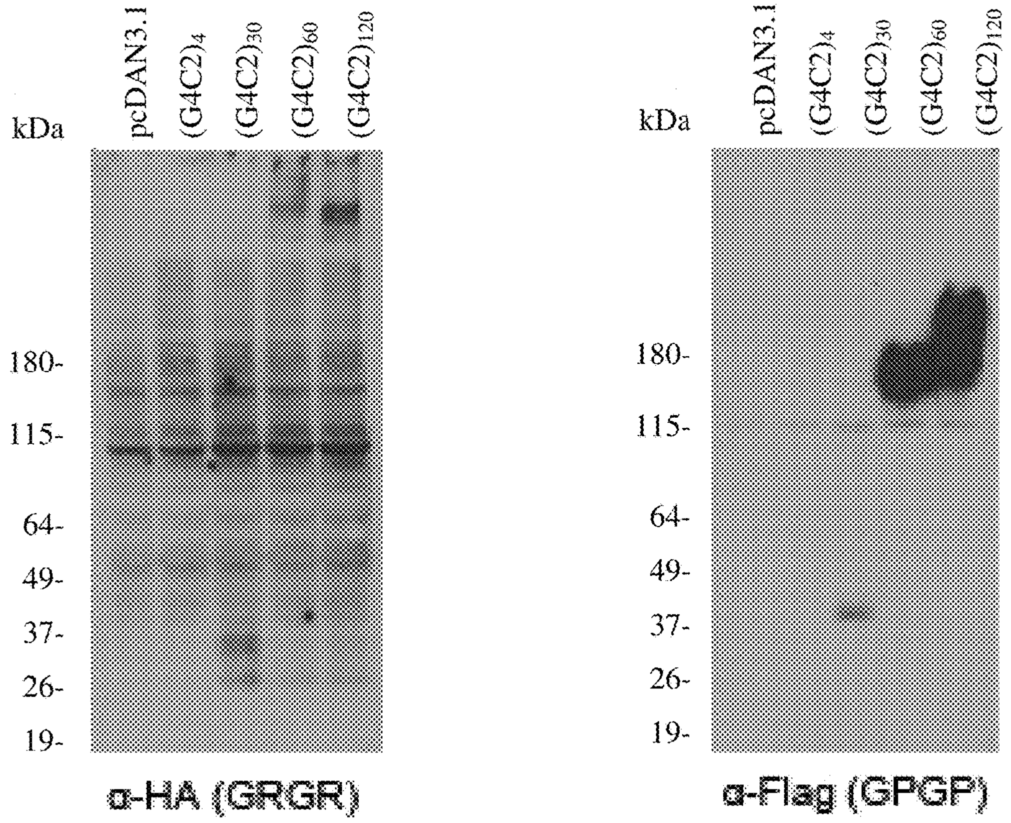
FIG. 2B is a photograph of a western blot depicting that GR and GP RAN translation proteins are expressed in cells transfected with 30, 60 or 120 GGGGCC repeat sequences.
Figure 3:
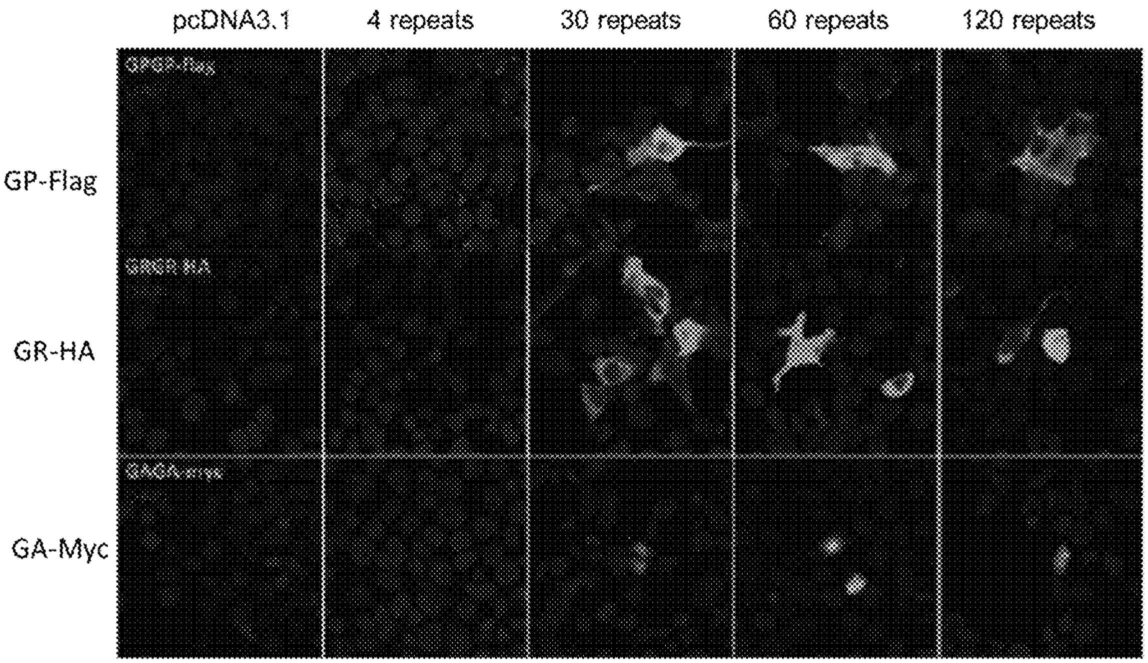
FIG. 3 is a photograph of an immunofluorescence staining of cells expressing GP, OR, or GA RAN proteins in cells transfected with 30, 60 or 120 GGGGCC repeat sequences.

A construct containing a CMV promoter, a (GGGGCC) expansion motif containing either 4, 30, 60, or 120 repeats of GGGGCC, and an HA, FLAG, or MYC tag were transfected into cells (FIG. 2A). It was shown by western blot that poly-(GR) and poly-(GP) proteins were produced in cells transfected with constructs containing 30, 60 or 120 repeats of GGGGCC (FIG. 2B). It was further shown using immunofluorescence of cells that GP-flag, GR-HA, and GA-Myc proteins were expressed in cells transfected with constructs containing 30, 60 or 120 repeats of GGGGCC (FIG. 3). These results show that GGGGCC repeat regions are capable of initiating translation independent of an AUG start codon (repeat-associated non-ATG (RAN) translation), and that poly-(GP), -(GR), and (GA)-repeat proteins are produced.

Figure 4:
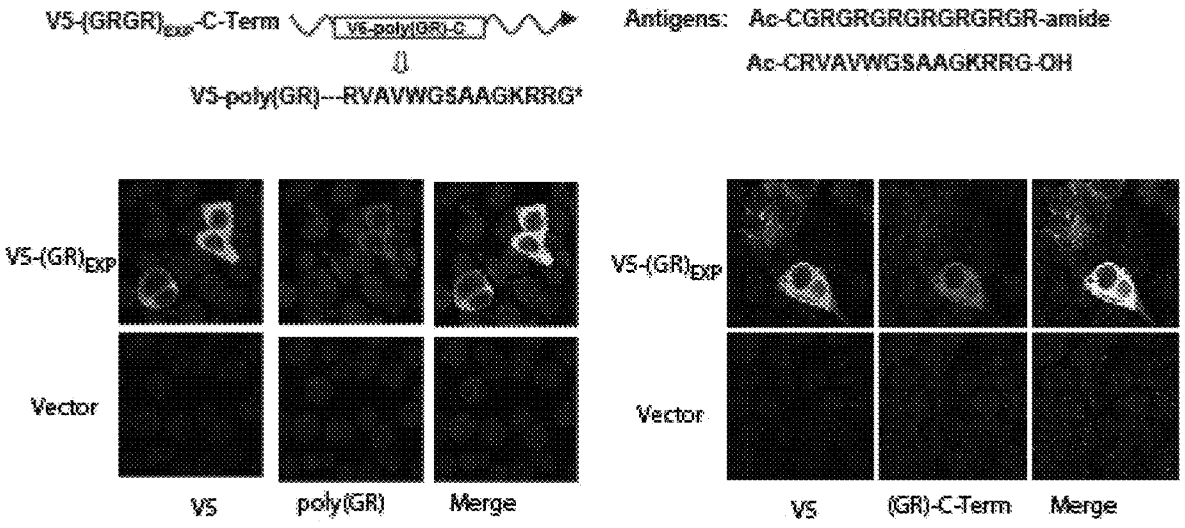
FIG. 4 is a diagram of the poly-(OR) and OR-c-terminus antigens and a series of photographs of immunofluorescence staining showing that the poly-(OR) and (GR)-c-terminal antibodies detect poly-(GR) RAN proteins.

Antibodies to a poly-(GR) sequence or to the C-terminus of the poly-(GR)-repeat protein were generated. Fluorescent staining using these antibodies showed that these antibodies were capable of detecting the poly-(GR) repeat protein (FIG. 4).

Figure 5:
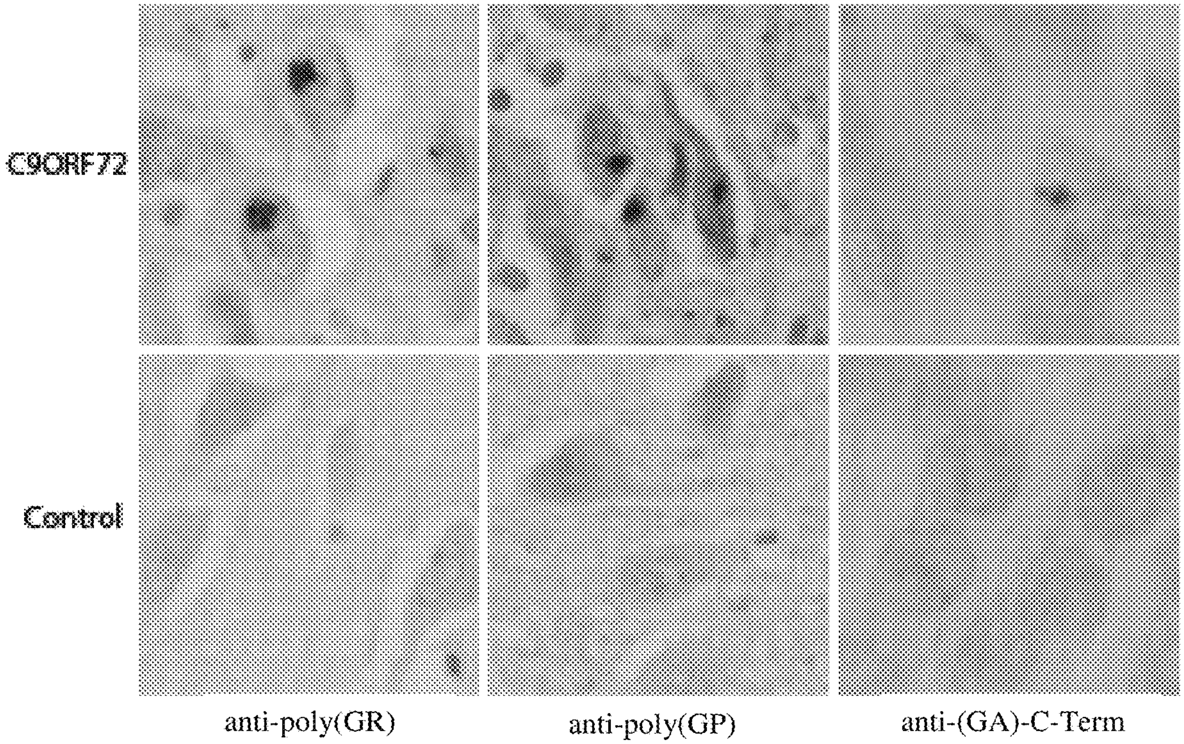
FIG. 5 is a series of photographs of tissue from C9ORF72 ALS patients or control patients showing that poly-(OR), poly-(GP), and poly-(GA) di-amino acid-repeat-containing proteins are expressed by C9ORF72 ALS patients.

Antibodies were further generated to a poly-(GP) sequence and the C-terminus of the poly-(GA)-repeat protein. The anti-poly-(GR), anti-poly-(GP), and anti-poly-(GA)-C-term antibodies were then used to stain sections of brain tissue from patients with C9ORF72 ALS or controls (FIG. 5).

Figure 1:
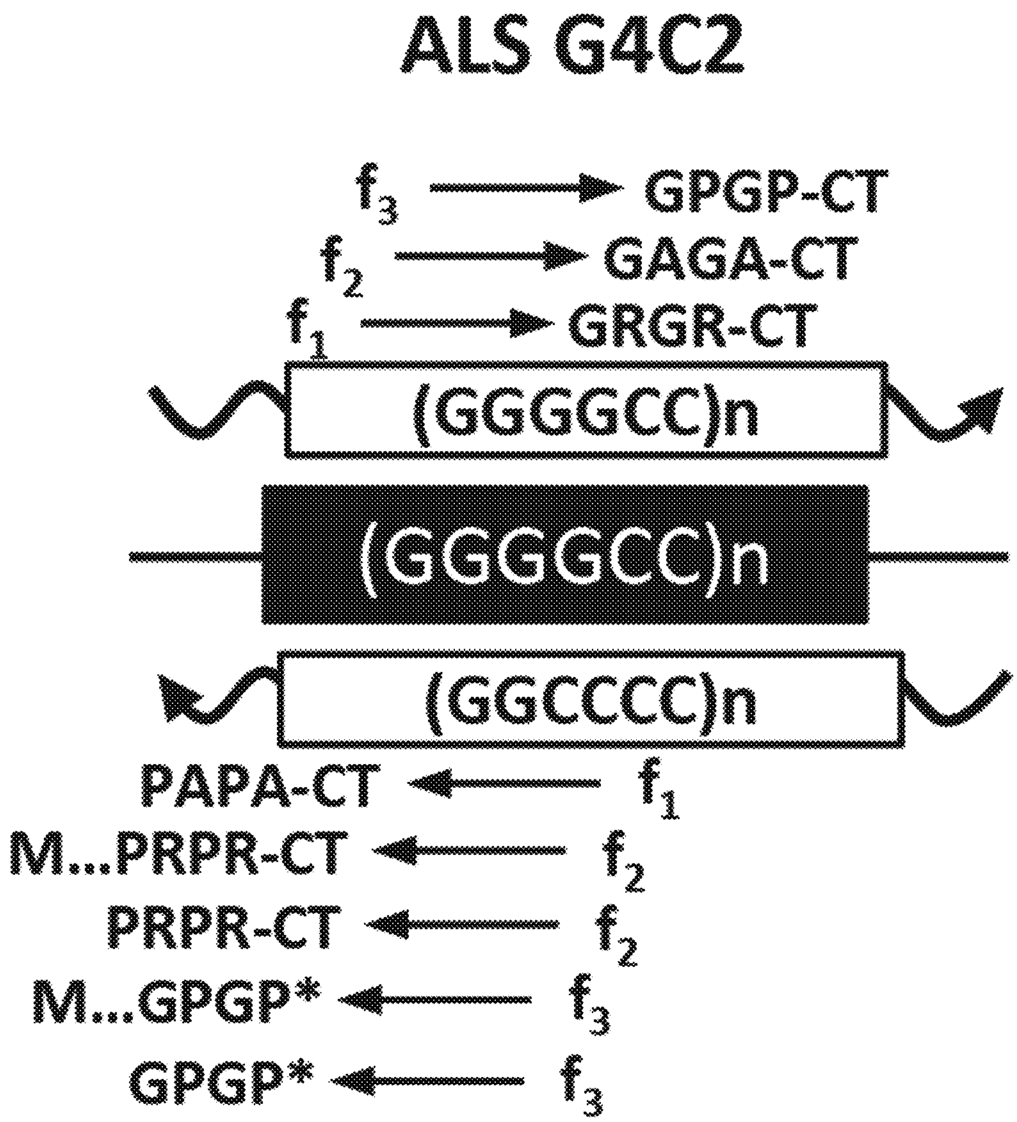
FIG. 1 is a drawing showing that transcripts are produced in the sense and anti-sense direction on the C9ORF72 gene, and that repeat-associated non-ATG (RAN) translation proteins are translated in all three reading-frames from both the sense and anti-sense C9ORF72 transcripts. The drawing also shows that Met . . . poly-(Pro-Arg) and Met . . . poly-(Gly-Pro) proteins are translated through ATG-initiated translation on the anti-sense transcript. CT=predicted to and/or shown to contain a c-terminal domain. *=end of protein (due to stop codon). M=Methionine.
Figure 6:
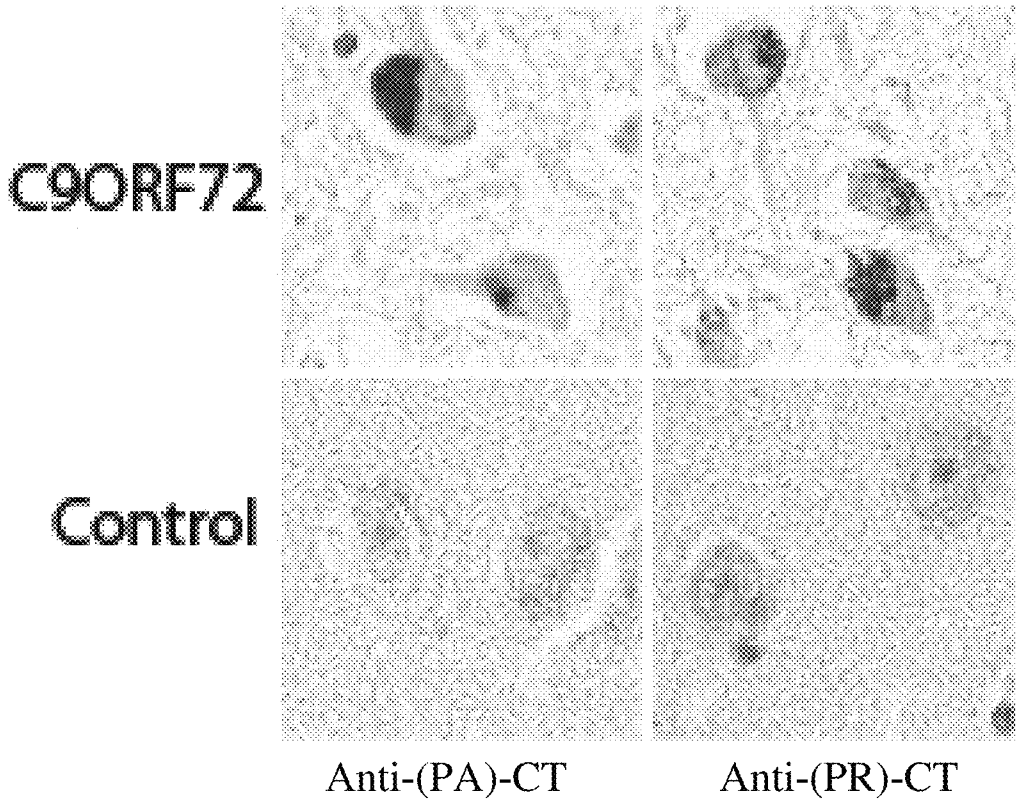
FIG. 6 is a series of photographs of tissue from C9ORF72 ALS patients or control patients showing that poly-(PA) and poly-(PR) di-amino acid-repeat-containing proteins are expressed by C9ORF72 ALS patients.

It was then hypothesized that transcripts of C9ORF72 may be produced in both a sense and anti-sense direction (see FIG. 1). It was further hypothesized that these anti-sense transcripts may also undergo RAN translation to produce further repeat proteins from the 5'-GGCCCC-3' repeats present in the anti-sense transcript. As shown in FIG. 6, both poly-(PA) and poly-(PR) proteins were detectable in brain tissue samples from patients with C9ORF72 ALS but not in controls. These results indicate that di-amino acid-repeat-containing proteins, such as RAN proteins are produced from both a sense and anti-sense transcript produced from the C9RF72 locus.

Figure 7A:
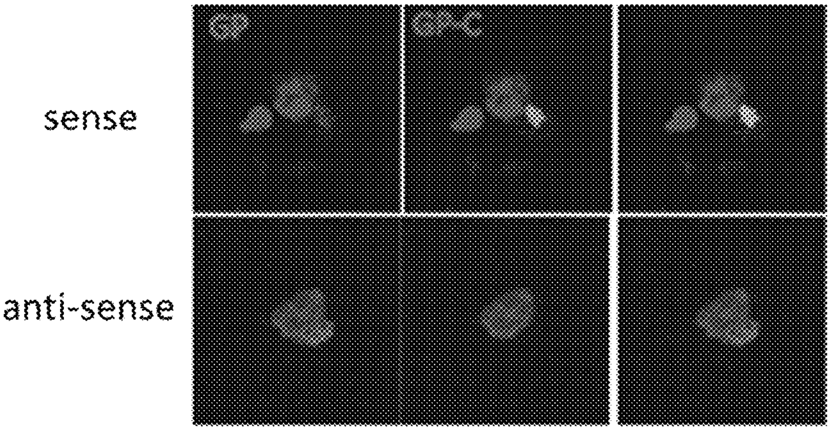
FIG. 7A is a series of photographs of immunofluorescence staining showing antibodies generated to recognize the GP repeat motif (GP) or the unique C-terminal region of the same GP-RAN proteins (GP-C) colocalize in 20% of patient cells. Cells that stain for and GP-C and GP express GP-RAN protein in the sense direction and that cells showing only GP staining express RAN-GP or Met . . . GP from the anti-sense strand.
Figure 7B:
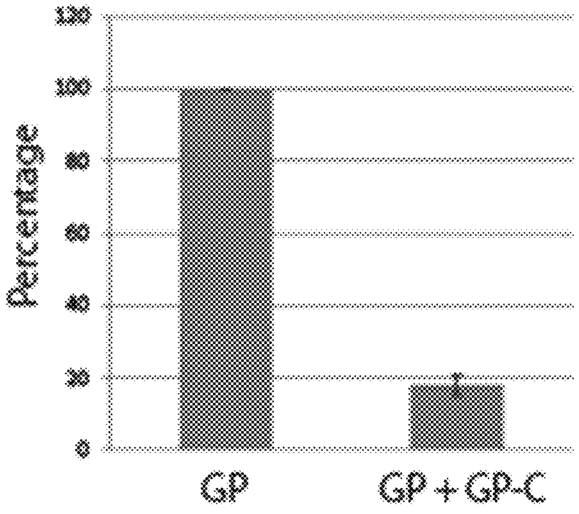
FIG. 7B is a graph depicting the percentage of GP and GP+GP-C in patient cells.

FIG. 7 shows that approximately 20% of aggregates detected with the anti-GP antibody (GP) also co-localize with antibodies directed against the unique C-terminus of the sense GP protein (GP-C). Consistent with the increases levels of antisense transcripts that seen in affected brains, these co-localization data suggest the more ~80 percent of the GP dipeptide aggregates are expressed from C9ORF72 antisense transcripts.

Figure 12:
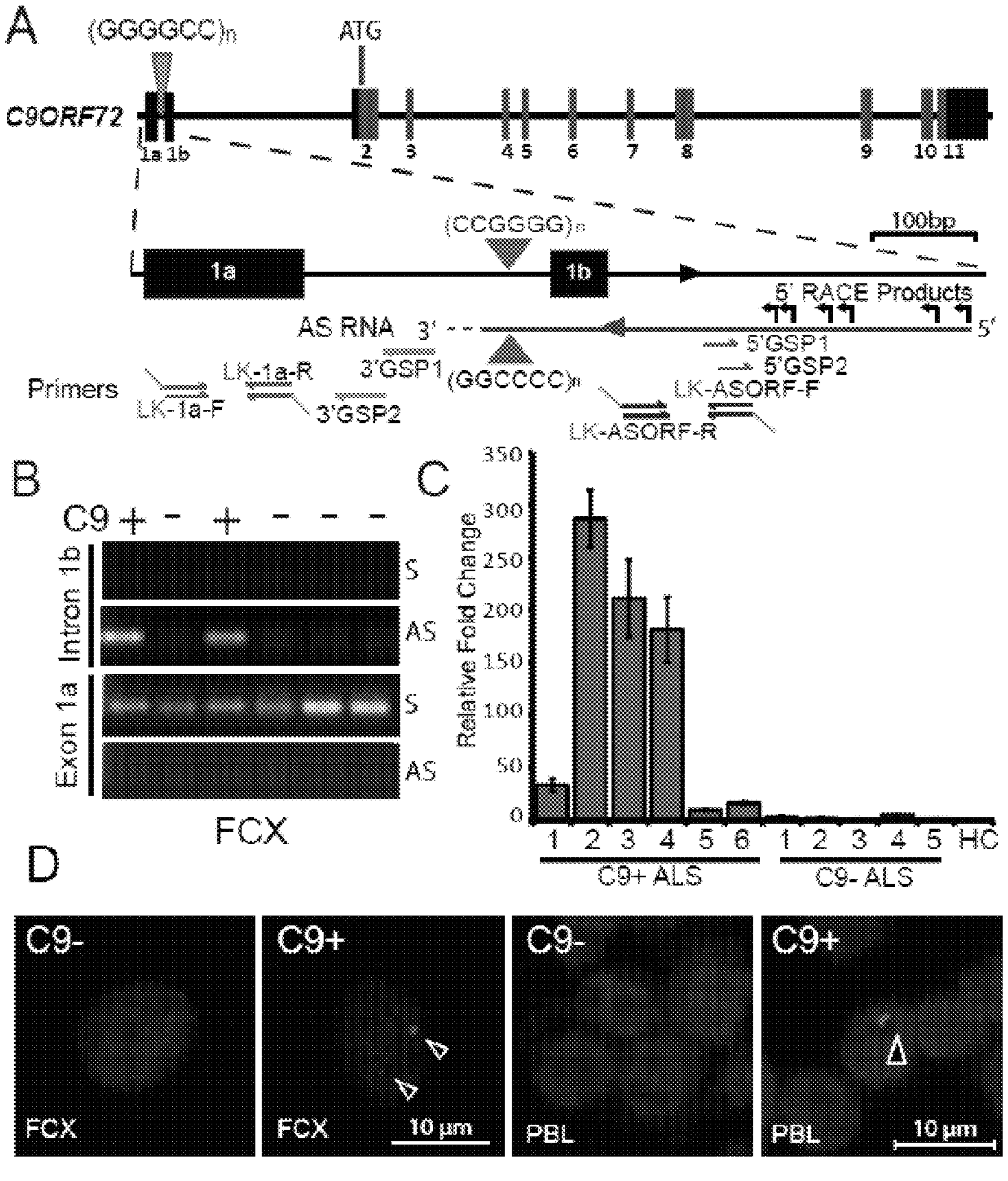
FIG. 12 is a series of schematics, graphs and images showing that G2C4 antisense transcripts are elevated by strand specific RT-PCR and accumulate as RNA foci in C9ORF72 patient tissues. (A) Schematic diagram of C9ORF72 gene and antisense transcripts and relative location of primers for strand-specific RT-PCR and RACE primers. (B) Strand-specific RT-PCR of sense (S) and antisense (AS) transcripts (across intron 1b and exon 1) from frontal cortex of C9(+) and C9(−) ALS patients. (C) strand-specific qRT-PCR showing elevated antisense mRNA in C9(+) compared to C9(−) ALS patients. (D) In situ hybridization with G4C2-Cy3 probe showing G2C4 antisense RNA foci (arrowheads) in C9(+) frontal cortex and peripheral blood leukocytes (PBLs) which are absent in C9(−) cases. Nuclear foci in FCX are indicated by arrow heads. FCX=frontal cortex. PBL=peripheral blood leukocytes.

Additionally, the anti-sense transcript was found to be dramatically elevated in subjects with ALS compared to controls (FIG. 12). The primers for the qPCR assay for detecting the anti-sense transcript levels are shown in the table below.

| | | |
|---|---|---|
| ORF F2 | AGTCGCTAGAGGCGAAAGC (SEQ ID NO: 36) | primer in c9orf72 antisense orf |
| ORF R2 | CGAGTGGGTGAGTGAGGAG (SEQ ID NO: 37) | |
| ORF F2 + IK | CGACTGGAGCACGAGGACACT GAAGTCGCTAGAGGCGAAAGC (SEQ ID NO: 38) | |
| ORF R2 + 1k | CGACTGGAGCACGAGGACACT GACGAGTGGGTGAGTGAGGAG (SEQ ID NO: 39) | for RT 1st strand |
| Linker | CGACTGGAGCACGAGGACACT GA (SEQ ID NO: 40) | for RT-pcr with ORF F1 and F2 |

Further, di-amino acid repeat-containing proteins were found to be present in the blood (including in the serum and plasma) and in the brain of subjects with ALS (FIGS. 9 and 10) but not in control subjects.

Example 2

Figure 8:
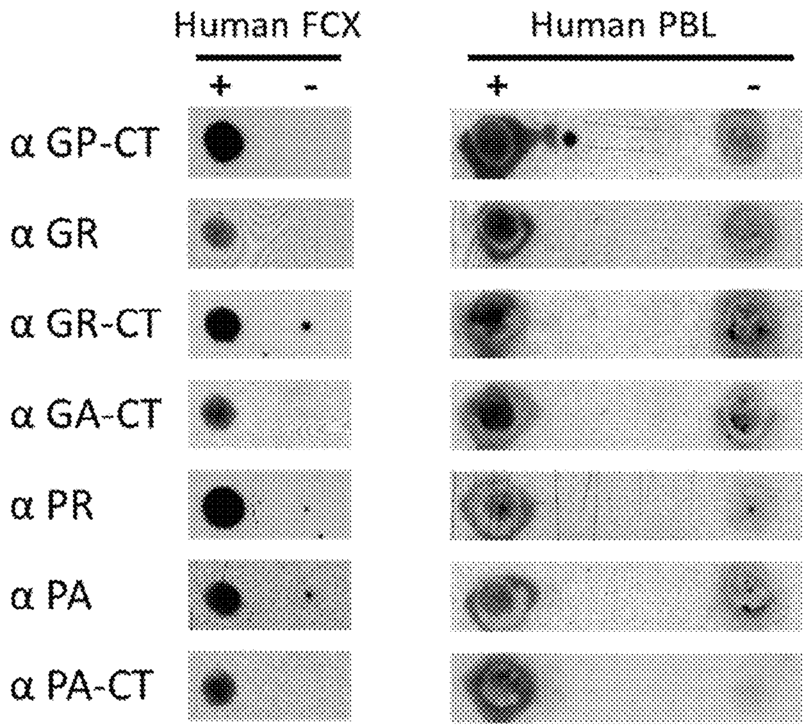
FIG. 8 is a picture of a dot blot showing that di-amino acid repeat-containing proteins are found in the blood (PBL) and the brain (FCX, frontal cortex) of subjects with ALS, but not controls.
Figure 9:
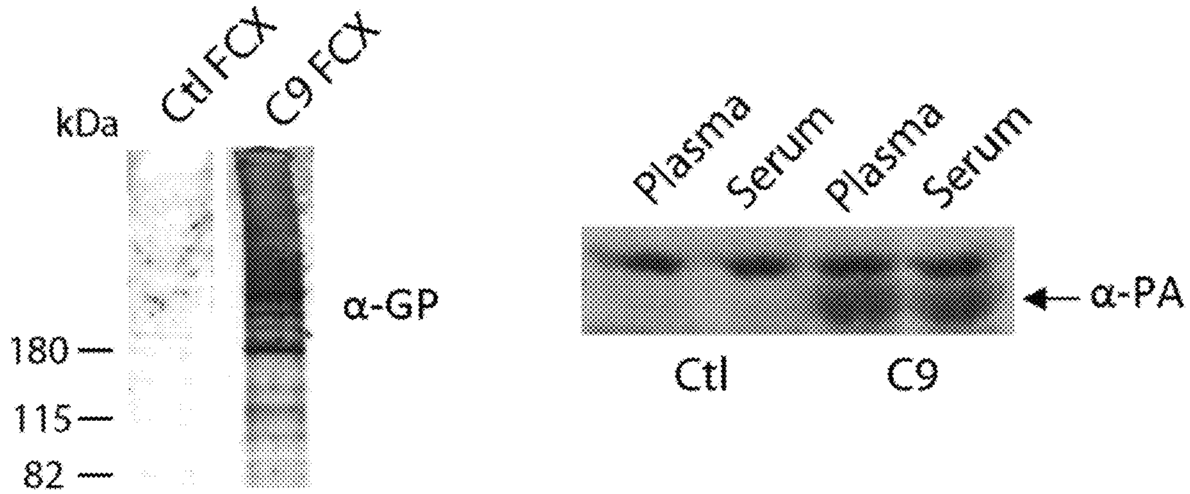
FIG. 9 is a photograph of a western blot showing that GP-repeat proteins are present in the brain (FCX) of subjects with ALS but not controls and that PA-repeat proteins are present in the plasma and serum of subjects with ALS but not controls.

According to some aspects of the disclosure, di-amino acid repeat-containing protein (such as RAN protein) accumulation in blood and cerebral spinal fluid (CSF) substantively contribute to C9ORF72 ALS/FTD and that plasmapheresis and bone marrow transplantation will reverse progression of the disease. Accoiding to some aspects of the disclosure, di-amino acid repeat-containing protein accumulation in blood and circulating CSF infiltrates the brain parenchyma and leads to protein accumulation, neuroinflammatory changes, CNS dysfunction and neuronal death. Aspects of the disclosure are based in part on the following. First, blood brain barrier (BBB) impairment is an early feature of disease in ALS patients (4, 5) and higher rates of ALS and other neurological diseases are found in patients who have had traumatic brain injuries (6). In some embodiments, without wishing to be bound by theory, ALS is in part caused by BBB disruptions that allow for the CNS entry of immune cells and other harmful substances that accelerate ALS/FTD. Secondly, as described herein di-amino acid repeat-containing proteins were found to accumulate in ALS patient blood samples (FIGS. 8 and 9).

Although plasmapheresis and bone marrow transplants have been tested as therapeutic strategies for ALS in the past, it is not clear if any of these cases were C9ORF72 positive or if treatment was early enough to have an effect. Accordingly, in some embodiments, ALS treatment (e.g., plasmapheresis or BMT) is initiated when above-normal levels of one or more di-amino acid repeat-containing proteins are detected in the blood of a subject.

The data presented herein on di-amino acid repeat-containing protein accumulation in C9ORF72 ALS patient tissues and blood indicates that reduction of blood (and perhaps also CSF) di-amino acid repeat-containing-protein load may help treat ALS in C9ORF72 ALS patients. According to some aspects of the disclosure, reduction may be achieved, for example, using plasmapheresis or a bone marrow transplant.

Methods

A detailed evaluation is performed on gene carriers from a C9ORF72 family (CNSA-1) and patients in the clinic including a gene-positive patient with early signs of motor neuron disease or fronto-temporal cognitive dysfunction, or both. Di-amino acid repeat-containing protein expression is correlated with repeat length in CNSA family samples and additional samples collected in clinic. Di-amino acid repeat-containing protein expression in blood is determined in longitudinally collected samples and correlated with disease onset and clinical severity. These methods are expected to characterize di-amino acid repeat-containing protein expression in C9ORF72 positive expansion study subjects and to determine if di-amino acid-repeat-containing protein expression occurs throughout life or increases with age and if di-amino acid repeat-containing protein levels quantitatively correlate with disease severity.

Plasmapheresis is tested to determine if lower di-amino acid repeat-containing-protein load in the blood and CSF reverses signs of the disease. Plasmapheresis is performed on five C9ORF72 positive individuals with early signs of the disease. Six plasmaphereses, each with 2-litter exchange with normal human albumin, is performed over two weeks, followed by one plasmapheresis weekly for the next six months. The study may be prolonged, if required. The primary outcome measure is the Appel ALS Rating Scale (AALSRS). Clinical evaluations including neurological examination, speech evaluation, neuropsychological testing, the ALS Functional Rating Scale (ALSFRS), EMG, and needle muscle biopsy for immunohistopathological evaluations of the vastus lateralis muscle are performed to assess disease progression immediately before and after the treatment period. Venipuncture and lumbar puncture are also performed before and after the 6-month (or if applicable, also after the prolonged) treatment period to assess the concentration of serum and CSF levels of RAN translation and ATG-translation products.

Bone marrow transplant in an animal model is tested to determine if BMT prevents di-amino acid repeat-containing-protein accumulation in blood and the brain. In a first cohort of animals, bone marrow from RANT-positive mice are ablated and replaced with wild-type donor marrow to test if protein aggregate load in the brain decreases. In a parallel set of experiments, RANT-negative animals are transplanted with RANT-positive bone marrow to test if CNS protein accumulation occurs in animals that only express the transgene in hematopoietic cells. Both groups of treated animals are compared to wild-type and untreated RANT control animals using a combination of behavioral, functional and neuropathological assessments.

Figure 10:
FIG. 10 is a schematic of the RAN translation mouse model construct containing 6× stops, a CAG repeat region, tags for detecting each CAG repeat frame, and a terminator sequence.
Figure 11:
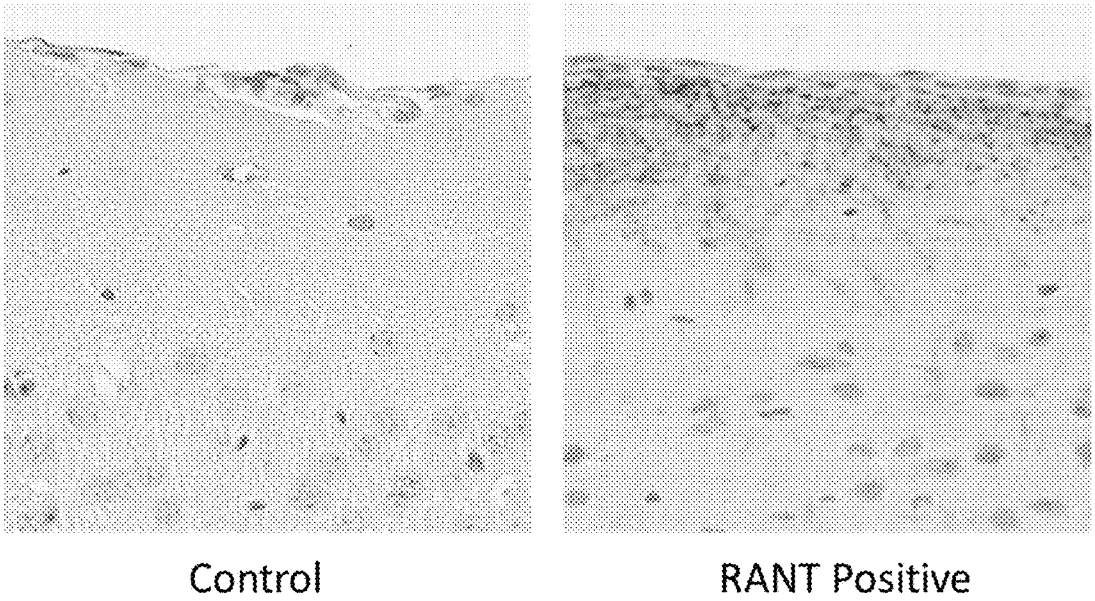
FIG. 11 depicts two photographs showing that poly-Gln proteins accumulated in the brain of RAN translation (RANT) mice containing the construct in FIG. 10, but not in control mice.

A RAN translation mouse model has been generated. Transgenic mice were generated using a construct containing 6 stop codons (two in each reading frame) immediately upstream of a CAG expansion mutation and followed by 3 separate epitope tags in each reading frame (FIG. 10). The CAG repeat generates poly-Gln RAN proteins, which have been previously associated with diseases in humans such as fragile X syndrome. The RANT mouse model produced poly-Gln RAN proteins, which were found to localize at high levels under the pia surface in the brain which is exposed to the cerebral spinal fluid (FIG. 11). This RANT mouse model is used in the studies outlined in Example 2. Accordingly, detection of poly-amino acid repeat containing proteins (e.g., mono- or di-amino acid repeat containing proteins) may be indicative of a risk for a brain disorder associated with the poly-amino acid repeat containing proteins. Accordingly, methods described herein may be used to detect or treat other neurological diseases.

Example 3

Introduction

The chromosome 9p21-linked form of ALS/FTD, the most common cause of familial FTD and ALS identified to date, is caused by an expanded GGGGCC ($G_4C_2$) hexanucleotide repeat in intron 1 of chromosome 9 open reading frame 72 (C9ORF72) (1, 2). The C9ORF72 mutation is found in 40% of familial and 7% of sporadic ALS cases and 21% of familial and 5% of sporadic FTD patients (3). The discovery of the C9ORF72 expansion has generated substantial excitement because it connects ALS and FTD to a large group of disorders caused by microsatellite expansion mutations (4).

Traditionally, microsatellite expansion mutations located in predicted coding- and noncoding regions were thought to cause disease by protein gain-, or loss-, of-function or RNA gain-of-function mechanisms (4). Protein loss-of-function has been proposed to underlie C9ORF72-driven ALS/FTD because the expansion mutation leads to decreased levels of variant 1 transcripts and potential decreases in C9ORF72 protein expression (1, 2). Additionally, because the C9ORF72 $G_4C_2$ expansion mutation is located in an intron, several studies have pursued the hypothesis that C9-linked ALS-FID results from a toxic RNA gain-of-function mechanism in which $G_4C2$ expansion RNAs sequester important cellular factors in nuclear RNA foci. Multiple $G_4C_2$ RNA binding proteins have been identified, but so far there is no demonstration that any of these candidates directly bind endogenous expansion transcripts or co-localize with RNA foci observed in patient cells or autopsy tissue (5-8).

In this mechanism, hairpin-forming microsatellite expansion transcripts express proteins in one or more reading frames without an AUG-initiation codon (9). While a variety of names have recently been ascribed to these RAN translated proteins (e.g. homopolymeric, dipeptide. RANT), it is proposed that all proteins expressed across microsatellite expansion mutations in the absence of an ATG-initiation codon be referred to as RAN proteins to prevent confusion as additional expansion mutations that undergo RAN translation are identified.

Here it is shown that C9ORF72 ALS/FTD antisense transcripts containing the GGCCCC ($G_2C_4$) expansion accumulated in patient brains as nuclear, and infrequent cytoplasmic, foci. Additionally, a novel panel of antibodies directed to both the repeat motifs and unique C-terminal regions was developed and both sense and antisense RAN proteins were demonstrated to accumulate in C9ORF72 patient CNS autopsy tissue. The discovery of antisense $G_2C_4$ RNA foci and three novel antisense RAN proteins in C9ORF72 patient brains suggests that bidirectional transcription and RAN translation are fundamental pathologic features of C9ORF72 ALS/FTD.

Results

Antisense RNA Foci in C9ORF72-Expansion Patients

Figure 19D:
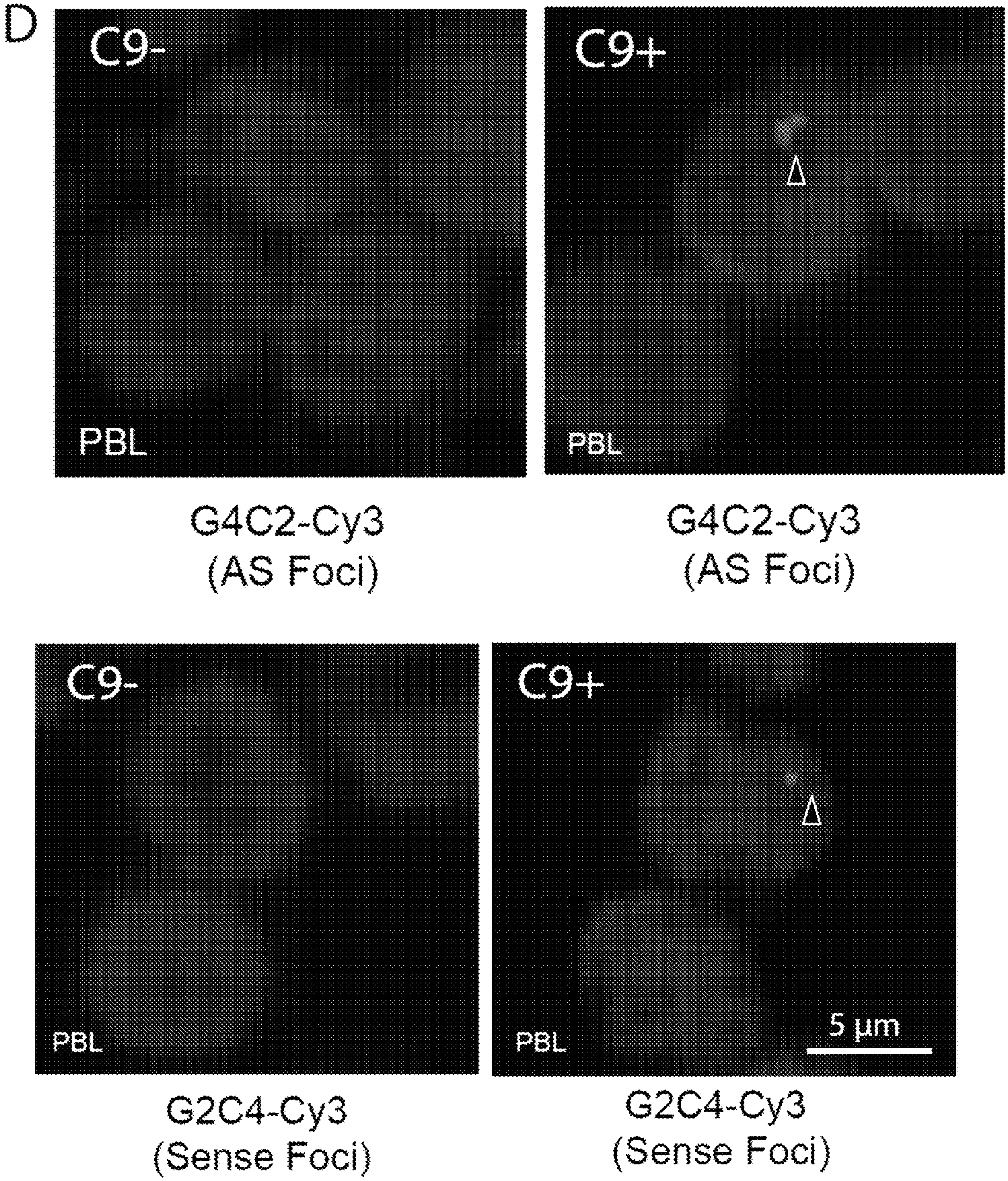

A series of experiments was performed to test the hypotheses that antisense (AS) C9ORF72 expansion transcripts form AS $G_2C_4$ RNA foci and express AS proteins by RAN translation or from short AS open-reading frames (AS-ORFs). First, it was confirmed that C9ORF72 antisense transcripts are expressed using a linkered strand-specific RT-PCR strategy to compare expression of the sense and antisense transcripts in intron 1b, 5' of the antisense $G_2C_4$ expansion, and exon 1a. For the antisense strand in intron 1b, strand-specific RT-PCR was performed using LK-ASORF-R primer for the RT reaction and ASORF-F and the LK for PCR to specifically amplify antisense-cDNAs (FIG. 12A). Similar strategies were used to amplify sense transcripts from the same region of intron 1b and sense and antisense transcripts in exon 1a. Intron 1b antisense transcripts were detected by RT-PCR in frontal cortex from C9(+) ALS/FID patients but not C9(−) ALS/FTD or normal controls (FIG. 12B) and qRT-PCR shows these transcripts are dramatically increased among six C9(+) ALS/FTD cases (FIG. 12C). In contrast, intron 1b sense transcripts were not detected by RT-PCR (FIG. 12B) in frontal cortex. In blood, both intron 1b sense and antisense transcripts are detectable and the dramatic C9(+) elevation of the intron 1b antisense transcripts was not observed. 5' RACE showed intron 1b AS transcripts begin at varying sites 251-455 basepairs (bp) upstream of the $G_2C_4$ repeat (FIGS. 12A, 19B). In contrast, 3'RACE, using 3'GSP1 or 3'GSP2 primers located 40 and 90 bp 3' of the $G_2C_4$ repeat, did not detect transcripts. These data showed that the 3' end of the AS transcript does not overlap the sense exon 1a region, located 170 bp 3' of the antisense $G_2C_4$ repeat. Consistent with this result, sense but not antisense transcripts are detected by strand specific linkered-RT-PCR using primers overlapping exon 1a (FIG. 12B). To determine if antisense transcripts include the $G_2C_4$ repeat expansion. RNA fluorescence in situ hybridization (FISH) was performed using a Cy3-labelled (G4C2)4 probe to detect putative antisense $G_2C_4$ RNA foci. The results showed nuclear (FIG. 12D) and rare cytoplasmic (FIG. 19C) $G_2C_4$ RNA foci accumulate in C9(+) but not C9(−) ALS frontal cortex. The detection of foci in the cytoplasm showed that antisense expansion transcripts can be found in the same cellular compartment as the protein translation machinery, presumably where RAN translation occurs. Because RNA foci in peripheral tissues may provide biomarkers of the disease, peripheral blood leukocytes (PBLs) were examined and both sense and antisense RNA foci were detected in C9(+) but not C9(−) PBLs (FIG. 12D, FIG. 19D). It was discovered that the RNA-FISH signal from the Cy3-G4C2 probe detecting AS-foci may be competed with excess unlabeled G4C2 oligo, and these foci were resistant to DNase I and sensitive to RNase I digestion (FIG. 19E, F). Taken together, this shows that C9ORF72 antisense transcripts are elevated in the frontal cortex in C9(+) ALS but not C9(−) ALS or normal controls. It was also shown for the first time that antisense transcripts containing the $G_2C_4$ expansion mutation are expressed and accumulate in nuclear and rare cytoplasmic RNA foci in C9(+) frontal cortex. Additionally, it was shown that sense and antisense foci accumulate in blood, providing potential biomarkers of C9ORF72 ALS/FTD in a readily accessible tissue.

RAN Translation of GGCCCC Repeat Expansion In Vitro

To test if the antisense $G_2C_4$ expansions undergo RAN translation, a triply tagged $G_2C4$ minigene was generated, $(G_2C_4)_{EXP}$-3T, lacking an ATG initiation codon, by inserting a 6× STOP codon cassette (two stops in each frame) upstream of $G_2C_4$ expansions of 40 or 70 repeats and three different C-terminal epitope 8 tags to monitor protein expression in all reading frames [e.g., ($G_2C_4$EXP transcripts translated in three frames results in Gly-Pro (GP), Pro-Ala (PA) and Pro-Arg (PR) RAN proteins] (FIG. 13A). Immunoblotting detected two epitope-tagged RAN proteins, PR-Myc and GP-Flag, but not PAHA (FIG. 13B). The (PR)40- and (PR)70-3×Mye proteins migrated at approximately their predicted sizes of 20 and 27 kDa, respectively. In contrast, the (GP)40- and (GP)70-3×Flag proteins migrated substantially higher than their predicted sizes (10-15 kDa) at 50 and 75 kDa, respectively (FIG. 13B). The faint lower molecular weight bands on this blot may result from repeat contractions seen during bacterial culture or differences in translational start site. Immunofloresence (IF) showed antisense RAN proteins are expressed in all three reading frames (FIG. 13C). The detection of PA-HA by IF but not western blotting may be caused by a lower frequency of cells expressing RAN PA-HA from these constructs. Additionally, recombinant GP-Flag and PA-HA proteins had a cytoplasmic localization whereas PR-Myc proteins were distributed in both the nucleus and cytoplasm. These localization differences may result from different properties of the repeat motifs or the C-terminal flanking sequences found in this epitope tagged construct. In an additional series of experiments also it was shown that sense G4C2-expansion constructs containing 30, 60 and 120 repeats express GP-Flag, GR-HA and GA-Myc RAN proteins (FIG. 20). In summary, these data showed that recombinant $G_2C_4$ and $G_4C_2$ expansion transcripts express RAN proteins in all six reading frames.

Dual Immunological Strategy to Detect RAN Proteins Since amino acid repeats can be found in a range of different proteins, a dual immunological strategy was used and antibodies that recognize the predicted repeat motifs described herein or their corresponding unique C-terminal regions were developed. A schematic diagram showing eight putative C9ORF72 RAN proteins is shown in FIGS. 13D and 21. Predicted proteins include six putative RAN proteins and two putative proteins with additional ATG-initiated N-terminal sequence. Unique C-terminal regions are predicted in five of the six predicted reading frames. To test for the accumulation of these proteins in vivo a series of polyclonal antibodies against the predicted repeat motifs or available corresponding C-terminal regions, were developed (FIGS. 13D, 21). Antibodies to test for putative antisense proteins [rabbit α-PA, α-PA-CT, α-PR, α-PR-CT, α-GP α-GP-CT (sense), and mouse α-GP] were generated and their specificities demonstrated in cells transfected with constructs expressing epitope-tagged recombinant protein by western blot and IF detection (FIGS. 13E, 22). Additional antibodies detecting repeat and C-terminal regions expressed in the sense direction are characterized in FIG. 23.

Antisense $G_2C_4$ RAN Proteins Accumulate in Brain

Several approaches were used to determine if novel antisense (AS) proteins are expressed in C9ORF72 expansion positive autopsy tissue. To overcome the obstacle that aggregated proteins are difficult to isolate from human brain, a sequential protein extraction protocol (23) was used on frozen C9(+) and C9(−) ALS frontal cortex autopsy samples. Antisense PA and PR proteins were detected with α-PA, α-PA-CT, α-PR, α-PR-CT on immuno-dot blots of 1% Triton-X100 insoluble, 2% SDS soluble extracts from a subset of C9(+) but not C9(−) ALS patients (FIG. 14A). Additional immuno-dot blots showing evidence for sense-RAN protein (GP. GR, GA) 10 accumulation in C9(+) ALS/FTD frontal cortex are shown in FIG. 24. α-PA, α-PR and α-GP antibodies also detected high molecular weight smears in 2% SDS insoluble fractions from C9(+) ALS frontal cortex samples after resuspending the pellets in sample buffer containing 8% SDS (23) (FIG. 3B). The differences in migration pattern seen for the recombinant proteins (FIG. 13B), which migrate as one or more bands, and the smears observed in patient tissue extracts (FIG. 14B) reflect differences in the RAN proteins due to much longer repeat tracts in patient samples and their extraction from highly insoluble aggregates. Immunohistochemistry (IHC) was next used to show that protein aggregates were detectable in the perikaryon of hippocampal neurons from C9(+)

ALS/FTD autopsy tissue but not in C9(−) ALS patients or control subjects using antibodies against the repeat motifs (α-PA, α-PR, α-GP) as well as antibodies directed to predicted C-terminal sequences beyond the PA and PR repeat tracts (α-PA-CT and α-PR-CT) (FIG. 14C, 25). Previous studies using antibodies directed against the GP repeat motif, detected aggregates, which were assumed to be expressed from the sense strand (10, 11). It is noted that GP repeat-containing proteins are predicted to be expressed from both sense and antisense transcripts (FIG. 13D) In the sense direction the predicted RAN GP protein contains a unique C-terminal (CT) sequence. In contrast, the antisense GP protein has a stop codon immediately after the repeat. To distinguish sense-GP RAN proteins from antisense-GP proteins, a double label IF experiments was performed on C9(+) human hippocampal autopsy sections using rabbit α-GP-CT to detect the Cr region of the sense-GP protein and mouse a-GP to detect both sense and antisense GP expansion proteins. Double labeling showed two types of inclusions: a) putative sense inclusions double labeled with mouse α-GP and rabbit α-GP-CT sense and; b) putative antisense inclusions singly labeled with mouse-α-GP (FIG. 14D). Approximately 18% of inclusions showed the sense pattern with double labeling and 82% 11 of inclusions showed the antisense pattern and were positive for α-GP and negative for α-GP-CTsense (FIGS. 14E,F). These data showed the importance of characterizing protein aggregates with both repeat and C-terminal antibodies. Taken together, these results show that insoluble, aggregate-forming antisense-RAN proteins are expressed from all three antisense reading frames.

$G_2C_4$ Expansions and RAN Proteins are Toxic to Cells

Figure 13:
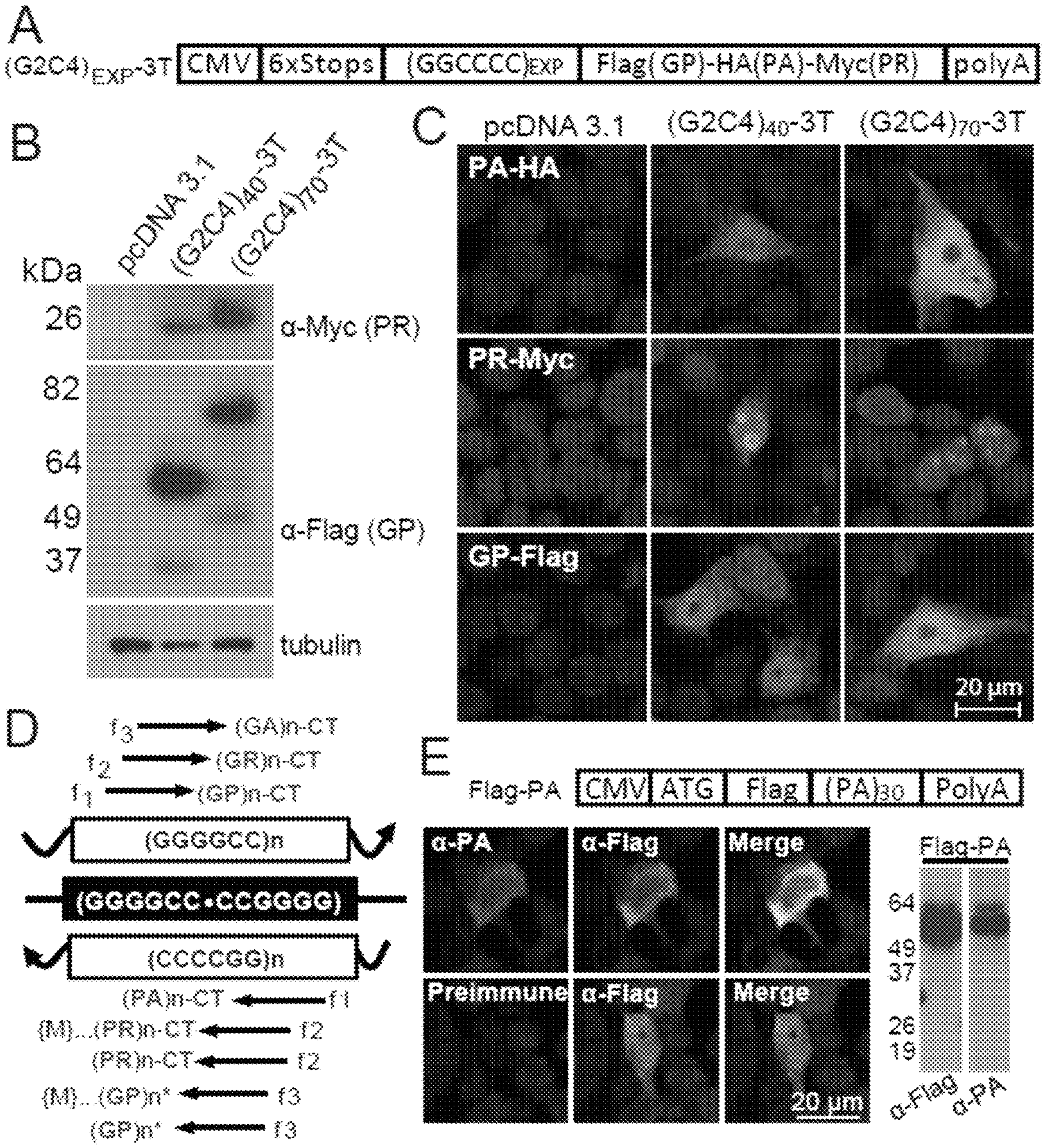
FIG. 13 is a series of schematics, graphs and images showing in vitro evidence for RAN translation of antisense $G_2C_4$ expansion and dual immunological detection strategy. (A-C) Immunoblots (B) and IF staining (C) of HEK293T cells 48 hours post-transfection with the $(G_2C_4)_{EXP}$-3T construct (A). (B) PR and GP expansion proteins detected by western and (C) PA, PR and GP detected by IF in transfected cells. (D) Diagram of putative proteins translated from sense and antisense transcripts. CT=C-terminal, f1-3: reading frame 1-3. (E) Abbreviated example of validation of α-PA rabbit polyclonal antibody. IF staining of HEK293T cells transfected with constructs with 5' Flag epitope tagged PA protein and corresponding immunoblots. See FIGS. 22 and 23 for additional controls and validation of eight additional antibodies generated against repeat motifs and CT regions.
Figure 14A:
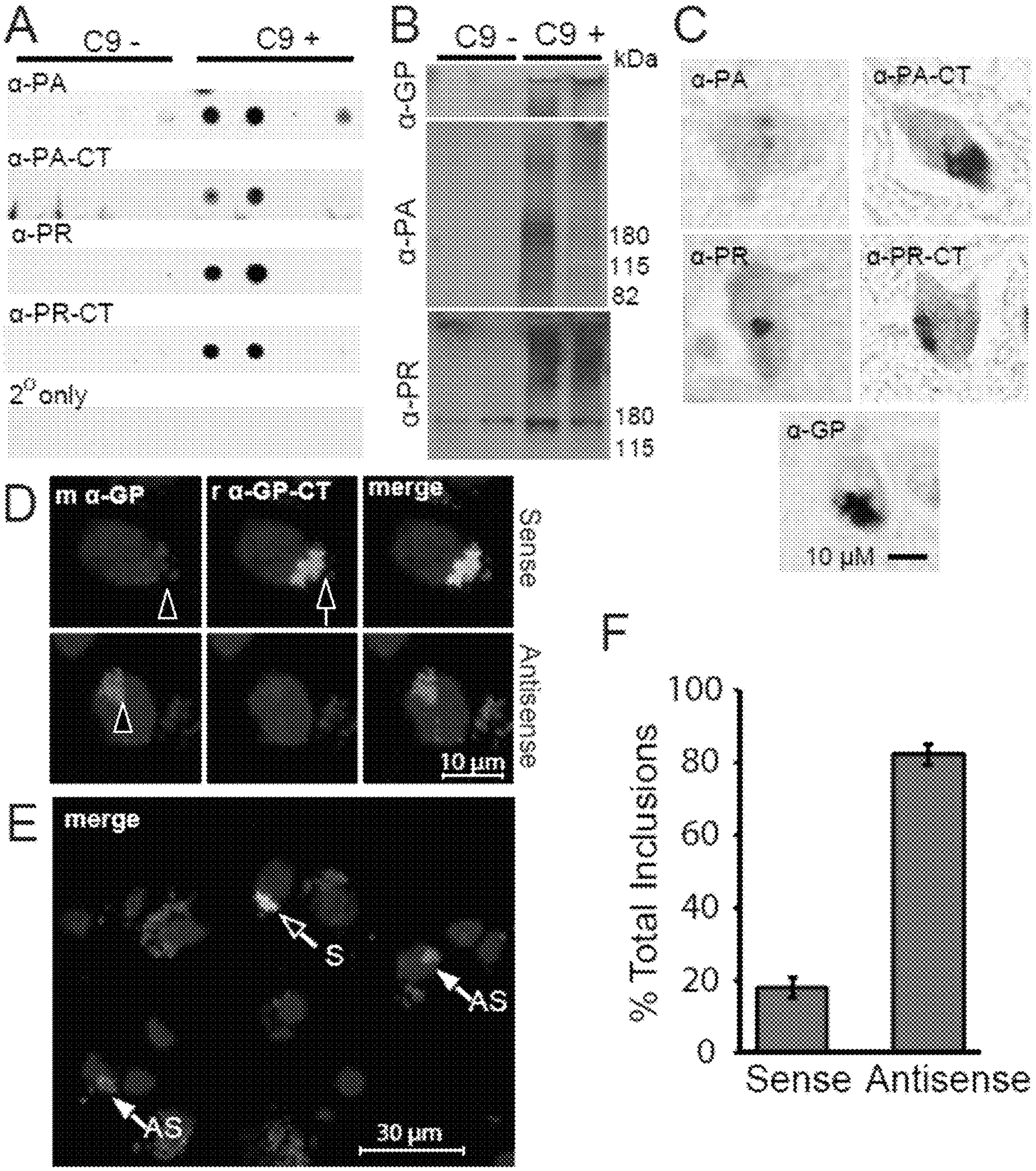
FIGS. 14A and 14B are a series of images and graphs showing in vivo evidence for RAN-translation of the $G_2C_4$ AS repeat and toxicity studies. (A) Dot blot of C9(+) and C9(−) frontal cortex lysates probed with α-PA, α-PA-CT, α-PR, α-PR-CT antibodies. (B) Immunoblots of C9(+) and C9(−) ALS frontal cortex lysates. (C) IHC detection of PA, PR and GP protein aggregates in hippocampal neurons from C9(+) ALS patients detected with α-PA, α-PA-CT, α-PR, α-PRCT and α-GP antibodies. (D) IF staining with mouse α-GP (arrowhead) and rabbit α-GP-CT (arrow) of C9(+) hippocampal tissue with sense inclusions positive for both antibodies (upper panel) and antisense inclusions positive for only GP repeat antibody (lower panel). (E) IF staining of larger region showing sense (S) and antisense (AS) staining. (F) Quantitation of double (sense) and single (antisense) labeled aggregates. (G-J) RAN and PR toxicity studies (G) $G_2C_4$ expansion constructs (+/−ATG-PR-3T)+/−ATG initiation codon in PR frame and 3'epitope tags. (H) Protein blots showing levels of PR and GP in cells transfected with constructs in (G). (1) LDH and (J) MTT assays of transfected HEK293T cells.
Figure 14B:
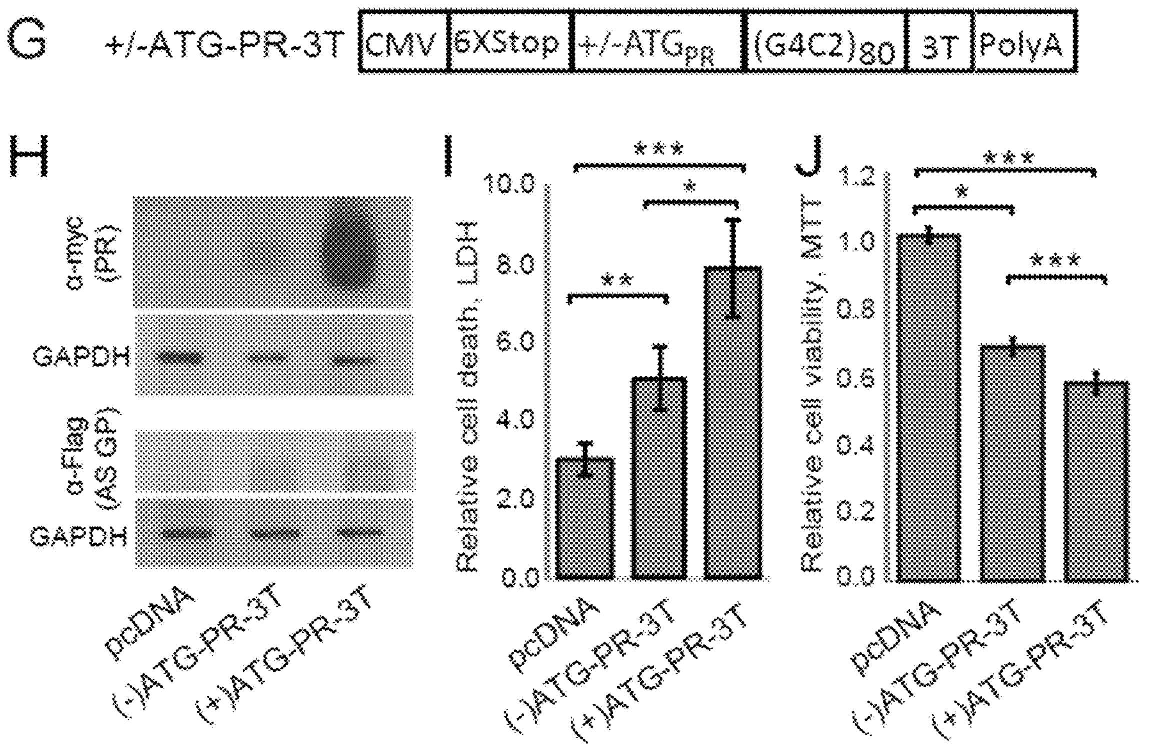
Figure 26A:
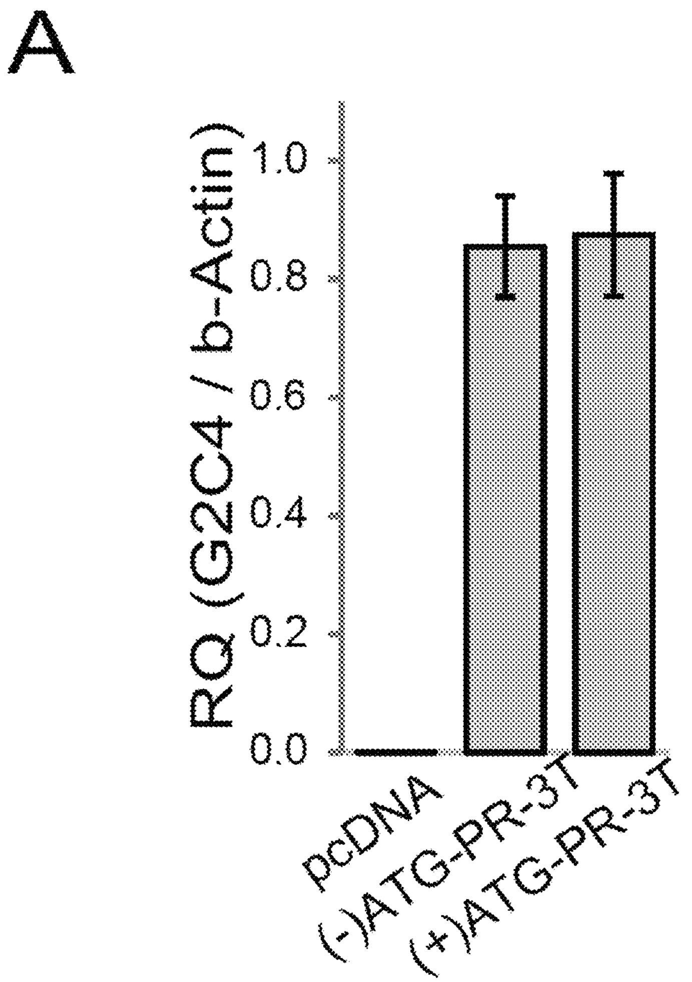
Figure 26D:
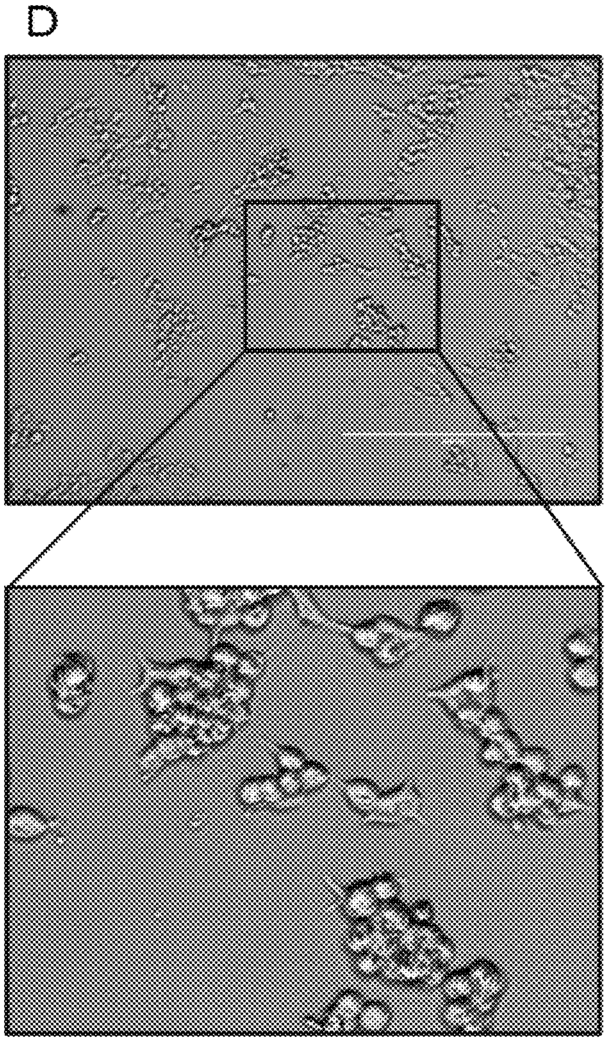

In addition to antisense GP and PR RAN proteins expressed by RAN translation, two of the antisense reading frames have upstream AT initiation codons that may result in both ATG-initiated OP and PR proteins (M-GPAS and M-PRAS) (FIGS. 13D and 21). It was shown that the presence of an ATG-initiation codon does not prevent RAN translation from also occurring in all three reading frames (9). Therefore antisense GP and PR proteins may be expressed by both AUG-initiated and/or RAN translation. To explore the effects that an AT-initiation codon has on RAN protein expression for the $G_2C_4$ expansion, an additional minigene construct was generated by placing an ATG initiation codon in front of the $G_2C_4$ repeat (FIG. 14G). The PR frame was selected for analysis because an ATG initiation codon naturally occurs in this reading frame. Western blotting shows that HEK293T cells transfected with (+)ATG-PR-3T express substantially higher levels of PR protein compared to (−)ATG-PR-3T transfected cells (FIG. 14H). In contrast, qRT-PCR and Western blotting showed transcript levels (FIG. 26A) and levels of RAN-translated GP (FIG. 14H) were comparable. Similar to FIG. 13, RAN-translated PA was not detectable by Western blot. The effects of these constructs on cell viability was then tested using complementary assays; lactate dehydrogenase (LDH) detection and methylthiazol tetrazolium (MTT). For the LDH assay, cells transfected with the (−)ATG-PR-3T or (+)ATG-PR-3T construct showed 1.9 and 2.9 fold increases in cell death compared to vector control cells ($p=0.008$ and 0.001), respectively. Additionally, (+)ATG-PR-3T transfected cells, which express elevated levels of PR protein showed a 1.5 fold increase in cell 12 death compared to cells transfected with the (−)ATG-PR-3T construct ($p=0.034$). The MTT assay showed similar results. Cells transfected with (−)ATG-PR-3T and +ATG-PR-3T constructs showed dramatic decreases in the number of metabolically active cells, 33% ($p<0.00001$) and 43% ($p<0.00001$), respectively compared to untreated cells or empty vector controls (FIG. 14J). Additionally, elevated PR expression in cells transfected with (+)ATG-PR-3T had significantly lower levels of metabolic activity compared to (−)ATG-PR-3T cells ($p<0.05$). By light microscopy cell detachment and changes in cell morphology were evident in -ATG-PR-3T compared to control cells and these phenotypes worsened in (+)ATG-PR-3T cells which express elevated levels of PR (FIG. 26B-D). Taken together, these data demonstrated that: 1) the $G_2C_4$ expansion mutation is toxic to cells—this toxicity may be caused by effects of the DNA. $G_2C_4$ RNA and/or RAN-translated PR. GP or PA proteins; 2) increased PR protein expressed in cells transfected with the (+)ATG-PR-3T construct increases cell toxicity and death above levels caused by the DNA, $G_2C_4$ RNA and RAN protein effects. Therefore the PR protein was shown to be intrinsically toxic to cells.

All Six RAN Proteins Form Aggregates in the Brain

Figure 15A:
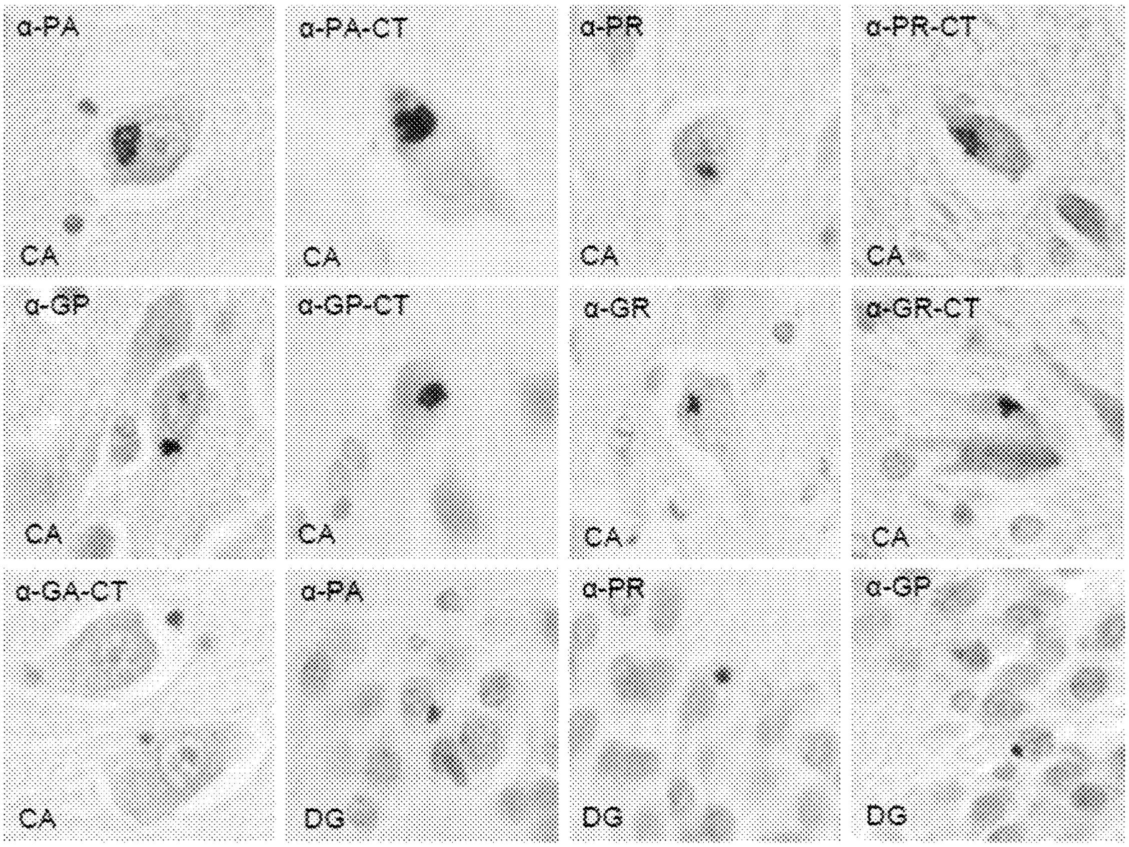
FIGS. 15A and 15B are a series of images showing in vivo evidence for RAN translation in both antisense and sense directions of C9ORF72. Cytoplasmic inclusions detected by IHC using antibodies against sense (α-GR, α-GR-CT, α-GA, α-GP-CT) and antisense (α-PA, α-PA-CT, α-PR, α-PR-CT) and α-GP which recognizes GP proteins made in both the sense and antisense directions. Aggregates were found in neurons of cornu ammonis (CA) and dentate gyrus (DG) regions of the hippocampus and the motor cortex (MC) of C9(+) ALS autopsy tissue.
Figure 15B:
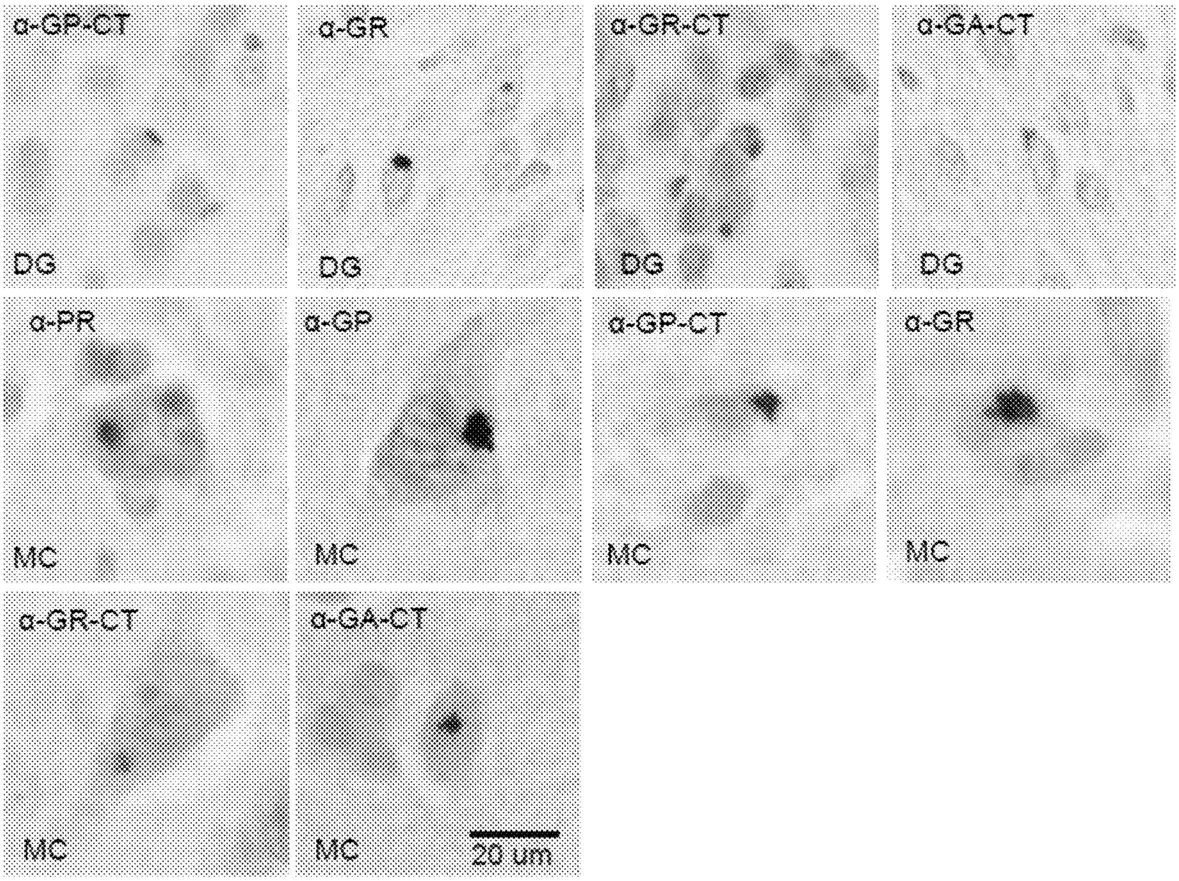

To determine if all six RAN proteins from both sense and antisense RNA strands are expressed in C9(+) ALS patients. IHC staining was performed on sections of paraffin-embedded brain tissues using nine polyclonal antibodies against repeat-expansion and/or C-terminal sequences of these proteins. In C9(+) cases there were abundant globular and irregular-shaped neuronal cytoplasmic inclusions (NCIs) in the hippocampus, the majority of which were in the dentate gyrus and in pyramidal cells in the CA regions. These RAN inclusions were also detected in C9(+) motor cortex (FIG. 15). GP positive inclusions were detected in all examined C9(+) cases but not in C9(−) cases or normal control sections in the hippocampus as well as in the motor cortex using α-GP. In the CA regions of the 13 hippocampus and in the motor cortex, clusters of aggregates were frequently found in C9(+) cases with aggregates in >20% of neurons (FIG. 27). Fewer aggregates were detected with the α-GP-CT sense antibody, consistent with double labeling experiments (FIG. 14D-F) that showed most GP aggregates are translated from C9ORF72 antisense strand. PA inclusions were detected in hippocampus in four out of six C9(+) cases tested and in one out of two motor cortex samples (FIG. 27). In C9(+) cases, the frequency of PA inclusions were significantly lower in the hippocampus and motor cortex compared with GP inclusions, but high-intensity regional staining with extremely large PA inclusions found in >50% of neurons were found in one patient (FIG. 27). PR positive inclusions were also seen in hippocampus in all C9(+) cases examined and in motor cortex in one out of two C9(+) cases tested. Similar to the PA staining, PR inclusions are less frequent but intense regional staining was occasionally observed. In the sense direction, GR positive inclusions were found in the hippocampus and motor cortex in all C9(+) cases examined, but appeared less frequent than the GP aggregates. GA inclusions were only occasionally detected by IHC as small perinuclear inclusions in hippocampus and in motor cortex (FIG. 15, 27). The apparent differences in the frequency of various types of aggregates may result from differences in protein conformation and epitope availability or differences in the affinities of these antibodies, which were designed to different epitopes. Taken together, this data showed that all six RAN proteins form aggregates in the C9(+) autopsy brains.

Inclusions of RAN Proteins in Upper and Lower Motor Neurons

Figure 16A:
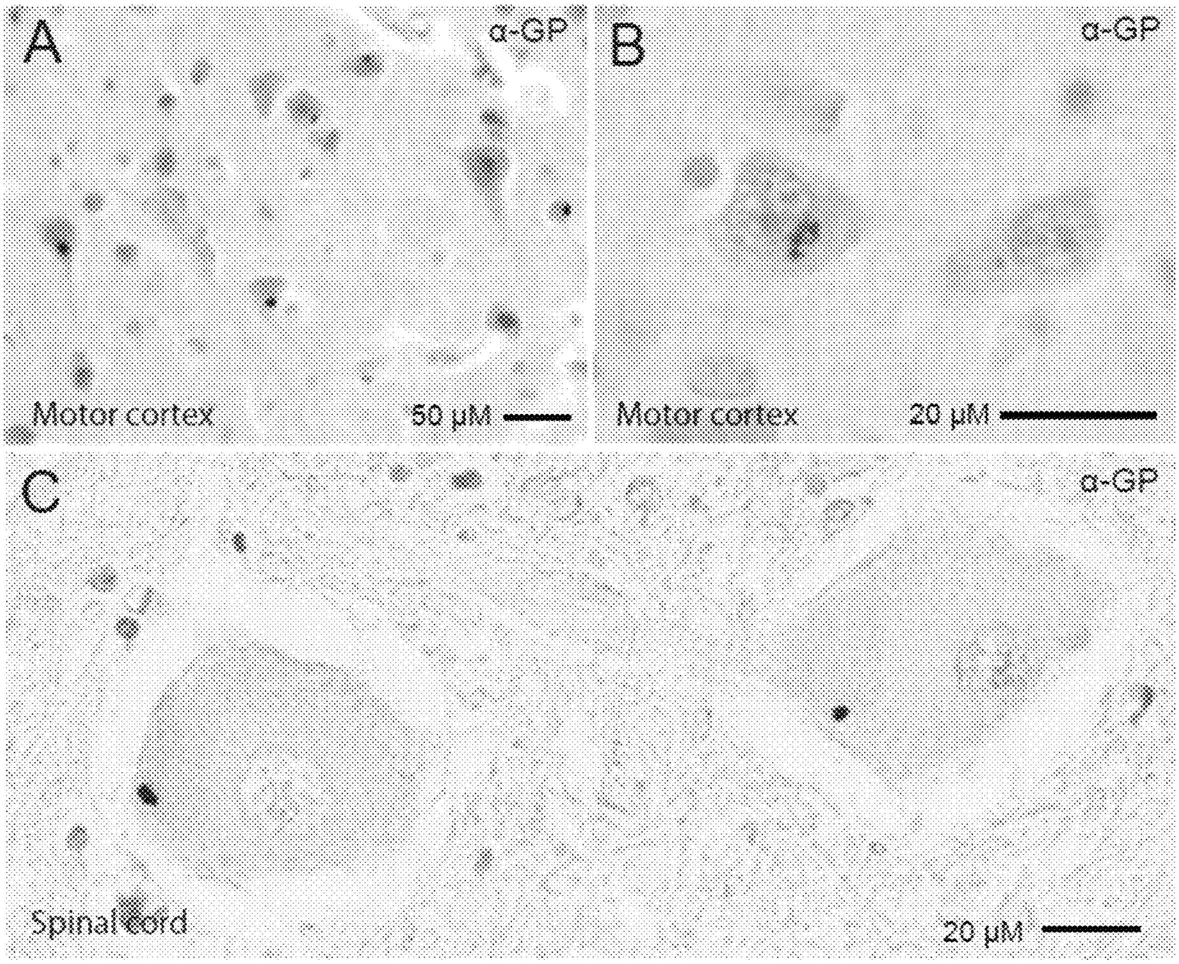
FIGS. 16A and 16B are a series of images of clustered RAN protein aggregates and RAN aggregates in motor neurons. IHC showing cytoplasmic α-GP aggregates in: (A) in layer Ill of motor cortex. (B) upper motor neuron in layer V of the motor cortex; (C) lower motor neurons in the spinal cord (L-S.C). (D) in cornu ammonis, CA. (E) and dentatus gyrus, DG regions of the hippocampus. (F and G) IHC showing abundant PA and PR cytoplasmic inclusions in the pre-subiculum (PrSub) from one patient.
Figure 16B:
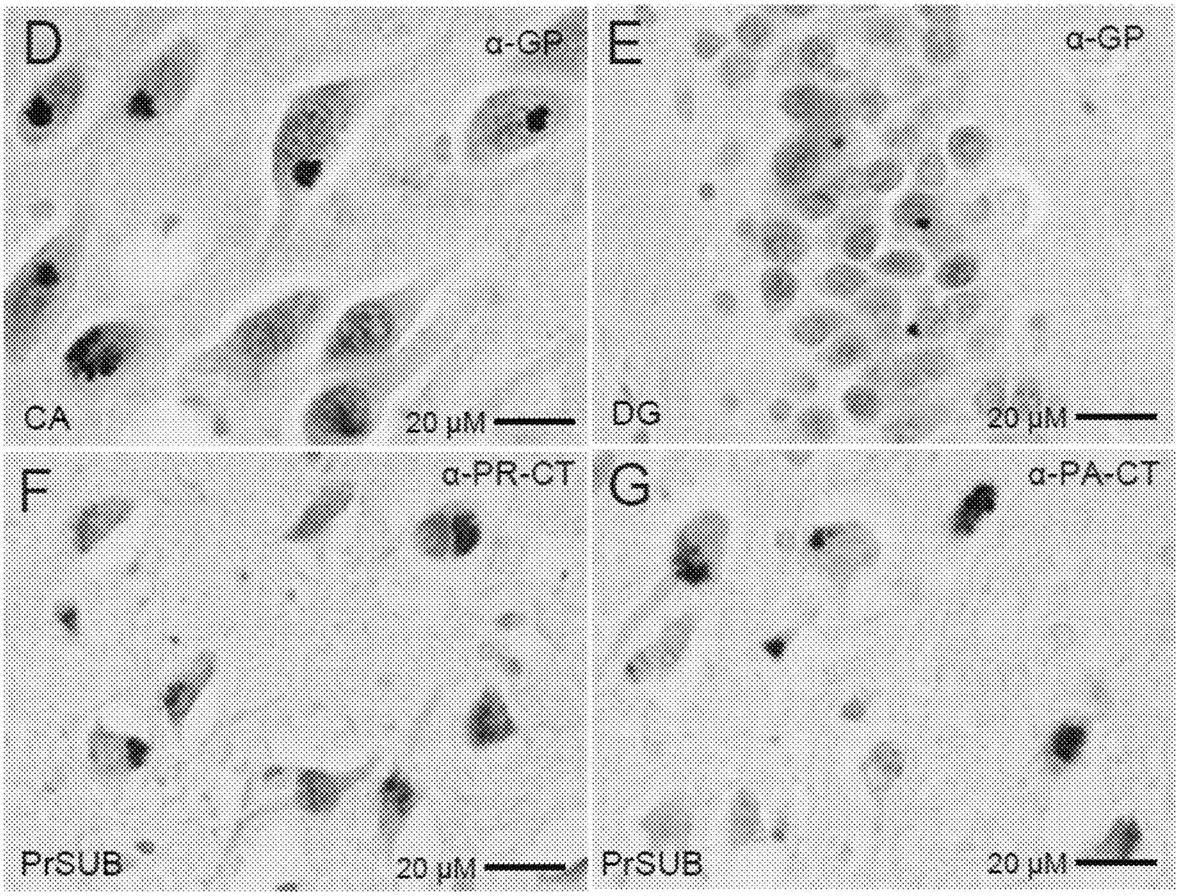

A central feature of ALS is the gradual degeneration and death of upper motor neurons in motor cortex and lower motor neurons in the brain stem and spinal cond. To test if RAN proteins accumulate in upper and lower motor neurons, IHC was performed using all nine antibodies against predicted proteins in both sense and antisense directions. In C9(+) cases, abundant GP-positive neuronal cytoplasmic inclusions were seen in all layers of motor cortex, with frequent GP aggregates in pyramidal neurons of layer III and throughout layer V (FIG. 16A). Although cell death and atrophy made motor-neurons in layer V difficult to identify, GP inclusions in remaining upper motor neurons were found (FIG. 16B). Additionally, PA-, PR-, GR- and GA-positive inclusions were also found in the motor cortex (FIG. 15, 27). Using a similar series of experiments performed in spinal cord sections. GP aggregates in all three cases examined and aggregates in lower motor neurons in two out of three C9(+) patients were detected, but not in C9(−) ALS cases or normal controls (FIG. 16C). This is the first report of RAN protein accumulation in motor neurons. The discovery of GP-aggregates in both upper and lower motor neurons links C9 RAN-protein accumulation to the neurons selectively vulnerable in ALS.

High Density Clustering of RAN-Protein Aggregates

Figure 17:
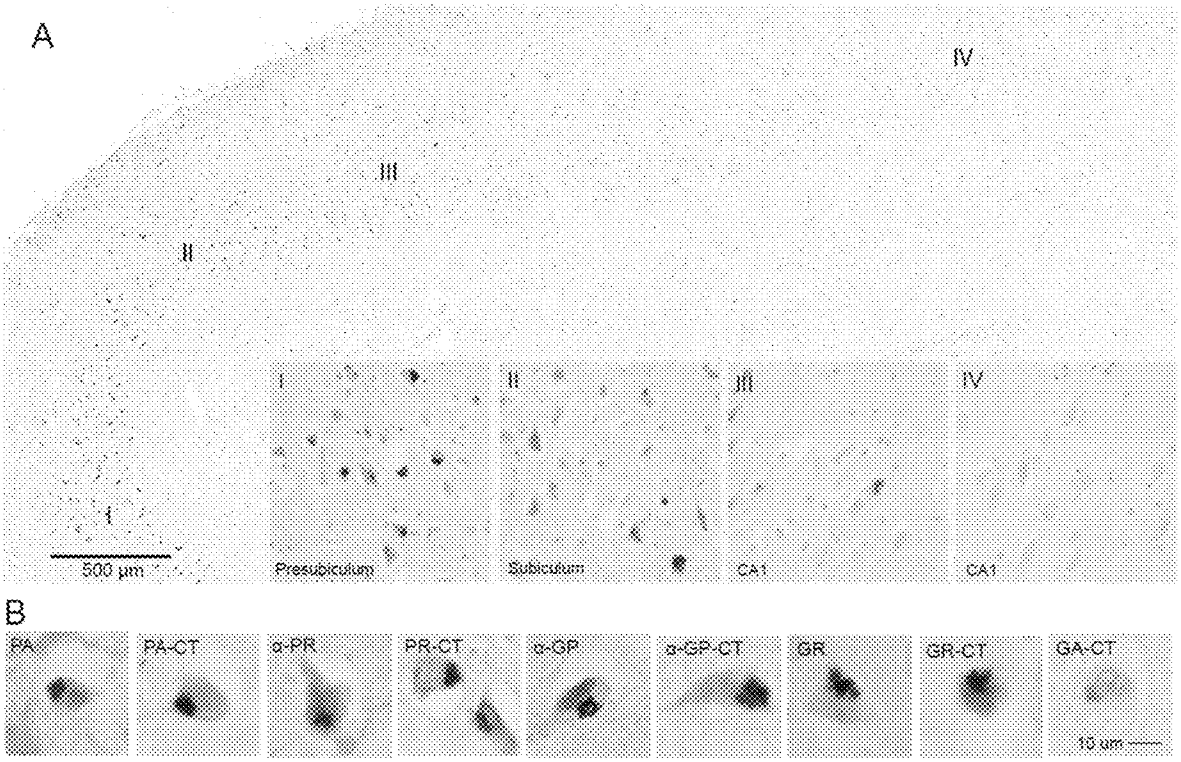
FIG. 17 is a series of images of clustered staining of RAN proteins. (A) Low power image of IHC staining with α-PA-CT shows variations in staining intensity (dark spots are positive) in regions I-IV with insets showing higher-power images. (B) Examples of aggregates from region I show immunoreactivity against all nine antibodies with similar staining for antibodies against repeat and unique C-terminal epitopes.

Both sense and antisense proteins accumulated in neurons of C9ORF72 autopsy brains. In general, two types of aggregation patterns were observed: 1) isolated cytoplasmic aggregates and 2) high-density clustered cytoplasmic aggregates in which ~10 to more than 50% of neurons were positive. Clustered aggregates were most frequently detected for GP and were found in the dentate gyrus (DG) and CA1-4 of the hippocampus (FIG. 16D, E). The clustered GP aggregates in DG were smaller and less frequent than the large cytoplasmic aggregates in CA regions. Additional clustered GP aggregates were frequently found in subiculum and presubiculum of the hippocampus as well as 15 the motor cortex. Immunostaining of serial sections showed that multiple proteins are often found in the same region. For example, intense clustered staining for PA, PR, GP, GA and OR proteins was found in the same region of the presubiculum in serial sections from one C9 (+) patient (see FIG. 16F,G). Immunostaining for PA showed that some brain regions have abundant aggregates whereas other regions in the same section are relatively spared. For example, FIG. 17A illustrates a gradient of PA inclusions (presubiculm>subiculum>CA1) across hippocampal regions in a single section in one patient. PA inclusions in this patient were numerous (>50% of neurons) in presubiculum (I), moderate in subiculum (II), and rare in CA1 hippocampal regions (Ill and IV). Consistent with the focal regional staining seen in this section, PA staining was not detected in sections from a separate block of hippocampal tissue taken from the same patient. These data shows that expression of the PA RAN protein is variable from cell to cell or that aggregation of PA in one cell triggers aggregation in neighboring cells as has been proposed in a mouse model of Parkinson's disease (24). Next, serial sections from this C9(+) case were used to show that antibodies directed against both the repeat motifs ((α-PA, α-PR, α-GP, α-GR) and corresponding C-terminal regions (α-PA-CT, α-PR-CT, α-GP-CT, α-GR-CT α-GA-CT) detect aggregates in the same densely staining region of the presubiculum (region I) (FIG. 17B). These results showed that both sense and antisense RAN protein aggregates accumulate in this region. The detection of similar aggregates in using antibodies that recognize either the repeat motifs or specific C-terminal regions confirms that these antibodies are recognizing proteins expressed across both the $G_2C_4$ and $G_4C_2$ expansion transcripts and provides new tools to understand the biological impact of RAN translation in C9ORF72 ALS/FTD.

Discussion

There has been much excitement about the discovery that an intronic microsatellite expansion mutation in C9ORF72 causes a common form of both familial and sporadic ALS/FTD (1, 2). The three major pathological mechanisms being considered for this disease include haploinsufficiency (1, 2). RNA gain-of-function (5-8), and RAN translation (9, 11-13). To date, efforts to understand the molecular mechanisms of this disease have focused exclusively on understanding the consequences of the C9ORF72 expansion mutation in the sense direction. The results reported here show that C9ORF72 expansion mutation is also expressed in the antisense direction and show that antisense RNA foci and antisense RAN proteins contribute to C9ORF72 ALS/FTD. We show for the first time: 1) antisense C9ORF72 but not sense transcripts are elevated in C9(+) autopsy tissue; 2) antisense $G_2C_4$ expansion transcripts form RNA foci that accumulate in C9+brain and blood; 3) RAN translation occurs across antisense $G_2C_4$ expansion constructs in cell culture; 4) that sense and antisense RAN proteins accumulate in C9(+) autopsy brains using a dual immunological approach with both repeat and C-terminal antibodies; 5) RAN protein aggregates accumulate in upper and lower motor neurons linking RAN translation directly to the key pathologic feature of ALS. Since the initial report that $G_4C_2$ RNA foci accumulate in C9ORF72 ALS/FTD patient tissues (1, 2), a leading hypothesis is that $G_4C_2$ sense transcripts sequester and dysregulate RNA binding proteins similar to the sequestration of MBNL proteins in DM1, DM2 and SCA8 (4). Several groups have already reported $G_4C_2$ binding proteins and are testing their potential role in disease (5-8). The discovery that antisense $G_2C_4$ foci also accumulate in patient cells shows that $G_2C_4$ antisense RNAs and binding proteins may play a role. Additionally, the discovery of sense and antisense foci in C9(+) peripheral blood may prove useful as an easily accessible biomarker of C9ORF72 ALS/FTD. Biomarkers that monitor both sense and antisense transcripts may be particularly important as therapies that decrease expression of one strand may increase expression of the other strand. Using a dual immunological approach it was shown that $G_2C_4$ antisense transcripts express novel antisense proteins (PA, PR, GP) by RAN translation and/or from two short ORFs (Met-AS-PR and Met-AS-GP).

Materials and Methods cDNA constructs. CCCGGGGCC$(GGGGCC)_2$GGGGCCC (SEQ ID NO: 64) and CCCGGGGCC$(GGGGCC)_{28}$GGGGCCC (SEQ ID NO: 65) fragments that contain upstream 6×Stop codons were synthesized and cloned into pIDTSmart vector by Integrated DNA Technologies. 6×Stops-$(GGGGCC)_4$-3T and 6×Stops-$(GGGGCC)_{30}$-3T constructs were generated by subcloning NheI/XhoI fragment into pcDNA3.1 vector containing triple epitopes. To expand the size of the GGGGCC repeats, SmaI/XhoI fragment was subcloned into PspOMI blunted with T4 DNA polymerase/XhoI of pcDNA-6×Stops-$(GGGGCC)_{EXP}$-3T. To reverse the orientation of GGGGCC repeats in pcDNA-6×Stop-3T construct, SmalI/ClaI fragment was subcloned into pBluescript SK+ to generate pBluescript-$(GGGGCC)_{EXP}$. The AfeI/XhoI fragment pBluescript-$(GGGGCC)_{EXP}$ was subcloned into pcDNA-6×Stop-3T to make pcDNA-6×Stop-$(GGCCCC)_{EXP}$-3T construct.

RT-PCR. 1) Strand-specific RT-PCR in autopsy tissues: Total RNA was isolated from Frontal cortex autopsy tissues and peripheral blood lymphocytes (PBL) of ALS patients and healthy controls with TRIzol (Invitrogen). To detect transcripts from both strands, cDNA was generated from 0.25 μg of total RNA using the SuperScript III system (Invitrogen) with linkered strand specific reverse primers and PCR with strand specific forward and linker (LK) primers. The PCR reactions were done as follows: 94° C. for 3 min, then 35 cycles of 94° C. for 45s, 58° C. for 45s and 72° C. for 1 min followed by 6 min at 72° C. Bands were cloned and sequence to verify their specificity of the PCR amplification. 2) RT-PCR for toxicity assay in 293T cells: Total RNA from cells was extracted using miRNeasy Mini kit (Qiagen) according to the manufacturer's protocol. Total RNA was reverse transcribed using the Superscript III RT kit (Invitrogen) and random-hexamer primers. The expression of the different G4C2-3×Tag constructs were analyzed by RT-PCR and qPCR using primer set: 3×Tag-Fw and 3×Tag-Rv. β-Actin expression was used as a reference gene amplified with primer set ACTB3 and ACTB4. Primer sequences are listed in FIG. 27.

Real time RT-PCR. Two step quantitative PCR was performed on a MyCycler Thermal Cycler system (Bio-Rad) using SYBER Green PCR Master Mix (Bio-Rad) and ASORF strand-specific cDNA and primer sets. Control reactions were performed with human beta-actin primers ACTB3 and ACTB4 using oligo dT synthesized total cDNA as template. Two stage PCR was performed for 40 cycles (95° C. 30s, 60° C. 30s) in an optical 96 well plate with each sample cDNA/primer pair done in triplicate. The relative fold changes were generated by first normalizing each experimental Ct value to their beta actin Ct value and then normalized to the healthy control antisense ΔΔCt. Primer sequences are listed in FIG. 28.

Rapid Amplification of 5' and 3' cDNA ends (5' and 3' RACE). Four μg of total RNA from 2 C9(+) ALS patients and 2 C9(−) ALS patients frontal cortex autopsy tissues were used for 5' and 3' RACE (5' RACE systems and 3' RACE: Life Technologies). In 5'RACE, Primer ASORF R was used for gene specific first strand cDNA synthesis and nested reverse primers are 5'GSP1 and 5'GSP2. In 3'RACE, nested forward primers are 3'GSP1 and 3'GSP2. The 3' RACE and 5' RACE products were gel-extracted, cloned with TOPO TA Cloning (Invitrogen) and sequenced. Primer sequences are listed in FIG. 28.

Production of polyclonal antibodies. The polyclonal rabbit antibodies were generated by New England Peptide and the polyclonal mouse antibody was generated by the Interdisciplinary Center for Biotechnology Research (ICBR) at the University of Florida. In sense strand (GGGGCC), antisera were raised against synthetic poly(GP), poly(GR) peptides and C terminal regions of predicted GP, GR, and GA RAN proteins (FIG. 21). In antisense strand (GGCCCC), antisera were raised against synthetic poly(PA), poly(PR) peptides and the C terminal regions of predicted PA and PR RAN proteins. Peptides used to generate antibodies to both antisense and sense proteins and their use for Western blot, immunofluorescence (IF) and immunohistochemistry (IHC) is summarized in Table S3.

Cell culture and transfection. HEK293T cells were cultured in DMEM medium supplemented with 10% fetal bovine serum and incubated at 37° C. in a humid atmosphere containing 5% CO2. DNA transfections were performed using Lipofectamine 2000 Reagent (Invitrogen) according to the manufacturer's instructions.

Human Samples. Frozen frontal cortex tissue samples for biochemical and histological analysis included samples from six C9(+) ALS, five C9(−) ALS controls and one normal control were used in this research. Additionally, paraffin embedded fixed tissues from C9(+) ALS/FTD and C9(−) ALS/FTD cases as well as a normal control. Peripheral blood lymphocytes (PBL) were isolated from the buffy coat of freshly collected whole blood following brief centrifugation at 2000×g. Red blood cells (RBC) were preferentially lysed and removed using RBC Lysis Buffer (Roche), PBLs centrifuged, washed once with PBS and dried on slides. This study was conducted in compliance with the Declaration of Helsinki. Institutional review boards of the University of Florida and Johns Hopkins University approved the study. Written, informed consent was obtained from participants or relevant parties at the time of enrollment.

Immunofluorescence. The subcellular distribution of polymeric proteins was assessed in transfected HEK293T cells by immunofluomscence. Cells were plated on 8 well tissue-culture chambers and transfected with plasmids the next day. Forty-eight hours post-transfection, cells were fixed in 4% paraformaldehyde (PFA) in PBS for 30 min and permeabilized in 0.5% triton X-100 in PBS for 15 min on ice. The cells were blocked in 1% normal goat serum in PBS for 30 min. After blocking, the cells were incubated for 1 hour at RT in blocking solution containing the rabbit anti-Myc (Abcam), mouse anti-HA (Covance), mouse anti-Flag (Sigma), rabbit anti-OR and rabbit anti-GR-CT primary antibodies at a dilution of 1:400. The slides were washed three times in PBS and incubated for 1 hour at RT in blocking solution containing Goat anti-rabbit conjugated to Cy3 (Jackson ImmunoResearch, PA) and goat anti-mouse conjugated to Alexa Fluor 488 (Invitrogen) secondary antibodies at a dilution of 1:200. The slides were washed three times in PBS and mounted with mounting medium containing DAPI (Invitrogen).

RNA-FISH. Slides with cells were fixed in 4% PFA in PBS for 10 min and incubated in prechilled 70% ethanol for 30 min on ice. Following rehydration in 40% formamide in 2×SSC for 10 min, the slides were blocked with hybridization solution (40% formamide, 2×SSC, 10 mg/ml BSA, 100 mg/ml dextran sulfate and 10 mg/mi yeast tRNA) for 10 minutes at 55° C. and then incubated with 200 ng/ml denatured RNA probe in hybridization solution at 55° C. for 2 hours. After hybridization the slides were washed 3 times with 40% formamide in 2×SSC and briefly washed one time in PBS. Autofluorescence of lipofuscin was quenched by 0.25% of Sudan Black B in 70% ethanol and the slides were mounted with mounting medium containing DAPI (Invitrogen). The specificity of the RNA foci was determined by treating cells prior to FISH detection with either RNAse (100 ug/mL in 2×SSC), DNase (1 U/ul in DNaseI buffer) or Protease K (120 ug/mL in 2 mM CaCl2, 20 mM Tris, pH 7.5). Treated cells were incubated at 37° C. for 30 minutes, washed 3 times with PBS then 3 times with 2×SSC. Subsequent FISH detected was performed as described above. Antisense foci specificity was determined using standard FISH detection to first hybridize slides with 10-fold excess unlabeled (G4C2)4 oligo followed by hybridization with either G4C2-cy3 (antisense probe) or $G_2C_4$-cy3 (sense probe). Subsequent treatment and detection were performed as described above.

Western blotting. Transfected cells in each well of a six-well tissue-culture plate were rinsed with PBS and lysed in 300 μL RIPA buffer with protease inhibitor cocktail for 45 min on ice. DNA was sheared by passage through a 21-gauge needle. The cell lysates were centrifuged at 16,000×g for 15 min at 4° C., and the supernatant was collected. The protein concentration of the cell lysate was determined using the protein assay dye reagent (Bio-Rad). Twenty micrograms of protein were separated in a 4-12% NuPAGE Bis-Tris gel (Invitrogen) and transferred to a nitrocellulose membrane (Amersham). The membrane was blocked in 5% dry milk in PBS containing 0.05% Tween-20 (PBS-T) and probed with the In anti-Flag (1:2000), anti-Myc (1:1000), anti-HA (1:1000), or rabbit polyclonal antibodies (1:1000) in blocking solution. After the membrane was incubated with anti-rabbit or anti-mouse HRP-conjugated secondary antibody (Amersham), bands were visualized by the ECL plus Western Blotting Detection System (Amersham). Sequential extraction of patient frontal cortex autopsy tissue was performed as follows: tissue was homogenized in PBS containing 1% Triton-X100, 15 mM MgCl2, 0.2 mg/ml DNase I and protease inhibitor cocktail and centrifuged at 16,000×g for 15 min at 4° C. The supernatant was collected. The pellet was resuspended in 2% SDS and incubated at room temperature for 1 hour, then centrifuged at 16,000×g for 15 min at 4° C. The supernatant was collected and the 2% SDS insoluble pellet was resuspended in 8% SDS, 62.5 mM Tris-HCl pH 6.8, 10% glycerol and 20% 2-Mercaptoethanol for protein blotting (25).

Protein slot blot. 1% Triton-X100 soluble fraction and 2% SDS soluble fraction from the sequential extraction was immobilized onto nitrocellulose membranes with Bio-Dot 96-well microfiltration system (Bio-Rad) under vacuum. The membranes were washed in PBS-T and blotted with each rabbit polyclonal antibody (1:2000) using the same protocol as western blotting.

Immunohistochemistry. Ten-micrometer sections were deparaffinized in xylene and rehydrated through graded alcohol, incubated with 95-100% formic acid for 5 min. and washed with distilled water for 10 min. HIER was performed by steaming sections in citrate buffer, pH 6.0, at 90° C. for 30 min. To block nonspecific immunoglobulin binding, a serum-free block (Biocare Medical) was applied for 30 min. Rabbit polyclonal antibodies were applied at a dilution of from 1:5000 to 1:15,000 in serum-free block (Biocare Medical) and incubated overnight at 4° C. linking reagent (streptavidin and/or alkaline phosphatase, Covance) was applied for 30 min at room temperature. These sections were incubated in 3% H2O2 for 15 min to bleach endogenous peroxidase activity. Then labeling reagent (HRP, Covance) was applied for 30 min at room temperature. Peroxidase activity was developed with NovaRed substrate (Vector) and sections were counterstained with hematoxylin.

Cell toxicity assays. All the transfection experiments were performed using Lipofectamine 2000 (Invitrogen), according to the manufacturer's instruction and at a 60% cell confluence. 500 ng of each vector was transfected in 35 mm wells. Cell death was determined by measuring Lactate dehydrogenase (LDH) cell release, using CytoTox 96 non-radioactive cytotoxicity assay (Promega) according to the manufacturer's instructions. Absorbance was recorded at 490 nm and total LDH release was measured by lysing the cells with 1% Triton X-100. In each experiment, determinations were performed in quintuplicates for each experimental condition and average data calculated. Statistical significance was determined using the two tailed unpaired Student t test for single comparisons ($p<0.05$) and the analysis of variance (ANOVA) when multiple pairwise conditions were compared.

Cell viability assays. HeK293T cells were transfected in 96 well plates and cell viability was determined 42 hours post-transfection with the 3-(4,5-dimethythiazol-2-yl)-2,5-diphenyl tetrazolium bromide (MTT) assay. MTT was added to cell culture media at 0.5 mg/mL final concentration and incubated for 45 minutes at 37° C. Cells were then lysed with 100 μL of DMSO upon medium removal and absorbance was measured at 595 nm. In each experiment, determinations were performed in quintuplicates. Statistical significance was determined using Student's t test ($p<0.05$).

Example 4. BAC Transgenic Mouse Model of C9ORF72 ALS to Test the Hypothesis that Both Sense and Antisense Transcripts Contribute to ALS/FTD Rationale: A mouse model of C9ORF72 ALS/FTD that recapitulates the sense and antisense transcripts is critical for modeling this disease. BAC clones were isolated from a human patient which contain ~800 G4C2 repeats. These BAC clones were used to generate 8 founder lines. These mice are useful, for example, to answer the following questions: Does both RAN protein expression and RNA gain of function contribute to C9ORF72 ALS/FTD? Are sense and antisense mechanisms both important in C9ORF72 pathogenesis?

Approach: BAC clones containing the full human C9ORF72 gene plus flanking sequences were isolated from a human patient with ~800 GGGGCC repeats and inserted into the pCC1BAC™ plasmid (Epicentre®). The BAC insert chosen for use in the mouse extended from bp 27,625,470 to 27,527,137 of human genome reference sequence on Chromosome 9 (FIG. 29). The coordinates above do not include extra repeats from this patient. It was found that the BAC insert DNA contained about 800 repeats in some clone preps but was very unstable. Pronuclear injections were performed and 8 FVB founder lines were generated—2 independent lines which were confirmed expansion mutations. The BAC repeat size in the mice was ~500 repeats but varied between progeny and may grow or shrink in size as the mouse colony is expanded and additional generations of mice are propagated in the laboratory. BAC expansion mice expressed both sense and antisense versions of the C9ORF72 gene. Sense and anti-sense GGGCC RNA foci were present in mice that had the GGGGCC repeats, but not in control mice (FIGS. 30-31).

At least two expansion and two control lines are selected for detailed characterization. Behavioral characterization includes rotorod analysis, grip strength, balance beam and open field assessments. Molecular characterization of sense and antisense transcripts and RAN proteins are performed by RT-PCR, RACE, immunoblot, immunohistochemistry and immunofluorescence. Immunohistochemistry, immunofluorescence and FISH studies are performed to correlate sites of RNA foci and C9-RAN proteins accumulation with pathological changes. RAN-protein accumulation in the CNS, CSF, muscle, blood and other tissues are examined at various times during development.

Relevance: Results from these studies will lead to a better understanding of the role that RAN translation plays in C9ORF72 ALS/FTD. Additionally, these studies will help to prioritize individual protein targets by determining which proteins are found most frequently in autopsy tissue and identifying overt differences in the toxicities of individual RAN proteins. Information from cellular and mouse models will also inform future studies on the effectiveness of various treatment strategies.

REFERENCES

1. DeJesus-Hernandez M, et al (2011) Expanded GGGGCC hexanucleotide repeat in noncoding region of C9ORF72 causes chromosome 9p-linked FTD and ALS. *Neuron* 72(2):245-256.

2. Renton A E, et al (2011) A hexanucleotide repeat expansion in C9ORF72 is the cause of chromosome 9p21-linked ALS-FTD. *Neuron* 72(2):257-268.
3. Majounie E, et al. (2012) Frequency of the C9orf72 hexanucleotide repeat expansion in patients with amyotrophic lateral sclerosis and frontotemporal dementia: a cross-sectional study. *Lancet Neurol* 11(4):323-330.
4. Nelson D L, Orr H T, & Warren S T (2013) The unstable repeats—three evolving faces of neurological disease. *Neuron* 77(5):825-843.
5. Reddy K, Zamiri B, Stanley S Y, Macgregor R B, Jr., & Pearson C E (2013) The disease-associated r(GGGGCC)n repeat from the C9orf72 gene forms tract length-dependent uni and multimolecular RNA G-quadruplex structures. *J Biol Chem* 288(14):9860-9866.
6. Mori K, et al. (2013) hnRNP A3 binds to GGGGCC repeats and is a constituent of p62-positive/TDP43-negative inclusions in the hippocampus of patients with C9orf72 mutations. *Acta Neuropathol* 125(3):413-423.
7. Xu Z, et al. (2013) Expanded GGGGCC repeat RNA associated with amyotrophic lateral sclerosis and frontotemporal dementia causes neurodegeneration. *Proc Natl Acad Sci USA* 110(19):7778-7783.
8. Almeida S, et al. (2013) Modeling key pathological features of frontotemporal dementia with C9ORF72 repeat expansion in iPSC-derived human neurons. *Acta Neuropathol.*
9. Zu T, et al. (2011) Non-ATG-initiated translation directed by microsatellite expansions. *Proc Natl Acad Sci USA* 108(1):260-265.
10. Ash P E, et al. (2013) Unconventional translation of C9ORF72 GGGGCC expansion generates insoluble polypeptides specific to c9FTD/ALS. *Neuron* 77(4):639-646.
11. Mori K, et al (2013) The C9orf72 GGGGCC Repeat is Translated into Aggregating Dipeptide-Repeat Proteins in FTLD/ALS. *Science.*
12. Todd P K, et al. (2013) COG repeat-associated translation mediates neurodegeneration in fragile X tremor ataxia syndrome. *Neuron* 78(3):440-455.
13. Ash P E A, et al. (2013) Unconventional Translation of C9ORF72 GGGGGCC Expansion Generates Insoluble Polypeptides Specific to c9FTD/ALS Neuron.
14. Strausberg R L, et al. (2002) Generation and initial analysis of more than 15,000 full-length human and mouse cDNA sequences. *Proc Natl Acad Sci USA* 99(26):16899-16903.
15. Venter J C, et al. (2001) The sequence of the human genome. *Science* 291(5507):1304-1351.
16. Beausoleil S A, Villen J, Gerber S A, Rush J, & Gygi S P (2006) A probability-based approach for high-throughput protein phosphorylation analysis and site localization. *Nat Biotechnol* 24(10):1285-1292.
17. Sopher B L, et al. (2011) CTCF regulates ataxin-7 expression through promotion of a convergently transcribed, antisense noncoding RNA. *Neuron* 70(6):1071-1084.
18. Chung D W, Rudnicki D D, Yu L, & Margolis R L (2011) A natural antisense transcript at the Huntington's disease repeat locus regulates HTT expression. *Hum Mol Genet* 20(17):3467-3477.
19. Wilburn B, et al. (2011) An antisense CAG repeat transcript at JPH3 locus mediates expanded polyglutamine protein toxicity in Huntington's disease-like 2 mice. *Neuron* 70(3):427-440.
20. Ladd P D, et al. (2007) An antisense transcript spanning the CGG repeat region of FMR1 is upregulated in premutation carriers but silenced in full mutation individuals. *Hum Mol Genet* 16(24):3174-3187.
21. Moseley M L et al. (2006) Bidirectional expression of CUG and CAG expansion transcripts and intranuclear polyglutamine inclusions in spinocerebellar ataxia type 8. *Nat Genet* 38(7):758-769.
22. Cho D H, et al. (2005) Antisense transcription and heterochromatin at the DM1 CTG repeats are constrained by CTCF. *Mol Cell* 20(3):483-489.
23. Li H. Wyman T, Yu Z X, Li S H, & Li X J (2003) Abnormal association of mutant huntingtin with synaptic vesicles inhibits glutamate release. *Hum Mol Genet* 12(16):2021-2030.
24. Luk K C, et al. (2012) Pathological alpha-synuclein transmission initiates Parkinson-like neurodegeneration in nontransgenic mice. *Science* 338(6109):949-953.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

What is claimed is:

1. A method of producing an antibody, the method comprising administering to a subject a poly-(Pro-Ala) di-amino acid repeat-containing protein.

2. The method of claim 1, wherein the poly-(Pro-Ala) di-amino acid repeat-containing protein comprises the sequence set forth in SEQ ID NO: 20.

3. The method of claim 1, further comprising the step of isolating the antibody from the subject.

* * * * *

SEQUENCE LISTING

```
<160> NUMBER OF SEQ ID NOS: 65

<210> SEQ ID NO 1
<211> LENGTH: 31
<212> TYPE: PRT
<213> ORGANISM: Artificial sequence
<220> FEATURE:
<223> OTHER INFORMATION: Synthetic polypeptide

<400> SEQUENCE: 1
```

```
Trp Ser Gly Arg Ala Arg Gly Arg Ala Arg Gly Gly Ala Ala Val Ala
1               5                   10                  15

Val Pro Ala Pro Ala Ala Ala Glu Ala Gln Ala Val Ala Ser Gly
            20                  25                  30


<210> SEQ ID NO 2
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 2

Gly Arg Gly Arg Gly Gly Pro Gly Gly Gly Pro Gly Ala Gly Leu Arg
1               5                   10                  15

Leu Arg Cys Leu Arg Pro Arg Arg Arg Arg Arg Arg Arg Trp Arg Val
            20                  25                  30

Gly Glu


<210> SEQ ID NO 3
<211> LENGTH: 54
<212> TYPE: PRT
<213> ORGANISM: Artificial sequence
<220> FEATURE:
<223> OTHER INFORMATION: Synthetic polypeptide

<400> SEQUENCE: 3

Gly Val Val Gly Ala Gly Pro Gly Ala Gly Pro Gly Arg Gly Cys Gly
1               5                   10                  15

Cys Gly Ala Cys Ala Arg Gly Gly Gly Gly Ala Gly Gly Gly Glu Trp
            20                  25                  30

Val Ser Glu Glu Ala Ala Ser Trp Arg Val Ala Val Trp Gly Ser Ala
        35                  40                  45

Ala Gly Lys Arg Arg Gly
    50


<210> SEQ ID NO 4
<211> LENGTH: 24
<212> TYPE: PRT
<213> ORGANISM: Artificial sequence
<220> FEATURE:
<223> OTHER INFORMATION: Synthetic polypeptide

<400> SEQUENCE: 4

Pro Ser Ala Arg Leu Leu Ser Ser Arg Ala Cys Tyr Arg Leu Arg Leu
1               5                   10                  15

Phe Pro Ser Leu Phe Ser Ser Gly
            20


<210> SEQ ID NO 5
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 5

Pro Leu Ala Arg Asp Ser
1               5


<210> SEQ ID NO 6
<211> LENGTH: 780
<212> TYPE: DNA
```

<213> ORGANISM: H. sapiens

<400> SEQUENCE: 6

```
ccccatttcg ctagcctcgt gagaaaacgt catcgcacat agaaaacaga cagacgtaac     60

ctacggtgtc ccgctaggaa agagaggtgc gtcaaacagc gacaagttcc gcccacgtaa    120

aagatgacgc ttggtgtgtc agccgtccct gctgcccggt tgcttctctt ttgggggcgg    180

ggtctagcaa gagcaggtgt gggtttagga ggtgtgtgtt tttgtttttc ccaccctctc    240

tccccactac ttgctctcac agtactcgct gagggtgaac aagaaaagac ctgataaaga    300

ttaaccagaa gaaaacaagg agggaaacaa ccgcagcctg tagcaagctc tggaactcag    360

gagtcgcgcg ctaggggccg gggccggggc cggggcgtgg tcggggcggg cccgggggcg    420

ggcccggggc ggggctgcgg ttgcggtgcc tgcgcccgcg gcggcggagg cgcaggcggt    480

ggcgagtggg tgagtgagga ggcggcatcc tggcgggtgg ctgtttgggg ttcggctgcc    540

gggaagaggc gcgggtagaa gcgggggctc tcctcagagc tcgacgcatt tttactttcc    600

ctctcatttc tctgaccgaa gctgggtgtc gggctttcgc ctctagcgac tggtggaatt    660

gcctgcatcc gggccccggg cttcccggcg gcggcggcgg cggcggcggc gcagggacaa    720

gggatgggga tctggcctct tccttgcttt cccgccctca gtacccgagc tgtctccttc    780
```

<210> SEQ ID NO 7
<211> LENGTH: 780
<212> TYPE: DNA
<213> ORGANISM: H. sapiens

<400> SEQUENCE: 7

```
gaaggagaca gctcgggtac tgagggcggg aaagcaagga agaggccaga tccccatccc     60

ttgtccctgc gccgccgccg ccgccgccgc cgccgggaag cccggggccc ggatgcaggc    120

aattccacca gtcgctagag gcgaaagccc gacacccagc ttcggtcaga gaaatgagag    180

ggaaagtaaa aatgcgtcga gctctgagga gagcccccgc ttctacccgc gcctcttccc    240

ggcagccgaa ccccaaacag ccacccgcca ggatgccgcc tcctcactca cccactcgcc    300

accgcctgcg cctccgccgc cgcgggcgca ggcaccgcaa ccgcagcccc gccccgggcc    360

cgcccccggg cccgccccga ccacgccccg gccccggccc cggcccctag cgcgcgactc    420

ctgagttcca gagcttgcta caggctgcgg ttgtttccct ccttgttttc ttctggttaa    480

tctttatcag gtcttttctt gttcaccctc agcgagtact gtgagagcaa gtagtgggga    540

gagagggtgg gaaaaacaaa aacacacacc tcctaaaccc acacctgctc ttgctagacc    600

ccgcccccaa aagagaagca accgggcagc agggacggct gacacaccaa gcgtcatctt    660

ttacgtgggc ggaacttgtc gctgtttgac gcacctctct ttcctagcgg gacaccgtag    720

gttacgtctg tctgttttct atgtgcgatg acgttttctc acgaggctag cgaaatgggg    780
```

<210> SEQ ID NO 8
<211> LENGTH: 33
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GA repeats

<400> SEQUENCE: 8

Gly Ala Trp Ser Gly Arg Ala Arg Gly Arg Ala Arg Gly Gly Ala Ala

```
1               5                   10                  15

Val Ala Val Pro Ala Pro Ala Ala Ala Glu Ala Gln Ala Val Ala Ser
            20                  25                  30

Gly


<210> SEQ ID NO 9
<211> LENGTH: 34
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: AG repeats

<400> SEQUENCE: 9

Ala Gly Ala Trp Ser Gly Arg Ala Arg Gly Arg Ala Arg Gly Gly Ala
1               5                   10                  15

Ala Val Ala Val Pro Ala Pro Ala Ala Ala Glu Ala Gln Ala Val Ala
            20                  25                  30

Ser Gly


<210> SEQ ID NO 10
<211> LENGTH: 36
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GP repeats

<400> SEQUENCE: 10

Gly Pro Gly Arg Gly Arg Gly Gly Pro Gly Gly Gly Pro Gly Ala Gly
1               5                   10                  15

Leu Arg Leu Arg Cys Leu Arg Pro Arg Arg Arg Arg Arg Arg Arg Trp
            20                  25                  30

Arg Val Gly Glu
        35


<210> SEQ ID NO 11
<211> LENGTH: 37
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: PG repeats

<400> SEQUENCE: 11

Pro Gly Pro Gly Arg Gly Arg Gly Gly Pro Gly Gly Gly Pro Gly Ala
1               5                   10                  15

Gly Leu Arg Leu Arg Cys Leu Arg Pro Arg Arg Arg Arg Arg Arg Arg
            20                  25                  30

Trp Arg Val Gly Glu
        35


<210> SEQ ID NO 12
<211> LENGTH: 56
<212> TYPE: PRT
```

-continued

<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: GR repeats

<400> SEQUENCE: 12

Gly Arg Gly Val Val Gly Ala Gly Pro Gly Ala Gly Pro Gly Arg Gly
1               5                   10                  15

Cys Gly Cys Gly Ala Cys Ala Arg Gly Gly Gly Gly Ala Gly Gly Gly
            20                  25                  30

Glu Trp Val Ser Glu Glu Ala Ala Ser Trp Arg Val Ala Val Trp Gly
        35                  40                  45

Ser Ala Ala Gly Lys Arg Arg Gly
    50                  55

<210> SEQ ID NO 13
<211> LENGTH: 57
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: RG repeats

<400> SEQUENCE: 13

Arg Gly Arg Gly Val Val Gly Ala Gly Pro Gly Ala Gly Pro Gly Arg
1               5                   10                  15

Gly Cys Gly Cys Gly Ala Cys Ala Arg Gly Gly Gly Gly Ala Gly Gly
            20                  25                  30

Gly Glu Trp Val Ser Glu Glu Ala Ala Ser Trp Arg Val Ala Val Trp
        35                  40                  45

Gly Ser Ala Ala Gly Lys Arg Arg Gly
    50                  55

<210> SEQ ID NO 14
<211> LENGTH: 27
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: AP repeats

<400> SEQUENCE: 14

Ala Pro Ala Pro Ser Ala Arg Leu Leu Ser Ser Arg Ala Cys Tyr Arg
1               5                   10                  15

Leu Arg Leu Phe Pro Ser Leu Phe Ser Ser Gly
            20                  25

<210> SEQ ID NO 15
<211> LENGTH: 26
<212> TYPE: PRT
<213> ORGANISM: Artificial sequence
<220> FEATURE:
<223> OTHER INFORMATION: Synthetic polypeptide

<400> SEQUENCE: 15

Pro Ala Pro Ser Ala Arg Leu Leu Ser Ser Arg Ala Cys Tyr Arg Leu

-continued

```
1               5                   10                  15

Arg Leu Phe Pro Ser Leu Phe Ser Ser Gly
            20                  25


<210> SEQ ID NO 16
<211> LENGTH: 8
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: PR repeats

<400> SEQUENCE: 16

Pro Arg Pro Leu Ala Arg Asp Ser
1               5


<210> SEQ ID NO 17
<211> LENGTH: 9
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (1)..(2)
<223> OTHER INFORMATION: RP repeats

<400> SEQUENCE: 17

Arg Pro Arg Pro Leu Ala Arg Asp Ser
1               5


<210> SEQ ID NO 18
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 18

Arg Gly Arg Gly Arg Gly Arg Gly Arg Gly Arg Gly Arg Gly Arg Gly
1               5                   10                  15

Arg Cys


<210> SEQ ID NO 19
<211> LENGTH: 18
<212> TYPE: PRT
<213> ORGANISM: Artificial sequence
<220> FEATURE:
<223> OTHER INFORMATION: Synthetic polypeptide

<400> SEQUENCE: 19

Arg Pro Arg Pro Arg Pro Arg Pro Arg Pro Arg Pro Arg Pro Arg Pro
1               5                   10                  15

Arg Cys


<210> SEQ ID NO 20
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 20
```

```
Ala Pro Ala Pro Ala Pro Ala Pro Ala Pro Ala Pro Ala Pro Ala Cys
1               5                   10                  15

Lys Lys Lys Lys
            20


<210> SEQ ID NO 21
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 21

Gly Pro Gly Pro Gly Pro Gly Pro Gly Pro Gly Pro Gly Pro Gly Pro
1               5                   10                  15

Gly Cys Lys Lys
            20


<210> SEQ ID NO 22
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 22

Cys Arg Arg Arg Arg Trp Arg Val Gly Glu
1               5                   10


<210> SEQ ID NO 23
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 23

Cys Tyr Arg Leu Arg Leu Phe Pro Ser Leu Phe Ser Ser Gly
1               5                   10


<210> SEQ ID NO 24
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 24

Cys Arg Val Ala Val Trp Gly Ser Ala Ala Gly Lys Arg Arg Gly
1               5                   10                  15


<210> SEQ ID NO 25
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 25

Cys Arg Pro Arg Pro Leu Ala Arg Asp Ser
1               5                   10


<210> SEQ ID NO 26
<211> LENGTH: 13
<212> TYPE: PRT
<213> ORGANISM: Artificial sequence
```

<220> FEATURE:
<223> OTHER INFORMATION: Synthetic polypeptide

<400> SEQUENCE: 26

Cys Ser Gly Arg Ala Arg Gly Arg Ala Arg Gly Gly Ala
1 5 10

<210> SEQ ID NO 27
<211> LENGTH: 32
<212> TYPE: PRT
<213> ORGANISM: Artificial sequence
<220> FEATURE:
<223> OTHER INFORMATION: Synthetic polypeptide

<400> SEQUENCE: 27

Ala Trp Ser Gly Arg Ala Arg Gly Arg Ala Arg Gly Gly Ala Ala Val
1 5 10 15

Ala Val Pro Ala Pro Ala Ala Ala Glu Ala Gln Ala Val Ala Ser Gly
20 25 30

<210> SEQ ID NO 28
<211> LENGTH: 35
<212> TYPE: PRT
<213> ORGANISM: Artificial sequence
<220> FEATURE:
<223> OTHER INFORMATION: Synthetic polypeptide

<400> SEQUENCE: 28

Pro Gly Arg Gly Arg Gly Gly Pro Gly Gly Gly Pro Gly Ala Gly Leu
1 5 10 15

Arg Leu Arg Cys Leu Arg Pro Arg Arg Arg Arg Arg Arg Arg Trp Arg
20 25 30

Val Gly Glu
35

<210> SEQ ID NO 29
<211> LENGTH: 55
<212> TYPE: PRT
<213> ORGANISM: Artificial sequence
<220> FEATURE:
<223> OTHER INFORMATION: Synthetic polypeptide

<400> SEQUENCE: 29

Arg Gly Val Val Gly Ala Gly Pro Gly Ala Gly Pro Gly Arg Gly Cys
1 5 10 15

Gly Cys Gly Ala Cys Ala Arg Gly Gly Gly Gly Ala Gly Gly Gly Glu
20 25 30

Trp Val Ser Glu Glu Ala Ala Ser Trp Arg Val Ala Val Trp Gly Ser
35 40 45

Ala Ala Gly Lys Arg Arg Gly
50 55

<210> SEQ ID NO 30
<211> LENGTH: 25
<212> TYPE: PRT
<213> ORGANISM: Artificial sequence
<220> FEATURE:
<223> OTHER INFORMATION: Synthetic polypeptide

<400> SEQUENCE: 30

Ala Pro Ser Ala Arg Leu Leu Ser Ser Arg Ala Cys Tyr Arg Leu Arg
1 5 10 15

Leu Phe Pro Ser Leu Phe Ser Ser Gly 20 25

<210> SEQ ID NO 31
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 31

Arg Pro Leu Ala Arg Asp Ser
1 5

<210> SEQ ID NO 32
<211> LENGTH: 99
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (92)..(93)
<223> OTHER INFORMATION: PR repeats

<400> SEQUENCE: 32

Met Gln Ala Ile Pro Pro Val Ala Arg Gly Glu Ser Pro Thr Pro Ser
1 5 10 15

Phe Gly Gln Arg Asn Glu Arg Glu Ser Lys Asn Ala Ser Ser Ser Glu
20 25 30

Glu Ser Pro Arg Phe Tyr Pro Arg Leu Phe Pro Ala Ala Glu Pro Gln
35 40 45

Thr Ala Thr Arg Gln Asp Ala Ala Ser Ser Leu Thr His Ser Pro Pro
50 55 60

Pro Ala Pro Pro Pro Pro Arg Ala Gln Ala Pro Gln Pro Gln Pro Arg
65 70 75 80

Pro Gly Pro Ala Pro Gly Pro Ala Pro Thr Thr Pro Arg Pro Leu Ala
85 90 95

Arg Asp Ser

<210> SEQ ID NO 33
<211> LENGTH: 74
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (73)..(74)
<223> OTHER INFORMATION: GP repeats

<400> SEQUENCE: 33

Met Arg Gly Lys Val Lys Met Arg Arg Ala Leu Arg Arg Ala Pro Ala
1 5 10 15

Ser Thr Arg Ala Ser Ser Arg Gln Pro Asn Pro Lys Gln Pro Pro Ala
20 25 30

Arg Met Pro Pro Pro His Ser Pro Thr Arg His Arg Leu Arg Leu Arg
35 40 45

Arg Arg Gly Arg Arg His Arg Asn Arg Ser Pro Ala Pro Gly Pro Pro
50 55 60

Pro Gly Pro Pro Arg Pro Arg Pro Gly Pro
65 70

<210> SEQ ID NO 34
<211> LENGTH: 68
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (67)..(68)
<223> OTHER INFORMATION: GP repeats

<400> SEQUENCE: 34

```
Met Arg Arg Ala Leu Arg Arg Ala Pro Ala Ser Thr Arg Ala Ser Ser
1               5                   10                  15

Arg Gln Pro Asn Pro Lys Gln Pro Pro Ala Arg Met Pro Pro Pro His
            20                  25                  30

Ser Pro Thr Arg His Arg Leu Arg Leu Arg Arg Arg Gly Arg Arg His
        35                  40                  45

Arg Asn Arg Ser Pro Ala Pro Gly Pro Pro Pro Gly Pro Pro Arg Pro
    50                  55                  60

Arg Pro Gly Pro
65
```

<210> SEQ ID NO 35
<211> LENGTH: 41
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (40)..(41)
<223> OTHER INFORMATION: GP repeats

<400> SEQUENCE: 35

```
Met Pro Pro Pro His Ser Pro Thr Arg His Arg Leu Arg Leu Arg Arg
1               5                   10                  15

Arg Gly Arg Arg His Arg Asn Arg Ser Pro Ala Pro Gly Pro Pro Pro
            20                  25                  30

Gly Pro Pro Arg Pro Arg Pro Gly Pro
        35                  40
```

<210> SEQ ID NO 36
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 36

```
agtcgctaga ggcgaaagc                                                 19
```

<210> SEQ ID NO 37
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 37

```
cgagtgggtg agtgaggag                                                 19
```

<210> SEQ ID NO 38
<211> LENGTH: 42
<212> TYPE: DNA

<213> ORGANISM: Artificial sequence
<220> FEATURE:
<223> OTHER INFORMATION: Synthetic polynucleotide

<400> SEQUENCE: 38
cgactggagc acgaggacac tgaagtcgct agaggcgaaa gc 42

<210> SEQ ID NO 39
<211> LENGTH: 42
<212> TYPE: DNA
<213> ORGANISM: Artificial sequence
<220> FEATURE:
<223> OTHER INFORMATION: Synthetic polynucleotide

<400> SEQUENCE: 39
cgactggagc acgaggacac tgacgagtgg gtgagtgagg ag 42

<210> SEQ ID NO 40
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 40
cgactggagc acgaggacac tga 23

<210> SEQ ID NO 41
<211> LENGTH: 91
<212> TYPE: PRT
<213> ORGANISM: Artificial sequence
<220> FEATURE:
<223> OTHER INFORMATION: Synthetic polypeptide

<400> SEQUENCE: 41

```
Met Gln Ala Ile Pro Pro Val Ala Arg Gly Glu Ser Pro Thr Pro Ser
1               5                   10                  15

Phe Gly Gln Arg Asn Glu Arg Glu Ser Lys Asn Ala Ser Ser Ser Glu
            20                  25                  30

Glu Ser Pro Arg Phe Tyr Pro Arg Leu Phe Pro Ala Ala Glu Pro Gln
        35                  40                  45

Thr Ala Thr Arg Gln Asp Ala Ala Ser Ser Leu Thr His Ser Pro Pro
    50                  55                  60

Pro Ala Pro Pro Pro Pro Arg Ala Gln Ala Pro Gln Pro Gln Pro Arg
65                  70                  75                  80

Pro Gly Pro Ala Pro Gly Pro Ala Pro Thr Thr
                85                  90
```

<210> SEQ ID NO 42
<211> LENGTH: 72
<212> TYPE: PRT
<213> ORGANISM: Artificial sequence
<220> FEATURE:
<223> OTHER INFORMATION: Synthetic polypeptide

<400> SEQUENCE: 42

```
Met Arg Gly Lys Val Lys Met Arg Arg Ala Leu Arg Arg Ala Pro Ala
1               5                   10                  15

Ser Thr Arg Ala Ser Ser Arg Gln Pro Asn Pro Lys Gln Pro Pro Ala
            20                  25                  30

Arg Met Pro Pro Pro His Ser Pro Thr Arg His Arg Leu Arg Leu Arg
        35                  40                  45
```

```
Arg Arg Gly Arg Arg His Arg Asn Arg Ser Pro Ala Pro Gly Pro Pro
    50                  55                  60

Pro Gly Pro Pro Arg Pro Arg Pro
65                  70


<210> SEQ ID NO 43
<211> LENGTH: 66
<212> TYPE: PRT
<213> ORGANISM: Artificial sequence
<220> FEATURE:
<223> OTHER INFORMATION: Synthetic polypeptide

<400> SEQUENCE: 43

Met Arg Arg Ala Leu Arg Arg Ala Pro Ala Ser Thr Arg Ala Ser Ser
1               5                   10                  15

Arg Gln Pro Asn Pro Lys Gln Pro Pro Ala Arg Met Pro Pro Pro His
            20                  25                  30

Ser Pro Thr Arg His Arg Leu Arg Leu Arg Arg Arg Gly Arg Arg His
        35                  40                  45

Arg Asn Arg Ser Pro Ala Pro Gly Pro Pro Pro Gly Pro Pro Arg Pro
    50                  55                  60

Arg Pro
65


<210> SEQ ID NO 44
<211> LENGTH: 39
<212> TYPE: PRT
<213> ORGANISM: Artificial sequence
<220> FEATURE:
<223> OTHER INFORMATION: Synthetic polypeptide

<400> SEQUENCE: 44

Met Pro Pro Pro His Ser Pro Thr Arg His Arg Leu Arg Leu Arg Arg
1               5                   10                  15

Arg Gly Arg Arg His Arg Asn Arg Ser Pro Ala Pro Gly Pro Pro Pro
            20                  25                  30

Gly Pro Pro Arg Pro Arg Pro
        35


<210> SEQ ID NO 45
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 45

gcccacgtaa aagatgacgc                                                  20


<210> SEQ ID NO 46
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 46

cctcctaaac ccacacctgc                                                  20


<210> SEQ ID NO 47
<211> LENGTH: 43
<212> TYPE: DNA
<213> ORGANISM: Artificial sequence
```

<220> FEATURE:
<223> OTHER INFORMATION: Synthetic polynucleotide

<400> SEQUENCE: 47
cgactggagc acgaggacac tgacctccta aacccacacc tgc 43

<210> SEQ ID NO 48
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 48
cgactggagc acgaggacac tga 23

<210> SEQ ID NO 49
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 49
gctttcgcct ctagcgact 19

<210> SEQ ID NO 50
<211> LENGTH: 23
<212> TYPE: DNA
<213> ORGANISM: Artificial sequence
<220> FEATURE:
<223> OTHER INFORMATION: Synthetic polynucleotide

<400> SEQUENCE: 50
tctagcgact ggtggaattg cct 23

<210> SEQ ID NO 51
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 51
ctgcggttgt ttccctcctt 20

<210> SEQ ID NO 52
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 52
tttcttgttc accctcagcg a 21

<210> SEQ ID NO 53
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 53
ctgggaacgg tgaaggtgac a 21

<210> SEQ ID NO 54
<211> LENGTH: 19
<212> TYPE: DNA
<213> ORGANISM: Artificial sequence
<220> FEATURE:
<223> OTHER INFORMATION: Synthetic polynucleotide

<400> SEQUENCE: 54
gggagaggac tgggccatt 19

<210> SEQ ID NO 55
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 55
acgacatcga ttacaaggac g 21

<210> SEQ ID NO 56
<211> LENGTH: 20
<212> TYPE: DNA
<213> ORGANISM: Artificial sequence
<220> FEATURE:
<223> OTHER INFORMATION: Synthetic polynucleotide

<400> SEQUENCE: 56
atcagcttct gctcgctatg 20

<210> SEQ ID NO 57
<211> LENGTH: 106
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (78)..(79)
<223> OTHER INFORMATION: AP repeats

<400> SEQUENCE: 57

```
Gly Glu Pro Pro Leu Leu Pro Leu Pro Leu Pro Gly Ser Arg Thr Pro
1               5                   10                  15

Asn Ser His Pro Pro Gly Cys Arg Leu Leu Thr His Pro Leu Ala Thr
            20                  25                  30

Ala Cys Ala Ser Ala Ala Ala Gly Ala Gly Thr Ala Thr Ala Ala Pro
        35                  40                  45

Pro Arg Ala Arg Pro Arg Ala Arg Pro Asp His Ala Pro Ala Pro Ala
    50                  55                  60

Pro Ala Pro Ala Pro Ala Pro Ala Pro Ala Pro Ala Pro Ala Pro Pro
65                  70                  75                  80

Ala Pro Ala Ser Ala Arg Leu Leu Ser Ser Arg Ala Cys Tyr Arg Leu
                85                  90                  95

Arg Leu Phe Pro Ser Leu Phe Ser Ser Gly
            100                 105
```

<210> SEQ ID NO 58
<211> LENGTH: 119
<212> TYPE: PRT
<213> ORGANISM: Artificial sequence
<220> FEATURE:
<223> OTHER INFORMATION: Synthetic polypeptide
<220> FEATURE:

<221> NAME/KEY: REPEAT
<222> LOCATION: (108)..(109)
<223> OTHER INFORMATION: PR repeats

<400> SEQUENCE: 58

Met Gln Ala Ile Pro Pro Val Ala Arg Gly Glu Ser Pro Thr Pro Ser
1 5 10 15

Phe Gly Gln Arg Asn Glu Arg Glu Ser Lys Asn Ala Ser Ser Ser Glu
20 25 30

Glu Ser Pro Arg Phe Tyr Pro Arg Leu Phe Pro Ala Ala Glu Pro Gln
35 40 45

Thr Ala Thr Arg Gln Asp Ala Ala Ser Ser Leu Thr His Ser Pro Pro
50 55 60

Pro Ala Pro Pro Pro Pro Arg Ala Gln Ala Pro Gln Pro Gln Pro Arg
65 70 75 80

Pro Gly Pro Ala Pro Gly Pro Ala Pro Thr Thr Pro Arg Pro Arg Pro
85 90 95

Arg Pro Arg Pro Arg Pro Arg Pro Arg Pro Arg Pro Arg Pro Arg Pro
100 105 110

Arg Pro Leu Ala Arg Asp Ser
115

<210> SEQ ID NO 59
<211> LENGTH: 94
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (89)..(90)
<223> OTHER INFORMATION: GP repeats

<400> SEQUENCE: 59

Met Arg Gly Lys Val Lys Met Arg Arg Ala Leu Arg Arg Ala Pro Ala
1 5 10 15

Ser Thr Arg Ala Ser Ser Arg Gln Pro Asn Pro Lys Gln Pro Pro Ala
20 25 30

Arg Met Pro Pro Pro His Ser Pro Thr Arg His Arg Leu Arg Leu Arg
35 40 45

Arg Arg Gly Arg Arg His Arg Asn Arg Ser Pro Ala Pro Gly Pro Pro
50 55 60

Pro Gly Pro Pro Arg Pro Arg Pro Gly Pro Gly Pro Gly Pro Gly Pro
65 70 75 80

Gly Pro Gly Pro Gly Pro Gly Pro Gly Pro Gly Pro Gly Pro
85 90

<210> SEQ ID NO 60
<211> LENGTH: 56
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (17)..(18)
<223> OTHER INFORMATION: GP repeats

<400> SEQUENCE: 60

Gly Pro Gly Pro Gly Pro Gly Pro Gly Pro Gly Pro Gly Pro Gly Pro
1 5 10 15

```
Gly Pro Gly Pro Gly Pro Gly Arg Gly Arg Gly Gly Pro Gly Gly Gly
            20                  25                  30

Pro Gly Ala Gly Leu Arg Leu Arg Cys Leu Arg Pro Arg Arg Arg Arg
        35                  40                  45

Arg Arg Arg Trp Arg Val Gly Glu
    50                  55


<210> SEQ ID NO 61
<211> LENGTH: 98
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (39)..(40)
<223> OTHER INFORMATION: GR repeats

<400> SEQUENCE: 61

Arg Leu Thr Arg Arg Lys Gln Gly Gly Lys Gln Pro Gln Pro Val Ala
1               5                   10                  15

Ser Ser Gly Thr Gln Glu Ser Arg Ala Arg Gly Arg Gly Arg Gly Arg
            20                  25                  30

Gly Arg Gly Arg Gly Arg Gly Arg Gly Arg Gly Arg Gly Val Val Gly
        35                  40                  45

Ala Gly Pro Gly Ala Gly Pro Gly Arg Gly Cys Gly Cys Gly Ala Cys
    50                  55                  60

Ala Arg Gly Gly Gly Gly Ala Gly Gly Gly Glu Trp Val Ser Glu Glu
65                  70                  75                  80

Ala Ala Ser Trp Arg Val Ala Val Trp Gly Ser Ala Ala Gly Lys Arg
                85                  90                  95

Arg Gly


<210> SEQ ID NO 62
<211> LENGTH: 65
<212> TYPE: PRT
<213> ORGANISM: Artificial sequence
<220> FEATURE:
<223> OTHER INFORMATION: Synthetic polypeptide
<220> FEATURE:
<221> NAME/KEY: REPEAT
<222> LOCATION: (29)..(30)
<223> OTHER INFORMATION: GA repeats

<400> SEQUENCE: 62

Gln Ala Leu Glu Leu Arg Ser Arg Ala Leu Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Trp Ser Gly Arg Ala Arg Gly Arg Ala Arg Gly Gly Ala Ala
        35                  40                  45

Val Ala Val Pro Ala Pro Ala Ala Ala Glu Ala Gln Ala Val Ala Ser
    50                  55                  60

Gly
65


<210> SEQ ID NO 63
<211> LENGTH: 98334
<212> TYPE: DNA
<213> ORGANISM: H. sapiens
<220> FEATURE:
<221> NAME/KEY: repeat_region
```

<222> LOCATION: (51933)..(51938)
<223> OTHER INFORMATION: GGGGCC repeats

<400> SEQUENCE: 63
aagcttgata atattatcaa atattagata aatgtaatat tagaagaaaa ctttttttgaa 60 aagatatata aaaataattt cattcaaaat ttttatattt aatttaaatt tttaatgaaa 120
atatatctaa gttttgtacg ctttaaatgt aattatgttt gataatttaa tcatttacta 180
ttcgttctct attgctgccc taacaaatta ccatagttca gtggcttaca aaacacaaat 240
ttattatctt accattctgt gagtcaaaat tccaaaatag gtgtcactag gctaaaatga 300
aggactgcat ttcttcctgc aggctccagg agagatctat gtcttactct tttcggcttc 360
taaaggctgc ccacattcct cgactagtgg cgtccctcct tcgtctctaa acccagcaac 420
aacaggttga gtcctcatgt cacatctttc ttacctttct gtcatctcat ctcgctgact 480
gctgctggga aaaattctcc acttttaagg gctatcatga ttagactatg cccactagat 540
aatacaagat ctcagatcct taacttccat cacatctgca aagtcgcttt tgcctcataa 600
aagagtctga ggtttagacg ggagatctta agggggctat taatatgcct accataatca 660
ctgagaataa gtacaagtta agattataat agcaatagaa tatacaaacg tgaagctcca 720
aaagaacaac aacaacaaaa aaggtgaaca ggaaaaagaa actgaaaatc tttaaaaagg 780
cagtctgttt aaatctataa aaactggaaa aaaatgagag tggacaaata tctggtaagc 840
atgatggact taaaatttgt gactagggca ttacattttt tatattaata taatgaagat 900
tgaattactg atcaaaacaa ttaaaaagca agagaactat tctcatcaaa tctgcaacac 960
gaaaagttca gacaaaattc caacaacttc acattctgaa ctaaatgagg actaattacc 1020
agttcgagca atgagaatat atgaggtcct ccgtttgcac tttgccaggg atctgaaaac 1080
gttgggagta ggtcggcttc accctgaagc cagaccatcg acagccagtt ttccctccct 1140
tctccaccca caggtcttag gccctcatcc ttcccagcct cagaactagt ctccaaagaa 1200
gaggaaagtt agaggagaga gtaaatcgtt gaataggatg aaggagatgt gggaaaaaga 1260
aaaagagagg ctgcaagaga gagggtccca gggataactc tgctcttgga agggtggcca 1320
cagtcatgtg gtcccaagag gcaacaacaa gcttaggaag ccagagaaac cagttacaat 1380
cactgctact cttttcgatt ctgtgttgtt taagaaatat cacccgccag gagttctcca 1440
gaaacatttt ccctgattcc atgtaagtgc tcaaccagtg aatggtaatc ccattttggt 1500
ttagtctgta ccatccccta ttccaaaata aagggaaaaa tggtgggttt atatcttaaa 1560
ttttctactt tactaaactc aagggaaata gccaagcaaa aacgaaagct gagactcttg 1620
ctaattatcc tttccataga atgtttgcta aaattccttg tcaaggaagg aataacaaag 1680
ctagtccacg ctctgtatag ggtgtttcca attagttata ctttaaagta taagtattta 1740
acaaaatcta taaattttgt taattattta cttgtagtga aaaatgagcc attctcaagc 1800
aaatcacttt ttattacaca ttccagagaa taaccataaa aggacattta ttatagcaaa 1860
aataaccaca tctggatgga acttcaatca ccagtattta ctaaataaat gcccagaaaa 1920
aaaatagttc atctttaatt tcagtcatca ttaataaaag ctgaagtacc tcttcagatc 1980
ttttgatcat tttctgttgg attgttttct ttttactgag ttgcaaatgc tctttatata 2040
ttttggatac aaagctttat cacataggca ttttgcaagt attttttcca agttttttta 2100
tcttttcatt tatttaataa tatctttcaa agaacgggaa ttttataatt tttatgaagt 2160
ccatttataa ttttttcttt tatgggttgg tgggggttgg gggttgtgtt gtcctaagaa 2220

-continued

```
atcttggctc aacacaaaaa gattagtttc tatattttct tctagaagtt ttatagtacg   2280

atctcagatc catttcagat gatgaataag cacataaaaa aaggatactc atcgttagtc   2340

attagagaaa tgcatattaa aaccataagg aaatactact atatacatat attagatagg   2400

atgaagagca actggaatct catacagtgc tgattgaaat gcaaaatggc aaaacaactt   2460

tagaaaccaa tttggaagca gctgtactga catggaattt tgagctggaa gaatcttaga   2520

aaaagaatac tttaccacct cccccattct cttcaccctg ggaactgtt aaatgaggaa   2580

attgtggttc aaggaggaac ttgtctatat gctttctcag ctttcccgtg gtaattacca   2640

tcttgataat ataacgtaat gtatgtatat gttatcaaat aatataatat cttcatcata   2700

tatttatcat cttcataatg ttagctgtct agtggtaact tttttttgct ctttattgcc   2760

tccctctttt ttccctcttt gttgtttttt gtcatacaat tatgatatat gtgtatatat   2820

tctcactgta aagatgtaaa caacacaaag attattgaac aaatcacgaa agtaaccctt   2880

ccttcattct taccctatcc aaccctcatc tcctcagaag aatacaccat tttagttgta   2940

aatgtttttc tagctctttt tcaatgtttc tacctatatg catgtatgta taatgtatat   3000

acatacatat atacatacat attgatatat acatatatag aggtatggtt ttttaactta   3060

aatggaattg cattgtggat attgtcctat gacttgcttt caaccaaatt atatgtcttg   3120

gaaatacata catatattta aaaaatatgt tatgtatatg taacatacta tatgtgcata   3180

atatatatta catagatata ataaggccta ggaagaaatt gtgtgcaacc tctagtacat   3240

cttcctctat atctactgta catacataca acccattctt tttttaattt ttttattttt   3300

ttagacagaa tcttgctctg tcgcccaggc tggagtgcag tggcacaatc tcggctcact   3360

gcaagctcca cctcctgggt tcacgccatt ctcctgcctc agcctcccaa gtagctggga   3420

atacaggcac ctgccatcag gcccagctaa tttttttttg tatttttagt acagatgggg   3480

tttcaccgtg ttagccagga tggtctccat ctcctgacct cgtgatccgc ccacctcatc   3540

ctcccaaagt gctgggattt acaggcgtga gccaccgcgc ccagccacaa ctcattgcag   3600

agtagtccaa aatatggatg gactgtagct taattactta ttctcccatt gatagacact   3660

taggactttt ctaattttta taatttaaaa atatgctgca attaacaaac attcttgtgt   3720

atctttttgc tgtatgtatg catatttctt tagtatgggt tttggaagag gaatcacaaa   3780

ggaggcatag aatataaata tttttatttt gaaaaataca gttgtaattt aataacccac   3840

caaaagactc taacagttta gattcacatc aacagtgtaa gaacatgtct gttttactgc   3900

atccttaccc ccactggtta taatactttt aattaacaat cttatggatg aagaatacta   3960

tcgcaatgtt gttttaatgc atttttccaa ttactagtga gattgaacat taattctttt   4020

attttatgga tcactggctt ttctccttct gtgaactacc tgttcacatc ctctgctttt   4080

cagctcttga gctgttatct ttttcttatt gatttatatg agctctttat atattcaaga   4140

tgttaatcat ttgtatttta tgtatatggc aatgattttc ttccaaacca atgcttgtct   4200

tttatttatt tatttattta tttatttatt tgagaccgag tctcgctctg tcgcccaggc   4260

tggagtgcag tggcgcgatc tcggctcact gcaagctccg cctcccgggt tcacgccatt   4320

ctcctgcctc agcctcctga gtaggtggga ctacaggcgc ccgctgccac acccggctaa   4380

tttttgtat ttttagtaga gacagggttt caccgtgtta gccaggatgc tctctatctc   4440

ctgacctcgt gatccgcccg cctcggcctt ccaaagtggt cggattacag gcatgagcca   4500

ccacgcctgg ccaatgcttg tctttttatc tctgtttatg gcatctttca tactatggac   4560

atttttattt ttattttta tgttgattta ttcttgaatt gtatacatgt taattatacc   4620
```

-continued

```
taagttattg taatacctt aaagccaagt tctacacata tatttaattt gctttcccaa   4680
taggtctctg agggaacaca ttttttcaaa tcactttgtt tcatcttttt taggtgttga   4740
tcaattatta aggagtttga aataatcatt taaacggaat tcttcagatg aaaacataaa   4800
gacatttatc gggtcagagc attggtcggt tcacatactc aggatcagtg gcctgggtgg   4860
gcaggcactg ggtgaatgga gagctgcagg tattggaaga gagcccagtt ggatatgtag   4920
tttccaaaga tcatcaaggc agacaaccaa agggaaaccg tgggaaacac ctgctttggg   4980
ccatctaaga tgagatgata aagtaaggaa agagttgagc ccaacacagt gatagccaat   5040
ctgaaagcgg gcagaactga caagaccaaa caagtaggtg aactggctgc aggcagccag   5100
ccaccacagg gacagcgtgt actccaggga caagctcaag gctataggta gttagttcaa   5160
ggctactagg gtgagaagag caggaactga gttctatacc agtgcttctc aaaactaatg   5220
tgcatcctaa tcacctggaa atcttgtaaa aatgtagatt ctgattcagt gagtctgaag   5280
cagagcttaa gatactacat gcttaacaag agcctagttg atgctgacac tgctggtccc   5340
tggagctctc tttgagtagc aggcttctgg aaggcttgtg tcactaagca cagagaagcc   5400
tcacttatca aatctgcacc aaaacaggaa aactaatgtg aagaataatg tgatgcacac   5460
gtcagagcat gaggcagttg ctttgtccct gaggttgcgc tccagatggc ttcctaagat   5520
gcgacaggct gatcttgtgc gtgggggtcc cggaggcttg ggccacggga gagacaggac   5580
ctcagaggct gggagacagg cagagacaga agagtgacat cctgctgctt ttgaatttgc   5640
acattctgta gaataataac agcagtaaac tgttacacaa tatctattct cagcatcttg   5700
aagccctttc acatattgtt acttccatta atggggccct ttgctgctat ttctactttt   5760
ctcttcagct atcaacaata tggctttcca cacctccatc agacagtagc cagatgaaat   5820
aaaatgtgcc agaatgaaaa cttgttcatt tgtctacttt ttgccaagac tagacaggca   5880
ggaaattgaa tgtattttta cagaaaaggt tttcaaaact ttttcccctc tgtggctcat   5940
ttaggtaaac taaaaggcat aagacccacc taaaacatgg gttcccgctt tttattggag   6000
aaagaacata gtactttaaa aaaatacata aaataataaa aaggaaagac aaagataatg   6060
aaggttgtac atggtaccaa atttttgtat cccataataa cacatgagta gatcactact   6120
aagtaggttt tagtgacata taggaaacat taaaatctac agaaatttgc attattttct   6180
gtcaaaaagg atcatttcac agcctttcag gggggaaccca ttgcccacag gaactcatgc   6240
attccatgct ttgaggatca ctagatctaa gaagccttcc ttggaggttc tagcctccaa   6300
cccttatttt agtaaaagaa gctccagttt tatctgtttc taagtcagac taccacacaa   6360
cattgggctt aaagaaaggt ttccagggct aaagcagact ttgaggatta ctaattccga   6420
gttaaatttc tgtgtattat ctctggattt gacttattca cactggacta tcactcataa   6480
atatacataa tacagagtta actatttaaa tttataaaga gagtattttc cttttttatg   6540
agcaaaacat gctgccaact acttggacca catactgatc cataaatact gacagctttg   6600
taattggaaa taataaatac acactaatga agcatctcaa aagggaagag ccacaggtaa   6660
tctgagtgat taggcattca tgttaggtta ggctttgatc attgttttta atcgcaattt   6720
cattgcagtg catctataaa tccatgtcca gaagtatgaa gtggttctat agtaagaata   6780
agatgctaca gataatgcga ctaaataaga cactataggt aatgacacag attcaagtct   6840
tattgttgat gggaagaggt caataatgga tgatataata tactacagca atgagaatta   6900
ttgaatgttt tccagactca cttgtataat tggccataac agcaaacaaa aaacaggttc   6960
```

-continued

```
tgatagcaaa atgatataca gtactaacaa aggtgaatct tgaggtgaac cttctcttta   7020
taagtttaaa tagtttaccc ccgacctttt cccatagtag aacagcctaa aaagtatctt   7080
tcagtagaat gctagtgctt atgaggtttt cttaagatat catttttcaa ttaaaattta   7140
tttcacaaaa gactcacatc cttgccagcc ttcagggtga gtgttgattc aggctgtgtc   7200
caacggcaac gatgagtgaa cttctcaccc tcagaatcac atgagcattc ctgagatgtt   7260
ttatcagagt gataccaact tcattattag aatattgagt ccctatttcc tatattcaat   7320
gtcctttcaa gccctaactt tgtccgggtt gaaggcaaag atccaaataa tcacatttgt   7380
ctttgataac tgaaactggg agaactggga ctgtctcaag agttctacgt gactgtaggt   7440
tgcaagtact gtggttgcat ctccaaatat taaccaatcc cagtgacaat tcaatggggt   7500
ctcctgaacc atgatcctca tgtctccagt gaaggaaatg ggcaaagggg attcaaaaat   7560
ccccttttgga ggaataggaa acttctgctt tccttcattt cataacattt gcgatggaac   7620
aaaggctttt ttagaatgga gcaaccagat cctttttttgg gggaatcagc ttaaatgtcc   7680
cttcttctca tactactttt atctatgtga tcctattctt ttctgttgtg gattgaatca   7740
tgtccctcaa aaagattgaa tttagagtgt gctctaaatt caatgtggag aaatttggac   7800
acagaggcag acacacaggg agaaccccgt gtgacaatgg aggaagagga tgcatttatg   7860
ctgccacaag ccaaggaaca ccaaagattg tcagcagcca ccagaagcta ggataaaggc   7920
atggcacatc actccctctg agcccccaaa aggagccaag actgctaata ctctgatctc   7980
ggacttctgg cctgaaacag tgagagaata aggttctgtt gtttcaagct acccagcttg   8040
cggtattttg tcacagaagc acaaggaatc aagtacattt tctttctcag cacttgtgat   8100
aatttgattt tttctttact cagtggttgt ttcacaccta tgtccccatc agactgtaag   8160
cttaaagaga cctggatctg gtctgtcttc accactgttg attcattacc agcacagtgc   8220
ctggcccatg gtcactgaat aaacgtttgt tgagagaatg aatgtgctta accagaagta   8280
ctattgacct attaggccaa gttcaaggtg cctaacagct cagctgtgaa ggatacctct   8340
cctttcagtc ctctgttaca tatgtccctg atagatgtgt tatttgtatc tcctcctggc   8400
cctcaagttt gtttgagggc aggacccttt tttgtatatc tgtagagctt cgtagtacct   8460
aaatactact ttgcatatat aataaagttt cgataaatat tcattaaata aagaaataaa   8520
tgaaatgact aagttttcta agatgttaca actagattga agatatttag ctcattattt   8580
aacaagaaaa ctatggttaa ttatggtgtc ctgtgtgaaa atggttatag tttgtttttt   8640
aattaatata agcatgtatg tgcattatca gtatacacaa tttgtggtat gagtgttttg   8700
tgtccctgca cacagaccac ggaaatcctg agaaacaaac tgccacccca gagcaggtgc   8760
ctaacacaga gacttttaat ccttaaagtt tttctataac taagcaatgt tttttcaaat   8820
gcaataacac tgatatgcag acatattgat tgtccactca caaagccatt cctcaatatc   8880
attacaacat gcctctttga atgtcattaa aaatagatgt ctcatttttc taggacaagt   8940
tggctgaagt tctgcttgaa aactggtaat agaaaataca atttctcaac ccgctttggc   9000
cttttaattc tgttctacaa ccttgccagt tcactttcaa agtcaaggga tgcatcttgc   9060
aaaaccatga catcttttga gtaactcctt ctgttcttaa cacatattcc caggagctta   9120
ataaatattg tttttgcaac ttgtttagtg gcaaaataat gagtccttgg tgtatgctta   9180
tcctctgctt tgctattaga gaagatatat tcagactgtt ttaaacaaat taattcaagg   9240
gcagggaaca gtcctaaaac ctgttaaaat tcaaatactt ggtcactgta tgtgcagcat   9300
gtgtgttcta gaaagtccta ttattttaaa atataaattg aatcttgttg agaaattaat   9360
```

```
gtcatatgaa tatattaata actgaaatgc tgccaagttt acaaaaagcc ctcaatgaaa   9420
ctgtgacctt gtatagacaa gggcctgtgg agggacattt ttaaaccatc tcttttttta   9480
tttcctcatg agatctacaa tgtaagtgca ttaaagttga tgaatgaatt gcagtgcaac   9540
ttttcctgcc tcttttgcct ttcatttgtc tatatttcaa gcttcactga agtgatagat   9600
tttgggcttt gccacattgt cctctgattg cttccctctg ctcctccttt tcctagtgaa   9660
tctttgtttt actggtggaa aaatctacat ctttgtatct tggcatttta ctttcacatt   9720
atctcataga ttttatttca agttgctata aagttatcaa cttttatttt taactaatat   9780
tatttttaac aattagaaaa ttgttgacca ggtaattcca gcactttggg aagctgaagc   9840
gggaggatca cgtgagccca ggagctcgag accagcctgg gcaatgcaag gagactgtct   9900
ctacaaaata taaaaataca ttagccaggt ttggcggtgc atgcctgggg tccagctatt   9960
caggaagctg aggtgggagg atcacttgag ctggagaggt tgaggctgca gtgagcagtg  10020
atcgcaccac tgcactccag tctgggtgac agagggagac cctatctcga aaaaaaggaa  10080
aagaagagga ttttgctggc aagatggctg aataggaata gctccgttct gcagctccca  10140
gtgagatcaa tgcagaaggc aggtgatttc tgcatttcca acagaggtac ctggttcatc  10200
tcactgggac tggttggacg gtgggtgcag cccatggagg gtgagcagaa gtagggtggg  10260
gcgttgcctc actcaggaag tgcaaggggt ccctcttcta gccaagtgaa gccgtcaggg  10320
actgtgccat aagaacagtg cactctggtc caggcttttc ccacagtctt tgcaacccac  10380
agaccaggag ataacaagcg gtgcctatgc caccagggcc cggggtttca agcacaaaac  10440
tgggtggcca tttgggcaga catcaagcta gctgcaggag tttttatttt catacccccag  10500
tggtgcctgg aacgccagtg agacagaacc gttcactccc ctggataagg ggcagaatcc  10560
agggagccaa gtggtctggc ttggcgggtc ccacacccac ggcgcccagc aagctaagat  10620
ccactggctt gaaactctcg cttccagcac agcagtctga ggtccacctg agacgcccgg  10680
gcttggtgtg gggaggggca tccaccattg ctgaggcttg agtaggcggt tttaccctca  10740
cggtgtaaac aaagctgcct ggaaggtcca gctgggcaca gcccaccaca gctcaccaag  10800
gccgctgtgg ccagagtgcc cctctggatt cctcctctct gggcaaggca tctctgaaaa  10860
aaaggcagca gcgccagtca gagacttata gataaaaccc ccatcaccct gggacagagc  10920
acctcaggga aggagtggct gtgggtgcag tttcagcaga tttaaacgtt cctgcctgac  10980
agctctgaga gagcaacaga tctcccagca cagcgttcaa gctctgttaa agatcagact  11040
gcctcctcaa gtgggtccct gactcccatg tctcctgatt gagagacacc tcccagtagg  11100
ggctgacaaa cacctcataa aggagagctc cagctggcat ctggcaggtg cccctctggg  11160
acgaagcttc cagaggaagg aacaggcagc aatctttgct gttctgcagt ctcagctgat  11220
gatacccagt caaacaggtc ctggagtgga cctccagcaa actccagcag acctgcagca  11280
gaggggcctg accgttagaa ggaaaattaa caaatagaaa ggaatagtat caacatcaac  11340
aaaaaggacg tccactcaga gaccccatcc aaaagtcacc aacatcaaag accaaaggta  11400
gataaatcca caaagatggg gagaaaccag tgcaaaaaag tctgaaaatt ccaaaaacca  11460
gaacgcctct tctcctccaa agaatcacca ctcctcacta gcaaggtaac aaaactggac  11520
agagaatgag tttgacaaat tcacagaatt agtgttcaga aggtgggcaa taacaaactc  11580
ctccaagcta acggagcatg caaggaagct aagaaccttg aaaaaagtta gagcaattgc  11640
taactagaat aaccagttta gagaagaaca taaatgacct gatggagctg aaaaacacag  11700
```

-continued

```
cacgagaact ttgtgaagca tacacaagta tcaatagcca aatcgatcac gtggaagaaa  11760
ggatatcaga gattaaagat caacttaatg aaataaattg agaagacaag attagagaaa  11820
aaagaatgaa aaggaatgaa caaagcctcc aagcaatata ggactatgtg aaaagaccaa  11880
atctatgttt gactggtgta ccagaaagtg acggggagca tggaaccaag ctggaaaaca  11940
ctcttcagga tattatccag gagaacgtcc ccaacctagc aaaacaggcc aacatttaaa  12000
ttcaagaaat acagacaaca ccacaaagat actcctcgag aagaccaacc ccaagacaca  12060
taatcgtcag attcaccaag gttgaaatga agaaaaaaat gttaagggca gccagagaga  12120
aaggtcaggt tacccacaaa ggaagcccat cagactaaca gcagatctct ctgcagaaac  12180
cctacaagcc agaagagagt gggggccaat attcaacatt tttaaagaaa agaattttca  12240
acccagaatt tcatgtccag ccaaactaag cttcataagt gaaggagaaa taaaatcctt  12300
tacagacaac caaatgctga gagattttgt caacagcaag cgtgccttac aagagctcct  12360
gaaggaagca ctaaacgtgg aaaggaacaa tcggtaccag ccactgcaaa agcacaccaa  12420
atttaaagt ccattgacac tatgaaaaaa ctgcatcaac taacaggcaa aataaccagc  12480
tagcatcata atgacaggat caaattaacc ttaattaagt tagccttaaa tgtaaacggg  12540
ctaaatgccc cagttaaaag acacagactg gccacctgta taaagagtaa agacccatca  12600
gtgtgctata ttcaggagac ccatctcaca tgaaaagaca cacataggct caaaataaag  12660
ggatggagga atatttacta agcaaatggg aagcaaagaa aacaaaaagc aggggttgca  12720
atcctagtct ctgataaaac agactttaaa ccaacaaaga tcaaaataga caaacaaggg  12780
cattacataa tggtaaaggg atcaatgcaa caagaacagc taactatcct aaatatatat  12840
gcacccaata caggagcacc cagattcata aagcaagttc ttagagacct acaaagagac  12900
ttagactccc acacaataat aatgggagac tttaacactc cactgtcaat attagacaga  12960
tcaatgagat aggaaattaa caaggatact caggacttga actcagttct ggatcaagtg  13020
gtcctaatag atacctacag aactctccac cccaaatcaa cagaatttac attcttctca  13080
gcaccacatc gcacttattc taaaattcac cacatagttg gaagtaaaac actcctcagc  13140
aaatgcaaaa gaacggaaat cataacagtc tcttagacca cagtgcagtc aaattagaac  13200
tcaggattaa gaaactcact caaaaccgca caactacatg gaaactgaac ctgttcctga  13260
atgactactg ggtaaataat gaaatgaagg gcaaaataaa gaagttcttt gaaaccaatg  13320
acaacaaaca cacaatgtac cagaatctct gggacacatt taaagcagtg ttaagaggga  13380
aatttatagc actagatgcc caaaaaagaa agcagaaaag atctaaaatc gacaccctag  13440
catcacaatt aaaagaacta gagaagcaag agcaaacaaa ttcaaaagct agcagaagac  13500
aataaataag atcagagcag aactgaagag gagagagaca tgaaaaaccc ttcaaaaaaa  13560
tcaatgaatc caggagctgg ttttttgaag agattgacaa aacagataga ccactagcca  13620
gacaataaag aaggagagaa gaatcaaata gatgcaataa aaaatgataa aggggggtatc  13680
accactgatc ccacagaaat acaaactacc atcagagaga atactataaa caactacaca  13740
aataaactag aaaatctaga agaaatggat aaattcctgg acacatacac cctcccaagt  13800
ctaaaccagg aagaagttga atccctgaat agaccaataa caagttctga aattcaggta  13860
gtaattaata gcctaccaac caaaaaaagt ccaggaccag acagattcac agccgaattc  13920
tatcagaggt acaaacagga gctggtacca ttccttctga aactattcca atagaaaaag  13980
agggaatcct ccctaactga ttgtatgaag ccagcatcat cgtgatacca aaacctggca  14040
gagacacaac aaaaaaaaga aattttcagg ccaatatccc tgatgaacat tgatgcgaaa  14100
```

```
atcctcaata aaatactggc aagcggaatc cagcagcgca tcaaaaagct tatccgccag  14160
gatcaagtcg gcttcatctc tgggatgcaa ggctggttca acatacgcaa atcaataaac  14220
catcattctc agcaaattat cacaagaaca gaaaaccaaa caccgcatgt tctcactcat  14280
aagagggagt tgaacaatga gaacacgtgg acccaaggag gggaacatca catactgcgg  14340
cctgtcgagg gatttggggt tgagggagtg atagcattag gagaaatacc taatgtaggt  14400
aacaggttga tgggtgcagc aaaccacaat gcgatgtgta tacctaccta acaaacctgc  14460
acgttctgca catgcactcc agaacttaaa gtataataat aaaaggcgct gcctcaggat  14520
gtaaagtgta acaaggggggc tggggtgggc agcgtgggcc tctgagacct ttggttgccc  14580
gtgtccgcag ctcgccccgc agccggctcc acaatggtcc gctccgtttg ccacgtgcgg  14640
attcgggttc cagactgaag gctgcgtgtt ctctgccgcc cacagcccaa gtttattgtg  14700
gcaaccgccg gagcagcctt ccccgctgtg gaggagcctg gggctacccc tcagcggtat  14760
ttggggctgg tcctgggggga gctaagcagg gttgtggcag cactgcctga aagtgtgaga  14820
ccagactcta atccttatgg ttttccatgg gagttggtga tatgtgcagc tgtacatgga  14880
ttttttgctg ttctcttttt ttgtgtggag aagttttaga tcggttggga gtcggcttta  14940
tgtgggaaga gaaaaaaagc ttgctgtaat gctttctgga ctaattgaag aaaagcataa  15000
actacttgaa aaatttagcc atgttcaaaa agagtatgaa ggctatgaag tagagtcatc  15060
tttaaagaat gccagctttg agaaggaggc aacctgtgaa aagctaaaca ggtccaattc  15120
tgaacttgag gatgaaatac tctgtctaga aaaagagtta aaataagaga aatctaaaca  15180
ttctgaacaa ggtgaattga tggtggatat ttgcaaaagg atacagtctc tagaagatga  15240
gtcaaaatcc ctcaaatgac aagtagctga agccaaaatg aacttgacga tatttcaaat  15300
gaatgaagaa cgactgaaga tagcaataaa agatgctttg aatgaaaatt ctcaactcca  15360
ggaaaacgag agacagcttt tgcaagaagc tgaggtatgg aaagaacaag tgagtgaact  15420
taataaacag aaaataacat ttgaagactc caaagtacat gcagaacaag ttctaaatga  15480
taaagaaaat cacatcaaga ctctgaacgc ttgctaaaaa tgaaagatca ggctgctatg  15540
cttggagaag acataacgga tgatggtaac ttggaattag aaatgaacag tgaatcggaa  15600
aatggtgctt acttagataa tcctccgaaa ggagctctga agaaactgat ttatgctgct  15660
aagttaaatg cttctttaaa aaccttacaa ggagaaagaa accaaattta tagtcagtta  15720
tctgaagttg ataaaggaag agcttacaga gcatattaaa aatcttcaga ctgaacaagc  15780
atctttgcag tcagaaaaca cacattttga aagtgagaat cagaagcttc aacaaaaact  15840
taaagtaatg attgaatttt atcaagaaaa tgaaatgaaa ctccagagga aattaacagt  15900
agatgaaatt accggttaga aaaggaagaa aaactttcta aagtacacga aaagatcagc  15960
cgtgccactg aagagttgga gacctataga aagtgagcca aagatcttga agaagagttg  16020
gcgagaacta ttcattctta tcaaggatgg attatttccc acgagaaaaa agcacataat  16080
aattggttgg cagcttggac tgctgaaaga aacctcaatg gtttaaggaa agaaagtgct  16140
cacaacagac aaaaattaac tgaagcagag tttaaatttg aacttttaga aaaagatcct  16200
tatgcacttc atgttccaaa tacagcattt ggcagagagc attccccata tggtccctca  16260
ccactgggtc ggccttcatc ctaaacaaga gcttttctct gagggcccac tgagactctc  16320
atctttgcta acaggaggag gaggaagagg ctcaagaggt ccagggaatc ctctggacca  16380
tcagattacc aatgaaagag gagaatcaag atgtgacagg ttaaccaatc ctcacagggc  16440
```

ttctctgaca ctgggtccct gtcacctcca tgggaacagg accgtaggat gatgtttctt 16500
ccaccaggac aatcatatcc tgattcagct cttcctccac aaaggcaaga cagattttat 16560
tctaattctg gcacactgtc tggaccagca gaactcagaa ggtttaatat gacttctttg 16620
gataaagtgg atgggtcaat gctttcagaa atggaatcca gcagaaatga taccaaagat 16680
gaccttggta atttaaatgt gcctgattca tctctccctg ctgaaaatga agcaactggc 16740
ccttactttt ctcctccacc tcttgctcca atcagaggtc cattgtttcc ggggggataca 16800
aggagcctgt tcatgagaag aggacctcct ttccccccac ctcctccagg aaccatgttt 16860
ggagcttctc aagattattt tccaccaagg gatttcccag atccaccaca tgctccattt 16920
gcaatgagaa atgtctatcc agcgaggcgt ttcctcctta ccttccccca aaacctggat 16980
ttttccccat aaaccccaca ttctgaaggt agaagtgagt tccctgcagg gctgattctg 17040
ccttcaaatg agcctgctac tgaacatcca gaaccacagc aagaaacctg acaatatttt 17100
tgctctcttc aaaagtaatt ttgactgatc tcattttcag tttaagtaac tgctgttact 17160
taagtgatta cacttttgct cccactgaag cttaatggaa ttataattct caggatagtg 17220
ttttctaaat aaagatgatt taaatatgaa tcttatgagt aaattatttc cattttatgt 17280
tattctggat agtataacta ttttaatttg ataaactaat ccacgattat ataaacaata 17340
atgggagttt tatatatgta atcttgcagg tagggaggct ttaaattata aaggttgtgt 17400
ctttatgcca agaactgtat taactgtggt tgtagacaaa tgtgaaagta attttatgct 17460
tcattaaata aattttagtt gatttttttt taaaaaaaga aaatggttaa tctatcattt 17520
aggtgcatca tcagttgttt aaccattctc tcttactgaa cattgggttg tttaaaaagt 17580
gttgttattt ttgaatcatg gttcagtgaa caattttgga cacataactt tttatctgat 17640
gagttatttc ctaaggatcc agctcagaaa ctcagcacat aaacctaata agaaaaaaac 17700
aatttgaagt ggctaacctc ttatcccaat aaaaatgttg tatttatgtt tggatttaga 17760
tgcctttcag tggtcatacc ttcacctaac ttttatggat tctactttta acatgtagag 17820
tgactgttta aatcacctaa actcactgag ttttaagttc ctttttattc aacaagactg 17880
gattgtatgt tccagctcct caaacttagt taccaaccac catcctagag aagtgaattc 17940
acatgaggcc tgtccagaag aacaatctcc ctttcagtgt cctcatgcat gcagtgacca 18000
gagaccaacc ttgataaatt atggaaaaag tacagcacat tctggaagag ccatgaaaga 18060
tccagatcat ctggtgctgg ataagaatat taatggacag gctgggcgcg gtggctcacg 18120
cctgtaatcc tagcactttg ggaggccgag gcgggcggaa catgaggtca ggagatcgag 18180
accatcctgg ctaacacggt gaaaccccgt ctctactgaa aatacaaaaa attagccggg 18240
catggtggcg ggcgcctgta gtcccagcta cacgagaggc tgaggcagga gaatggcgtg 18300
aacccgggag gcagagcttg tagtgagccc agatggcgcc attgcacttc agcctgggcg 18360
acagagtgag actccgtttc aaaaaaaaaa aaaaaagaat attaatggac aaaaagatta 18420
atgaaagaac atattgaagc atccaattac ctggtgtctg ctcaaatgag gaatcggtga 18480
gataggtcag ttagcagtca agatttataa aagagacgat ggccttggga ggggctgccc 18540
tactcgactt tttaatggct agaagctatt aagggctaag ccagaaccct tcagtatggt 18600
tcagtgagga tcccaatttg gggtccaaaa gtaaatgaca actcccagga accattaaga 18660
ataaaaatca tggagcatta ctgagaattt atgttatcta agtctgagga aaattaatgt 18720
taaggaagct ttcaaaagtc taatatttac accgaattcc agggcaccat gctctaagac 18780
aaagcactct ggtcctgccc ctctcctttc ctcatgtttt ttggttcttg ggatccttaa 18840
gggtcaatgt tattcttaaa atacagagca tcctggaaac taaaaaagtg gaagatattc 18900
aaattctaat gaatgtactg gcagtattgt agatcatgga gtataacata aagacaagaa 18960
tccctagcct cttccaccat actttgtaat ggtaaggaga aaggatagaa ttttgagaag 19020
tctgggaaga caatgtatga taacatctgg agaagctctg cataagttac ttttgttcag 19080
gcttaagaaa aattctagct tgcccctgca ctgtcatcag gtatcatgaa agtaaataaa 19140
acctttaaag attcttcaag ccagcagact tctatcttct ctatactatc ctgtgatcct 19200
aaactcttaa cagttactac gtataatttc cctacatttg ctactagtat tttatcatac 19260
acaatattac actcaatatt tcaaaagtgg atgattcatc tcccgaagag actgcaaaat 19320
tcatgagtta agatttgaga atactatttt agacaagatt tagtcagatt ttagagagtt 19380
agaaacctgt aacaattctc taacaatact gcttctcctt ttgtgtatta aggaattttt 19440
gtctatcaaa gatagtacga ggtagaccag aagataactt gccttcaaaa tgtctggaat 19500
gtaaaatggc aacagtagta tttggggact tcgtagggga tggccaatat acacccattc 19560
ttagaggtac tgatgatata atgtataaga caaaatcaag tggtctccat caccatataa 19620
tgtttaaaat ggcaaagagg gagcagaaca aacacccttt gcaaatctct tcatagaatc 19680
taccgtaata aacttgtact tgcttaaagt gtgtctcttc agtggtctta ttaccactac 19740
tttggggaaa atgaggctgc ttaaaagatt aacagacatt acattttaca tatctgtggc 19800
agagaaaaca ctatgtattc accaaaccac ttcttttcct tcccagtcac tcgggaagag 19860
gtcatttctt tgtccccttt catctaattg aggtgccgtg actacttcta gacaggcaat 19920
gtgagcagaa ggtatgcacg ccacgtatag gcctggtctt caaaaatccc tcagatatga 19980
tcttcttctc tcgtctcttt catggacaaa ctacaggcca tgtaataagg atggtggggt 20040
tccaaactga aagagcctgg atttctgatt tactgttttg agaagagttc accagggaaa 20100
cagcctggaa atacgcacag gaaaatatgc acaggaccct gtgtgagcaa gatataaaga 20160
tctattacat ggtgccatta aggtgagagt attgtgctta tagtatccag cattaattat 20220
cctcactact acaacttctt tgtatccatc atgtggaaaa gtagagtatt taataaatga 20280
ttattgagtt tattaccttt tttatattcc aatcattgct aattgtacgt tacctcattt 20340
caaggtaaag gtgaccaagg gctaaagcag tgctatccaa accaagccag acatcaaaat 20400
cacacaaaac cttttgaaaa tacaactttg aagatgccat tcacatagat atttattcag 20460
tgggttttca aatggaaccc tggaatctac agtctttaac aaggcttccc aagttattct 20520
gatatacagc aggcaaatct gagaaccact ggacaagaag aaaataaagg ctatatcttt 20580
cgacaacaaa gacaatgcct taaacataga atgtattcaa ttaaagcttg tagaaagata 20640
ggtttgtgaa caggcacagg gactagcctc gagcaaatta ataagggcag caatgttttt 20700
cactgaaacc attattcccc ctattttatt tcttctgggg ctctgtgttt cctttctcct 20760
atcaaaatcc attctaaggt tggaggttgg gggtatctct tgcctactcc atacagcaag 20820
gaataaaatt agtatttctc gaactatctg tgacagcaga cccattgtag gccagtactt 20880
ttgtaaaatg caataaaaat taacttctag agaatgaaat tttaaaatca cagacattca 20940
aaatacaaat tccaattttt ttattattaa ctgtaagaaa tttaaaatta aatctcaata 21000
aataaaatta aagcaaacat aagatagaaa aaaataagca ttatggattg gcccagtctg 21060
caaactgtat acactttgcc aaacatgggc ataaattact aagaagcaaa atcttccatc 21120
tgtaaacatt tccatttcca ttgacaatat gtgtgaggga aaggagggat gcttctgttt 21180

```
tagaatgcca ggcgtcagct aacaagtgac aaatacgtat tgagactgag atctccccag  21240
cctctcagta gtcagcaaga acatgttgag gcctctgttt ttgactaaaa aattggccag  21300
tgcatgggca acatgcatag gtcctgaatg aaaaaaatag cagcagcaga aatttaaaag  21360
aattttcaca gctaggccac agtaaattct caagcccttc atcagaagcc actgtggggc  21420
ctcatttatg cctttgtttt tattaaattg gatgtgatct taagattctt ctgtcaaaat  21480
tccactagca tgtgaaggca ccaaaagttt aaaatgtaaa attaacccaa gttaagctat  21540
tccattatta agcaatagca gatatatttg ttattatatg agaagaaagt taacagggag  21600
ctaagattga tgttactgat aagaaacaga aacaagactt taaaattaaa taaatgaatt  21660
atttatttaa taagaaccaa ttgacagatt ctcgataaag actgtaagat gtcttaaaac  21720
attaggtgta tggagataac atttgtaact ttgacaattt atatgatgag aaaaatcaag  21780
gaatgttatt gtttattggc agagttctag aattacaatt ccatcattct gttttgggga  21840
agtttccctt gaagtaaatg ataacagggc ttgaaatagt acacctcagc attttgttta  21900
taaaactgtg gaataggtaa ggtttgtatt gtaactgaac ccaggttcag ctgcttgctg  21960
ctctaaagct agacataaga gaggaaggtt ggtgggagga aaagcgattt taatcggaga  22020
agcagcaaac caagaagatg gtgaacaata gtcacagaac catcttaaat tttaaaattt  22080
accatagagt gttcaaagga aaacttggta tgggaggcat gcaggagggg tgcagggggc  22140
ggggtctgtg tgtcttgttc caatggctat ctcagatagt cacccatctg gaggtctagt  22200
tggtattatt ttgaattcag cccagtggtg gtggactgtc agtgactcct cgctaagcag  22260
gaggattctg cactcagggc tccatgcatg gtttgtttca agattggcct ctggaatttc  22320
tcaagcaaga acataattaa ataagcaggc attgccagag gggagtgtct ggaaaggaaa  22380
ggaatgaaga gatgaaagga aagtgggtgg ttaaactata tttttaaaac tgaggttccc  22440
agttatagta tgtttcgcac gctcccccca ttttagcacc cctgacagaa tttagtaatc  22500
tcctcatctt gtcctctact tcaggtcccc tatctgtcct tgtactctcc agggtttcct  22560
tttcttcttc acgaccttcc ttccctgcaa ttttataagc tattcctatc ccagtgattt  22620
agtttcagct tataaaactg tgtctttgcc attgtaatca aattgaaggg cctctgcttc  22680
atggttggat tctgtgacca ggagactctt acgaggagtt ggccaggtct ctgttaggaa  22740
agcaaaaaag aacaatggag gcaattatcc cattgatttc agctataaat cctattttgc  22800
ctgaattgtc tgaacgatga gtattctgtg aaaatgctgc tctctagtgc aatagaactg  22860
caaataatgc acatctattt cttataatct catccaacat acccacagag attcagatct  22920
aacaaaacag aggtgatttg gttattgaat cataatataa atatggggaa gaggagggaa  22980
atttcaagcc tgaggaaact gtagtaggag taagtatgct gtgtttaaga ggtcacagat  23040
aaaattaata ttaccaatcc atcaataggc aattactaat agcttactac acacacagga  23100
ataaaatgtg aagacagagg aagtgtaaaa tggagccgcc aactctacgg agttgtttgc  23160
aatttggtct ggtagaaagc tatgaaataa ggaagtacat gattgagagc tagagaatgt  23220
ggcacaggct ctgaacccgg accgttcaat gtagtaagct ctagccacac tggacacttg  23280
caatgtggct tgtccaaact gacatgtgct ttaagtataa aatataatcc agatttctaa  23340
gacttcaaaa aaaatggaaa tatctcatta ataatcttaa gtttattaca ggtagaaatg  23400
atagattaaa taaactatat tgtcaaaatt catttgatct gtttctacag tataacaaac  23460
ttacttgtgt ggtttgcatt ttatttctac tggataacat ggctttaaaa atggtatttt  23520
agaggaagga aagcttggta gagaatggac taatccggat ccctggaaga aatggacctt  23580
```

```
gaatgggtct tgatgacttg gagaggcaga gagagaaaaa gaaaagtcaa acatagggaa  23640
ttggttgata aaatgaaggt gaggggagaa ggaacagagg gaggagaaga tccagtttga  23700
gggatattac agcgagcagc ctgagaaaga aggataagaa aggagagaaa aaatgcaagg  23760
gaagtaaccc ttcaaagcca gtcagaagtt tctgggttcc tcagcagcca gaaaagaagc  23820
cgttgaaaag atctgagtaa cggagattct ggacgaaaac tgaagttatg gaagggaagt  23880
ttagacatgg gttattaaac gctttagcgc attagaagtt tcttatgtaa tcactaaatt  23940
cagatcctga aataatgcca caagaactat acagctcagc cacccaattc aataagaagt  24000
tacagcacag tctcacacat atccaattaa ccttggcctt tagtcaacat ctgggttctt  24060
tttgtcattt tcaaatacta tcacccagag gtgctatgat ttatattggg gaggggatta  24120
aaagaaaata agtaagttgg tgataagaaa aagctttcag atgattccat ctgaattaac  24180
agccctcttt agttgtctag gaaagaggat gctttttctt gaaagtgctt tgaaatgatg  24240
atgtgcttgt tagtaaacat caattatttt caaatcgtaa tgtttgcaag tttgtcttcc  24300
tgtagctcac cctttatgta ggtccagaat atgattgtca caaatatctg ggtgagcaag  24360
actatgaaat gtggtcataa agtaagtgat tatttctaaa ctcatctttg tcactcgtag  24420
tgcttcacaa agcacctttt cctggactac aattcatttt aattgatccc atcagcacta  24480
tatctgtatc ctgagtgact tcacaatacc ctctatttca agagaaacca atcaggttat  24540
gggtttgtta gtaataaaaa ttaccaagga gcagtttgtg gatggtaaaa gcaatgcaaa  24600
ttctaaagag aagtcataag agcaataata agcatcctcc tcacttcttg gaagtgaaca  24660
attccaagct ccctgaagca acacttaacc tatcatatta aacagtaatg gacaaatatt  24720
agaaatgttg atgtcagctt tcagaatctg tgggcatcaa aacatcactt aagttctccg  24780
aagtattctc tgtcaagttt ccttctacag tattcttttc ctactaggac agagccttaa  24840
gccctagaag aataatttg cttgtgtgtt aattatttgt ttactggttc attccagagt  24900
gtgagctgga aaaaggggga agtgtcataa atagtttttt atggcccatg gtttttcaac  24960
tacgtcacta ttggtagcag tttccactgc aggatctatt tgcaaagcct aggaaattag  25020
cattaagcaa gctgctagga agacttcaac agtaactagg ccacaggcct cacacatttt  25080
tcctccaccc cagcctcctc tggagagtac ttgctaaacc tctgtgacac ataatgaagc  25140
aaagaaagtg atagaacaac agaattacac gggcagatcc ttgtttcttc ttctctctct  25200
aaagaattcc ttggactgaa aagcagttta ttttggagga gtgagaaagt ggtgacagaa  25260
ttagaagggc ctgggagggc ttcattttag gagacagttt taggctgaaa agagatttca  25320
tgagtgtgat ttacctgagg tgacttttgg gggctcttat aaaaaggaag ttcatgctga  25380
atgggaggtg gcttctgaga tgcagattct ggtgagctaa gagggctcgg taaagaggag  25440
gcaggagtta agtagcgtga actatgcagt agcagccttc ttcccccctt gcttggggca  25500
ggtcatcaca acccttctca ataaaggggt ccaggaacca ctaggaataa atgggcattt  25560
gcacttcagg tgaaacccat ttgtcataac tgcttggact ttaagcttac aaataaaaag  25620
aaccacatat ttccctttgc agcttgattt agttaatgtc attttgagaa agaaagaaga  25680
cattgttatc ccgtcccttt tttttttttt tttttttttt tatgaagaga ctgggactca  25740
gagaagtcaa gtgattttcc cagaaccaga aaacacagaa gtagcagagc tgagatgact  25800
actccggtct tctgattcca aattccaaat tcattcttct aagcgatttc ccaaaacggg  25860
aaatgggttt atcttctatt tatgggaagt gatagtggta ttctatttag agaacttata  25920
```

```
taaaatctta ctttaaaata aataatattt caaaaagtaa gcttaattta aagaaaataa  25980
tcaagaaagt ctggtatatt tttacaaata taccaaatga ccttgctcta aaatacatct  26040
actttccagc aagccaaagt gaaacaattt gaaataagtg gcatttactg accactccct  26100
aaagttcaca caaaagaggt agtactctaa cttaaatata caaggtgaag aaatagctta  26160
ctcagcctgt tgggcttcct cttctacact cttgggaaat gccctccgtg ttaaccaaga  26220
attctcaggc cttggaggga gttttccatt ctcagtaaac tgagattgca gttgcggaaa  26280
ttaagaggta tctgtccagc acttcattcc cttaaggtca ggatctgtgc ttttaataat  26340
gacaattagc taacatatac aattaagcca tgcaaatgaa gtaagagaaa gctagaggag  26400
aaattcagga gccagttgcc ttttccagac atcttgtaca aatagtgttc aaaggactaa  26460
ttcaaaagat gggattcttc gcttgaaccc aggaggtgga gtttgcagtg agcggagatc  26520
gctccactgc actccagcct gggtgacaaa gtgagacccc atccaaaaaa aaaaaaaaaa  26580
aaaaaaaaaa aagatgggat tctttttaa aaaataaatt ttactgcgta tttttaaggt  26640
atacaacgtg atgttataag atggatatag atagtgaaaa ggtaactgta gtgaagcaaa  26700
ttaacatatt catcatctca catagttatc ttttatttgt tttgttttga tgggattttt  26760
aagatagtag aaaggaatgg tagacaataa acatttgagg gaaagtgggg ctttgtagaa  26820
ctcctaaaat gacagcacgc acaaatgtcc ccattatgtc taaagggtaa ctcgttccta  26880
cttctaggga cagctgaggg acatcaatgt aaatttctaa atgacttcct gaacttttta  26940
tttttatttt ttgtattttt agaggaaatt ataataacat caagccacct ctggaccata  27000
tcgctgctga tatcatcagc aaatggcact attcctaaat cctaagatgc acttttccct  27060
tcacatttca acatttgtga aactcgattg tacctacacc tgattttata tacaatgcag  27120
cctttccttt tcttttgtca ttgcatctta cgcctgattt ctccttggaa ttgagtaaat  27180
ataatgctta catgtgttaa taagaattga ggtcactcat aatttttgaa atatgccacc  27240
aaatataagc ctttctacat attgttgact ttgaagtcat ttcttttttt aactactaaa  27300
caataacact ttttgttgag aaaaattgca tatgaacaag agaccaagca ggtagagaga  27360
aaaaaacttt taataatcaa gagaatgtta ctgtgtccca aaggctaaag tcaccttact  27420
atcaagagag aaggacagga acagagagaa ccaggtaaat tacgaattga aaattccatg  27480
gttcatttat ctttattttt aataattcca tttgtgtgat tgtgttgacc acaaggtcat  27540
aatgttactc ttcatactga cttctcatgt aaattataaa taagttttta tgctaatgat  27600
ttatggagta agctattcat ctttccgaca gagagttacc tacaaagaaa taattattct  27660
acctctgaga tgaaatatca tgaaaggagt ggtttccaga tattttgact tttaaaagct  27720
taaagaatat atgtagtata aaattctaaa gcaggcaaaa ttaatccttt tagcaatcaa  27780
gatagcggct acttttggtg agaaggacaa ggtagtgata gagaaggggc tcaggggtct  27840
ttcctgaaga cagtgaggtg ggcaatggta ttttccttga cctggatggt gattaaacag  27900
atgtgtttac tttgtgataa ttgactaggc tgtgcaccta tgaactgcat acttttccat  27960
atatgtactg tattcttata cttaaaaaga agtttaaaaa taaatgcaac agatatagga  28020
cttcctatat tactcgttga ccaaaaaaat ggattcattt ttctttcagg taaaacgtac  28080
tagtggtttt aatattatat tgaccaggga gtaaatgttt accttaggaa ccttaatctt  28140
gatgttctcc aaagtcatta tctgttcttt ctgattatca gaatagagta tatctctata  28200
taaatgaaaa tttctggtca ttctcaaaaa ataacactaa gcatgaaaat cagaaatatt  28260
gatcttgttt tgtaatgatg tttctattga tgtgaagtag tttctagtag agttgctgtc  28320
```

-continued

```
ctaacacaca aatgaaattg cactgtttgg aagacacaac tgtgaatgac ttgcttcagt  28380
aaggaatttc caacatgatg gtttagggat agaggtgctc gattcctctg tctccggtta  28440
cccaggttat tgaggacagg gaggtcaata agtaatgccc tcctcccacc catagcacaa  28500
aacagagcgg ggttcagaga ataggtaagg ctttggccag ggtgttgagg agacttacat  28560
ccctgggaac cagtcagaat gggggcgctg aaaacaatgt tttaaattct agcacccagc  28620
aacatatgtg tgaagattaa atgtactcgt gctaaattca cttgctccat tactgaattt  28680
gggtggtgtc tgttaaagat gggaacaaag gcattcaggt cctggtatct tctaccactc  28740
ccagcatgaa cagactcatg tcagtgggta agggatggta tttcccgaga aggctttgaa  28800
ctcttgtagt gggtcaaata atggcccccc acttaaaaat gttcatgtcc aaatccctgg  28860
aagctgtgaa aaggggtttt tgcacatgta attaagtcaa agatattgaa attagatcat  28920
cctggattac ataggtgggc cctacattta atgacaagta tcctcataac agaagaggag  28980
aaggtgatgt gagatttgga gcagcagaga ttggagtgat gtggccacca atcaaggaaa  29040
ccaaggactt ccagcagcca ccagaagctg gaagaggcaa ggaaggactc ttccctaaag  29100
cctttaaagg agcacagccc tactaacacc ttgcttttgg gctctggccc gcaaaactgt  29160
gaaaggatac attgctgtta tttgaagcca cagttcgtag taaatttatt acagcagccc  29220
tagaaactga tacaactcct aaatacaccc ttagcaacac tgctcaacaa gaagtaggca  29280
atttcctcct gactgaaaaa tactgatact gttatgggat ccttgggggt gttgcttttc  29340
tgtccagaaa cctctgtggc ggtggcacct ttgcatgagt tttgctcggg tccactgggc  29400
ccactcatcc tggcaggctg cgctcagctg acactactgg cgtggatccc atgcctccaa  29460
agagactgga gcgaagcggt gagggatgtg tgaggaagtg agcgtggggt ctggcacaca  29520
gtcaggctca atggctgcta cagcgggatg ggcagcttca ggtgctggca cgggtgctgg  29580
ctcactgcaa ggctgtggct gcaccaagca gcgcagcaac ggaacgcatt ggtgcctgga  29640
aacttggaga ctccaggaac ctcagggctc caaaaggcaa atcacagccc tagcttcggg  29700
agctcccagg tctgggctgc caaagggctg cagctcttct ctcctctctc tctcttcgct  29760
cctctccctt tctctcttca ctcctccctc tttctctctt cactcctcct gtcgcctatg  29820
aacagcgaat tcaaccttcc agttttcaga ctaggaatgc tggagttgtc cttgattact  29880
ctgaattgtt cactccgcat atgggcactg aggatacgtt gatgaactac acagacaaaa  29940
aggatagaaa ttcctgtcaa gactacattc aatagggatg aagcaggcaa taatgaataa  30000
acatactaag ttgaatatga ctatttaaat atatataaca catatgactt gtataatgtt  30060
aaatatttta agtttttaa attcttccct tcatagattt tacattatag tagaagaggc  30120
atttttgttg ttgttctttt tgttttggat tcagagggta aatgtgcggg gttgttacat  30180
gggtatattg cataatgctg atgatggtcc catcacccag gtggtaaaca tagtacgtaa  30240
taggtgaatt tttagcccgt gcttccctct cccatctagt cgtcctgagt gtttatcgtt  30300
gctacgttta tgtcaatgtg tattcaatat ttagctccca cttataattg agaatatgca  30360
gtatttcgtt ttttgttctc gtgttaattt gtttaggata atggcctaca aagaacatga  30420
tttcattatt tttatggaca tgtagtattt catggtgtat atgtaccacg gtttctttat  30480
acaatcccac tgttgatggg cacctaggtt gattctattg ctgttgtgaa tagggctgca  30540
atgaacatac aagtgcatgt atctttttgg taacaaaaat tttatatttg gattacccag  30600
tagaattgct gggttgaata atagttttgg tttaagttct ctgagaaatc tccaaactgc  30660
```

-continued

```
tttccacagt agctgaacta atttacattt ccactagcag tgtataagcg ttctcttttc  30720
tccacaatct tttcaccagc atctgttatg ttttggcttt ttaatagcct tttgatgact  30780
gtgaaatggt atctcactgt ggtttggatt tccatttctc taatgattag tgaatgttga  30840
gcattttttt catatgttta ttggccgttt gtatgtcttc ttttgataag cgtctgttca  30900
tgtcctttac acattttcaa ttaaaatatt tgtttttttgc ttgctgattt aagttctttg  30960
tatattctgg aaattagatc tttgtcagat gcatagtttg caaatatttt ctcccattct  31020
gtagcctgtt tactctgttg gtaatttctt ttgctgtaca gaaactcttt aattaggtcc  31080
cacttgccta tttttagttt tgttgcaatt attctctgga acttagccat aaattgtttg  31140
ccaaagccaa cgtggagaag gatattttct aggttttctt ctaggatttt atagtttaag  31200
ttttacattt aaatctttaa tccatcttga gttaattttt gtatatgttg agaagcagga  31260
gtctaatttc attcttctgc atagggctag ccattatctt ggcaccattt attgaataga  31320
gagtcctttc cttattgctt atttctgtca attttgttga atatcagatc gtcgtaggtg  31380
tatgggtcca tttctgggtt ttctattctg ttctatttgt ctctgtgtct gtttttgtac  31440
cagaaccatg ctgcttggtt actgtagcct tttagtatag tttgaagttg ggtaatgtga  31500
tgtctctggc ttcgttcttt ttgcttagga ttgctttggc tattcaggct ccttttttggt  31560
tccatatgaa ttttagaata tttttctgat tctgtgaaaa atgacttgat attttgctag  31620
ggatagcatt ggagtggtaa cttgctttgg acagtgtggc cattttaatg atattgatta  31680
ttccaatcca tgagcatgga gtatttttat atttattcag tcatcttgat ttctttcagc  31740
agtgttttgt agttcaccct gtagaacatt tcacttccat ggttagatgt attcctattt  31800
tgtggctatt gtaaatggca ttgtattttt ttttatttgg ccctaaacta gaatgttatt  31860
ggtgtataga attgctactg atttttgtac attgattttg tatccttaaa ctttactgaa  31920
gttatttatc agttctagga gacttttgga gaagtcttta gggtttttcta tgtatgaaat  31980
catatcatca gcaaagagag acagtttgac ttcttcttct ttttggatgc catttatttc  32040
tttctcttgc ctagttgctc tgactaggac ttccagggca atgctgaata ggagtggtga  32100
gagtgggcat ccttgtcttg ttccagtact caagagaaat gcttccagca tttacctgtt  32160
tagtatgatg ttggctgtgg tttgtcatag gtggatctta ttattctaag gtatattcct  32220
ttgatgccta gcctgtcgag ggtttttaat catgaatgga tattgaattt tattgaaggt  32280
tttttctgaa actattgaga tgatcatatg gtttttgttt tttcattctg tttatgtggt  32340
gaatcacact tattgatttg ttatgttgaa ccagccttgc atcccaggaa taaagcctac  32400
ttgattgttg tgaattaact ttttgatgtg cttcttgatt tagtttgctc atattttgtt  32460
gaggatttttc gtgtttatgt taatcagaga tattgtcctg aagttttctt ttttcattgt  32520
gtctctggca gattttgata tcaggatgat gctggcattg tagaatgagt tagggaggag  32580
cccctctcct taatattatg gaatagtttc agtaagatta ctatcagttc ttctttgtat  32640
gcttggtaga attcagttgt gaatccatct ggtccagggc taaatttggt tggtaggttt  32700
tttattactg attcaatttt ggaacttgtt ataggtctgt tcaagttttc acttccgtcc  32760
tggttcaatc ttgggaggtt gtatgtttcc aggaatttat ccatttcctc tagatttcct  32820
actttgtgtg catagaggtg ttcataacgg tctctgaaaa tctttggcat ttctgtggga  32880
ttggtcgtaa tgtcattttt gtcatttctt gtgctttttg gaacttctgt ctgtttttcc  32940
tcgtttttct agctagcagt ctattagtct tgtttattct tatgaaaaac caactctttg  33000
tttcactaac attttatgga cttttgcatc tcaattttat ttagtcatta tctgatttta  33060
```

gttatgtctt ttcctctgct agctgtgaga ttgaattgtg ctcttttttt ctagttcctc 33120
tagtgttatg ttagattgtt tagttgagat ctttctaacc tcttgatgaa ggcattttag 33180
cactataaac tttcctctta acactgcttt tgctacatcc caaagatttt ggaaagttgt 33240
gtctctattt tcattaattt caaataattt tttgatttct gccttaattt cattgttcac 33300
ccaacagtta ttcgggagca tgtggcttaa tttccatgct tttgtgtagt tttgagagat 33360
cttcttggta ttgatttcta ttgttatttc actatgattt gagagtggcc tttgtatgat 33420
tttaattttt tttaatttat tgagacttgc tttatgactg agcatgtggg gcaatcttag 33480
aatacgttcc atgtgcatat gagaagaatg tgtgttctgt cattgttggc ttgagtatcc 33540
tagagaggtc tattaggtcc aactggtcaa gtgtcaagtt taattccaga attccttcgt 33600
cagttttctg cctcagtgat ctgtctaatg ctatcagtgg agtgataaag cccccactaa 33660
tattgtgctg ccatctacgt tttattgtag gccaataatt tgttttatga atctgagtgc 33720
tccagtgttg ggtgcatata tgtttagaat agttaagtct ttttgttcaa ttgaaccttt 33780
tatcatttta taatgccctt ctttgtcctt cctgattgtt gttggtttaa agtatgtttt 33840
aatctgattt aagggtagca actcctgctc tttttgtttt ttcatttgca tggtagatct 33900
ttcttcattc tttcactttg agcctgtgag tgtcattcat gtaggatgca tcttctgaaa 33960
acagcagaca gttgtgtctt gtctttttat ccagcttacc actttatgca ttttaaaggg 34020
agagtgtaga ctgtttacat ttagggttag cattgacatg tgagattttg ctcctgtcat 34080
tgtgttgttt agctggttgt tttgtagact tcattgtgta ataagtgtat ttttattggt 34140
agcaggtttc gtctttcatt tccatgttta gcaatcactt acggatttcc tgtaagaatc 34200
atctggtggt aatgaatctc cttggtgctt gcttgtctga gaaggattgt atttctcctt 34260
cacttatgaa actcagtttg gtgggatatg agttcttggt tgaaatttat tttctttaat 34320
aatgctgaaa atataggccc ccccatatct tctggcttgt aaggtttctg ctgacagaac 34380
tgttgctggc ctgatgaggt tctttttgta ggtgacctga cctttctcac tagctgcctt 34440
aacaattttt tcttttgcat tgaccttggt gaatctgatg actatgtgac ttggcaatgg 34500
ttgtcttgta tagtgtctca caggagttct ctgtatttct tgaatttgta tgcccacctc 34560
tctggtgaga taggggaaat tttcatggac tgcatcctca gatgtatgtt ctaagttgct 34620
tactctcttt ctcaggaatg actgtgagtc atagacttgg tctctttaca taacctcata 34680
aatcttgaag gttttgttca tgttttaaat tcttttttct ttatttttgt ccaaccaagt 34740
tgattcaaat aactggtctt caaactctga gattctttcc tcagcttggt ctgttctgct 34800
gttaatgcct ctgactatat tatgaaattt ttgaagttga tccctcaatt tctgaagttc 34860
agttttgttc tttcttaaaa tagctatttc atctttaagc tctttgatca tttttctgga 34920
ttccttgagt tccttgtatt gggtttcaat gatctcctgg atcttgatgt acttccttgc 34980
catccagatt ctgaattcta tgtatgtcat ttgagtcatt ttaatctggt taaaatcctt 35040
tgctggagga cttgtgtgtt tgtctggagg taaggagaca ccagcttttt tgaattgcta 35100
gagttcttga gatgactctt taacatatga gggctggtgt tccattaaca atagtgtaca 35160
ttgagtatag tcagttggct tcattctgag tgctttcaaa gggccaaagc tctgtacagc 35220
atctttattt gtggctagat ttttgcttta ggtttcacag gtgctgtata ttggaaaaat 35280
gtttttggtg ttgtcatttg gggtgcaatc cagtaggtga tgcttaagag tggtagctgg 35340
cagataggct cttactcagt ccacagctct tttgtatttt ggtgcagtcc tcagtagtgc 35400

-continued

```
tctgtggtgg tagggagaga tgaccccctc accagataca ttcctgggcc ttgggggagc  35460
cctctcttat tactggcact gcacctgcat ttcatttatt aggtgtcctg ggctgcaggg  35520
tgccctcagg cagaggctgc ggctggaaaa tagaccatac ccttccctgg ctggccctgc  35580
acaaggaggc acaccctgtt cctgagccag tccatgaacc cagctgtctc acccctctca  35640
gtgttctgag agtaggggat cccccactgc ttgagcacca tgagcccctc ctggctacag  35700
gcagtggggg taggtatagt ctctcaaccc actgtccaac tgatttccag ggtaacagag  35760
agctgtgcct gcccacagag ttcaggcaga ggccaggcca ttgtgctgga agctgatgct  35820
aagccttgtc tgatgatggg gagtgaagca atgtaacggc tccctaactg tggcttctct  35880
cagggctatg gcagctggca tgagactgct ccaggtccaa ggcctgtggg acttcctgtg  35940
gacttgagtt ttgcctctgc aaacactcca gcaactctct atgtcagtct agaggcccag  36000
ggacacggat caggtattgg gatgaagggg ttctccagtt cccaggattt cacaggtccc  36060
tgtggaaagt gaggatcccc caggggctct cactcactca ccctttctct atgttgggga  36120
gcttcccctg gctccatgcc catcttgggt ggccagctgc ccagcttcac tcttccctgt  36180
tctctgtgtc ccctcactcc cttaattgtc ctgatatcgt tccttaggtg atctacttgc  36240
agaggcagtg tttactcgcc acttgttttc tctctgtgag agtagcacac actagctgct  36300
actcatctag catcttgaat tcttcccatc tgaaaaagtt tcaactgcaa tcacagttaa  36360
agaaatacaa aaacaatagc actctaagtt acaacttctc acctatagaa ttcaaaaaca  36420
tccaaatgat taactaaaca tttgtttggt agatctgtgg gaaaacatga attccttgtg  36480
aattactgga gaaaatgaaa atgatgcaac acttatggaa gaaaatttgg ggatttttgg  36540
gggggagggg aacaatatat ttaaaactat aaatgcattt atcctagcaa ttctatgaat  36600
ggggatttat cttagggtac acctgcacac ttaggaaata atgtatgcag tcattcatta  36660
cagaattgtt tgtaatagca acaacctgaa aagcaactca tatatccatc catcacacag  36720
ggactggttt catgactacg gttcatgaat actctgcagc ccttagaaag aatgaggaag  36780
tggccgggca cggtggctca tgcctgtaat cccagcactt tgggaggccg aggcgggtgg  36840
atcacgaggt caggagatca agaccatcct ggctaacacg gtgaaacccc gtctctacta  36900
aaaacaatac aaaaaaatta gccaggcagg cgcctatagt cccagctatt cgggaggctg  36960
aggccggaga atggcatgaa cccgggaggc agagcttgca gtgagccgag ataacgccac  37020
tgcactccat ccagcctggg cgacagagcg agactccgtc aaaaaaaaaa aaaaagagga  37080
agttctctat gcgctgacat ggaaggaaga cagatggttg aatgaaaaaa gtacataatt  37140
agccataaag tgtaagactt tttgtctaaa aaagaagggt gatataattg catatttata  37200
ttttcttcca tttatattaa gagataataa aggtacacaa attggctaga ataaagtggt  37260
ttcctataaa gggtaagagt aattgagtgg atgaagacta gggttaggga tagatttctc  37320
agtgtattca ttttaatata tgtattcatt ttatatatgt actaattttt atatatgtat  37380
ttattttata ttttgatttt cttaacataa atatattatt ccttcataaa attaaacttg  37440
atacattttt gattactaga tatgtagaaa gcattatgtt cagtaccaca gtaatacttt  37500
caaaccagct acaattagta tttatgagca tctatgtgcc agacattgtg ttctgctttg  37560
gttggtgggg gtagaggagg aaaggaaacc atggcttaca taggagtgga agtcttgtct  37620
ttcactttgc acctctctcc ttcagaccta gcataaatat gaccttaggg gaggcagaac  37680
acatatgata aagagataac tagcaagaga cataatagta gctaaataaa tactgaagga  37740
aaaattcagg aagaggtagg aaggatatgc ctcatcactt ccacctgtta agaaaaactt  37800
```

-continued

```
tagacattct tgccaatatt ccttattgcc tgtcttttga acaaatgcca ttatcactag  37860
agtgaaatga tatttcattg tagttttgat ttgcatttct ctcatgatcg gtgatgttga  37920
gcaccttttt atatacctgt ttgccatttg tatgtcttct cttgaaaaat gtctattcag  37980
atctttgccc atttttaaat ggcgtaatac attttttcct attgagttgt ttgagttctt  38040
tatatattct ggttattaat cccttgtcag atgaataatt tgcaaatatt ttctcccatt  38100
ctgaggatta ccagaggctc agaggggtaa tggtggtggg ggagaataaa aatggttaat  38160
gagtacaaaa atatagatag gagtaataag atctagtatc tgatagcaca acagggtaat  38220
tacagccaac aaaaatttat tgtgcatttc aaaataacta agagtataat tggaatgtct  38280
gtaacacaaa gaagcaataa atgcttgagg tgatgtgagg ggatggatat ctaatttacc  38340
ttgatgtgat tattacatat tgtatgcctg catcaaaata gctcatgtat cttataagta  38400
tatacaccta ttatgtaccc attaaatttt ttaagaactt taaacaaatc aaatttaaca  38460
gagtttaatt gggcaaagaa tgatttgagg atcaggcaac ccccagaaac agaagaggtt  38520
caaagcaact cagtgctgtc acatggttgg agaggattta tgggcagaaa agggaaagag  38580
agatacagaa aatggaagtg aggtacacaa acagctggat tggttacagc ttgccatttg  38640
cgttatttga acataatctg aacagttggc tgtctttgct tgaccaaaac ttggtgtttg  38700
gtacaagagc agattacagt ctatttacac atccagttag tttacagttc actatacacg  38760
aagaagaaac ctttaagcag aacttaaaat atgcaaagag gaagctttaa gttaaactta  38820
atttaacaca cccaattatc aaaaaatgag tagctctgca aaagtggatt ttcctggtca  38880
tctttggtac ttccttaaaa aagagaaaag tagtactcac gataaaaaaa aaaaagtcct  38940
caagtcttta ttttattcct ttccaattta aaatgttaca tcatctgagg aaggtttttc  39000
cctttgaccg ctttcataga catttcttct gcatgggttg gccagaatca gaagagtaat  39060
tgtaactttc tgttcttgtc ctacagttac aaagcggttt cactttgtaa atgctctttg  39120
gatggcagga accaagcagc catgaaaaga ggagttacac ctttaaagga gtcattccat  39180
catgactctc aggactggaa catggaatac ctgaatggcc tctttggcac agataggcca  39240
cccttgaaag gtgttccaag ctaggaactc actaccactg ttacatcgat gcaactctgt  39300
gagaagtttt tatctggtga tggaaaatct catctcttca acacactgac tactaccagt  39360
ctcagaaccc tgtaaacaag attcattcat ctcaaattgg gttaaagcag tcaccctgcc  39420
ttacattagt ttggaataag gatgtgggga tggtggtaga ggaggggagt ggatgatgat  39480
ttttttattg ttatttgatt ctaaagaaac ttctatacat tttgcattta aaataattat  39540
gtttttaaca atgtttggat taattcaaaa taggatatta tatcctatta tattaaatat  39600
actatttaat catcttgttg accaaatgca acttaaacat gtaaaatggt aaatagcata  39660
ataattgtct tctaagcctg cactataaag tatttcagtg gcctcattat taaaggacca  39720
aggtgcccaa agaaacaaaa tttagtaatc ataaacaaga gacaaaccta cttcttttcc  39780
cccagagttc tggccacatt gaaataaggt gtttgaatgc ttaataagaa ttattttggc  39840
ccacacagtg gctcatgcct gtaatctcag cactttggga tgccaaggtg agcagatcac  39900
ttgaggccag gagttcaaga ccagcgtggc caacgtggtg aaaccccatc tctactaaaa  39960
atacaaaaat tagcccggtg tggtggtaca cgcctatagt cccagctact cgggagactg  40020
aggtgggaga atcacttgaa cccgggaggc caaggctgca atatcgagat cacaccactg  40080
cactctagcc tgggcaacag agtgagagtg agactctttc tcggaaaaaa aaaaaaagaa  40140
```

```
ttattttgaa caaagtgctg tcacctaagt tagcaaaact ccaagcaagg tttttggctc  40200
tgtaaggaaa gaattagcct actcatttgg aaatttagtg gtgtttgtaa tgcagaaagt  40260
gacagtgaga ctggaaaggg attggctttg gggcttgttc tgctttataa ataataatga  40320
atcttctcca acatgaagta atgtgaatta aaaaaaaaaa atctgtcctt agagtacaaa  40380
attacttcat aacccaatct gcatttctcc actccaagca tattttctgg gagttctact  40440
tagagagtga aagctgctgt gtgtgtgata attaatttta acaaacactt ggcaaactga  40500
gctggactat gtataagcta ccctagacta agcatgaatt tgaactgcac tttttatggt  40560
gttttttcca caatgacatt atttaggcat ttaaagttat ctgaactgca attttttgtt  40620
cttttttttt taatttgact ttttaaaaaa aattattcct gaataaagag gcagtttgta  40680
aaaactcgag aactgtgaga gataattgga tctttgtgta gcaaaactag aagggtgttg  40740
ggtatctgct ctttatcaaa tggaccactt acttttcttt tctttttgc cctgtgttca  40800
gaaaacaaat gtgcgtgtct cctgatttat aatgtatagt tcattaatgg agaaagtgct  40860
tgagaattag atcctaatgt catttcccat gcagcatctt cattcttttc taaagcacta  40920
tttggtaaaa acaactgata gtcgtcagag gtgatcagca atgtttgagc actatttcct  40980
ttttatatcc tgcacatgga atatggacag gcaaacaaat catttccaag taagaaaata  41040
aattttgagg gagttaatac tataatttga aagtaataac ctcctattta tccatctagt  41100
ttgttgttct gtactaaatt atttgtgcat gtctctgtgt ctataattta tgtgaaactt  41160
tgcacaatct taaataggac aaaatagaca ttctgtaatt tcccaggcaa gctatttaag  41220
gtgactatct ctctacatat ttgagatgaa aaacaataac atgacaatcc atcccttctt  41280
aggtttttgt aagcagactt actacctgtg actcagtttt gttctcacag ggtactaatt  41340
aatccttcac gataataact tgtcaaattc cattacttct gtaaaggcaa tactttatat  41400
ttgtttgtat tcaaatttta aactgatgtt aaatgccgtg ggtgcaactg caggttaaaa  41460
atatgtgttt gaatctctta ttctttttgc ttggcaatgt atgaaataac tgctctttct  41520
agaaatcttg atgatgaagt ggcctgttgt tttgtcacct aaaaatgcaa taatgttcaa  41580
attaagcttt tctttattaa catcacttga ttgtgtgcca tatttagagc ttagtgaaat  41640
tttaatctac acattgatta aatacatttt atttattctt gtttctaatg ggaactttct  41700
ttgtttctaa tgggaacttt cttaaattaa attacatcca acatttatta aagacctaaa  41760
acataggcaa ttactgtgct tagaggaaaa gcgcagacga aagtgaatca gacaagttcc  41820
ctgccctccg gaagctttca gtctagtgat gagaaagacg tatacacacc ttatgttgat  41880
ttaaaaaaaa aaaaagctct tacctggttg ctggcatatg aaagtgttag ttacagatct  41940
gccccaaact aaaggtgtca cctcgagtaa atctctttcc ctttcccttt caatctcttc  42000
atctataaac taggggttgg gaatacattt attaacaaac acaaattgag cgtctaccat  42060
gtgataatag tagctaaact tactgagcaa ttaccatggg gcaggtatca agataaaccc  42120
tttatgatgg taacctcatt taatcctcaa agcaattcca ttttcaagag gaggaaattg  42180
aggctcaaaa atgttaagta actcccccaa ggatgcaaag tgattgagcc agaattcaag  42240
actaggttgg tttgactcca aaactcatgc cattaaaccc tattgtgtca ctgcaaacaa  42300
ctctaatagt ttcaaattat tagttctatt aatattatat taccattatt tgccccccaaa  42360
atgtaaaatg taaatacaaa gagtttggtt tttgtattac tagtggaggt taaaggtgca  42420
caatggaatt attcaaactg ggaaaatcca ggaagacttc atggaggagg cagcatatgg  42480
ctgcagttaa taaggtttgc tcacacaaaa tggagaggtg aggacatttc aggcagagag  42540
```

aattatatga gaggttacag agcagtaaac agtcatgcgt ctgcaagatc aaagggaaag 42600
ggcggtaaga gagaagcttg aaagtcaagt ggagccagat tgtggaaaaa ctagagagtc 42660
atgccaagga ccttgacata tagaaaatgg gaagcccctg aaaggtgaag aacatgagag 42720
tgaaatgatt agtaactttt tggtttagga cttgtttctt ttgtgttttg gttgctttct 42780
tgttttgttt tgtttgtggt ttttaaattt acaaccaata agaatattta gtaaggtttc 42840
caaatacatc atgaatatat aaaactagcc tgactcaagg ataataattc tgggtagttg 42900
gagtgaagtt tcaatcagct acgtggcatt tgctaatcat ctgatatgag ctaacaataa 42960
aggagttaac aaataaactg tcagcctaca gtccagggtc tcaaatagca tgtgacatag 43020
ttgagaagca gttttccata tcatacatga aataactaaa gaaactactt acaaagcact 43080
ataccagtaa ctacaataaa atacaactat acatgcaaaa taatgctgaa agctgcaagt 43140
agaggggtaa agctaggcca gttgctcagg gaaccattct gaagtggatt tgggaagtat 43200
gtctagaagg ggagccattg ctgtgagagt gctgaggctc atctgctact agtcccccac 43260
tactcaggca tatggtaggt cagtaacaaa accatcattg tgcactgttc tttccatcta 43320
aattccatca aattatgacc aacctatcaa ggtactagtt caaattctct cttcctctat 43380
aagctagtgg tcttctctaa aatttaagaa gatcgtgctc atcttcctac ttcttgttct 43440
ctttcttctg tgttttctga ggctgcaatg aactaggaac ttcctctccc cagaactctg 43500
tattccaggc cttagatcac tcaaaactgt tgcttataaa gtgcagagaa tcaacagaga 43560
aggaatagag gttaatgtct ggtcaaagat gtgattctct tgttgaaaag ttcattagct 43620
tattatttat agaatcataa gtcccaggaa aaaccaaaag gaaatatata ttggatccta 43680
atgatattct ctttttttct tttttctttt cccccactcc attgcccagg ctggagtgca 43740
gtggcataat ctcagctcac tgcaacctcc acctcccggg ttcaagggac tctcctgcct 43800
cagccttcca agtagatggg attacaggca tgtgccacca catctggcta attttttttt 43860
gtatttttag tagagatggg gtttcaccat gttagtcagg ctggtgttga actcctgacc 43920
tcaaatgatc caccagcctc ggcctcccag tgtgctggga ttgcaggcgt gagccaccac 43980
acccggcctg atattctctt gcaagggcat tgtttacatt gtctatcatc agaactgtag 44040
agtgttggct ccaggcacag aacccctaga gttttgtaaa ccatttatat cacactggca 44100
accagaagta actttatata ctcaagaatc aagatttcac ctagaagtac ctcaggtagg 44160
tgttggttca ttcacattcc aaccaaaaga taatgtacca taaagtgcat accgcctagt 44220
ccgtaatgat taaggcaacc acataaaatc tcattattta aaagaaatta agtccaggca 44280
cggtggctca cacctgtaat ctcagcactt cgggaggcca aggagggcag atcacctgag 44340
gttgggagtt tgagaccagc ctgatcaaca tggagaaatc ccatctctac taaaaataca 44400
aaattagcgg ggcatggtgg tgcatgccta taatcccagc tactcaggag gctgaggcag 44460
gagaatcact tgaacccagg aggtggaggt tgagatcgtg ccattgcact ccagcctgga 44520
caacaagagt gaaactctgt ctcaaaaaag aaaaaaagaa aaagaaatta aatgcactat 44580
ggtttatgga gcggtattcc tcctccatgt cctacataag atctttcaca tgccagtcac 44640
agttaaatct aatttgctgt aatctggata aatgggagct aatcaacaag ctctcagctc 44700
tagctctgaa tcagcagcag atattgcatt tttgaaatac actaatagca agaatgcctt 44760
cctgacaaca actggcattt ttgacacagc aggaagttta tctggattct gatataatag 44820
ttattggaat catacatagg tacatagttt aaaaggctaa taagtcattt gttattgctt 44880

-continued

```
ttattatctc tgcatagtta gtaaaattga gattagaacc acttctcgaa tgtactgttc  44940
taaatcctta gcttgcttga tcacacatga ccctcacaat gatcctagga gaaattattc  45000
tgcatgccat tttgtagctg ggaaactga ggcacagaga aatacagtac tgcccaaaat  45060
gtcataacta atcaaaggca aagacaatac tcacaccagc tctgattcca gagcccactc  45120
tcttaaccat atgcttttct gcttccctag ttgtagagtc tttttgtatg actgcattaa  45180
ttatatgtga agagttcaaa aatttctata taaggtcttt taagggtgtc attctggttg  45240
aaaatggagg actaggcttc tcacttgaag acatatttct gtagaaaaac ctattttcat  45300
ttagatgcta cagttacttg atgtggttaa taaaccagtt aacagagtat gaaaaggata  45360
agggttaaag ccctcccaag ccatctttca tgctgctaat atgaatcaca ttactagata  45420
cttaaatatc attttctctt tggttcccag aagactgcat atatgctaga atatttgtcc  45480
tcctctttta ccctttcagg caataaagta ttttggacca ctgtactatg ttataattat  45540
tgtttctctc ctgatttttt tgctccaatc taatgaaaga catacaagct actatactgc  45600
tacacaatga ctaaatacct gttggattag gtggggggaa gatacacagt cactggctag  45660
aaagcatcat gcatacagag ccattttcac catatatttt atttctcatg atcatgtaga  45720
atttaggctt tggtgttgat tatttctctc ttaggaaaca tagttgtttc agggttgata  45780
tcacaaaaaa acagaaaaac ctattcgaga aaaggaaaat tatttgtctg taggccaaat  45840
tttgaagtag gaaaacctgc ttttggagtt gtattcccct cccaggcact taatccaagt  45900
tccagtctta ttctaaactg gggatgctag tattaaccac cataggagtt atctgagatg  45960
agttatcatc aacttggtac caggttgttg tcctctggac tcagtgagct ctagaattgc  46020
atgaaactgg cctaatttat caaagtatgt agccttgggt aaataattca agctctcaga  46080
ggtccagtta tctcctctgt aaaacatatc tacatcctag ggatgacaat atctacatcc  46140
tagagatgtc aggaggatta agtgtaattt tttttaattg tatgtattta aaatgggcaa  46200
cataatgttt tgatatacac gtgtatagtg attactacag tcaagcaaat taacatatcc  46260
atcatttcat agctaccttt tatgtatgtg ataagattat ctaaaatcta ttctcttacc  46320
aaatttccag tatacaatat tgatatggtt tgatccatat ccccatccaa atctcatgtt  46380
cagttgcaat ccccaacgtt ggagatggag cctggttgga ggtgattgga tcacaggggt  46440
ggcttctaat ggttcagcac catcctttct tggtactgta tagtgagtaa gttctcacga  46500
gatctggttg tttaaaagtg tgtaacacct cccccacttt ccctctctct gttcctcctg  46560
ctcccgctat gtgaagtgcc agctccctct ttgccttccg ccatgattgt aagttctctg  46620
aggcatcccc agaagctgat gctgccatgc ttcctataca gcctgcagaa ccatgagtca  46680
attaaacctc ttttctttgt aaattaccca gtctcaagta tttctttata gcaatgcaag  46740
aatggactaa tacagaaaat tgttactgag aagaagggca ttgctataaa gatacctgaa  46800
aatgtagaag tgactttgga accggctaac aggcagaagt tgaaacattt tagagggctc  46860
agaagaagac agaaagatga gagaaagttt ggaactcgct aggaacttgt tgagtggttg  46920
taaccaaaat actgatagtg atatagacag tgaagtccag gctgaggagg tctcagatgg  46980
aaatgagaaa tttattggga atgagtaaag gtcaggtttg ctatgcttta gcaaagagct  47040
tagctgcatt gttcctctgt tctagggatc tgtgaaatct tagacttaag aatgatgatt  47100
tagggtatct ggcagaagaa atttctaagc agcagagtgt tcaagaagta acctagctgc  47160
ttctaatagc ctatgctcat aggcatgagc acagaaatga cctgaaattg gaacttacac  47220
ttaaaaggga agcagagcat aaaagtttgt aaattttgca gcctggccat gtggtagtaa  47280
```

-continued agaaaagctc gttctcagga gaggaagtca agcaggctgc ataaatttgc ataactaaaa 47340
ggaaggcaag ggctgataac caaaacaatg gggagaaaga ctcataggac taacaggcat 47400
tttattttat tttattttta ttttattatt attatacttt aagttttagg gtacatgtgc 47460
acaatgtgca ggttagttgc atatgtatac atgtgccatg ctggtgtgct gcacccatta 47520
actcgtcatt tagcattagg tatatctcct aatgctatcc ctccccccctc ccccacccca 47580
caacagtccc cagagtgtga tgttcccctt cctgtgtcca tgtgttctca ttgttcaatt 47640
cccacctatg agtgagaaca tgtggtgttt ggtttttttga ccttgcaata gtttactgag 47700
aatgacgatt tccaatttca tccatgtccc tacaaaggac atgaactcat catttttttat 47760
ggctgcatag tattccatgg tgtatatgtg ccacattttc ttaatccagt ctatcactgt 47820
tggacatttg ggttggttcc aagtctttgc tattgtgaat agtgccacaa taaacatagt 47880
gtgcatgtgt ctttatagca gcaggattta tagtcctttg ggtatatacc cagtgatggg 47940
atggctgggt caaatggtat ttctagttct agatccctga ggaatcgcca cactgacttc 48000
cacaatggtt gaactagttt acagtcccac caacagtgta aaagtgttcc taataggcat 48060
tttaggcttt catggtggtc cctctcatca caggccccga ggcctaggag gactgaatca 48120
tttcctgggc caggcctagg gcccctgctc cctcttacag ccttgggact ctgctccctg 48180
aatcccagct gctcaaaggg gcccaggtac tgttacagta ggtagctaat caggcatgag 48240
tggggtaaga gagaagtccc caccacccac caggaatgtc aggcaaccat cagatgatgg 48300
tcaggcagtt gtcatactgc ctctctaaaa tagtaattgg ttgcagccag caccagggag 48360
aggcaacttc tcaatagata gaaacacctg aaattggtaa ctgggcgctt ccaataagat 48420
ctcaggaact gagagagtgg gcttaacatg cacattaaga ggcaaaatgg tgaagtatga 48480
cctttggggg cattccaccg gaaaagggaa gaaagcctca ggtaagcatg tatacaactc 48540
cagtaaacac actgcacacg ctcaccttcc aagtgcaagc agggcaccat gcatgcggca 48600
agctcaccct tagggaagga ccaagggaaa ggggcacaag atgtcagaag taggccagtg 48660
tataagatcc taggttcaag gtcaaacagg gcacttgacc tccaaggtgc ccacttgggc 48720
ctcttccaaa tgtactttcc tttcattcct gttctaaagc tttttaataa acttttactc 48780
ctgctctgaa acttgtcgca gtctcttttt ctgccttatg cctcttggtc aaattctttc 48840
ttctgaggag gcaagaattg aggttgctgc agacccacat ggatttgcag ctggtaactc 48900
agataacttt caccagtaag aatacagttc aggctgctgc ttcacagggt gccaggcata 48960
agccttggtg gcttccataa gctgtgaagc cggcgggcgc acataatgca agagttgagg 49020
cttaagaagc tctgcctaga ttttagagga tgtatgaaaa agcctggatg tccagacaga 49080
agcctgttac tggggtggaa tcctcatgga gaacatctac tagggaagca aggagaagaa 49140
atgtggggtt gcagccccca cagagagtcc cctggggcac tgcctagcag agctatgaca 49200
agacagccac cgtcctccag accccagaat ggtagatcca ccaacaactt gcaccctgca 49260
gcctggaaaa gctgcaagca ctcaatgcta gcccatgaga gcagctgtgg gagatgaacc 49320
ctggaaaacc acaggggtgg ttctgcccaa ggttttggga gcccactcat tgcatcagtg 49380
ttccctgggt gtgagtcaaa ggagattatt tcagagcttt aacatttaat gactgcccgg 49440
ctggctttca gacttgcaat ggggccctat agcctctttc ttttggcaga tttctccctt 49500
tcggaatggc agtatctgcc caatgcctat acccccattg tatctttgaa gcaattacct 49560
tgtttttgat tttacaggtt cataggtaga agggactagc ttcgtctcag gtgagacttg 49620

```
ggactttgga cttttgaatg aatgctggat cgagttaaga ctttggggaa ctgttggtaa  49680
ggcacgacag tattttgcaa tatgagaagg acattagatt tgggaggggc cagagttgga  49740
ataacatggt ttggatctct gtccccaccc aaatctcatg ttcaactgta atccccagtg  49800
ttggaggttg ggcctggtgg gaggtgagtg gattatgggg tggcttctaa tggttttgta  49860
cagtcccctc ttggtactat atagtgagtt ctgacaagat ctagttgttt aaacgtatgt  49920
agcacctccc atttctctct tcccccagtt cctgccatgt gaagtctggg gtctccctat  49980
gccttccatc atgattttaa gttccctatg gcctgcccag aagctgatcc agccatgctt  50040
cttgtacagc ctgcagaact gtgagccatt aaactttttct ttataaatta cccagtttca  50100
gttatttctt tatagcagtg taagaatgga ctaacacaat tattaacgct agtcctcatg  50160
ttgtacatta aatctctaga tgtattagac gtaactgcaa ctttgtaccc taccctacaa  50220
ttttctttcc ccccaagccc cccaaccaag ggtctactct gtttctataa attcagttgt  50280
tttttaattc cacgtataag tgaagtacaa ctcagtgtag aaacttggta aatgctagct  50340
acttgttata agctgtcagt caaaataaaa atacagagat gaatctctaa attaagtgat  50400
ttatttggga agaaagaatt gcaattaggg catacatgta gatcagatgg tcttcggtat  50460
atccacacaa caaagaaaag ggggaggttt tgttaaaaaa gagaaatgtt acatagtgct  50520
ctttgagaaa attcattggc actattaagg atctgaggag ctggtgagtt tcaactggtg  50580
agtgatggtg gtagataaaa ttagagctgc agcaggtcat tttagcaact attagataaa  50640
actggtctca ggtcacaacg ggcagttgca gcagctggac ttggagagaa ttacactgtg  50700
ggagcagtgt catttgtcct aagtgctttt ctacccccta cccccactat tttagttggg  50760
tataaaaaga atgacccaat ttgtatgatc aactttcaca aagcatagaa cagtaggaaa  50820
agggtctgtt tctgcagaag gtgtagacgt tgagagccat tttgtgtatt tattcctccc  50880
tttcttcctc ggtgaatgat taaaacgttc tgtgtgattt ttagtgatga aaaagattaa  50940
atgctactca ctgtagtaag tgccatctca cacttgcaga tcaaaaggca cacagtttaa  51000
aaaacctttg ttttttttaca catctgagtg gtgtaaatgc tactcatctg tagtaagtgg  51060
aatctataca cctgcagacc aaaagacgca aggtttcaaa aatctttgtg tttttttacac  51120
atcaaacaga atggtacgtt tttcaaaagt taaaaaaaaa caactcatcc acatattgca  51180
actagcaaaa atgacattcc ccagtgtgaa aatcatgctt gagagaattc ttacatgtaa  51240
aggcaaaatt gcgatgactt tgcaggggac cgtgggattc ccgcccgcag tgccggagct  51300
gtcccctacc agggtttgca gtggagtttt gaatgcactt aacagtgtct tacggtaaaa  51360
acaaaatttc atccaccaat tatgtgttga gcgcccactg cctaccaagc acaaacaaaa  51420
ccattcaaaa ccacgaaatc gtcttcactt tctccagatc cagcagcctc ccctattaag  51480
gttcgcacac gctattgcgc caacgctcct ccagagcggg tcttaagata aaagaacagg  51540
acaagttgcc ccgccccatt tcgctagcct cgtgagaaaa cgtcatcgca catagaaaac  51600
agacagacgt aacctacggt gtcccgctag gaaagagagg tgcgtcaaac agcgacaagt  51660
tccgcccacg taaaagatga cgcttggtgt gtcagccgtc cctgctgccc ggttgcttct  51720
cttttggggg cggggtctag caagagcagg tgtgggttta ggaggtgtgt gtttttgttt  51780
ttcccaccct ctctccccac tacttgctct cacagtactc gctgagggtg aacaagaaaa  51840
gacctgataa agattaacca gaagaaaaca aggagggaaa caaccgcagc ctgtagcaag  51900
ctctggaact caggagtcgc gcgctagggg ccggggccgg ggccggggcg tggtcggggc  51960
gggcccgggg gcgggcccgg ggcggggctg cggttgcggt gcctgcgccc gcggcggcgg  52020
```

-continued

```
aggcgcaggc ggtggcgagt gggtgagtga ggaggcggca tcctggcggg tggctgtttg  52080
gggttcggct gccgggaaga ggcgcgggta gaagcggggg ctctcctcag agctcgacgc  52140
atttttactt tccctctcat ttctctgacc gaagctgggt gtcgggcttt cgcctctagc  52200
gactggtgga attgcctgca tccgggcccc gggcttcccg gcggcggcgg cggcggcggc  52260
ggcgcaggga caagggatgg ggatctggcc tcttccttgc tttcccgccc tcagtacccg  52320
agctgtctcc ttcccgggga cccgctggga gcgctgccgc tgcgggctcg agaaaaggga  52380
gcctcgggta ctgagaggcc tcgcctgggg gaaggccgga gggtgggcgg cgcgcggctt  52440
ctgcggacca agtcggggtt cgctaggaac ccgagacggt ccctgccggc gaggagatca  52500
tgcgggatga gatgggggtg tggagacgcc tgcacaattt cagcccaagc ttctagagag  52560
tggtgatgac ttgcatatga gggcagcaat gcaagtcggt gtgctcccca ttctgtggga  52620
catgacctgg ttgcttcaca gctccgagat gacacagact tgcttaaagg aagtgactat  52680
tgtgacttgg gcatcacttg actgatggta atcagttgtc taaagaagtg cacagattac  52740
atgtccgtgt gctcattggg tctatctggc cgcgttgaac accaccaggc tttgtattca  52800
gaaacaggag ggaggtcctg cactttccca ggaggggtgg ccctttcaga tgcaatcgag  52860
attgttaggc tctgggagag tagttgcctg gttgtggcag ttggtaaatt tctattcaaa  52920
cagttgccat gcaccagttg ttcacaacaa gggtacgtaa tctgtctggc attacttcta  52980
cttttgtaca aaggatcaaa aaaaaaaaag atactgttaa gatatgattt ttctcagact  53040
ttgggaaact tttaacataa tctgtgaata tcacagaaac aagactatca tataggggat  53100
attaataacc tggagtcaga atacttgaaa tacggtgtca tttgacacgg gcattgttgt  53160
caccacctct gccaaggcct gccactttag gaaaaccctg aatcagttgg aaactgctac  53220
atgctgatag tacatctgaa acaagaacga gagtaattac cacattccag attgttcact  53280
aagccagcat ttacctgctc caggaaaaaa ttacaagcac cttatgaagt tgataaaata  53340
ttttgtttgg ctatgttggc actccacaat ttgctttcag agaaacaaag taaaccaagg  53400
aggacttctg tttttcaagt ctgccctcgg gttctattct acgttaatta gatagttccc  53460
aggaggacta ggttagccta cctattgtct gagaaacttg gaactgtgag aaatggccag  53520
atagtgatat gaacttcacc ttccagtctt ccctgatgtt gaagattgag aaagtgttgt  53580
gaactttctg gtactgtaaa cagttcactg tccttgaagt ggtcctgggc agctcctgtt  53640
gtggaaagtg gacggtttag gatcctgctt ctctttgggc tgggagaaaa taaacagcat  53700
ggttacaagt attgagagcc aggttggaga aggtggctta cacctgtaat gccagagctt  53760
tgggaggcgg aggcaagagg atcacttgaa gccaggagtt caagctcaac ctgggcaacg  53820
tagaccctgt ctctacaaaa aattaaaaac ttagccgggc gtggtgatgt gcacctgtag  53880
tcctagctac ttgggaggct gaggcaggag ggtcatttga gcccaagagt ttgaagttac  53940
cgagagctat gatcctgcca gtgcattcca gcctggatga caaaacgaga ccctgtctct  54000
aaaaaacaag aagtgagggc tttatgattg tagaattttc actacaatag cagtggacca  54060
accacctttc taaataccaa tcagggaaga gatggttgat tttttaacag acgtttaaag  54120
aaaaagcaaa acctcaaact tagcactcta ctaacagttt tagcagatgt taattaatgt  54180
aatcatgtct gcatgtatgg gattatttcc agaaagtgta ttgggaaacc tctcatgaac  54240
cctgtgagca agccaccgtc tcactcaatt tgaatcttgg cttccctcaa aagactggct  54300
aatgtttggt aactctctgg agtagacagc actacatgta cgtaagatag gtacataaac  54360
```

-continued

```
aactattggt tttgagctga tttttttcag ctgcatttgc atgtatggat ttttctcacc  54420
aaagacgatg acttcaagta ttagtaaaat aattgtacag ctctcctgat tatacttctc  54480
tgtgacattt catttcccag gctatttctt ttggtaggat ttaaaactaa gcaattcagt  54540
atgatctttg tccttcattt tctttcttat tctttttgtt tgtttgtttg tttgtttttt  54600
tcttgaggca gagtctctct ctgtcgccca ggctggagtg cagtggcgcc atctcagctc  54660
attgcaacct ctgccacctc cgggttcaag agattctcct gcctcagcct cccgagtagc  54720
tgggattaca ggtgtccacc accacacccg gctaattttt tgtattttta gtagaggtgg  54780
ggtttcacca tgttggccag gctggtcttg agctcctgac ctcaggtgat ccacctgcct  54840
cggcctacca aagagctggg ataacaggtg tgacccacca tgcccggccc attttttttt  54900
tcttattctg ttaggagtga gagtgtaact agcagtataa tagttcaatt ttcacaacgt  54960
ggtaaaagtt tccctataat tcaatcagat tttgctccag ggttcagttc tgttttagga  55020
aatactttta ttttcagttt aatgatgaaa tattagagtt gtaatattgc ctttatgatt  55080
atccaccttt ttaacctaaa agaatgaaag aaaaatatgt ttgcaatata attttatggt  55140
tgtatgttaa cttaattcat tatgttggcc tccagtttgc tgttgttagt tatgacagca  55200
gtagtgtcat taccatttca attcagatta cattcctata tttgatcatt gtaaactgac  55260
tgcttacatt gtattaaaaa cagtggatat tttaaagaag ctgtacggct tatatctagt  55320
gctgtctctt aagactatta aattgataca acatatttaa aagtaaatat tacctaaatg  55380
aatttttgaa attacaaata cacgtgttaa aactgtcgtt gtgttcaacc atttctgtac  55440
atacttagag ttaactgttt tgccaggctc tgtatgccta ctcataatat gataaaagca  55500
ctcatctaat gctctgtaaa tagaagtcag tgctttccat cagactgaac tctcttgaca  55560
agatgtggat gaaattcttt aagtaaaatt gtttactttg tcatacattt acagatcaaa  55620
tgttagctcc caaagcaatc atatggcaaa gataggtata tcatagtttg cctattagct  55680
gctttgtatt gctattatta taaatagact tcacagtttt agacttgctt aggtgaaatt  55740
gcaattcttt ttactttcag tcttagataa caagtcttca attatagtac aatcacacat  55800
tgcttaggaa tgcatcatta ggcgattttg tcattatgca aacatcatag agtgtactta  55860
cacaaaccta gatagtatag cctttatgta cctaggccgt atggtatagt ctgttgctcc  55920
taggccacaa acctgtacaa ctgttactgt actgaatact atagacagtt gtaacacagt  55980
ggtaaatatt tatctaaata tatgcaaaca gagaaaaggt acagtaaaag tatggtataa  56040
aagataatgg tatacctgtg taggccactt accacgaatg gagcttgcag gactagaagt  56100
tgctctgggt gagtcagtga gtgagtggtg aattaatgtg aaggcctaga acactgtaca  56160
ccactgtaga ctataaacac agtacgctga agctacacca aatttatctt aacagttttt  56220
cttcaataaa aaattataac tttttaactt tgtaaacttt ttaatttttt aacttttaaa  56280
atacttagct tgaaacacaa atacattgta tagctataca aaaatatttt ttctttgtat  56340
ccttattcta gaagcttttt tctattttct attttaaatt ttttttttta cttgttagtc  56400
gtttttgtta aaaactaaaa cacacacact ttcacctagg catagacagg attaggatca  56460
tcagtatcac tcccttccac ctcactgcct tccacctcca catcttgtcc cactggaagg  56520
tttttagggg caataacaca catgtagctg tcacctatga taacagtgct ttctgttgaa  56580
tacctcctga aggacttgcc tgaggctgtt ttacatttaa cttaaaaaaa aaaaaagtag  56640
aaggagtgca ctctaaaata acaataaaag gcatagtata gtgaatacat aaaccagcaa  56700
tgtagtagtt tattatcaag tgttgtacac tgtaataatt gtatgtgcta tactttaaat  56760
```

aacttgcaaa atagtactaa gaccttatga tggttacagt gtcactaagg caatagcata 56820
ttttcaggtc cattgtaatc taatgggact accatcatat atgcagtcta ccattgactg 56880
aaacgttaca tggcacataa ctgtatttgc aagaatgatt tgttttacat taatatcaca 56940
taggatgtac ctttttagag tggtatgttt atgtggatta agatgtacaa gttgagcaag 57000
gggaccaaga gccctgggtt ctgtcttgga tgtgagcgtt tatgttcttc tcctcatgtc 57060
tgttttctca ttaaattcaa aggcttgaac gggccctatt tagcccttct gttttctacg 57120
tgttctaaat aactaaagct tttaaattct agccatttag tgtagaactc tctttgcagt 57180
gatgaaatgc tgtattggtt tcttggctag catattaaat atttttatct ttgtcttgat 57240
acttcaatgt cgttttaaac atcaggatcg ggcttcagta ttctcataac cagagagttc 57300
actgaggata caggactgtt tgcccatttt ttgttatggc tccagacttg tggtatttcc 57360
atgtcttttt tttttttttt ttttttgacc ttttagcggc tttaaagtat ttctgttgtt 57420
aggtgttgta ttacttttct aagattactt aacaaagcac cacaaactga gtggctttaa 57480
acaacagcaa tttattctct cacaattcta gaagctagaa gtccgaaatc aaagtgttga 57540
caggggcatg atcttcaaga gagaagactc tttccttgcc tcttcctggc ttctggtggt 57600
taccagcaat cctgagtgtt cctttcttgc cttgtagttt caacaatcca gtatctgcct 57660
tttgtcttca catggctgtc taccatttgt ctctgtgtct ccaaatctct ctccttataa 57720
acacagcagt tattggatta ggccccactc taatccagta tgaccccatt ttaacatgat 57780
tacacttatt tctagataag gtcacattca cgtacaccaa gggttaggaa ttgaacatat 57840
ctttttgggg gacacaattc aacccacaag tgtcagtctc tagctgagcc tttcccttcc 57900
tgtttttctc ctttttagtt gctatgggtt aggggccaaa tctccagtca tactagaatt 57960
gcacatggac tggatatttg ggaatactgc gggtctattc tatgagcttt agtatgtaac 58020
atttaatatc agtgtaaaga agcccttttt taagttattt ctttgaattt ctaaatgtat 58080
gccctgaata taagtaacaa gttaccatgt cttgtaaaat gatcatatca acaaacattt 58140
aatgtgcacc tactgtgcta gttgaatgtc tttatcctga taggagataa caggattcca 58200
catctttgac ttaagaggac aaaccaaata tgtctaaatc atttggggtt ttgatggata 58260
tctttaaatt gctgaaccta atcattggtt tcatatgtca ttgtttagat atctccggag 58320
catttggata atgtgacagt tggaatgcag tgatgtcgac tctttgccca ccgccatctc 58380
cagctgttgc caagacagag attgctttaa gtggcaaatc acctttatta gcagctactt 58440
ttgcttactg ggacaatatt cttggtccta gagtaaggca catttgggct ccaaagacag 58500
aacaggtact tctcagtgat ggagaaataa cttttcttgc caaccacact ctaaatggag 58560
aaatccttcg aaatgcagag agtggtgcta tagatgtaaa gttttttgtc ttgtctgaaa 58620
agggagtgat tattgtttca ttaatctttg atggaaactg gaatggggat cgcagcacat 58680
atggactatc aattatactt ccacagacag aacttagttt ctacctccca cttcatagag 58740
tgtgtgttga tagattaaca catataatcc ggaaaggaag aatatggatg cataaggtaa 58800
gtgatttttc agcttattaa tcatgttaac ctatctgttg aaagcttatt ttctggtaca 58860
tataaatctt atttttttaa ttatatgcag tgaacatcaa acaataaatg ttatttattt 58920
tgcatttacc ctattagata caaatacatc tggtctgata cctgtcatct tcatattaac 58980
tgtggaaggt acgaaatggt agctccacat tatagatgaa aagctaaagc ttagacaaat 59040
aaagaaactt ttagaccctg gattcttctt gggagccttt gactctaata ccttttgttt 59100
ccctttcatt gcacaattct gtcttttgct tactactatg tgtaagtata acagttcaaa 59160
gtaatagttt cataagctgt tggtcatgta gcctttggtc tctttaacct ctttgccaag 59220
ttcccaggtt cataaaatga ggaggttgaa tggaatggtt cccaagagaa ttccttttaa 59280
tcttacagaa attattgttt tcctaaatcc tgtagttgaa tatataatgc tatttacatt 59340
tcagtatagt tttgatgtat ctaaagaaca cattgaattc tccttcctgt gttccagttt 59400
gatactaacc tgaaagtcca ttaagcatta ccagttttaa aaggcttttg cccaatagta 59460
aggaaaaata atatctttta aaagaataat tttttactat gtttgcaggc ttacttcctt 59520
ttttctcaca ttatgaaact cttaaaatca ggagaatctt ttaaacaaca tcataatgtt 59580
taatttgaaa agtgcaagtc attcttttcc tttttgaaac tatgcagatg ttacattgac 59640
tgttttctgt gaagttatct ttttttcact gcagaataaa ggttgttttg attttatttt 59700
gtattgttta tgagaacatg catttgttgg gttaatttcc taccccctgcc cccatttttt 59760
ccctaaagta gaaagtattt ttcttgtgaa ctaaattact acacaagaac atgtctattg 59820
aaaaataagc aagtatcaaa atgttgtggg ttgttttttt aaataaattt tctcttgctc 59880
aggaaagaca agaaaatgtc cagaagatta tcttagaagg cacagagaga atggaagatc 59940
aggtatatgc aaattgcata ctgtcaaatg tttttctcac agcatgtatc tgtataaggt 60000
tgatggctac atttgtcaag gccttggaga catacgaata agcctttaat ggagctttta 60060
tggaggtgta cagaataaac tggaggaaga tttccatatc ttaaacccaa agagttaaat 60120
cagtaaacaa aggaaaatag taattgcatc tacaaattaa tatttgctcc cttttttttt 60180
ctgtttgccc agaataaatt ttggataact tgttcatagt aaaaataaaa aaaattgtct 60240
ctgatatgtt ctttaaggta ctacttctcg aacctttccc tagaagtagc tgtaacagaa 60300
ggagagcata tgtacccctg aggtatctgt ctggggtgta ggcccaggtc cacacaatat 60360
ttcttctaag tcttatgttg tatcgttaag actcatgcaa tttacatttt attccataac 60420
tattttagta ttaaaatttg tcagtgatat ttcttaccct ctcctctagg aaaatgtgcc 60480
atgtttatcc cttggctttg aatgcccctc aggaacagac actaagagtt tgagaagcat 60540
ggttacaagg gtgtggcttc ccctgcggaa actaagtaca gactatttca ctgtaaagca 60600
gagaagttct tttgaaggag aatctccagt gaagaaagag ttcttcactt ttacttccat 60660
ttcctcttgt gggtgaccct caatgctcct tgtaaaactc caatatttta aacatggctg 60720
ttttgccttt ctttgcttct ttttagcatg aatgagacag atgatacttt aaaaaagtaa 60780
ttaaaaaaaa aaacttgtga aaatacatgg ccataataca gaacccaata caatgatctc 60840
ctttaccaaa ttgttatgtt tgtacttttg tagatagctt tccaattcag agacagttat 60900
tctgtgtaaa ggtctgactt aacaagaaaa gatttccctt tacccaaaga atcccagtcc 60960
ttatttgctg gtcaataagc agggtcccca ggaatggggt aactttcagc accctctaac 61020
ccactagtta ttagtagact aattaagtaa acttatcgca agttgaggaa acttagaacc 61080
aactaaaatt ctgcttttac tgggattttg ttttttcaaa ccagaaacct ttacttaagt 61140
tgactactat taatgaattt tggtctctct tttaagtgct cttcttaaaa atgttatctt 61200
actgctgaga agttcaagtt tgggaagtac aaggaggaat agaaacttaa gagattttct 61260
tttagagcct cttctgtatt tagccctgta ggattttttt tttttttttt ttttttggtg 61320
ttgttgagct tcagtgaggc tattcattca cttatactga taatgtctga gatactgtga 61380
atgaaatact atgtatgctt aaacctaaga ggaaatattt tcccaaaatt attcttcccg 61440
aaaaggagga gttgcctttt gattgagttc ttgcaaatct cacaacgact ttattttgaa 61500
caatactgtt tggggatgat gcattagttt gaaacaactt cagttgtagc tgtcatctga 61560
taaaattgct tcacagggaa ggaaatttaa cacggatcta gtcattattc ttgttagatt 61620
gaatgtgtga attgtaattg taaacaggca tgataattat tactttaaaa actaaaaaca 61680
gtgaatagtt agttgtggag gttactaaag gatggttttt ttttaaataa aactttcagc 61740
attatgcaaa tgggcatatg gcttaggata aaacttccag aagtagcatc acatttaaat 61800
tctcaagcaa cttaataata tggggctctg aaaaactggt taaggttact ccaaaaatgg 61860
ccctgggtct gacaaagatt ctaacttaaa gatgcttatg aagactttga gtaaaatcat 61920
ttcataaaat aagtgaggaa aaacaactag tattaaattc atcttaaata atgtatgatt 61980
taaaaaatat gtttagctaa aaatgcatag tcatttgaca atttcattta tatctcaaaa 62040
aatttactta accaagttgg tcacaaaact gatgagactg gtggtggtag tgaataaatg 62100
agggaccatc catatttgag acactttaca tttgtgatgt gttatactga attttcagtt 62160
tgattctata gactacaaat ttcaaaatta caatttcaag atgtaataag tagtaatatc 62220
ttgaaatagc tctaaaggga atttttctgt tttattgatt cttaaaatat atgtgctgat 62280
tttgatttgc atttgggtag attatacttt tatgagtatg gaggttaggt attgattcaa 62340
gttttcctta cctatttggt aaggatttca aagtcttttt gtgcttggtt ttcctcattt 62400
ttaaatatga aatatattga tgacctttaa caaatttttt ttatctcaaa ttttaaagga 62460
gatcttttct aaaagaggca tgatgactta atcattgcat gtaacagtaa acgataaacc 62520
aatgattcca tactctctaa agaataaaag tgagctttag ggccgggcat ggtcagaaat 62580
ttgacaccaa cctggccaac atggcgaaac cccgtctcta ctaaaaatac aaaaatcagc 62640
cgggcatggt ggcggcacct atagtcccag ctacttggga ggatgagaca ggagagtcac 62700
ttgaacctgg gaggagaggt tgcagtgagc tgagatcacg ccattgcact ccagcctgag 62760
caatgaaagc aaaactccat ctcaaaaaaa aaaaaagaaa agaaagaata aaagtgagct 62820
ttggattgca tataaatcct ttagacatgt agtagacttg tttgatactg tgtttgaaca 62880
aattacgaag tatttttcatc aaagaatgtt attgtttgat gttattttta tttttattg 62940 cccagcttct ctcatattac gtgattttct tcacttcatg tcactttatt gtgcagggtc 63000
agagtattat tccaatgctt actggagaag tgattcctgt aatggaactg ctttcatcta 63060
tgaaatcaca cagtgttcct gaagaaatag atgtaagttt aaatgagagc aattatacac 63120
tttatgagtt ttttggggtt atagtattat tatgtatatt attaatattc taattttaat 63180
agtaaggact ttgtcataca tactattcac atacagtatt agccacttta gcaaataagc 63240
acacacaaaa tcctggattt tatggcaaaa cagaggcatt tttgatcagt gatgacaaaa 63300
ttaaattcat tttgtttatt tcattacttt tataattcct aaaagtggga ggatcccagc 63360
tcttatagga gcaattaata tttaatgtag tgtcttttga aacaaaactg tgtgccaaag 63420
tagtaaccat taatggaagt ttacttgtag tcacaaattt agtttcctta atcatttgtt 63480
gaggacgttt tgaatcacac actatgagtg ttaagagata cctttaggaa actattcttg 63540
ttgttttctg attttgtcat ttaggttagt ctcctgattc tgacagctca gaagaggaag 63600
ttgttcttgt aaaaattgtt taacctgctt gaccagcttt cacatttgtt cttctgaagt 63660
ttatggtagt gcacagagat tgttttttgg ggagtcttga ttctcggaaa tgaaggcagt 63720
gtgttatatt gaatccagac ttccgaaaac ttgtatatta aaagtgttat ttcaacacta 63780
tgttacagcc agactaattt ttttattttt tgatgcattt tagatagctg atacagtact 63840

-continued caatgatgat gatattggtg acagctgtca tgaaggcttt cttctcaagt aagaattttt 63900
cttttcataa aagctggatg aagcagatac catcttatgc tcacctatga caagatttgg 63960
aagaaagaaa ataacagact gtctacttag attgttctag ggacattacg tatttgaact 64020
gttgcttaaa tttgtgttat ttttcactca ttatatttct atatatattt ggtgttattc 64080
catttgctat ttaaagaaac cgagtttcca tcccagacaa gaaatcatgg ccccttgctt 64140
gattctggtt tcttgtttta cttctcatta aagctaacag aatcctttca tattaagttg 64200
tactgtagat gaacttaagt tatttaggcg tagaacaaaa ttattcatat ttatactgat 64260
ctttttccat ccagcagtgg agtttagtac ttaagagttt gtgcccttaa accagactcc 64320
ctggattaat gctgtgtacc cgtgggcaag gtgcctgaat tctctataca cctatttcct 64380
catctgtaaa atggcaataa tagtaatagt acctaatgtg tagggttgtt ataagcattg 64440
agtaagataa ataatataaa gcacttagaa cagtgcctgg aacataaaaa cacttaataa 64500
tagctcatag ctaacatttc ctatttacat ttcttctaga aatagccagt atttgttgag 64560
tgcctacatg ttagttcctt tactagttgc tttacatgta ttatcttata ttctgtttta 64620
aagtttcttc acagttacag attttcatga aattttactt ttaataaaag agaagtaaaa 64680
gtataaagta ttcactttta tgttcacagt cttttccttt aggctcatga tggagtatca 64740
gaggcatgag tgtgtttaac ctaagagcct taatggcttg aatcagaagc actttagtcc 64800
tgtatctgtt cagtgtcagc ctttcataca tcattttaaa tcccatttga ctttaagtaa 64860
gtcacttaat ctctctacat gtcaatttct tcagctataa aatgatggta tttcaataaa 64920
taaatacatt aattaaatga tattatactg actaattggg ctgttttaag gctcaataag 64980
aaaatttctg tgaaaggtct ctagaaaatg taggttccta tacaaataaa agataacatt 65040
gtgcttatag cttcggtgtt tatcatataa agctattctg agttatttga agagctcacc 65100
tacttttttt tgtttttagt ttgttaaatt gttttatagg caatgttttt aatctgtttt 65160
ctttaactta cagtgccatc agctcacact tgcaaacctg tggctgttcc gttgtagtag 65220
gtagcagtgc agagaaagta aataaggtag tttattttat aatctagcaa atgatttgac 65280
tctttaagac tgatgatata tcatggattg tcatttaaat ggtaggttgc aattaaaatg 65340
atctagtagt ataaggaggc aatgtaatct catcaaattg ctaagacacc ttgtggcaac 65400
agtgagtttg aaataaactg agtaagaatc atttatcagt ttattttgat agctcggaaa 65460
taccagtgtc agtagtgtat aaatggtttt gagaatatat taaaatcaga tatataaaaa 65520
aaattactct tctatttccc aatgttatct ttaacaaatc tgaagatagt catgtacttt 65580
tggtagtagt tccaaagaaa tgttatttgt ttattcatct tgatttcatt gtcttcgctt 65640
tccttctaaa tctgtccctt ctagggagct attgggatta agtggtcatt gattattata 65700
ctttattcag taatgtttct gaccctttcc ttcagtgcta cttgagttaa ttaaggatta 65760
atgaacagtt acatttccaa gcattagcta ataaactaaa ggattttgca cttttcttca 65820
ctgaccatta gttagaaaga gttcagagat aagtatgtgt atctttcaat ttcagcaaac 65880
ctaatttttt aaaaaaagtt ttacatagga aatatgttgg aaatgatact ttacaaagat 65940
attcataatt tttttttgta atcagctact ttgtatattt acatgagcct taatttatat 66000
ttctcatata accatttatg agagcttagt atacctgtgt cattatattg catctacgaa 66060
ctagtgacct tattccttct gttacctcaa acaggtggct ttccatctgt gatctccaaa 66120
gccttaggtt gcacagagtg actgccgagc tgctttatga agggagaaag gctccatagt 66180
tggagtgttt tttttttttt ttttaaacat ttttcccatc ctccatcctc ttgagggaga 66240
atagcttacc ttttatcttg ttttaatttg agaaagaagt tgccaccact ctaggttgaa 66300
aaccactcct ttaacataat aactgtggat atggtttgaa tttcaagata gttacatgcc 66360
tttttatttt tcctaataga gctgtaggtc aaatattatt agaatcagat ttctaaatcc 66420
cacccaatga cctgcttatt ttaaatcaaa ttcaataatt aattctcttc tttttggagg 66480
atctggacat tctttgatat ttcttacaac gaatttcatg tgtagaccca ctaaacagaa 66540
gctataaaag ttgcatggtc aaataagtct gagaaagtct gcagatgata taattcacct 66600
gaagagtcac agtatgtagc caaatgttaa aggttttgag atgccataca gtaaatttac 66660
caagcatttt ctaaatttat ttgaccacag aatccctatt ttaagcaaca actgttacat 66720
cccatggatt ccaggtgact aaagaatact tatttcttag gatatgtttt attgataata 66780
acaattaaaa tttcagatat ctttcataag caaatcagtg gtctttttac ttcatgtttt 66840
aatgctaaaa tattttcttt tatagatagt cagaacatta tgccttttc tgactccagc 66900
agagagaaaa tgctccaggt tatgtgaagc agaatcatca tttaaatatg agtcagggct 66960
ctttgtacaa ggcctgctaa aggtatagtt tctagttatc acaagtgaaa ccacttttct 67020
aaaatcattt ttgagactct ttatagacaa atcttaaata ttagcattta atgtatctca 67080
tattgacatg cccagagact gacttccttt acacagttct gcacatagac tatatgtctt 67140
atggatttat agttagtatc atcagtgaaa caccatagaa taccctttgt gttccaggtg 67200
ggtccctgtt cctacatgtc tagcctcagg acttttttt ttttaacaca tgcttaaatc 67260
aggttgcaca tcaaaaataa gatcatttct ttttaactaa atagatttga attttattga 67320
aaaaaaattt taaacatctt taagaagctt ataggattta agcaattcct atgtatgtgt 67380
actaaaatat atatatttct atatataata tatattagaa aaaaattgta tttttctttt 67440
atttgagtct actgtcaagg agcaaaacag agaaatgtaa attagcaatt atttataata 67500
cttaaaggga agaaagttgt tcaccttgtt gaatctatta ttgttatttc aattatagtc 67560
ccaagacgtg aagaaatagc tttcctaatg gttatgtgat tgtctcatag tgactacttt 67620
cttgaggatg tagccacggc aaaatgaaat aaaaaaattt aaaaattgtt gcaaatacaa 67680
gttatattag gcttttgtgc attttcaata atgtgctgct atgaactcag aatgatagta 67740
tttaaatata gaaactagtt aaaggaaacg tagtttctat ttgagttata catatctgta 67800
aattagaact tctcctgtta aaggcataat aaagtgctta atacttttgt ttcctcagca 67860
ccctctcatt taattatata attttagttc tgaaagggac ctataccaga tgcctagagg 67920
aaatttcaaa actatgatct aatgaaaaaa tatttaatag ttctccatgc aaatacaaat 67980
catatagttt tccagaaaat acctttgaca ttatacaaag atgattatca cagcattata 68040
atagtaaaaa aatggaaata gcctctttct tctgttctgt tcatagcaca gtgcctcata 68100
cgcagtaggt tattattaca tggtaactgg ctaccccaac tgattaggaa agaagtaaat 68160
ttgttttata aaaatacata ctcattgagg tgcatagaat aattaagaaa ttaaaagaca 68220
cttgtaattt tgaatccagt gaatacccac tgttaatatt tggtatatct ctttctagtc 68280
ttttttccc ttttgcatgt attttcttta agactcccac ccccactgga tcatctctgc 68340
atgttctaat ctgctttttt cacagcagat tctaagcctc tttgaatatc aacacaaact 68400
tcaacaactt catctataga tgccaaataa taaattcatt tttatttact taaccacttc 68460
ctttggatgc ttaggtcatt ctgatgtttt gctattgaaa ccaatgctat actgaacact 68520
tctgtcacta aaactttgca cacactcatg aatagcttct taggataaat ttttagagat 68580

-continued

```
ggatttgcta aatcagagac catttttttaa aattaaaaaa caattattca tatcgtttgg  68640
catgtaagac agtaaatttt ccttttattt tgacaggatt caactggaag ctttgtgctg  68700
cctttccggc aagtcatgta tgctccatat cccaccacac acatagatgt ggatgtcaat  68760
actgtgaagc agatgccacc ctgtcatgaa catatttata atcagcgtag atacatgaga  68820
tccgagctga cagccttctg gagagccact tcagaagaag acatggctca ggatacgatc  68880
atctacactg acgaaagctt tactcctgat ttgtacgtaa tgctctgcct gctggtactg  68940
tagtcaagca atatgaaatt gtgtctttta cgaataaaaa caaaacagaa gttgcattta  69000
aaaagaaaga aatattacca gcagaattat gcttgaagaa acatttaatc aagcattttt  69060
ttcttaaatg ttcttctttt tccatacaat tgtgtttacc ctaaaatagg taagattaac  69120
ccttaaagta aatatttaac tatttgttta ataaatatat attgagctcc taggcactgt  69180
tctaggtacc gggcttaata gtggccaacc agacagcccc agccccagcc cctacattgt  69240
gtatagtcta ttatgtaaca gttattgaat ggacttatta acaaaaccaa agaagtaatt  69300
ctaagtcttt tttttcttga catatgaata taaaatacag caaaactgtt aaaatatatt  69360
aatggaacat ttttttactt tgcattttat attgttattc acttcttatt tttttttaaa  69420
aaaaaaagcc tgaacagtaa attcaaaagg aaaagtaatg ataattaatt gttgagcatg  69480
gacccaactt gaaaaaaaaa atgatgatga taaatctata atcctaaaac cctaagtaaa  69540
cacttaaaag atgttctgaa atcaggaaaa gaattatagt atacttttgt gtttctcttt  69600
tatcagttga aaaaaggcac agtagctcat gcctgtaaga acagagcttt gggagtgcaa  69660
ggcaggcgga tcacttgagg ccaggagttc cagaccagcc tgggcaacat agtgaaaccc  69720
catctctaca aaaaataaaa aagaattatt ggaatgtgtt tctgtgtgcc tgtaatccta  69780
gctattccga aagctgaggc aggaggatct tttgagccca ggagtttgag gttacaggga  69840
gttatgatgt gccagtgtac tccagcctgg ggaacaccga gactctgtct tatttaaaaa  69900
aaaaaaaaaa aaaatgcttg caataatgcc tggcacatag aaggtaacag taagtgttaa  69960
ctgtaataac ccaggtctaa gtgtgtaagg caatagaaaa attggggcaa ataagcctga  70020
cctatgtatc tacagaatca gtttgagctt aggtaacaga cctgtggagc accagtaatt  70080
acacagtaag tgttaaccaa aagcatagaa taggaatatc ttgttcaagg gacccccagc  70140
cttatacatc tcaaggtgca gaaagatgac ttaatatagg acccattttt tcctagttct  70200
ccagagtttt tattggttct tgagaaagta gtaggggaat gttttagaaa atgaattggt  70260
ccaactgaaa ttacatgtca gtaagttttt atatattggt aaattttagt agacatgtag  70320
aagttttcta attaatctgt gccttgaaac attttctttt ttcctaaagt gcttagtatt  70380
ttttccgttt tttgattggt tacttgggag cttttttgag gaaatttagt gaactgcaga  70440
atgggtttgc aaccatttgg tatttttgtt ttgtttttta gaggatgtat gtgtatttta  70500
acatttctta atcattttta gccagctatg tttgttttgc tgatttgaca aactacagtt  70560
agacagctat tctcattttg ctgatcatga caaaaataata tcctgaattt ttaaattttg  70620
catccagctc taaattttct aaacataaaa ttgtccaaaa aatagtattt tcagccacta  70680
gattgtgtgt taagtctatt gtcacagagt cattttactt ttaagtatat gtttttacat  70740
gttaattatg tttgttattt ttaattttaa ctttttaaaa taattccagt cactgccaat  70800
acatgaaaaa ttggtcactg gaattttttt tttgactttt attttaggtt catgtgtaca  70860
tgtgcaggtg tgttatacag gtaaattgcg tgtcatgagg gtttggtgta caggtgattt  70920
cattacccag gtaataagca tagtacccaa taggtagttt tttgatcctc acccttctcc  70980
```

-continued

```
caccctcaag taggccctgg tgttgctgtt tccttctttg tgtccatgta tactcagtgt  71040
ttagctccca cttagaagtg agaacatgcg gtagttggtt ttctgttcct ggattagttc  71100
acttaggata atgacctcta gctccatctg gtttttatgg ctgcatagta ttccatggtg  71160
tatatgtatc acattttctt tatccagtct accattgata ggcatttagg ttgattccct  71220
gtctttgtta tcatgaatag tgctgtgatg aacatacaca tgcatgtgtc tttatggtag  71280
aaaaatttgt attcctttag gtacatatag aataatgggg ttgctagggt gaatggtagt  71340
tctattttca gttatttgag aaatcttcaa actgcttttc ataatagcta aactaattta  71400
cagtcccgcc agcagtgtat aagtgttccc ttttctccac aaccttgcca acatctgtga  71460
tttttgact ttttaataat agccattcct agagaattga tttgcaattc tctattagtg  71520
atattaagca tttttcata tgcttttag ctgtctgtat atattcttct gaaaaatttt  71580
catgtccttt gcccagtttg tagtggggtg ggttgttttt tgcttgttaa ttagttttaa  71640
gttccttcca gattctgcat atccctttgt tggatacatg gtttgcagat atttttctcc  71700
cattgtgtag gttgtctttt actctgttga tagtttcttt tgccatgcag gagctcgtta  71760
ggtcccattt gtgtttgttt ttgttgcagt tgcttttggc gtcttcatca taaaatctgt  71820
gccagggcct atgtccagaa tggtatttcc taggttgtct tccagggttt ttacaatttt  71880
agattttacg tttatgtctt taatccatct tgagttgatt tttgtatatg gcacaaggaa  71940
ggggtccagt ttcactccaa ttcctatggc tagcaattat cccagcacca tttattgaat  72000
acggagtcct ttccccattg cttgtttttt gtcaactttg ttgaagatca gatggttgta  72060
agtgtgtggc tttatttctt ggctctctat tctccattgg tctatgtgtc tgtttttata  72120
acagtaccct gctgttcagg ttcctatagc cttttagtat aaaatcggct aatgtgatgc  72180
ctccagcttt gttcttttg cttaggattg ctttggctat ttgggctcct ttttgggtcc  72240
atattaattt taaaacagtt ttttctggtt ttgtgaagga tatcattggt agtttatagg  72300
aatagcattg aatctgtaga ttgctttggg cagtatggcc attttaacaa tattaattct  72360
tcctatctat gaatatggaa tgtttttcca tgtgtttgtg tcatctcttt atacctgatg  72420
tataaagaaa agctggtatt attcctactc aatctgttcc aaaaaattga ggaggaggaa  72480
ctcttcccta atgaggccag catcattctg ataccaaaac ctggcagaga cacaacagaa  72540
aaaagaaaac ttcaggccaa tatccttgat gaatatagat gcaaaaatcc tcaacaaaat  72600
actagcaaac caaatccagc agcacatcaa aaagctgatc tactttgatc aagtaggctt  72660
tatccctggg atgcaaggtt ggttcaacat acacaaatca ataagtgtga ttcatcacat  72720
aaacagagct aaaaacaaaa accacaagat tatctcaata ggtagagaaa aggttgtcaa  72780
taaaatttaa catcctccat gttaaaaacc ttcagtaggt caggtgtagt gactcacacc  72840
tgtaatccca gcactttggg aggccaaggc gggcatatct cttaagccca ggagttcaag  72900
acgagcctag gcagcatggt gaaaccccat ctctacaaaa aaaaaaaaaa aaaaaaatta  72960
gcttggtatg gtgacatgca cctatagtcc cagctattca ggaggttgag gtgggaggat  73020
tgtttgagcc cgggaggcag aggttggcag cgagctgaga tcatgccacc gcactccagc  73080
ctgggcaacg gagtgagacc ctgtctcaaa aaagaaaaat cacaaacaat cctaaacaaa  73140
ctaggcattg aaggaacatg cctcaaaaaa ataagaacca tctatgacag acccatagcc  73200
aatatcttac caaatgggca aaagctggaa gtattctcct tgagaaccgt aacaagacaa  73260
ggatgtccac tctcaccact ccttttcagc atagttctgg aagtcctagc cagagcaatc  73320
```

-continued

```
aggaaagaga aagaaagaaa gacattcaga taggaagaga agaagtcaaa ctatttctgt  73380
ttgcaggcag tataattctg tacctagaaa atctcatagt ctctgcccag aaactcctaa  73440
atctgttaaa aatttcagca aagttttggc attctctata ctccaacacc ttccaaagtg  73500
agagcaaaat caagaacaca gtcccattca caatagccgc aaaacgaata aaatacctag  73560
gaatccagct aaccagggag gtgaaagatc tctatgagaa ttacaaaaca ctgctgaaag  73620
aaatcagaga tgacacaaac aaatggaaat gttctttttt aacaccttgc tttatctaat  73680
tcacttatga tgaagatact cattcagtgg aacaggtata ataagtccac tcgattaaat  73740
ataagcctta ttctctttcc agagcccaag aaggggcact atcagtgccc agtcaataat  73800
gacgaaatgc taatattttt ccccttttacg gtttctttct tctgtagtgt ggtacactcg  73860
tttcttaaga taaggaaact tgaactacct tcctgtttgc ttctacacat acccattctc  73920
ttttttgcc actctggtca ggtataggat gatccctacc actttcagtt aaaaactcct  73980
cctcttacta aatgttctct taccctctgg cctgagtaga acctagggaa aatggaagag  74040
aaaaagatga aagggaggtg gggcctggga agggaataag tagtcctgtt tgtttgtgtg  74100
tttgctttag cacctgctat atcctaggtg ctgtgttagg cacacattat tttaagtggc  74160
cattatatta ctactactca ctctggtcgt tgccaaggta ggtagtactt tcttggatag  74220
ttggttcatg ttacttacag atggtgggct tgttgaggca aacccagtgg ataatcatcg  74280
gagtgtgttc tctaatctca ctcaaatttt tcttcacatt ttttggtttg ttttggtttt  74340
tgatggtagt ggcttatttt tgttgctggt ttgttttttg tttttttttg agatggcaag  74400
aattggtagt tttatttatt aattgcctaa gggtctctac ttttttaaa agatgagagt  74460
agtaaaatag attgatagat acatacatac ccttactggg gactgcttat attctttaga  74520
gaaaaaatta catattagcc tgacaaacac cagtaaaatg taaatatatc cttgagtaaa  74580
taaatgaatg tatattttgt gtctccaaat atatatatct atattcttac aaatgtgttt  74640
atatgtaata tcaatttata agaacttaaa atgttggctc aagtgaggga ttgtggaagg  74700
tagcattata tggccatttc aacatttgaa ctttttctt ttcttcattt tcttcttttc  74760
ttcaggaata tttttcaaga tgtcttacac agagacactc tagtgaaagc cttcctggat  74820
caggtaaatg ttgaacttga gattgtcaga gtgaatgata tgacatgttt tctttttttaa  74880
tatatcctac aatgcctgtt ctatatattt atattcccct ggatcatgcc ccagagttct  74940
gctcagcaat tgcagttaag ttagttacac tacagttctc agaagagtct gtgagggcat  75000
gtcaagtgca tcattacatt ggttgcctct tgtcctagat ttatgcttcg ggaattcaga  75060
cctttgttta caatataata aatattattg ctatctttta aagatataat aataagatat  75120
aaagttgacc acaactactg tttttgaaa catagaattc ctggtttaca tgtatcaaag  75180
tgaaatctga cttagctttt acagatataa tatatacata tatatatcct gcaatgcttg  75240
tactatatat gtagtacaag tatatatata tgtttgtgtg tgtatatata tatagtacga  75300
gcatatatac atattaccag cattgtagga tatatatatg tttatatatt aaaaaaaagt  75360
tataaactta aaaccctatt atgttatgta gagtatatgt tatatatgat atgtaaaata  75420
tataacatat actctatgat agagtgtaat atatttttta tatatatttt aacatttata  75480
aaatgataga attaagaatt gagtcctaat ctgttttatt aggtgctttt tgtagtgtct  75540
ggtctttcta aagtgtctaa atgatttttc cttttgactt attaatgggg aagagcctgt  75600
atattaacaa ttaagagtgc agcattccat acgtcaaaca acaaacattt taattcaagc  75660
attaacctat aacaagtaag tttttttttt ttttttgaga aagggaggtt gtttatttgc  75720
```

ctgaaatgac tcaaaaatat ttttgaaaca tagtgtactt atttaaataa catctttatt 75780
gtttcattct tttaaaaaat atctacttaa ttacacagtt gaaggaaatc gtagattata 75840
tggaacttat ttcttaatat attacagttt gttataataa cattctgggg atcaggccag 75900
gaaactgtgt catagataaa gctttgaaat aatgagatcc ttatgtttac tagaaatttt 75960
ggattgagat ctatgaggtc tgtgacatat tgcgaagttc aaggaaaatt cgtaggcctg 76020
gaatttcatg cttctcaagc tgacataaaa tccctcccac tctccacctc atcatatgca 76080
cacattctac tcctacccac ccactccacc ccctgcaaaa gtacaggtat atgaatgtct 76140
caaaaccata ggctcatctt ctaggagctt caatgttatt tgaagatttg ggcagaaaaa 76200
attaagtaat acgaaataac ttatgtatga gttttaaaag tgaagtaaac atggatgtat 76260
tctgaagtag aatgcaaaat ttgaatgcat ttttaaagat aaattagaaa acttctaaaa 76320
actgtcagat tgtctgggcc tggtggctta tgcctgtaat cccagcactt tgggagtccg 76380
aggtgggtgg atcacaaggt caggagatcg agaccatcct gccaacatgg tgaaaccccg 76440
tctctactaa gtatacaaaa attagctggg cgtggcagcg tgtgcctgta atcccagcta 76500
cctgggaggc tgaggcagga gaatcgcttg aacccaggag gtgtaggttg cagtgagtca 76560
agatcgcgcc actgcacttt agcctggtga cagagctaga ctccgtctca aaaaaaaaaa 76620
aaaatatcag attgttccta cacctagtgc ttctatacca cactcctgtt agggggcatc 76680
agtggaaatg gttaaggaga tgtttagtgt gtattgtctg ccaagcactg tcaacactgt 76740
catagaaact tctgtacgag tagaatgtga gcaaattatg tgttgaaatg gttcctctcc 76800
ctgcaggtct ttcagctgaa acctggctta tctctcagaa gtactttcct tgcacagttt 76860
ctacttgtcc ttcacagaaa agccttgaca ctaataaaat atatagaaga cgatacgtga 76920
gtaaaactcc tacacggaag aaaaaccttt gtacattgtt tttttgtttt gtttcctttg 76980
tacattttct atatcataat ttttgcgctt cttttttttt tttttttttt tttttttcca 77040
ttatttttag gcagaaggga aaaaagccct ttaaatctct tcggaacctg aagatagacc 77100
ttgatttaac agcagagggc gatcttaaca taataatggc tctggctgag aaaattaaac 77160
caggcctaca ctcttttatc tttggaagac ctttctacac tagtgtgcaa gaacgagatg 77220
ttctaatgac tttttaaatg tgtaacttaa taagcctatt ccatcacaat catgatcgct 77280
ggtaaagtag ctcagtggtg tggggaaacg ttcccctgga tcatactcca gaattctgct 77340
ctcagcaatt gcagttaagt aagttacact acagttctca caagagcctg tgaggggatg 77400
tcaggtgcat cattacattg ggtgtctctt ttcctagatt tatgcttttg ggatacagac 77460
ctatgtttac aatataataa atattattgc tatcttttaa agatataata ataggatgta 77520
aacttgacca caactactgt ttttttgaaa tacatgattc atggtttaca tgtgtcaagg 77580
tgaaatctga gttggctttt acagatagtt gactttctat cttttggcat tctttggtgt 77640
gtagaattac tgtaatactt ctgcaatcaa ctgaaaacta gagcctttaa atgatttcaa 77700
ttccacagaa agaaagtgag cttgaacata ggatgagctt tagaaagaaa attgatcaag 77760
cagatgttta attggaattg attattagat cctactttgt ggatttagtc cctgggattc 77820
agtctgtaga aatgtctaat agttctctat agtccttgtt cctggtgaac cacagttagg 77880
gtgttttgtt tattttattg ttcttgctat tgttgatatt ctatgtagtt gagctctgta 77940
aaaggaaatt gtattttatg ttttagtaat tgttgccaac tttttaaatt aattttcatt 78000
atttttgagc caaattgaaa tgtgcacctc ctgtgccttt tttctcctta gaaaatctaa 78060

-continued

```
ttacttggaa caagttcaga tttcactggt cagtcatttt catcttgttt tcttcttgct  78120
aagtcttacc atgtacctgc tttggcaatc attgcaactc tgagattata aaatgcctta  78180
gagaatatac taactaataa gatctttttt tcagaaacag aaaatagttc cttgagtact  78240
tccttcttgc atttctgcct atgtttttga agttgttgct gtttgcctgc aataggctat  78300
aaggaatagc aggagaaatt ttactgaagt gctgttttcc taggtgctac tttggcagag  78360
ctaagttatc ttttgttttc ttaatgcgtt tggaccattt tgctggctat aaaataactg  78420
attaatataa ttctaacaca atgttgacat tgtagttaca caaacacaaa taaatatttt  78480
atttaaaatt ctggaagtaa tataaaaggg aaaatatatt tataagaaag ggataaaggt  78540
aatagagccc ttctgccccc cacccaccaa atttacacaa caaaatgaca tgttcgaatg  78600
tgaaaggtca taatagcttt cccatcatga atcagaaaga tgtggacagc ttgatgtttt  78660
agacaaccac tgaactagat gactgttgta ctgtagctca gtcatttaaa aaatatataa  78720
atactacctt gtagtgtccc atactgtgtt ttttacatgg tagattctta tttaagtgct  78780
aactggttat tttctttggc tggtttattg tactgttata cagaatgtaa gttgtacagt  78840
gaaataagtt attaaagcat gtgtaaacat tgttatatat cttttctcct aaatggagaa  78900
ttttgaataa aatatatttg aaattttgcc tctttcagtt gttcattcag aaaaaaatac  78960
tatgatattt gaagactgat cagcttctgt tcagctgaca gtcatgctgg atctaaactt  79020
tttttaaaat taattttgtc ttttcaaaga aaaaatattt aaagaagctt tataatataa  79080
tcttatgtta aaaaaacttt ctgcttaact ctctggattt cattttgatt tttcaaatta  79140
tatattaata tttcaaatgt aaaatactat ttagataaat tgtttttaaa cattcttatt  79200
attataatat taatataacc taaactgaag ttattcatcc caggtatcta atacatgtat  79260
ccaaagtaaa aatccaagga atctgaacac tttcatctgc aaagctagga ataggtttga  79320
cattttcact ccaagaaaaa gttttttttt gaaaatagaa tagttgggat gagaggtttc  79380
tttaaaagaa gactaactga tcacattact atgattctca aagaagaaac caaaacttca  79440
tataatacta taaagtaaat ataaaatagt tccttctata gtatatttct ataatgctac  79500
agtttaaaca gatcactctt atataatact attttgattt tgatgtagaa ttgcacaaat  79560
tgatatttct cctatgatct gcagggtata gcttaaagta acaaaaacag tcaaccacct  79620
ccatttaaca cacagtaaca ctatgggact agttttatta cttccatttt acaaatgagg  79680
aaactaaagc ttaaagatgt gtaatacacc gcccaaggtc acacagctgg taaaggtgga  79740
tttcatccca gacagttaca gtcattgcca tgggcacagc tcctaactta gtaactccat  79800
gtaactggta ctcagtgtag ctgaattgaa aggagagtaa ggaagcaggt tttacaggtc  79860
tacttgcact attcagagcc cgagtgtgaa tccctgctgt gctgcttgga gaagttactt  79920
aacctatgca aggttcattt tgtaaatatt ggaaatggag tgataatacg tacttcacca  79980
gaggatttaa tgagacctta tacgatcctt agttcagtac ctgactagtg cttcataaat  80040
gctttttcat ccaatctgac aatctccagc ttgtaattgg ggcatttaga acatttaata  80100
tgattattgg catggtaggt taaagctgtc atcttgctgt tttctatttg ttctttttgt  80160
tttctcctta cttttggatt tttttattct actatgtctt ttctattgtc ttattaacta  80220
tactctttga tttattttag tggttgtttt agggttatac ctctttctaa tttaccagtt  80280
tataaccagt ttatatacta cttgacatat agcttaagaa acttactgtt gttgtctttt  80340
tgctgttatg gtcttaacgt ttttatttct acaaacatta taaactccac actttattgt  80400
tttttaattt tacttataca gtcaattatc ttttaaagat atttaaatat aaacattcaa  80460
```

aacaccccaa ttaaaagtca gagattgtta ataccacatg atctcactta cacacagaat 80520
tgaaaaactt ggaactcata gaagcagaga gtaaaaacat ggttaccagg tgctggggag 80580
aggcggtggg ctggggagat gttggtcaaa gttagacagg aggaataagt tcaagagatc 80640
tattgtacaa cttattcagt tagataggag gaataagcta aagatcaaga gatctattgt 80700
acaatgtgac tataaccaac aacatatatt gtacacttga aaattgctaa cagtatcttt 80760
taagtgttct ctctacaaat aaatatgtga ggtaatgtat atattaatta actgtagtca 80820
tttcacaatg tatacttatt tcaaaacatc atattgtatg ctataaatat atacaacttt 80880
tatttttcaa ttttagaaat gtccttaaaa aatcagattt tcagatcaga taaaaaagca 80940
agacccaact atatgctgcc aacaggaaac acaccttaaa aataaaggac gaacaaacag 81000
attaaaagta aaaggatgga gaaaagatac atcatattgg taattagaag aaaactggag 81060
tgacaatatg aaacaaaata gatttcagag caaagaatat taccaggggt aaaaatgatc 81120
attttataat gataaaagag tcagttcagc aaaaggatat aacagtccta aatgtttttt 81180
cacctcatag ctgtgtcaaa atagatgaag caaaaactga tagaactgta agaagtagac 81240
aagtccacaa ttatgtttgg agattttttt tttttttttt tttgtcgccc aggctggagt 81300
gcagtggcag gatctcagct cactgcaagc tccgcctccc aggttcacgc cattctcctg 81360
cttcagcctc cccagtagct gggactacag gcggccacca ccacgcctgg ctaatttttt 81420
tgtattttta gtagagacgg ggtttcaccg tgttagccag gatggtctcg atctcctgac 81480
ctcgtgatct gcctgcctcg gcctcccaaa gtgctgggat tacaggcatg agccactgca 81540
cgcagcctgg agattttaat atcctttcaa tgtttagtag aacaagaata cacaaaatca 81600
gtaaggatat agaagattag aacaagacta tcaaacaatt tgacttaaat gacatttgta 81660
gagcacagca gtccccaaca acaataaatc acacattctt tccaagagta catgaaacat 81720
gtaccaagat agaccgtatt ttgagccatg aaacaaatct tgataaattt aaaaggattc 81780
aagtcataga aaatatgttc tctgaccaca atggaattaa attattaacc aataacaaat 81840
atctgggaaa acctcaaaaa cttggacacc agcgctttta aaagactaaa taatttctaa 81900
attatctgtg ttggggggaa aagagaaatg gattagagag caaaaagggt atcagagtgc 81960
tgtggtacga tttttatgaa gagtggaaca gaatctgcct ttggcgtttc cccactacag 82020
cccattcttc acattgataa cagcatgatc cttctaaaat taaatctaac gatcacttct 82080
gcttaatggc tctccaacac ttacagaatt aggtccaaaa ttctagcaca gtttctgttc 82140
atctttctaa cctttcttcc cacaggtcta gctagtacgt atttctttta ttgcatttat 82200
tacactattc ctttgcttat ctatctcccc acctaggcta aagaacaaga ttcttgtctt 82260
tttcattttt gtgtctcagt gcctagcatg gtgccaggca cacagcatgc ttccagtaaa 82320
tgttagctgg atggatgtaa tgagtatatt aaatattaat ttatttgttt ttccccaaaa 82380
agaattattt cctgcaaatc aaggaaattg ctttctttat ataatcaaaa acttattttc 82440
ccagaagatt cttcattaaa aattaagcct atgcacaacc tagctctaaa gtttcaaaga 82500
ttttaggcag caatttttca atctttttga agtaatacat ttgaatcttt tcaaatttct 82560
gtttctgcat ttgtgccaca ccatctcatc tcttgctgaa atgtttttgt taaattaatt 82620
gcttgataaa ttgctaagta cttttcatca gaccaattag gacaatagta agtatccatc 82680
tgtggagcgc ggacattcaa gaaatctgat ccagtattta gaaagtcatt cctgagctga 82740
gttggctcaa actggcacct tctggcattt gcttgtgggt ggggaatgtg gaatgctttg 82800

-continued

```
aaagctgaat gagtttgtca agttttaaaa ttcccttatg gctaaaggaa aacaacattc  82860
attgtttaaa aacaccattg tttgtttttt ctgctttttt gttctttgga gcctgaatct  82920
gcaaaaacac tcacacccag cattttgctt catgtaccac tcctaagatg tttttagaga  82980
cttgaatagt gtctccgcac tactttttat tgtgattgtt cagaatgttc ataacaaatg  83040
gtaaaaagtc agttttagtg ctcaaattga gttttatgga gaaagaccat aatttatgtt  83100
tgtcattgta aattgatagg agaatttttg gaagtttgcg tcctagaacc agatttccaa  83160
ggctcagatc cttattttct cacttcctag ctgtgtgacc ttagacaagg tattaaacct  83220
gtctgtgctg cctcagtgtc ctcatctatt ctttaagagt aagaatagaa cctacccgat  83280
agagtcactt gaagattaag tgggttagta aattcagaat gcttggaaca gtaactagca  83340
cagaataagt gtccaataaa attgggttgc agctattatc agtattattc ctgtcataat  83400
catcatcacc attaagcaat taaatgtaga gttccaaaat ttgattatga aactacagtt  83460
atacagccat gattcccggt gataccacgt cagtaacaag attatttcct tagcttgagc  83520
cagtcactac ctcattgcat gtggcagagt gtgttgccgt aggcaaatgt cattgtaggg  83580
aatgaaaaaa aaattgcctg tgagctgctc tccagaggcc tcatcccatt ttcccatcgt  83640
ccactttact ccatctccac tgccactatt aggaccttat catttcttgt ctagattaat  83700
tcaacagctt ccttccttct agtctccatg atttcaccca ctagccatcc cctcccccttt  83760
gcccaatttt ctccatttat ggtagagtga tctttctaat aggaaactcc tgacttgcct  83820
taaaaagccc tcattgaggc cggacgtggt ggctcatgcc tgtaatccca gcactttggg  83880
aggccgaggc aggtggatca cgaggtcaag agattgagac catcgtgact aacacagtga  83940
aaccccatct gtactaaaaa tacaagaaat tagccaggcg tggtggcggg tgcctgtagt  84000
cgcagctact tgggaggctg aggcaggaga atggcgtgaa cccgggaggc agagcttgca  84060
gtgagccgag attgcgccac tgcactccag cctgggcgac agagtgagac tccgtctcaa  84120
aaaaaaaaag ccctcattga caaccttcaa cccacaatcc atggtgaagc acaggagcct  84180
tggggatctg cccccagcac acctctccac ccttgtctct cactgctcct gccttcatgg  84240
agagccctga tgaactattt gtagtttccc ctgactcacc ttgctgttac tgggcctgtg  84300
tgcgtgttgc tcccactacc tgcaatacgc ttacccactt cacctgggtg aactttactt  84360
aggattcacc ttaggtgggc atcatgttct tccaggcccc tcctctaact tttagttgag  84420
agtattccag acttaaggct ccatgggata gggatcttgt ctatgcacca gcttattccc  84480
aactgcctgg cacgtaatgc atttattaaa tatatattga attgattacc ctacttgggg  84540
ctcttgtttg cttctacact tacagttcta gcatagcact taactcatta tcatgcatca  84600
ttattatggg tttgttttgt ctcccattag actgtgagct ccacaaggct gtgtccttgt  84660
cttatacatc attgtatttc cagcttccaa catagtgctt gccatgacac aggaagtcag  84720
taagctctga atgaatgaat agtatctaca taccattaat ctgaggttta aagtttcccc  84780
aaattctgaa gcaaggggat ttacggactt ccctgacaat ttttggatgt catcccaatg  84840
ataccactaa cattttaagg gacagcttgc atatatacat ttttctggat ggcagttttt  84900
tttcccacag gcttcatcag atatttctcc atagccttcc tcagattctc aaaggggtct  84960
ctgattcccc caaaagataa gaaactgtca taaaaaatta tttctaaata tcaattgtta  85020
aataaaatgt ttgcaaagca gcctgatgaa tcatttcagg ccacttgacc ccgatgagtt  85080
agagagtttg tgctctgcaa tctgactgct tccagcagtc tcactgctgc tggactgtgg  85140
cacttccaat tggcagcagg gcaagtttct tctggatgaa tattctgtca taggggtccc  85200
```

ccttccacac atacctgtag gagcagtttg aaactcatat gcatggtctt cctggttcta 85260
ggcacatgag tcatttaagc tgctggagcc aggaccagct agtatgctag cccggcattc 85320
agaaagttaa aatttggggt caaaactgag aaccttcttt gatccacctt ggccagacat 85380
tttctctggc ttccattaat agcctcaaca tttttttttt ttctggccta gacccacaca 85440
ggcaagagac cagagcttct ctaaggagct aagggaaagc acattttaaa aataacttga 85500
gcaaatgaat tcatctggca aaagcaaccc cactacgtaa aataaacctt tttagtttcg 85560
caatagcagt tcctgaaaat gtaaacaacc tcagggtcta catgcactga atcatttgct 85620
gaacagaaag tccctggtcc aaattctgca agaataaaca ccttacaaaa ctaggggtca 85680
atgaccttca tatgggaaca aggagggtgt ggggggcagc aacccaccct gaggacaatg 85740
agaaagtctt gagacttgat attcaaaatg ctggctttct aaaccaaaaa ctggcatgag 85800
tggagggaga aggggagggt gggcacagtc tatgcctcag gctcttgctc agaccctacc 85860
aggcccctgc cttccctagg gaaagcgaga gtctactcac tgtcatgaag ccagaggaag 85920
gccctgcagg tttcactgtg tgttctgttg acaagatgat ggttccattg aaactgtaat 85980
aacatacttg gccaactaag cccatacgat cgtagtaact ttgtacccag tcctagcttt 86040
tcaaacataa tgataatatg ttctttctaa tgtggcccat actgttctaa tgaacttatg 86100
ctgagttttt ctgagtacta gaataatatt cgccataaat aatagatata attattctca 86160
tttaatattt gcgtagctct tctttaaagc agaaagtatt ttctcattcc ttactagaac 86220
ctttctgtgt gaggagcact gagctagaac ccatatctta gaatggtcag aatttggaga 86280
aattcaggga aaaggcactg gactcatttt taaagactag aaaatgcaac ctccagaaaa 86340
agattcaaga gtttttttact cccagagatg taggaaagat tggagtaaat cttaatatta 86400
tatttcaggt aaacaaagga tcactgtcaa aatagcagca tttattgagt aatggctgtg 86460
tgccaggtac tttacagttt cacatttaac cctcataata accttgtaaa gtggatatcc 86520
cctcagtaca tgatgagaac actgaagctt aggttaaatg attgtccaaa tcggacaatc 86580
attttcaaaa tctccccctt tttttctcct ttcttatctg caaggcagat tgccctttcc 86640
ctttcagtga aacttgtgca tgaccacatg actctctttg gccaatgaaa catgaacaag 86700
cagcgtttat cactttcaga tggaaggctt tgcatgagct ttgcctcctt ttcactctgc 86760
cacagtggcc actaacattc cagatagtgg cgctctgcag gctaggtcct atagtgggag 86820
ctatgggcag agccccccttt cccaccccca tcaagatgtg catgctgcat aagccatgca 86880
ttaatctttg cagttttaag ccactaagtt ttggagttat attaatcatt aatcatggtt 86940
ctcaagagaa acagagtggg ggagtggtat tcattatggg aattggctta catgattatg 87000
gaagctgagt agtcccccag tctgctgttt ttgagctgga gaactagagg agccagtggt 87060
ataattcagc ccaagcctga aggcctgaga aatgggatgg gggaattggg agggtgggtg 87120
tgctagggta ggataagtcc tgaagttcaa aggccagcca gaaggtggat gtttcagcac 87180
cagaagagag agcaaattcg cttttcttct gcctttttgt cctctctggg ccctcaatgg 87240
attggatgat gccctcccac attggtaagg gtggatcttc tatactcagt ctgctaattt 87300
cttccagaaa catcttcaca gacacatcca gaaataatgt tttaccagct atctcggtat 87360
cccttagcct agtccatatt taaaaattaa tgatcacaag cagttgtttg tttccacagc 87420
aaaacctggg tgacagacca agtgacccag atgactagaa tttgaccttc ttttgttgcc 87480
cacaccatac tctgaactaa catgctgtgc tgccttccaa gtggagaatg atggctaagt 87540
atcttctacc taatttgagt cacagaaaaa aaaaaaaaag gttattaact gcagtgacaa 87600
gaattgtgat tccccagggg gcagatcaag actgatagat aagagaagtg aggaacatct 87660
ggggaatgtc cattgaaaat ttactcagaa gagaagaata attaatataa taatatgata 87720
tattgaatta taataaataa tattttgatg tatttccttc caggcatgtt taagttatag 87780
actttgagta tattttctca aagggggttc tatgtaagag actatttctt aatatagttc 87840
ctagcttgga attgctcttg ctggtttaag ctgagcttat tttattacag acttcacaac 87900
aataacgttt tccttcacta gtcagtacac aagatggtct tcatttccag tttggaatcc 87960
cacactatca gagcctgaga caaggactag tatgcagtta gtttgtttgg gaggtgattc 88020
caggaagtgg gaatgagaga tcagtcagcc tgcaacacga aggaggaaaa gtcaatataa 88080
ggatgaattt ggcaattggc cgtttcatgc aactggggct aaattttgct tggctctcta 88140
agaaatgtaa agaatgcctc ccgtaattgc tcacctcaag tatttattca ttggctctca 88200
tgctccattg gttgtccatg agaactttag ccctccctcg ctgcagcaca gacactgtgc 88260
tttctcctag gctgagcaag ctcctgcatc tgtggaaacc gtcccggggc agatagtgaa 88320
ataatgactg ctgcgtgctt gagatctggg aaagaggcca catcataagt gcactgaaat 88380
cagagatgtg tcaagagatg tgacacaggg catctgaggt gtctactgca ccagctataa 88440
ctccctaaac gctaatctca gttcttacag aggggatgga tgcaagggaa cagtcatgat 88500
tgagagcacc gaagaagctc tgtatgaacc ttaggcaagt ttcctaatct ccaaaatgaa 88560
ggtaataata cccaccatcc aagatcttcg ggaggaatag atgaactaat gtatgtgaaa 88620
atgtccagca caggtcctaa cccatagtag gtgctcacca aatgttagtt ccctgccctc 88680
cacgttgtgt gtatccggag ctgcactaga tgctgaggca aatggtctca aatgtacttt 88740
aacacttaat gactgagatt ttttctgagc tgcctacagg ttattgacta tattcattat 88800
taataataat atatatggcc acttcaggca actggggcta aattttgctt ggctctctaa 88860
gaaatgtaaa gaatgcctcc tgtaattgct cacctcaagt atttattcat tggctctcgt 88920
gctttattgg ttgtccctga ggactttagc cctctctcac tgcagcacag acactgtgct 88980
ttctcctagt ttctgtggca agtgacagga gcccacctca aactaaagca aaagggactt 89040
cattggctct tgtagctagg aattccaggg ttggcactgg ctttgggcac tactggatgc 89100
aggaattcaa acaatgtctt caactctttc ttttggtgtt tctctcagct gtgcttctct 89160
tgtcgtttct tttttcccatt ttacagataa gttcatccgt aactgagaga ggtgaaaagg 89220
ggatggctgc agagaactct ggcttatatc atccttgctt gctgacctca aggtccatgt 89280
ataaattctc agagaagaag ccctctggtt ggtgatgctt ggaacatgcc ctggagggtg 89340
ggccccttga agtggagctt gctggaacca catgggctgg agcaaggcgc tagggccaga 89400
agagagaggt aggcagggct gctggccagg cactcttcac caagacaagg caagaggagg 89460
ggcatgattg aggcagtgat acagaaagca gacagtagag gtcgtggcaa gtgtgccgtt 89520
acttgctacc tgtggttgat gggagagtca caccacattt aggaggagag aatccatttg 89580
ccacttctga caatgccaca agaatcacat atttcatcca gaggttgaat ttggcccatg 89640
ctgagcttta aaatacagag ctgtcttgga acaatggctc agtacattca tttggtgtcc 89700
aacaaagcct gcctctgttg ccttccctct ctctgtgtgc ccttcaagat cttcattgtg 89760
ctttggggag agaaagagaa aatgtcatat cagggtagct caccccatgt gtcctggact 89820
caggaaaaga gtatcttatc accttactct tttgttatta taaaaaataa agttgaacgt 89880
cttcaaataa aataaagaag tatagaaaaa attttaaatt aacctgttat gattctacct 89940
agagaaccat tgtcaacatc ttggtatatg tacttccaga tactttccta tgaatatata 90000
cattgtagat tttttaatat taaaaggcta tcatgctgct ttgtatacag gctttcttta 90060
ctgatatgta atataataca cagacaaata tacaaatcct aagccatcaa ctcattgaat 90120
ttttattcat tgtttttaat acctgcattg tgttccattg ttaggctatg tcacaacata 90180
tttaattaag cccctattga tgaatattaa tttactctat ttgccagttc attccagtcc 90240
aacatttatt gagtgtctac ttacgggcca ggcactcttg tattcatcaa gatcaccaca 90300
ttatctgtat cagttattta ttgccacaat aaaactgcat aacaaatcac tccaaaatgt 90360
agcaccttaa aactacaact acttattatt tctcaagagt caatgggtca gctgagcagt 90420
tctgccgata ggggtcaagg tcaacacatt tcaactagac tacttgtaaa aaagaatgag 90480
tgtctgggta ggtgtgttct tctaaaaata aaacaaggaa tgaggaaatt gcaggtagga 90540
taagaggggt ggttggcaac caaaccccac aaaaggcaga caaattttaa ggaaacataa 90600
tgccagactc ctatgtcatc atccaagtag atgcagtgaa gtataacctg ggcgtagta 90660
gggtaggagt ggggagagca gaggagaagg aagggagatt gcttttcatc acttttggat 90720
tccctaataa cagacatgac tgccagtatt aaaatttaac aaaggatatc tgatcattaa 90780
ttttcctgta taagtcactg gtgatcttca acatctctcc ctcccttcct cccttccttc 90840
ctcccaccct cccttccttc cttctttcct cttttgcttt caacttcctt ttctcgtttc 90900
cttttgcttt ctttctcttc tcccttttt ctgtcactct gggcgtatgt agtagtgtaa 90960
aaaggttgac agagaaatca aatataacag gagcagggcc ctgagaaaag cacctggcat 91020
cctgtaggca aaccattgtt tctaaaagaa gggactgaga gattgaggag ctcaggacat 91080
tgccaaatga acaaggcaag cacatttatt cagtaccaaa caaacggaaa acggcctttc 91140
caaataactg acctataaaa cagccttttc acaagagtac cgtaattact ggccaacagc 91200
aacaatgaaa aacaactccc aaacaaagaa atatttctgg attaaaagcc atgagatctg 91260
gattctaaca agctgtgctc ctcaaactac aagtacaaaa tctggctcta aactaacaag 91320
ctatgagcct caaactgatg actggcatgt ttgggtctcc atctccttct tgggggttgg 91380
ggtcttagag accctttcc acgccctgat tctcttacta gtgtgtatgc tttccttttg 91440
acttctcatg ctgaccgtct gagcaggagt gagaagcaat ttcaaaggaa aacatcgttt 91500
atcatctgct gaaagaaacc aaaaagaaca caggaaaaca aaaagacaag gaaagggaat 91560
gaaaatgtaa ttcattttat taaaaagaag aattattctt ctgggacact ggatagaaac 91620
cttaatgagt tacctagcta tcataaatcc tctaacagag aagagaagag aaagaaacaa 91680
agacggaaga gggcaggata aaagaaagaa aaaaggaagg gaaaaatgaa ggaaggaagt 91740
tatctattca tttctacaga gactctgctg agcagtagac aagaagactt gggaaaaatt 91800
taactgaaac ttttccaaaa atcttttcag agggattttt tccctctgaa aagcatcatt 91860
agaggctgtt caatacccaa ggcaagcctc tttcatatta cttactgtac atgaaacact 91920
catgcaattg aggctagcca gaggccattt agaaattcaa taattattca acccaagggg 91980
ctttccaaat ggtgaagtag cttcttaaga ggaaattaat attgagcagt atagcaaacc 92040
taattggaat cttgagaaaa tagttctgtg tcgttagaac agctagaggc taaagaagat 92100
caggttggat gataccttca tttttgtctc tttccttaat tatgatgtaa agggaaaaat 92160
cttgtttatt ttctatgcca ggagggtaga gggtgatttg gagaggttcc aagtttatca 92220
aaatctacct tcagtctggc agtagaaaag tttacttcct tcatttcttt cctatagaca 92280

-continued ttcaaagaga gctaaggaga tccaaaaacc tttttttcta tatttgcaat gcaaggcagt 92340
tgggaattaa tgactgattt gttggtgagg gcagtgggca ttgatcacaa aagcagtaaa 92400
gctgtgtttc tcaaagagag aaagtctctt tgagatcttc attattttac tatttagaag 92460
agaaaggggc gttatatcac gttggaagca tccatgagtc actagtctct tctctatctt 92520
tctatgcctt tctgtattaa ttactttgaa agcacaacat tccaaaccca ttgagcacac 92580
agtggtctga tttctccact tgtgaaaggt gctaaagtct cactgtagga ttaatttggg 92640
ggtccaggct atgggcttgt agatatgact accttagact ttggttctcc tggcaactaa 92700
cccttttggg atcgtatcta agttgacctg tttcacagtg agagaactcc tctccattac 92760
tcagaatact gaggcagatc acaagtgtac cacacctggc taatgttaag ccagacagaa 92820
acatcaggct catctcttga gaagaagggt cgcttattaa ggatacaaac tatttttttt 92880
tttttttttt gagacagggt ctcattgccc aggttagagt gcagtggtgc aatcatagct 92940
cactgcagcc tcaaccacat gggtattttt aaataagaaa aaaataccat ctgatagata 93000
tgaaggagca ttgggtcact ataaacaaaa cagattctaa gagcaggaag aaagagtaca 93060
gtctcttttc aataattttt ttttaaactt gggaaagaac actcactcta ttcctataga 93120
ccagaaagca gataattgtc cattatgatt ccacatgaca ctatcttgtt cagctgtcac 93180
tgaaacaact ttgaacactg tcatatgttc ttcccagctc ctgaactctg acctttttat 93240
gccttagttc cactttcaca aaaagggatt gatgtaatgt gcatttcaga ggaaacgact 93300
atagacattt agtgtcatta taaatgttga gaagtatgct ggcagaaatt atgccttaag 93360
atcatatatg gattcttgta tggtttgaaa ttgcttaaaa gatatatatg atctctaaaa 93420
tgtgtgtgta tatatatatg atgtcttctt atatatctat atgtgatata tttatatata 93480
tataaatctg tgtatatcac atatataaat ttgctgttat ttgaattgcc attacctcag 93540
tgcttagggg aagccatgca cgtttgtttc ttttcagtac ccagagttaa ttaacataag 93600
ttatcacaga agctcccata agcattgaga caatttctct atacctgtga ctatttaagg 93660
ttttgaaaac aaaacagaag caggtaagga ggaagtacgc tttactattg aagatttatt 93720
aggtacacat ttagatttgt gaactcacat tgcttaggat gaaagggact cttgaggatg 93780
tctgctgttt gttagtgaac tgcctgtaac aattacaatt agcacacaca tgagcacaat 93840
gaactgggta gtcagactca gccaaaatga atagaaatag cctcttacca aatttacttt 93900
gagtagccct tggactctga gcactgctgc ccagagcaat atgactgtag gtccaagttt 93960
gtcaatgact atgcaaatgt gctttcttcg cttttactct attgtcatct gtctattaca 94020
atgttgctat ggtgacacct ttccaatatc cctgtgcttc tttggtatcc tctaagggga 94080
agctgtaatg aagtggcttg gcaaaagaat cctcttggaa tttttttttt ttcatatgct 94140
actgaaaacc agcatgattt tcctcttatg ggaaatgtat aaagtatgag ttggaaatga 94200
tggaaattaa tctgtactga cttgggcaag gaatgtgaat gttattcatt ctgttccaaa 94260
ctacctgaaa atattctctt tctgttccta ctttccagga gataacatct taagggacac 94320
tgaagcttgt gcgtgtgtga gtagaacacg tgctgggggc tcttgagctc atgagggagg 94380
ggctacatgt cggtggggtg ataactgtat gctggaaaca atgataggtg gtgaccctgg 94440
agcacttacc atgtgacagg tgttatgcta agcatgttgt atgcattcct tcattgaatg 94500
acagctacct atattatcct cattttataa gatgaggtaa cagagcttca gaaaggttag 94560
actcagctgc tatgggtctg tctgactctg gtgttcttcc tcttaaaaac tggggcactt 94620
tggaaatgag attcctcggt gatgaacaga aatattgctt agcggctgta tttttgtatc 94680
tggcagtttt cccatatttg agtcttatat tcacaatcgg tatctttaca ttacacaaaa 94740
gtgacacaga attagagtca tttaatccag ggttgatatc attaagtcat gactatttat 94800
taaatgtttc ttacaatatc tgagatgata ttgcaaaaga tgtaagtgat tttagaagtt 94860
ctcacttcgt agttagttgc agaaacctct tttggaggag ggatgttttc tctatatatc 94920
ctaatttcta cttaatatat ttccacacct ctttgaagtg tgtagtaaga atggtaaaat 94980
gcagtacttc gtcatttggt acagttcaat caatatgcat taagatgtga tcatatgggt 95040
aatagaaaaa tgtgaaagat ccaattcttt ttctccagaa ggcaggaagc tcatatttga 95100
tttctgttac tataaactat aaaaacgttt caaatgtagt ttacccgtaa ccatcaccct 95160
gcaagggtga tattgctccc cgccaattta cggaggagaa tactgaggct ttaaggttgt 95220
agatagacca agaccacaca agtagagagt ggcgggctgt gggttgagct ttaaaatcca 95280
ggttcatcca tgactcccag tgtgttctag taaatccact agaatctgag tattttccaa 95340
tgatttatgc tccgctctgt gtcaggcagt tcatggtatt tttcaacaat cagaaaatcc 95400
tggggaaggc aaactgtttc cccctctcta ggtgccttgg aagtggccgt tgtggaccca 95460
gagatcatcc tttctgatct gacaccttct tcactgccct ggcccagtgt cttttctgca 95520
aggctggaag ccccccttaga ctggtcatgt cccatctctt tccggaggga agatgatccc 95580
aaagacgact tttctctcca cggtgctgcc ataccgcagg cggccgccag gggtccccgc 95640
tcggcgtccc cgcgagacag tcgagccccg gccggctgcg cggcgcgctg ggtgcatgag 95700
ggggctgctc cggagcgacg gcggctgcag ctggagccag gcgctcgccc gtccgccggt 95760
tggctcgccg ggacctcgcg caccggcggc agagtccctt gcgtggattg gcaagcgacg 95820
ccccacctgc cccgagctca ccattttctt tcgcgctggc tgcagctgac ccggcgaagg 95880
gagccgaccg ggccctgggc tggaggtaaa accccacggt gagtaagaac ccgctccaag 95940
ctaggggagg cggcgcagcc cggtggctgc tcgctcccga tctcgcccgg gcgggcggcg 96000
aggtttgggg cgcacctggg cgcgggtgca agaaggtgcg ggaggcggcg gaccggtctt 96060
ctgcccgccg gccacgggct tccggggctg gagtcctctt cagacccctg ccggcgcctg 96120
ggtttctggc cggctcctcg tgtgcacttc ccggcaggaa caagggtcgc ccactttcca 96180
ccccgggatc ttgatttgtc cttgatttga aaagatataa atcaataaga tcgtccttct 96240
ttcggggtgc aagactccga gcccatcccc agccgcggac gcctgcaggg tgcgtgttgg 96300
gctgtgggtg gcgggaagac aaacttttac aaaagtgcgc ctgggctggg ggacaacgct 96360
tgggcgtcct gatcctgagg gaggagtctc ggcttggggc agcgtagggg aagtccgcac 96420
cgtcagccag gtcgccccccg gggctgacga tgcctcacgg aggtggggag cgtgtaaagg 96480
ccgtacaaat cgcgcttaac tttggggcca acaactgtca aacatctgga atcccagccc 96540
ctccctttcc ctgaactggg gaagaaggtg aaaacccttc aagttttctt tgattgcccc 96600
ttcccacctt cagacccctg ctgggagggt aaagcgccga cccctggtgc ctggcaagta 96660
ccagagactc taaatctctc gggatccccc ccctcgcgct ctttcctgac cctctcccct 96720
aaccctcccc acagagatct ctctacgcag ccgactgaga tcgtggcgaa tggccttttg 96780
tttctccgcg tttcccctat tgtttgcctt tccaacatct ggcggggctt ggggagagaa 96840
ggaagcccct ctggtccccc tccccggccc ccacgccagc tccggcaggg gatcccagct 96900
gggaaagtgg aggagcccga ccccagcgag gccgccccac cccgcccttg tggttagagg 96960
gcggagggaa agttgttcct tccccgcctc cgctgctgcc tgtggcccag ggcgcatttc 97020

-continued

```
tcagatctca gcccaggcgc gccgcaaagg ctcaaatccg agaaggtgct gctttcgaga  97080

cagtggaagc gcgttccgcc ccaatccaga gcgtccagtg gttggttcca gaggatttca  97140

atctctagcc aaaggcgttg gggctgggcc gctgctaggg cagtgggagg ggatcggggc  97200

acctttggta ggcggaaagc tgagattctg gggtccacaa gtttccaagg gcgggagggc  97260

aggctagtcg ccaaaaagag aacgaagatg caaataacga ggaagcctta tgacgttgcc  97320

tggaaatagt agtgtggtgg ttcactccgg aatgaacgtg gagttctggc tttgagtacc  97380

gctccaagtt taaatcccaa gtccccttc ttcattgtag aaaaagagga ctcagacgac  97440

gcaacacaga tacggctaga gcacagttcc tgcttccacg tcccagagaa caagtggctt  97500

aggatggtcc cgagttcccc tgtgggtgcg cttgttgggt tgcaggcggc cctgtttccc  97560

tgcacaagtc agatgcttac acattgtgtt cattcttagt gtggattatt gattaaagaa  97620

ctggggcaaa agcaaagtag ctactctgag aagtcagggt ccccagatgg tgcccagcga  97680

gttgtcttgc ctctgagggg aggctgactg agactgtgca cctgttagaa cctatgctac  97740

cccatagcct tgcagttgac ttgctgttgc cagcttttcc tgtgggatcc ccaatgagtc  97800

cctcttccaa ggaagctcaa ttacactttt gattcctcct caacccaggg gaagaaagag  97860

gcttctgtag gaacattatg atctatgtac ccactcagac attgtcagtg gataccagaa  97920

gcttggctct gcacagctct gagagttttc cctttgcgaa ctcaacagaa cttttgagtt  97980

tccatttaac ataaaagaag tgagactgct aagccaggaa tgcgacacat agagcacttt  98040

ctctagtgat ttctgggtat tatatctctt taccttccca acggtggaac caggaaaaga  98100

aaaaaaagca acatctttga agtactgcaa ggcactttac aaacatttca ttatgaaaat  98160

gatccccaag gaaggattcc tttgaaattt agcagcagca acccagaagc aacaaaaaag  98220

accaaagtta ctcaagaagt acccaaaggc atcattaaca aaataaaaga gcatttcttg  98280

tcttggccta ccccgctaag gaaaacaggg taattatagt ggaagttaag cttg        98334


<210> SEQ ID NO 64
<211> LENGTH: 28
<212> TYPE: DNA
<213> ORGANISM: Artificial sequence
<220> FEATURE:
<223> OTHER INFORMATION: Synthetic polynucleotide

<400> SEQUENCE: 64

cccggggccg gggccggggc cggggccc                                        28


<210> SEQ ID NO 65
<211> LENGTH: 212
<212> TYPE: DNA
<213> ORGANISM: Artificial sequence
<220> FEATURE:
<223> OTHER INFORMATION: Synthetic polynucleotide

<400> SEQUENCE: 65

cccggggccg gggcccgggg cccggggccc ggggcccggg gcccggggcc cggggcccgg     60

ggcccggggc ccggggcccg gggcccgggg cccggggccc ggggcccggg gcccggggcc    120

cggggcccgg ggcccggggc ccggggcccg gggcccgggg cccggggccc ggggcccggg    180

gcccggggcc cggggcccgg ggcccggggc cc                                  212
```